US012617770B2

(12) United States Patent
Ye et al.

(10) Patent No.: US 12,617,770 B2

(45) Date of Patent: May 5, 2026

(54) IRAK INHIBITOR AND PREPARATION METHOD THEREFOR AND USE THEREOF

(71) Applicant: WUHAN CREATERNA SCIENCE AND TECHNOLOGY CO., LTD., Wuhan (CN)

(72) Inventors: Guozhong Ye, Shanghai (CN); Chenli Ding, Shanghai (CN); Yawen Ding, Shanghai (CN); Qian He, Shanghai (CN); Chaodong Wang, Shanghai (CN)

(73) Assignee: WUHAN CREATERNA SCIENCE AND TECHNOLOGY CO., LTD., Wuhan (CN)

(*) Notice: Subject to any disclaimer, the term of this patent is extended or adjusted under 35 U.S.C. 154(b) by 1014 days.

(21) Appl. No.: 17/754,121

(22) PCT Filed: Sep. 23, 2020

(86) PCT No.: PCT/CN2020/117093

§ 371 (c)(1),
(2) Date: Mar. 24, 2022

(87) PCT Pub. No.: WO2021/057785

PCT Pub. Date: Apr. 1, 2021

(65) Prior Publication Data

US 2022/0298139 A1 Sep. 22, 2022

(30) Foreign Application Priority Data

Sep. 24, 2019 (CN) ........................ 201910906833.7

(51) Int. Cl.

*C07D 401/12* (2006.01)
*C07D 401/14* (2006.01)
*C07D 413/14* (2006.01)

(52) U.S. Cl.

CPC ......... *C07D 401/12* (2013.01); *C07D 401/14* (2013.01); *C07D 413/14* (2013.01)

(58) Field of Classification Search

CPC ... C07D 401/12; C07D 401/14; C07D 413/14
See application file for complete search history.

(56) References Cited

U.S. PATENT DOCUMENTS

| | | | | |
|---|---|---|---|---|
| 5,459,142 | A | 10/1995 | Tone et al. | |
| 7,842,711 | B2 | 11/2010 | d'Orchymont et al. | |
| 8,436,185 | B2 | 5/2013 | Foley et al. | |
| 8,507,528 | B2 | 8/2013 | Alisi et al. | |
| 9,951,086 | B2 | 4/2018 | Bothe et al. | |
| 10,160,753 | B2 * | 12/2018 | Gummadi | A61P 37/08 |
| 2016/0311833 | A1 | 10/2016 | Bothe et al. | |
| 2018/0201609 | A1 * | 7/2018 | Gummadi | A61P 3/00 |
| 2019/0071432 | A1 | 3/2019 | Bothe et al. | |
| 2019/0151295 | A1 | 5/2019 | Crew et al. | |
| 2022/0388982 | A1 | 12/2022 | Bothe et al. | |
| 2023/0250064 | A1 | 8/2023 | Ye et al. | |

FOREIGN PATENT DOCUMENTS

| | | | |
|---|---|---|---|
| CN | 111499612 | A | 8/2020 |
| JP | H 5-170747 | A | 7/1993 |
| JP | 2016506367 | A | 3/2016 |
| JP | 2017500326 | A | 1/2017 |
| JP | 2017535585 | A | 11/2017 |
| JP | 2018514539 | A | 6/2018 |
| JP | 2019520348 | A | 7/2019 |
| TW | 201725202 | A | 7/2017 |
| WO | WO 2009136663 | A1 | 11/2009 |
| WO | WO 2013042137 | A1 | 3/2013 |
| WO | WO 2014074657 | A1 | 5/2014 |
| WO | 2016083433 | A1 | 6/2016 |
| WO | WO 2016174183 | A1 | 11/2016 |
| WO | 2017/108744 | * | 6/2017 |
| WO | 2017108744 | A1 | 6/2017 |
| WO | 2017148902 | A1 | 9/2017 |
| WO | 2017207385 | A1 | 12/2017 |
| WO | 2017207481 | A1 | 12/2017 |
| WO | WO 2019089580 | A1 | 5/2019 |
| WO | WO 2019133531 | A1 | 7/2019 |
| WO | 2020135513 | A1 | 7/2020 |
| WO | WO 2021259163 | A1 | 12/2021 |

OTHER PUBLICATIONS

Flannery, Biochem Pharmacol, 2010, vol. 0, No. 12, 1981-1991. (Year: 2010).*

Flannery, Sinead et al.;"The interleukin-1 receptor-associated kinases: Critical regulators of innate immune signalling"; Biochem. Pharmacol; 2010; vol. 80, No. 12; pp. 1981-1991.

Priscilla, N. Kelly et.al.; "Selective interleukin-1 receptor-associated kinase 4 inhibitors for the treatment of autoimmune disorders and lymphoid malignancy"; The Journal of Experimental Medicine; Nov. 30, 2015; vol. 13, No. 212; pp. 2189-2201.

(Continued)

*Primary Examiner* — D Margaret M Seaman

(74) *Attorney, Agent, or Firm* — JONES DAY

(57) ABSTRACT

A compound represented by formula I are provided. The stereoisomer, racemate, tautomer, isotopic label, prodrug or a pharmaceutically acceptable salt of the compound, and a pharmaceutical composition containing the compound, a preparation method, and medical use of the compound are further provided. The structure is as shown in formula I.

Formula I

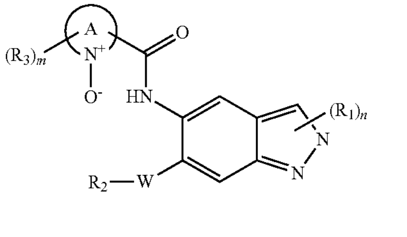

20 Claims, No Drawings

(56) References Cited

OTHER PUBLICATIONS

Chaudhary, Divya et al.;"Recent Advances in the Discovery of Small Molecule Inhibitors of Interleukin-1 Receptor-Associated Kinase 4 (IRAK4) as a Therapeutic Target for Inflammation and Oncology Disorders"; Journal of Medicinal Chemistry; Jan. 2015, vol. 58, No. 1; pp. 96-110.

Database Registry, CAS Registry No. 1259116-59-0; N-(1H-indazol-5-yl)-1-oxidopyridin-1-ium-2-carboxamide; Jul. 9, 2015 (5 pages).

Database Registry, CAS Registry No. 1797805-52-7; N-(1H-indazol-5-yl)-1-oxidopyridin-1-ium-4-carboxamide; Jan. 12, 2011 (5 pages).

International Searching Authority, English translation of the International Search Report and Written Opinion for International Patent Application No. PCT/CN2020/117093 (Pub No. WO 2021057785) mailed Dec. 21, 2020 (11 pages).

Yuan et al., 1984, "Organic Heterocyclic Chemistry: Basic Principles and Synthetic Drugs," People's Medical Publishing House, 1st Edition, p. 131, in Chinese with machine English translation (5 pages).

* cited by examiner

IRAK INHIBITOR AND PREPARATION METHOD THEREFOR AND USE THEREOF

CROSS-REFERENCE TO RELATED APPLICATIONS

This application is a U.S. national entry of PCT International Application No. PCT/CN2020/117093, filed Sep. 23, 2020, which claims priority to Chinese Patent Application No. 201910906833.7 filed with China National Intellectual Property Administration on Sep. 24, 2019 and entitled "IRAK INHIBITOR AND PREPARATION METHOD THEREFOR AND USE THEREOF". the content of which is incorporated herein by reference in its entirety.

TECHNICAL FIELD

The present invention relates to the field of pharmaceutical chemistry, particularly to a compound suitable for treatment of cancer and inflammatory diseases related to interleukin-1 receptor-associated kinase (IRAK), and more particularly to a compound for regulating a function of IRAK-4.

BACKGROUND

Interleukin-1 receptor-associated kinase (IRAK) family are intracellular serine-threonine protein kinases, including: IRAK1, IRAK2, IRAK-M and IRAK4. A common feature of these four members is the typical N-terminal death domain that mediates the interaction between the MyD88 family adapter and the central kinase domain, wherein IRAK1 and IRAK4 have activity. IRAK4 is a key factor downstream of the Toll-like receptor (TLR)/interleukin-1 receptor (IL-1R)-mediated inflammatory signaling pathway. When the binding of ligand to a pathogen-specific molecule (e.g., lipopolysaccharide, polypeptide and viral DNA) recognized by the extracellular portion of TLR, the intracellular portion recruits MyD88 and other factors to form complexes and initiate IRAK1 autophosphorylation, thereby activating downstream serine-threonine kinase TAK1, promoting NF-κB and MAPK signaling pathways, producing proinflammatory cytokines, chemokines and destructive enzymes, and ultimately leading to inflammatory responses that mediate innate immunity. IL-1R is involved in host defense and hematopoiesis and serves as a bridge connecting the innate immunity and acquired immunity. (Flannery, et. al, Biochem. Pharmacol., 2010, 80 (12):1981-1991).

Rheumatoid arthritis (RA) is a chronic, inflammatory, systemic autoimmune disease prominently characterized by non-suppurative inflammation in joints and joint tissues. RA is mainly manifested by synovitis of joints, which eventually causes damage to various tissues (such as cartilages of joints, ligaments and tendons) and multiple organs. Studies have shown that a variety of immune cells participate and mediate the autoimmune inflammation in RA patients, including T/B lymphocytes, macrophages, neutrophils, and the like. Meanwhile, a large number of researches have demonstrated the direct association between cytokines and RA, such as interleukins (IL-1/IL-6) and TNF-α.

Studies have shown that IRAK4 inhibitors can effectively block the production of the proinflammatory cytokine tumor necrosis factor (TNF) in LPS or CpG-induced human leukocytes; in mice with collagen-induced arthritis, IRAK4 inhibitors can significantly inhibit the release of TNF, thereby controlling disease progression; in mice with MyD88-dependent inflammatory gout, IRAK4 inhibitors are able to dose-dependently block leukocyte infiltration (Priscilla N. et. al., J. Exp. Med., 2015, 13 (212):2189-2201).

Therefore, it is believed that the excessive activation of IRAK4-dependent TLR/IL-1R signaling pathway is closely related to the development and progression of rheumatoid arthritis. It has been confirmed in various studies that IRAK4 activation is closely related to the onset and progression of diseases such as tumors, gout, systemic lupus erythematosus, multiple sclerosis, metabolic syndrome, atherosclerosis, myocardial infarction, sepsis, inflammatory bowel disease, asthma, and allergy (Chaudhary D, et. al., J. Med. Chem. 2015, 58 (1):96-110).

SUMMARY

In order to solve the problems in the prior art, the present invention provides a compound of formula I or a stereoisomer, a racemate, a tautomer, an isotopically labeled compound, a prodrug or a pharmaceutically acceptable salt thereof, Formula I

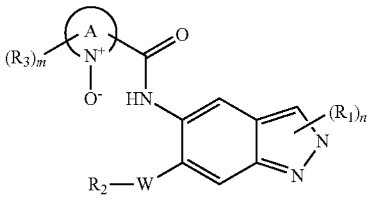

wherein, ring A is 5-14 membered heteroaryl or 5-12 heterocyclyl containing at least one of N;

$R_1$, $R_2$ and $R_3$ are each independently selected from hydrogen, halogen, CN, OH and the following groups optionally substituted with one, two or more R: ($C_1$-$C_{12}$)aliphatic hydrocarbyl, ($C_1$-$C_{12}$)aliphatic hydrocarbyl optionally comprising one, two or more heteroatoms, $C_{3-12}$ cycloalkyl, 3-12 membered heterocyclyl, $C_{6-20}$ aryl or 5-14 membered heteroaryl, and —$NR_aR_b$;

W is selected from O, S, NH and is a single bond;

$R_a$ and $R_b$, are each independently selected from H and ($C_1$-$C_{12}$)aliphatic hydrocarbyl; each R is independently selected from halogen, CN, OH, SH, $NR_aR_b$, and the following groups optionally substituted with one, two or more R': ($C_1$-$C_{12}$)aliphatic hydrocarbyl, ($C_1$-$C_{12}$) aliphatic hydrocarbyl optionally comprising one, two or more heteroatoms, $C_{3-12}$ cycloalkyl, 3-12 membered heterocyclyl, and $C_{6-20}$ aryl or 5-14 membered heteroaryl;

each R' is independently selected from halogen, CN, OH, SH and $NR_aR_b$; and n is selected from 1, 2 and 3; and m is selected from 1, 2, 3, 4, 5 and 6.

According to one embodiment of the present invention, the "($C_1$-$C_{12}$)aliphatic hydrocarbyl optionally comprising one, two or more heteroatoms" may be selected from ($C_1$-$C_{12}$)aliphatic hydrocarbyloxy, ($C_1$-$C_{12}$)aliphatic hydrocarbylthio, ($C_1$-$C_6$)aliphatic hydrocarbyloxy($C_1$-$C_6$)aliphatic hydrocarbyl, ($C_1$-$C_6$)aliphatic hydrocarbylthio($C_1$-$C_6$)aliphatic hydrocarbyl, N—($C_1$-$C_3$)aliphatic hydrocarbylamino($C_1$-$C_6$)aliphatic hydrocarbyl, and N,N-di-($C_1$-$C_3$)aliphatic hydrocarbylamino($C_1$-$C_6$)aliphatic hydrocarbyl:

the "5-14 membered heteroaryl or 5-12 membered heterocyclyl containing at least one N" refers that the heteroaryl or heterocyclyl contains at least one nitrogen atom, and further may contain other one or more heteroatoms selected from N, O and S, for example, selected from pyridine, pyrrole, piperidine and tetrahydropyrrole;

the ($C_1$-$C_{12}$)aliphatic hydrocarbyl may be selected from ($C_1$-$C_{12}$)alkyl, ($C_2$-$C_{12}$)alkenyl and ($C_2$-$C_{12}$)alkynyl, and preferably, the ($C_1$-$C_{12}$)aliphatic hydrocarbyl may be selected from ($C_1$-$C_6$)alkyl, ($C_2$-$C_6$)alkenyl and ($C_2$-$C_6$)alkynyl;

the "halogen" is selected from F, Cl, Br and I; and the "$C_{3-12}$ cycloalkyl" may be selected from cyclopropyl, cyclobutyl, cyclopentyl and cyclohexyl.

According to one embodiment of the present invention, the $R_1$, $R_2$ and $R_3$ may be each independently selected from the following groups optionally substituted with one, two or more R: methyl, ethyl, n-propyl, isopropyl, n-butyl, isobutyl, tert-butyl, n-pentyl, isopentyl, neopentyl, n-hexyl, ethenyl, 1-propenyl, 2-propenyl, 1-methylethenyl, 1-butenyl, 1-ethylethenyl, 1-methyl-2-propenyl, 2-butenyl, 3-butenyl, 2-methyl-1-propenyl, 2-methyl-2-propenyl, 1-pentenyl, 1-hexenyl, ethynyl, 1-propynyl, 2-propynyl, 1-butynyl, 1-methyl-2-propynyl, 3-butynyl, 1-pentynyl, 1-hexynyl, cyclopropyl, cyclobutyl, cyclopentyl, cyclohexyl, methoxy, ethoxyl, propoxy, butoxy, pentyloxy, methoxymethyl, ethoxylmethyl, propoxymethyl, methoxyethyl, ethoxylethyl, propoxyethyl, methoxypropyl, ethoxylpropyl, propoxypropyl, N-methylaminomethyl, N-methylaminoethyl, N-ethylaminoethyl, N,N-dimethylaminomethvl, N,N-dimethylaminoethyl, N,N-diethylaminoethyl, amino, N,N-dimethylamino, N,N-diethylamino, tetrahydropyrrolyl, piperidinyl, pyridyl, pyrazinyl, pyrrolyl, imidazolyl, pyrazolyl, oxazolyl, isoxazolyl,

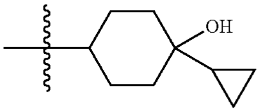, 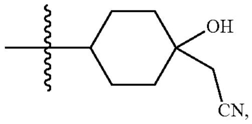

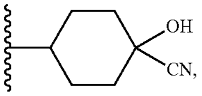 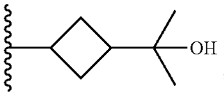

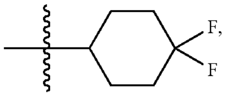 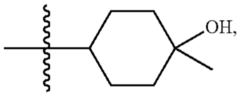

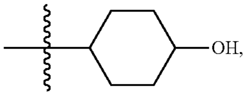 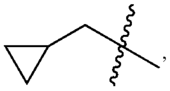

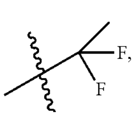 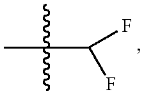 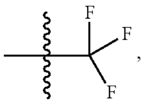

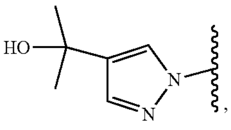 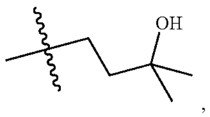

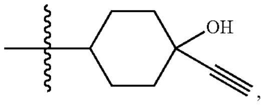 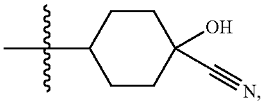 and

-continued

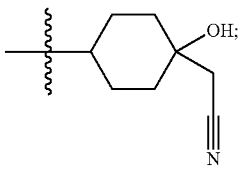

and the "⌇" denotes the connection site of the group.

According to an embodiment of the present invention, in the compound of formula I or the stereoisomer, the racemate, the tautomer, the isotopically labeled compound, the prodrug or the pharmaceutically acceptable salt thereof, the compound of formula I may be selected from the following structures of formula Ia, formula Ib, formula Ic, formula Id and formula Ie:

formula Ia

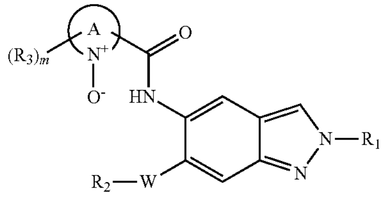

formula Ib

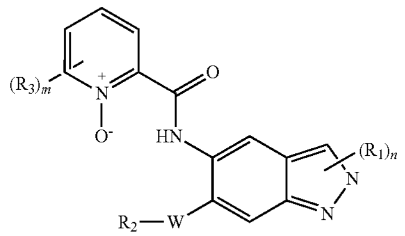

formula Ic

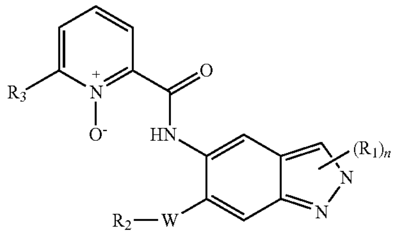

formula Id

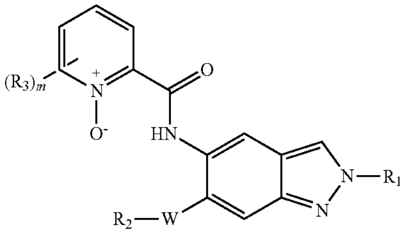

-continued formula Ie

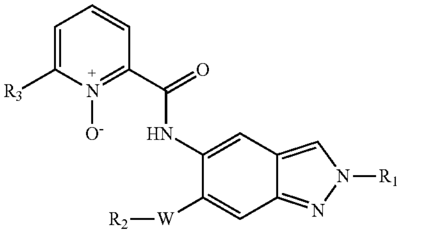

in the formula Ia, formula Ib, formula Ic, formula Id and formula Ie, $R_1$, $R_2$, $R_3$, m, n and W are as defined in formula I.

According to an embodiment of the present invention, in the compound of formula I or the stereoisomer, the racemate, the tautomer, the isotopically labeled compound, the prodrug or the pharmaceutically acceptable salt thereof, the compound of formula I may be selected from the following structures:

001

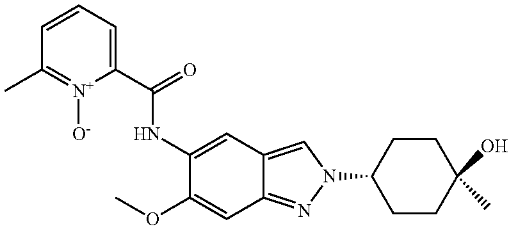

002

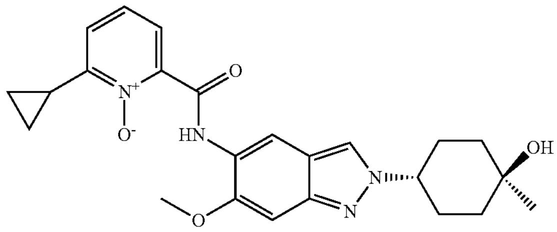

003

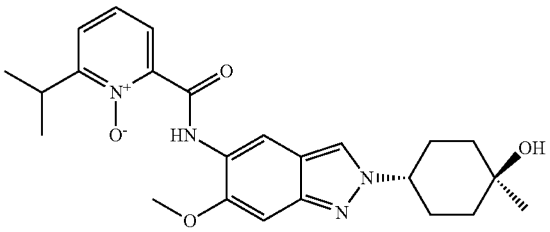

004

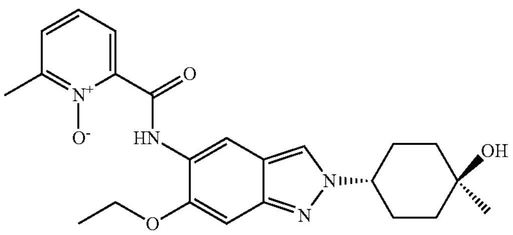

-continued

005

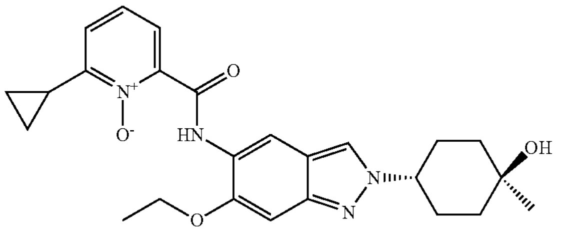

006

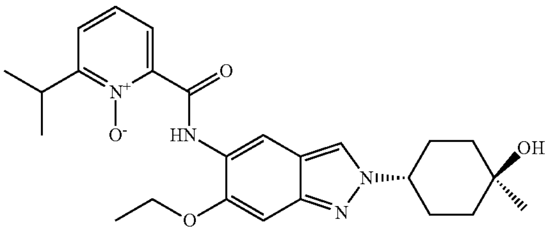

007

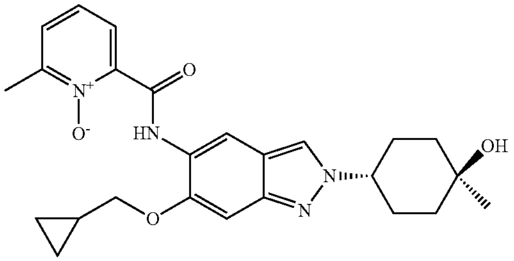

008

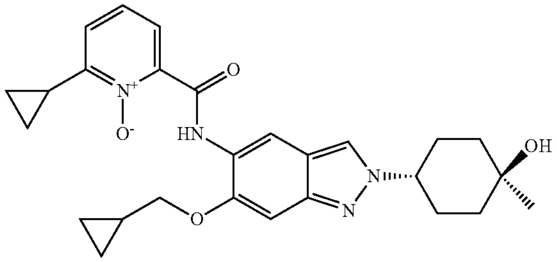

009

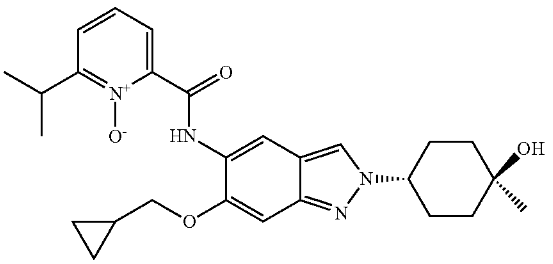

010

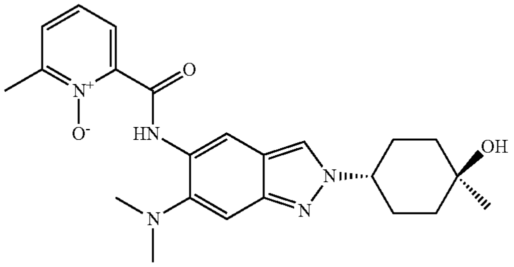

-continued
011
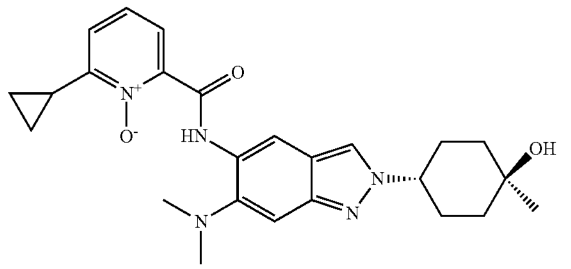
012
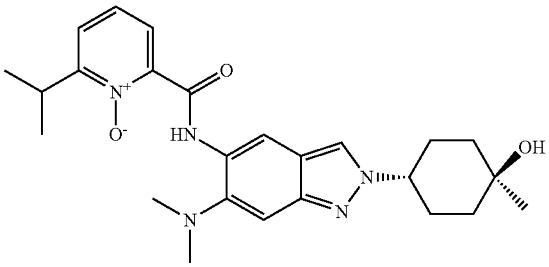
013
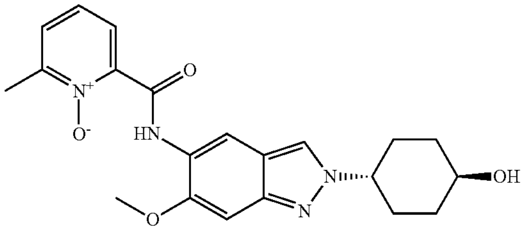
014
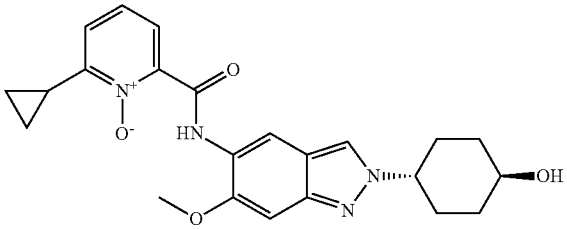
015
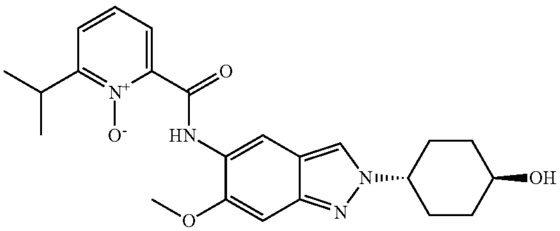
016
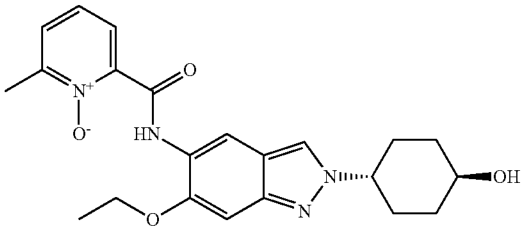
-continued
017
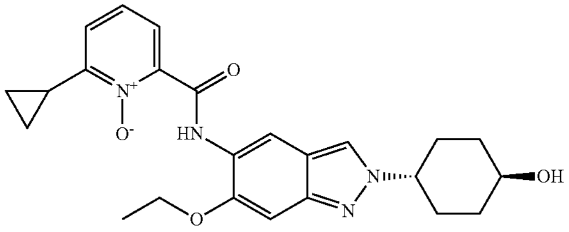
018
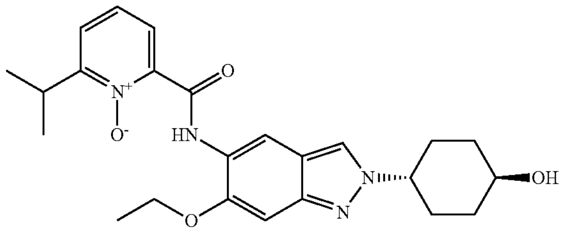
019
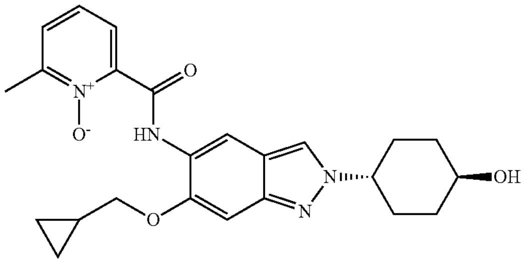
020
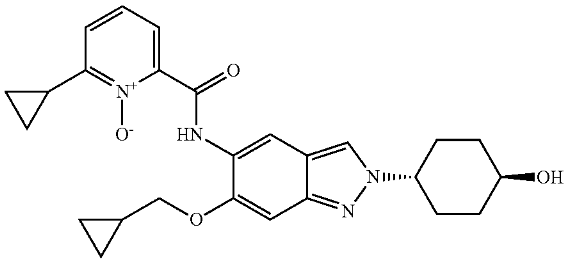
021
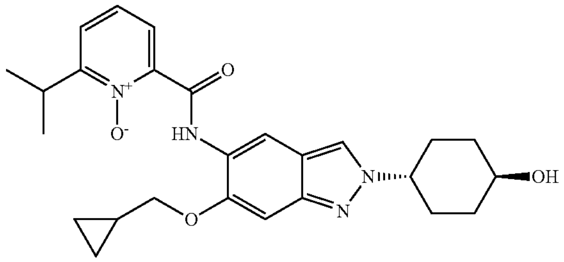

-continued
022
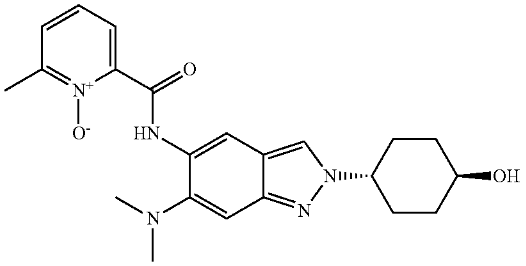
023
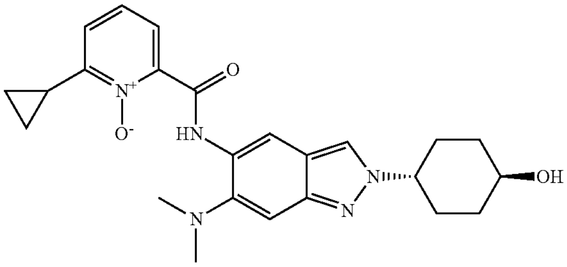
024
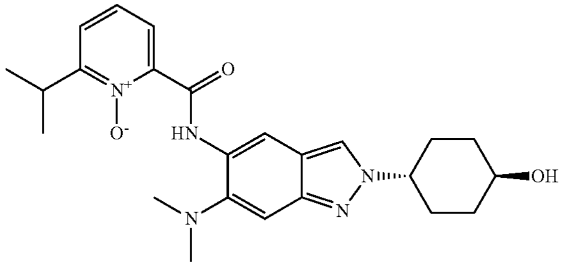
025
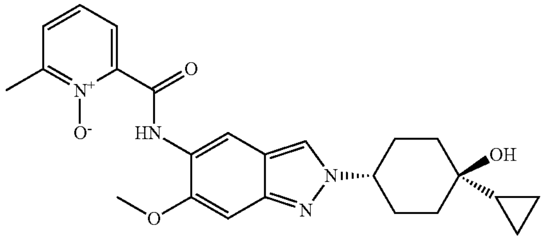
026
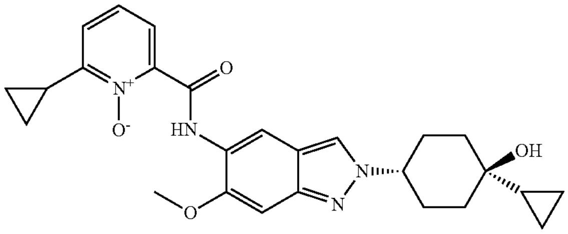
-continued
027
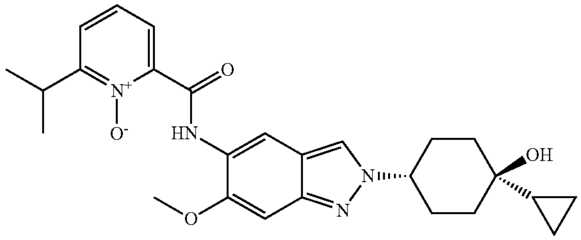
028
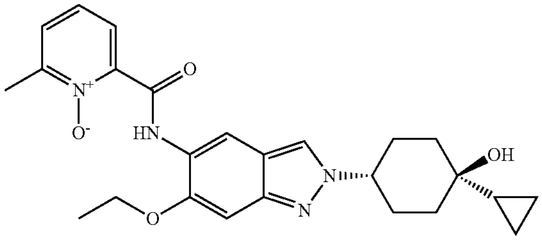
029
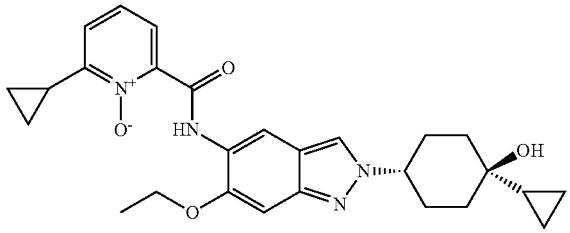
030
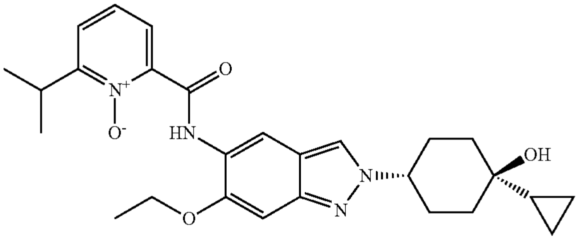
031
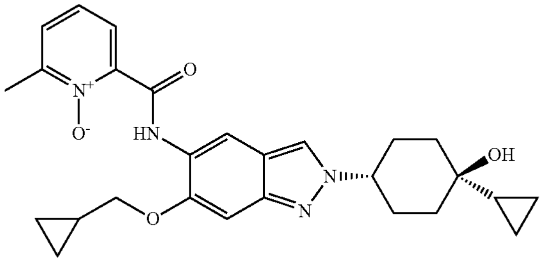
032
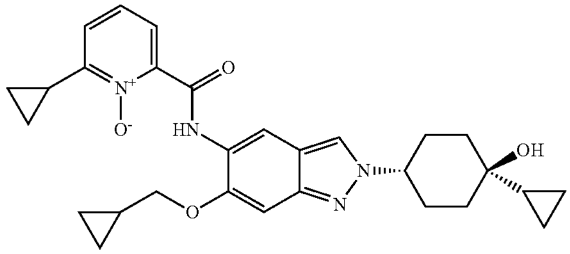

033
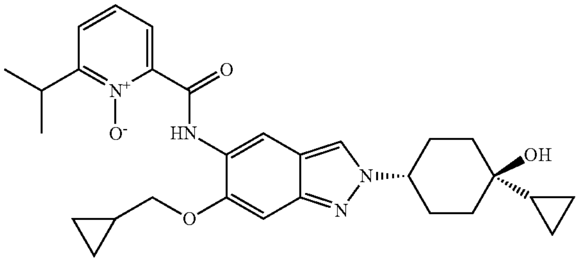
034
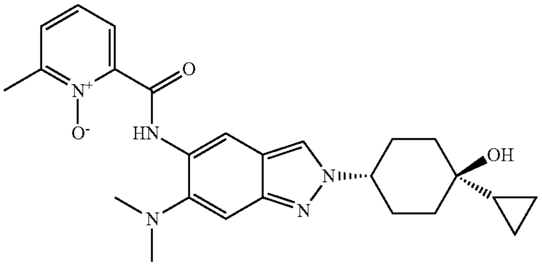
035
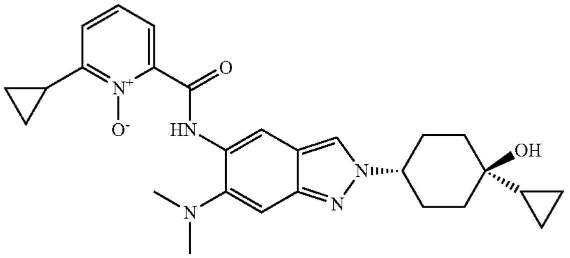
036
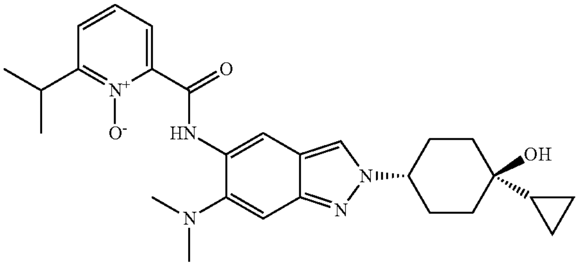
037
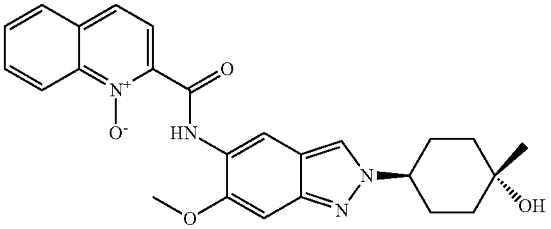
038
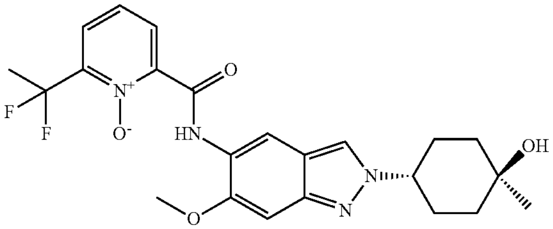
039
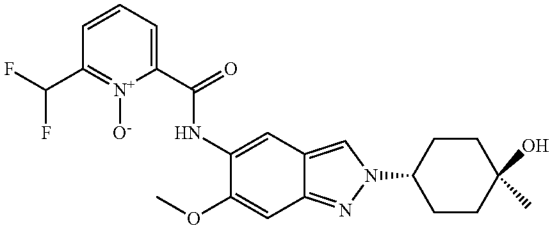
040
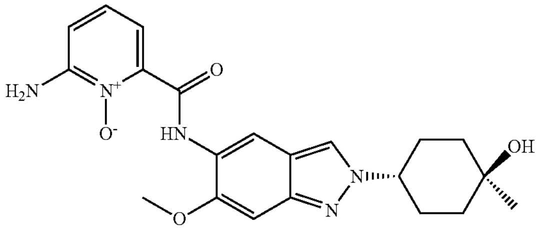
041
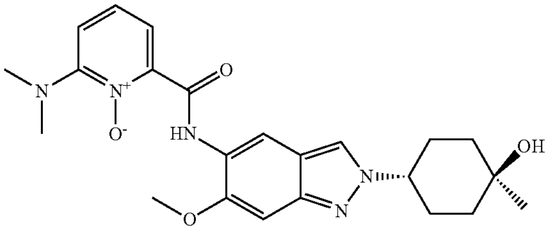
042
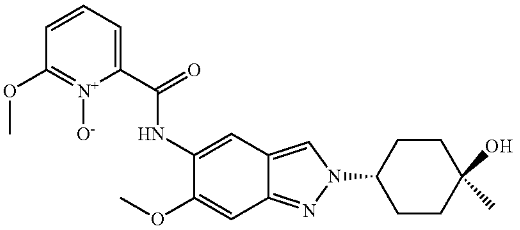
043
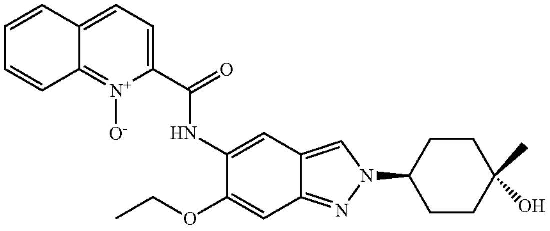

044
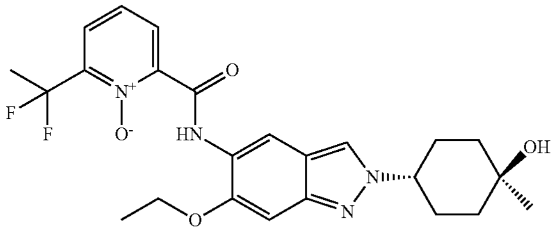
045
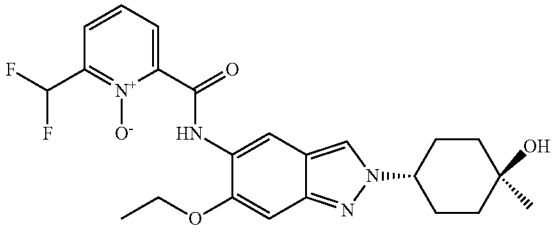
046
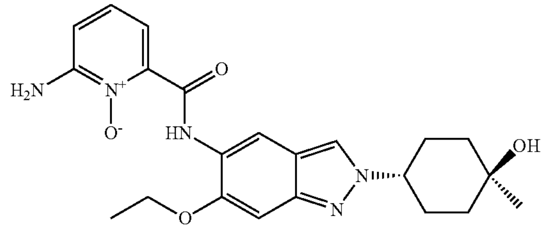
047
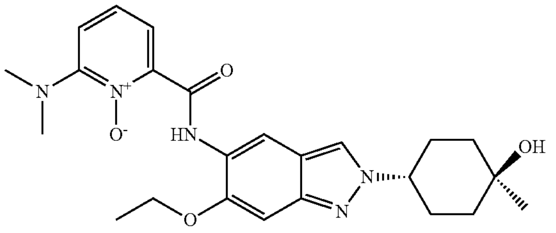
048
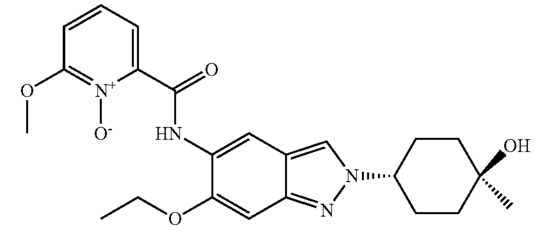
049
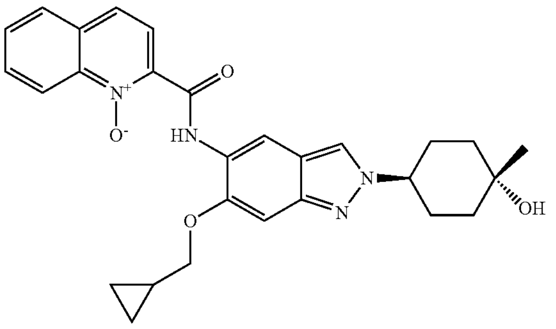
050
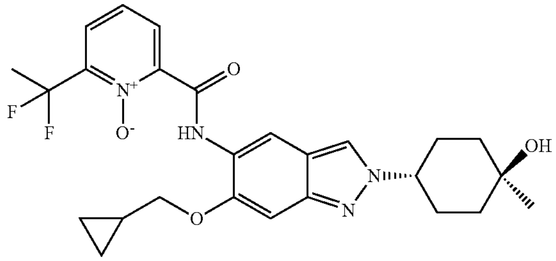
051
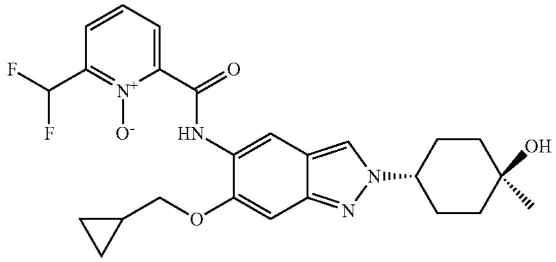
052
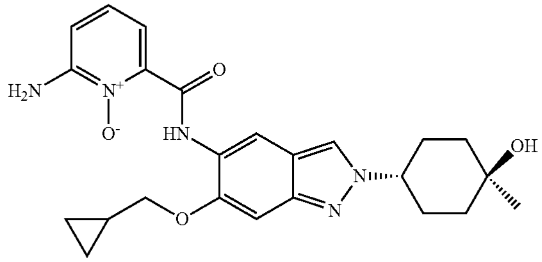
053
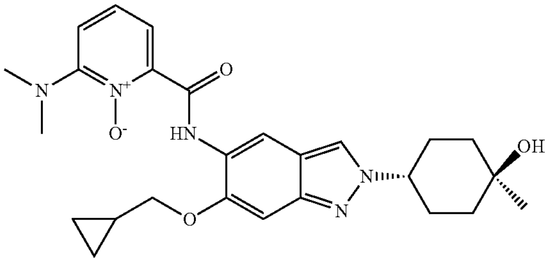
054
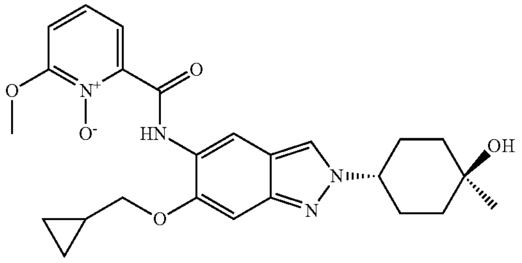

-continued
055
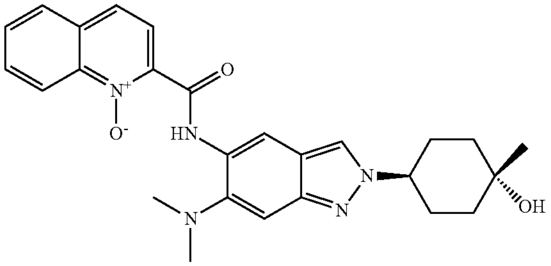
056
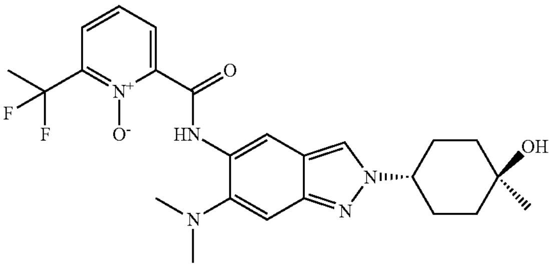
057
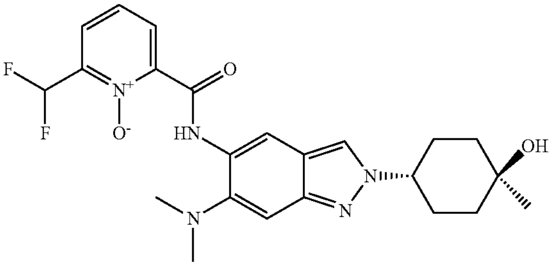
058
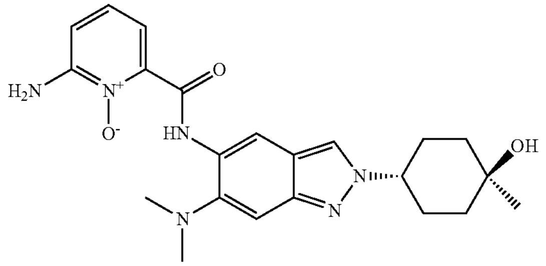
059
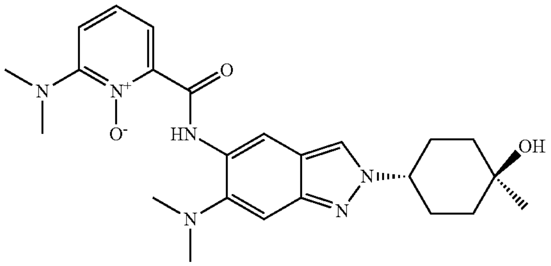
-continued
060
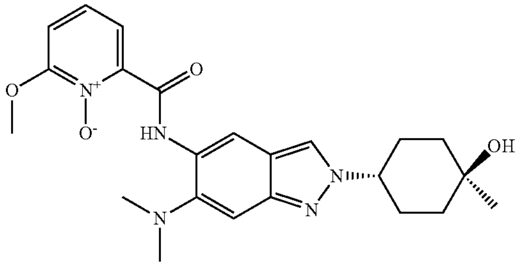
061
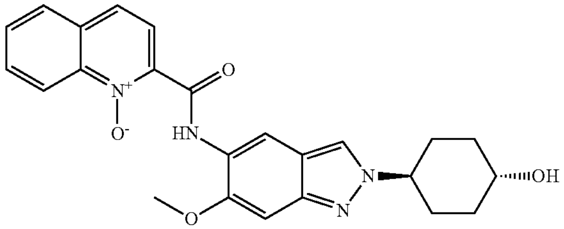
062
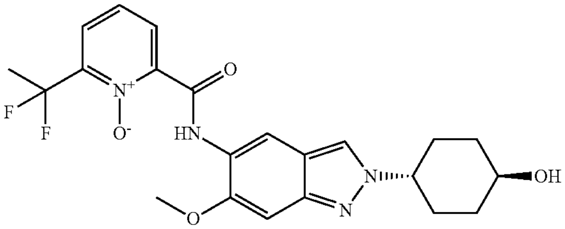
063
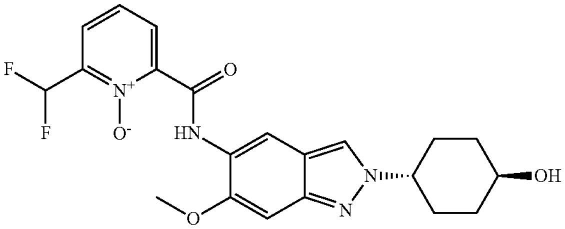
064
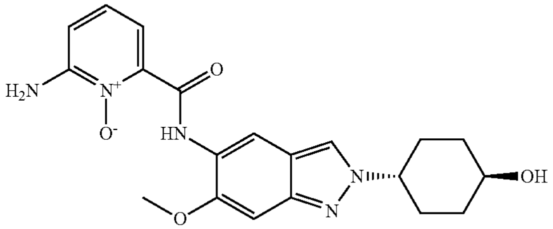
065
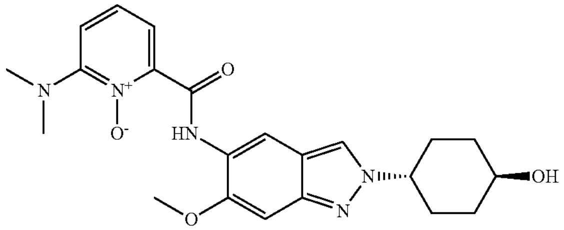

-continued
066
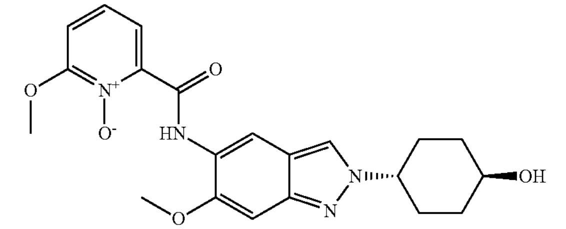
067
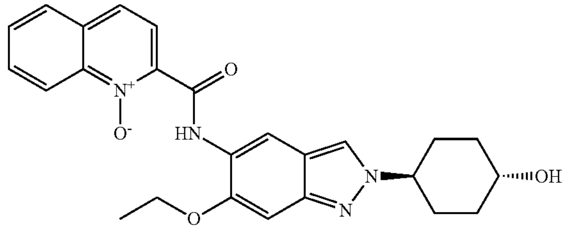
068
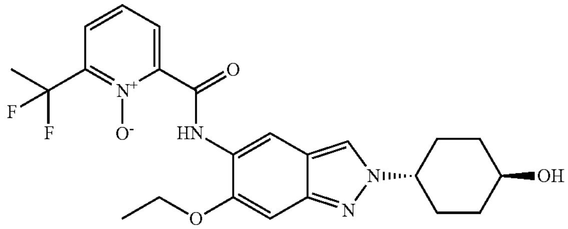
069
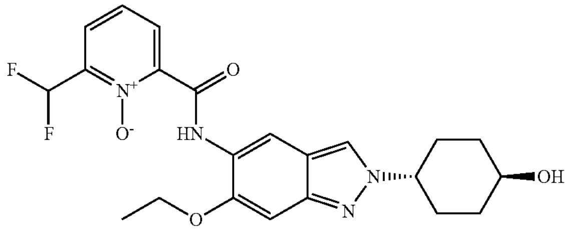
070
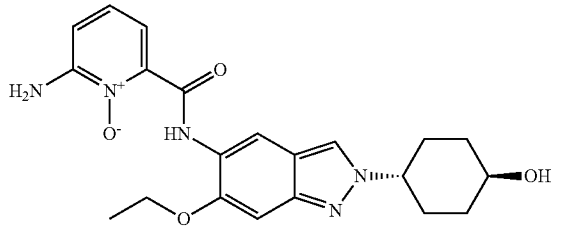
071
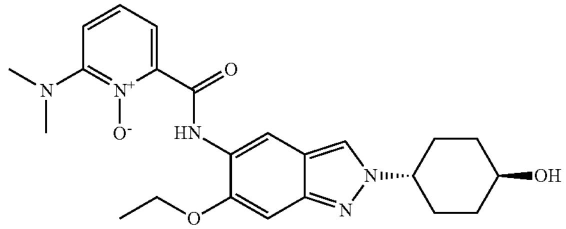
-continued
072
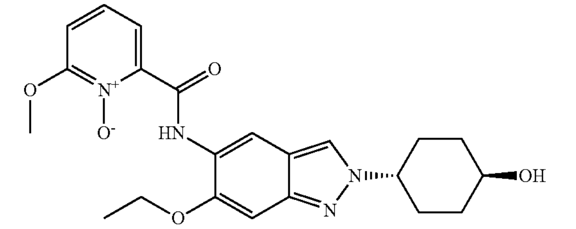
073
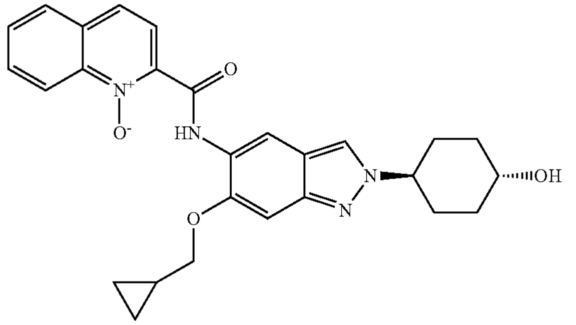
074
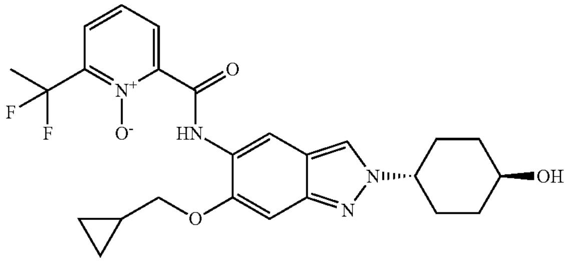
075
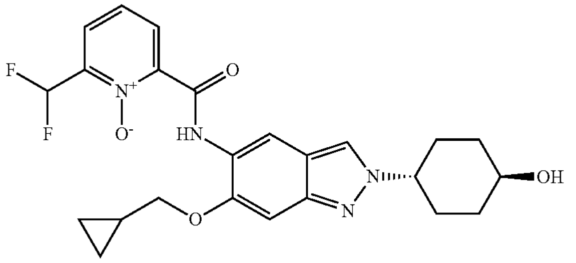
076
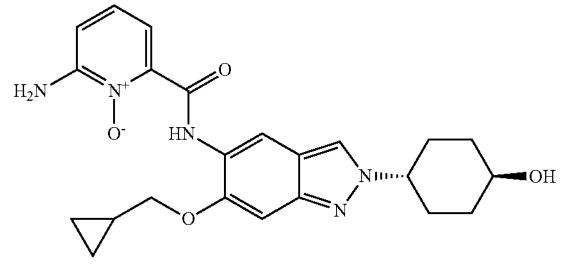

-continued
077
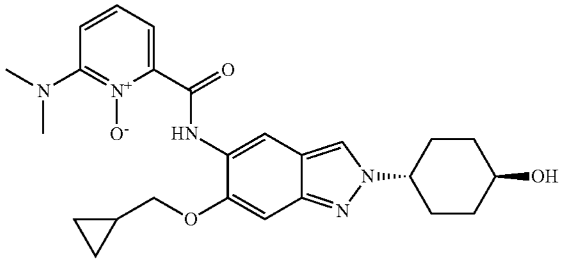
078
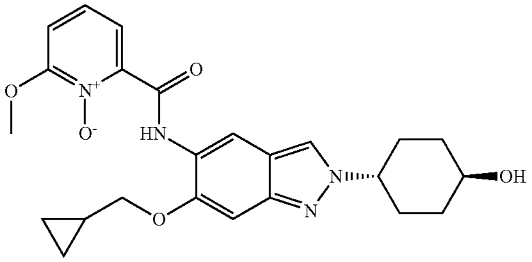
079
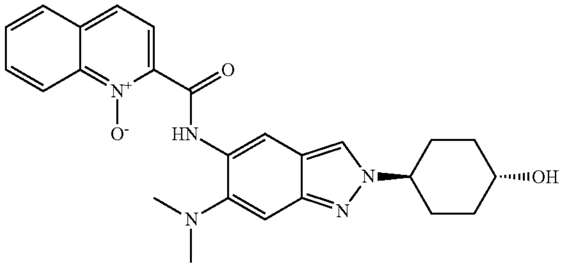
080
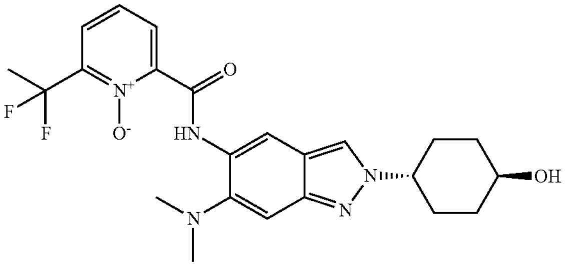
081
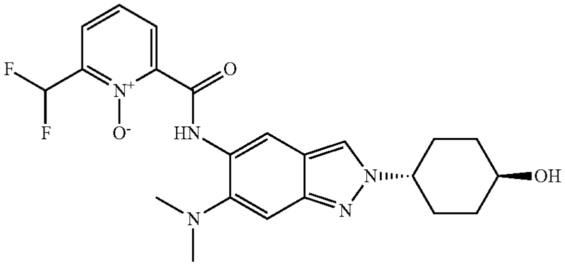
-continued
082
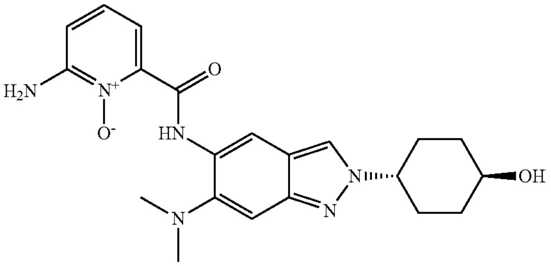
083
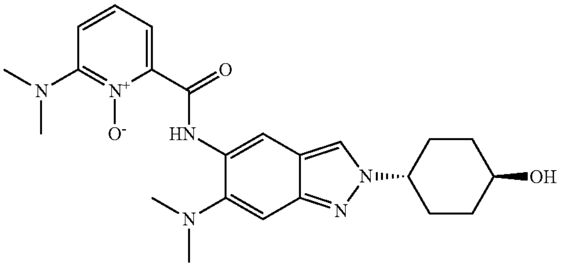
084
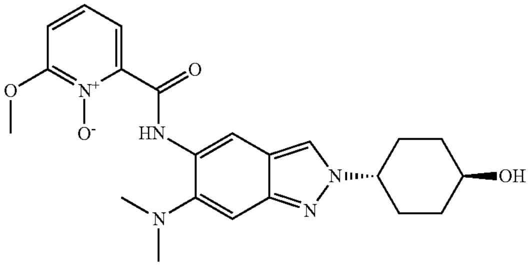
085
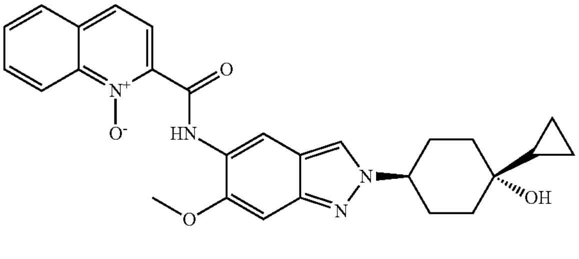
086
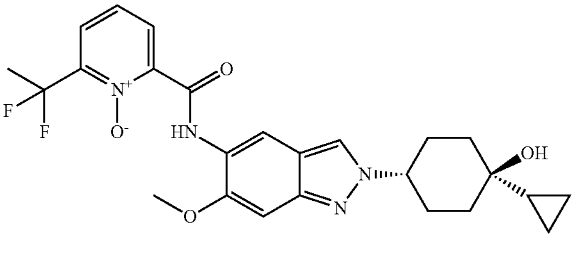

-continued
087
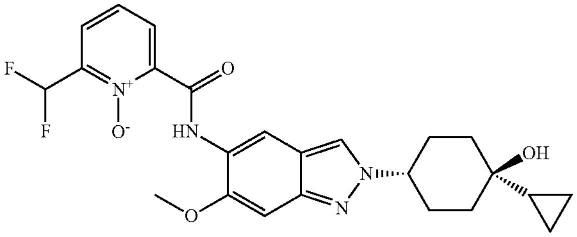
088
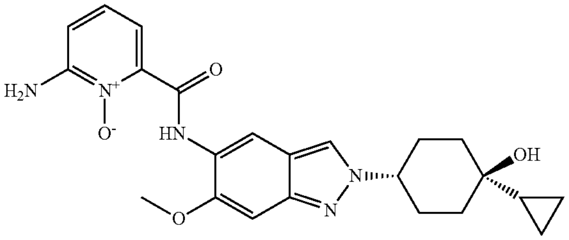
089
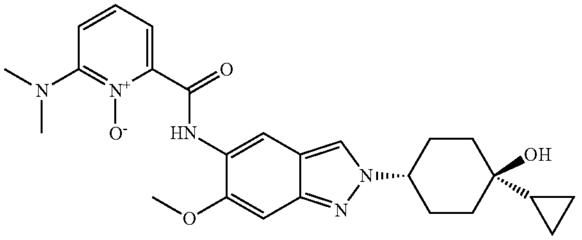
090
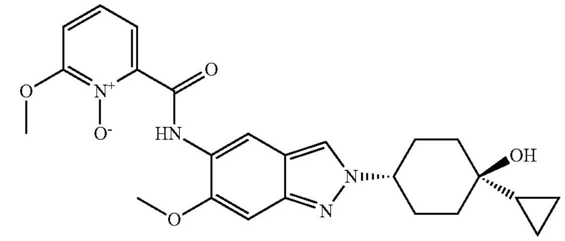
091
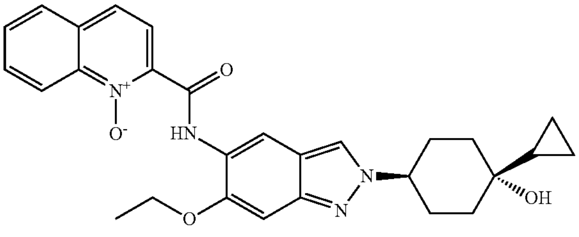
092
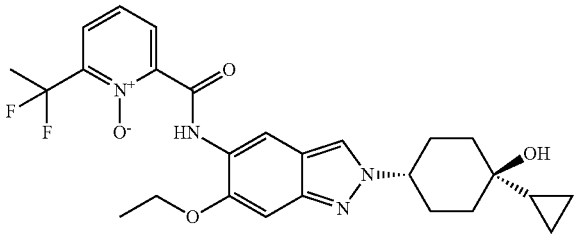
-continued
093
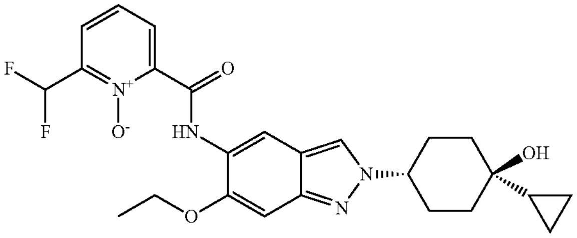
094
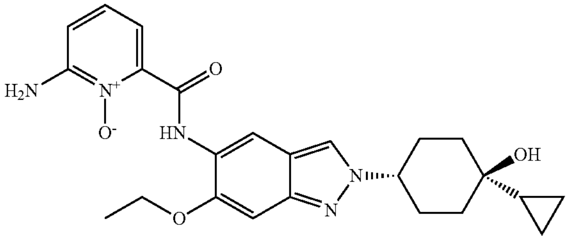
095
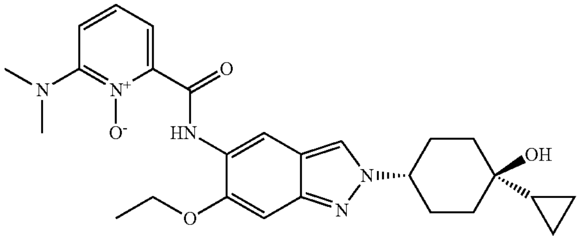
096
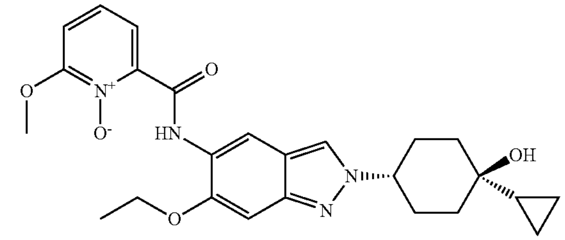
097
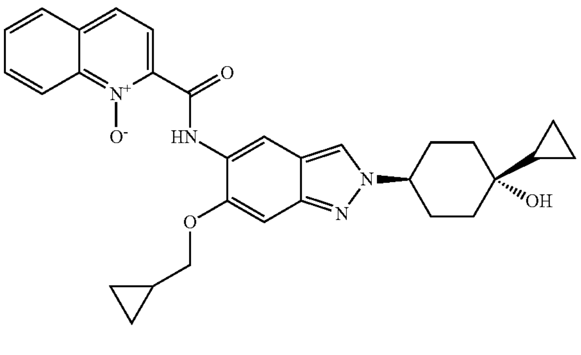

-continued
098
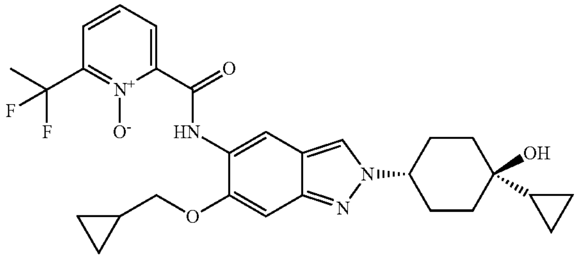
099
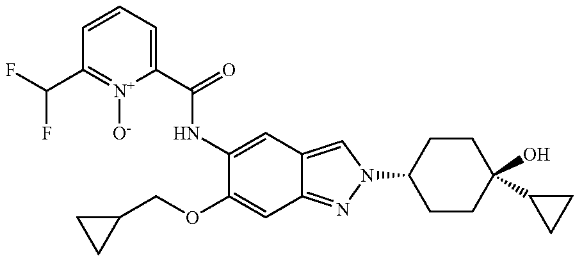
100
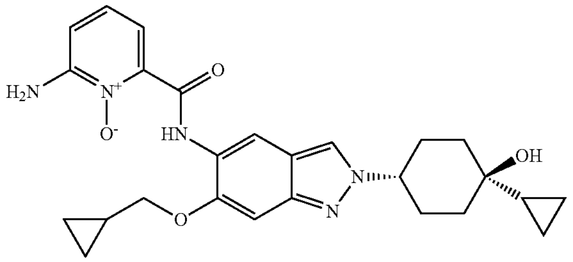
101
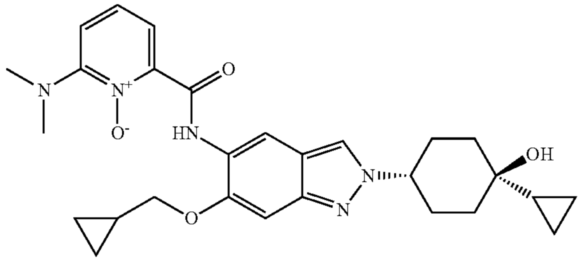
102
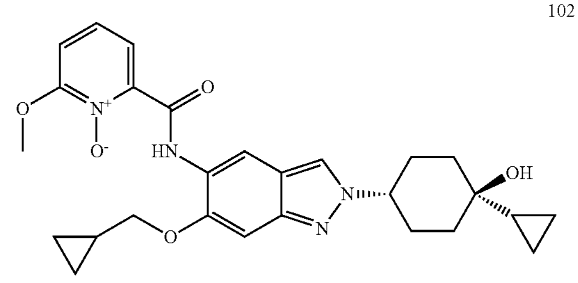 [SMILES: COc1cccc(C(=O)Nc2cc3cn([C@H]4CC[C@@](O)(C5CC5)CC4)nc3cc2OCC2CC2)[n+]1[O-]]
-continued
103
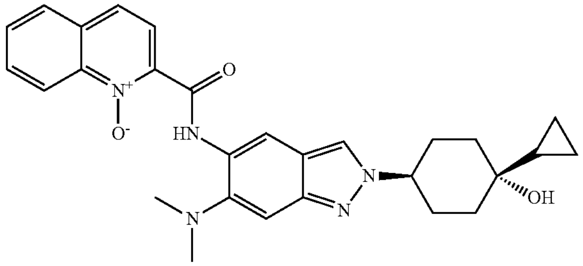
104
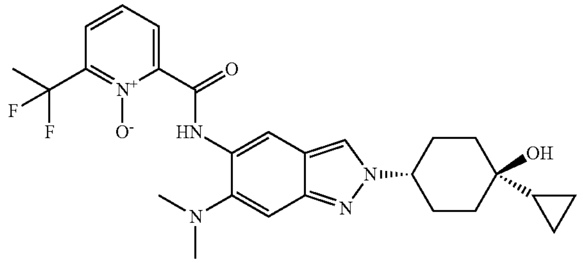
105
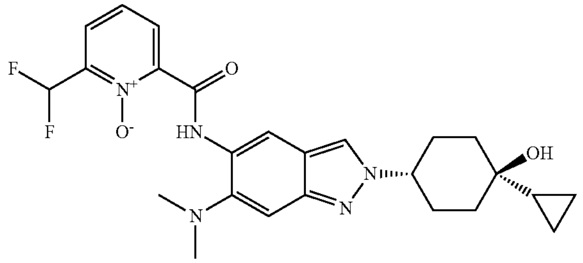
106
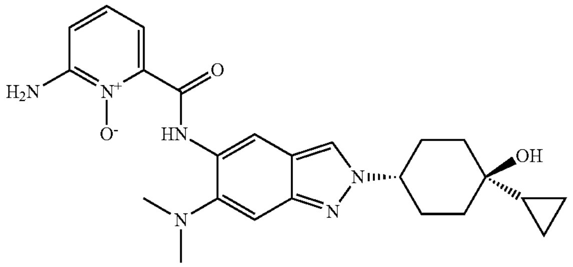
107
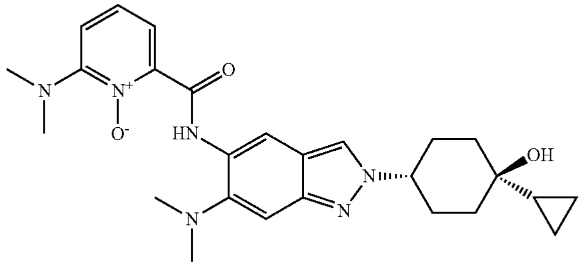

-continued
108
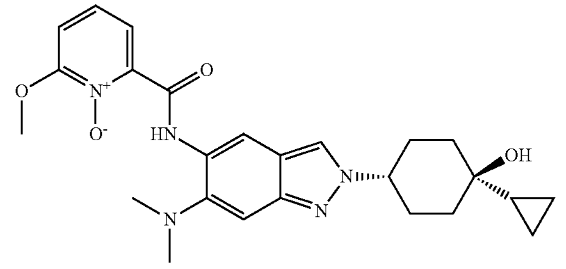
109
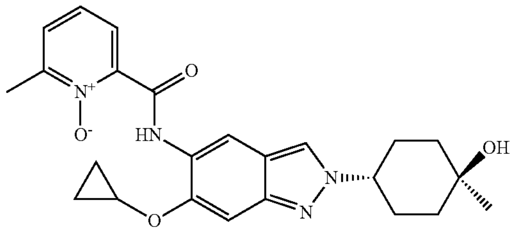
110
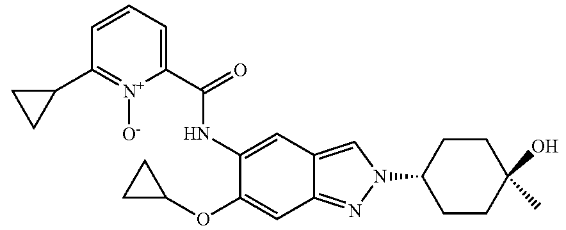
111
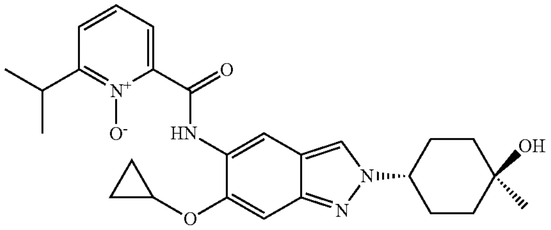
112
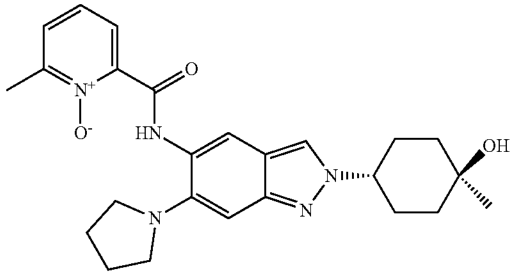
113
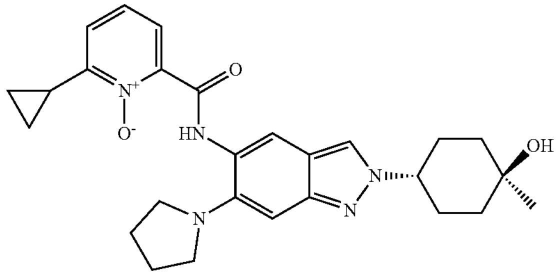
-continued
114
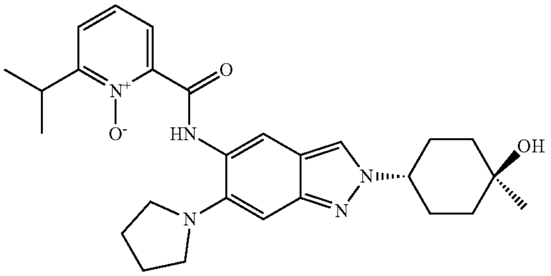
115
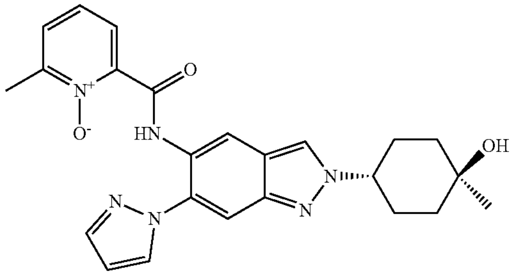
116
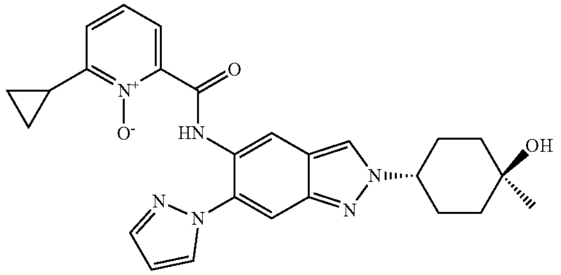
117
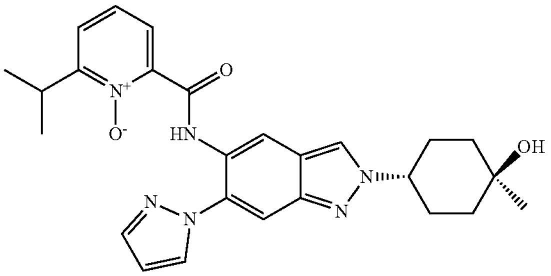
118
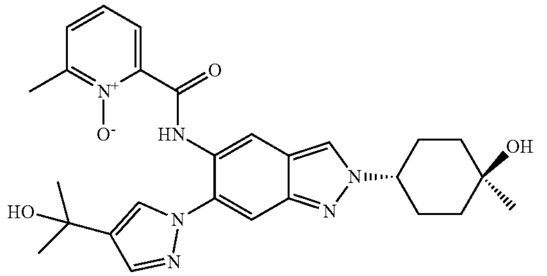

-continued
119
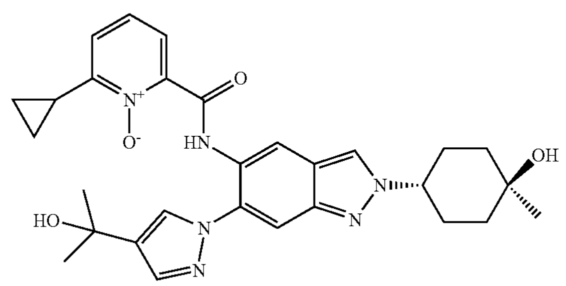
120
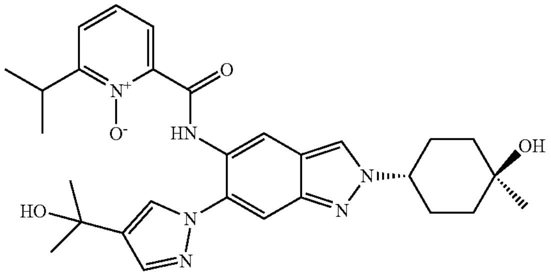
121
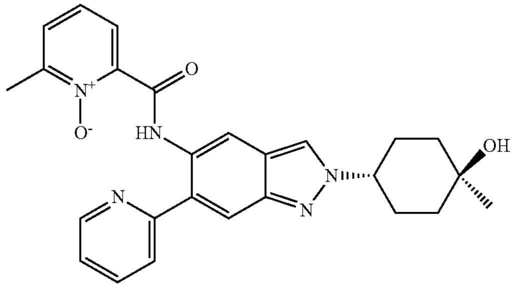
122
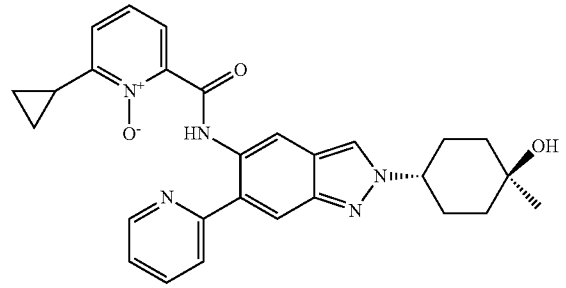
123
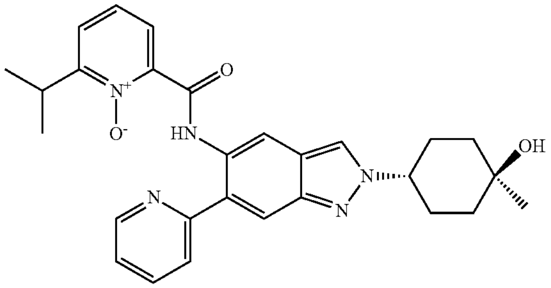
-continued
124
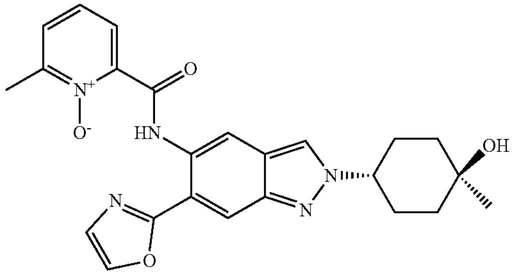
125
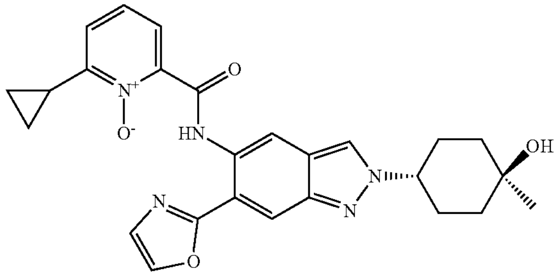
126
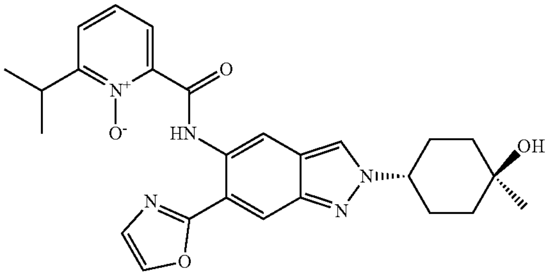
127
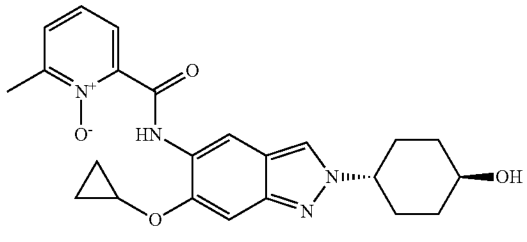
128
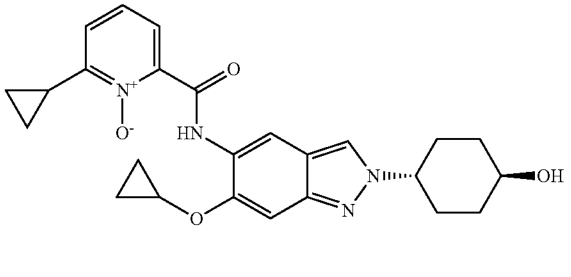

-continued
129
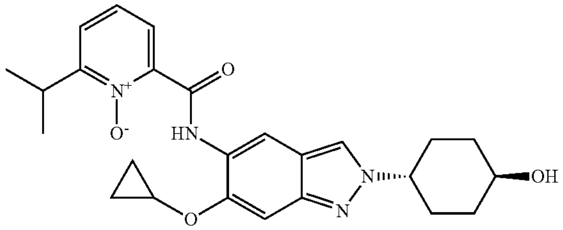
130
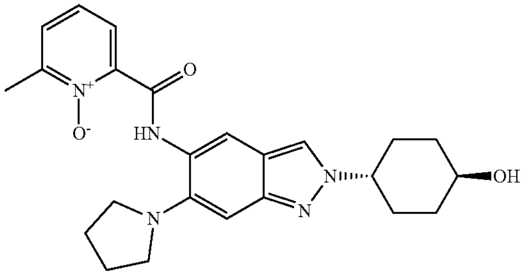
131
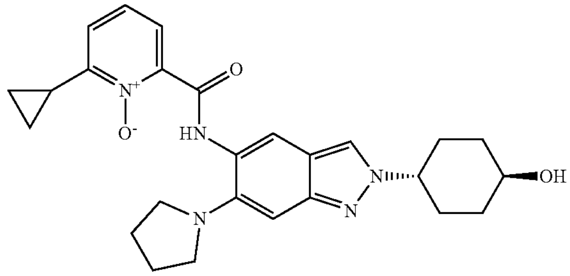
132
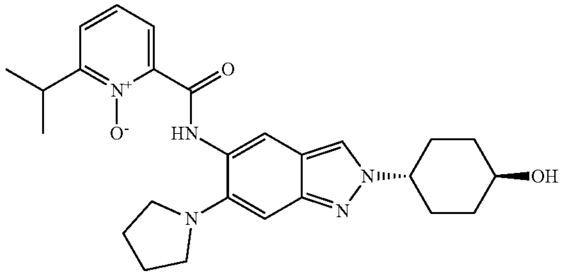
133
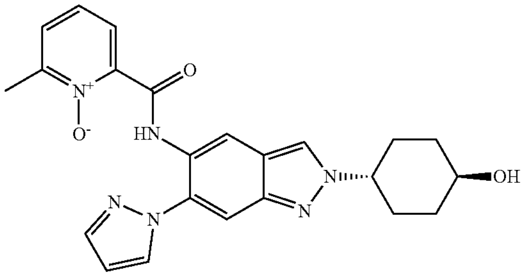
-continued
134
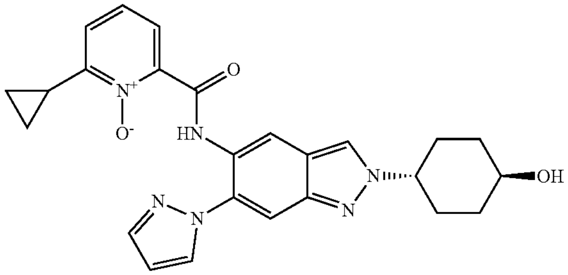
135
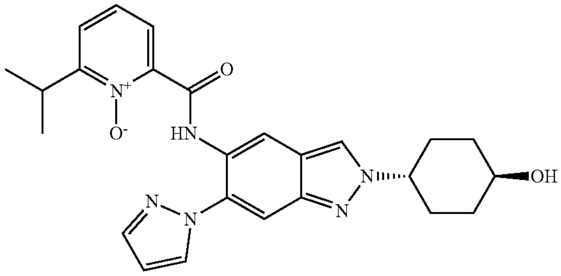
136
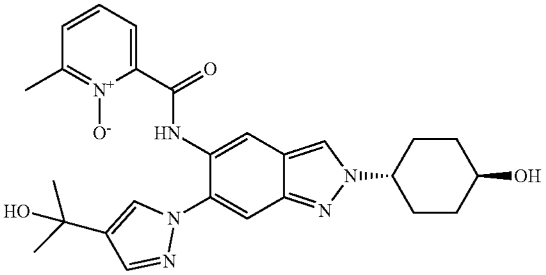
137
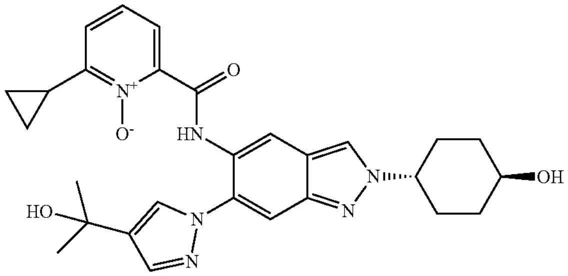
138
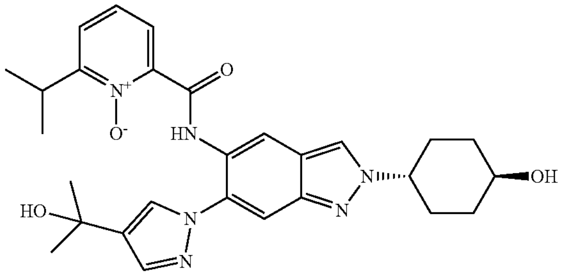

-continued
139
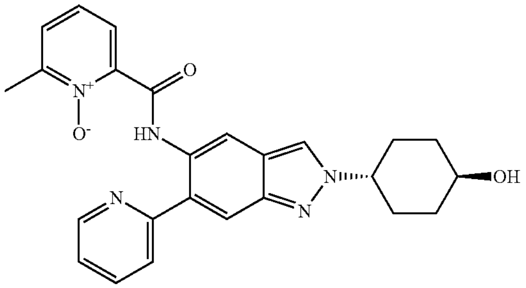
140
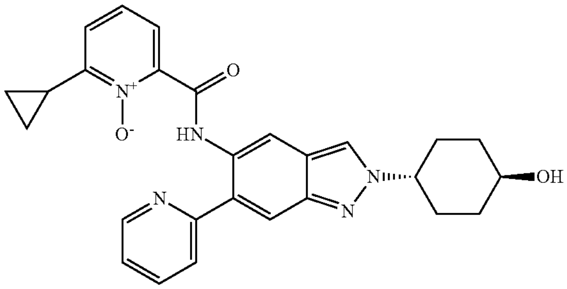
141
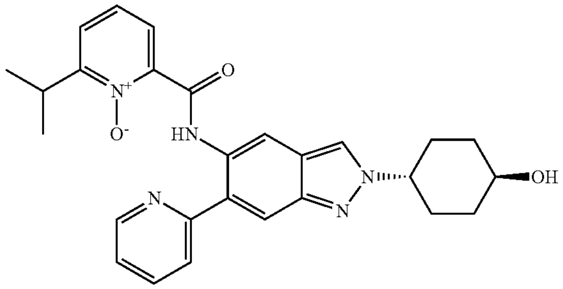
142
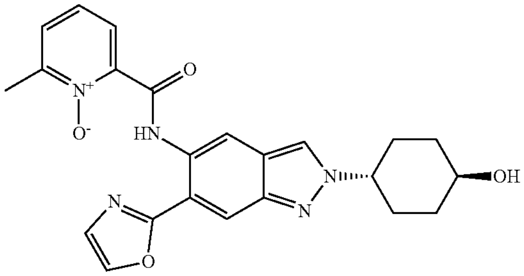
143
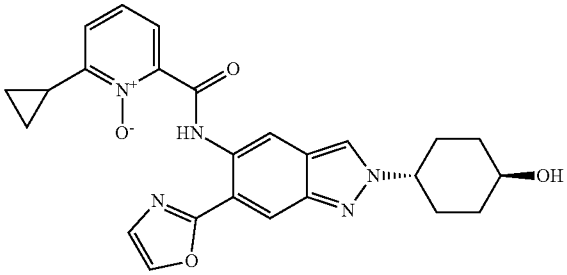
-continued
144
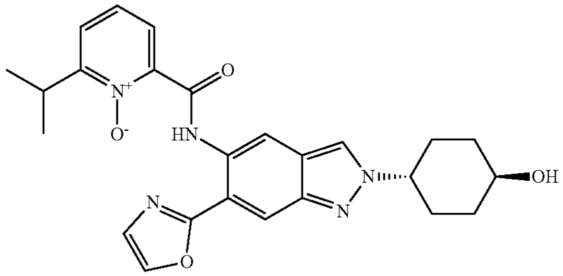
145
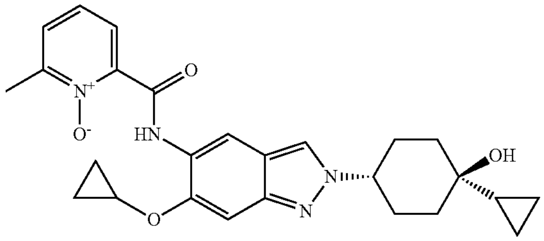
146
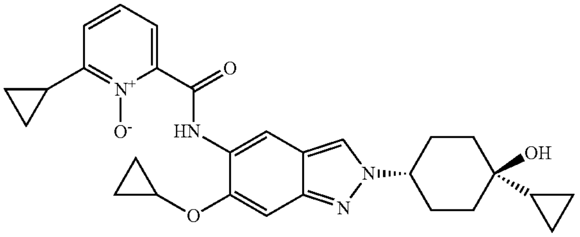
147
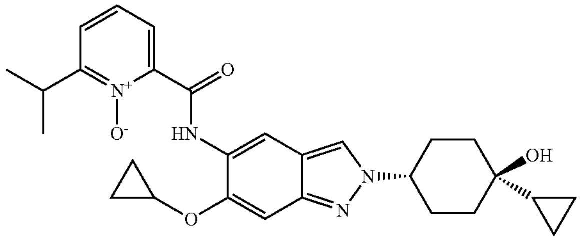
148
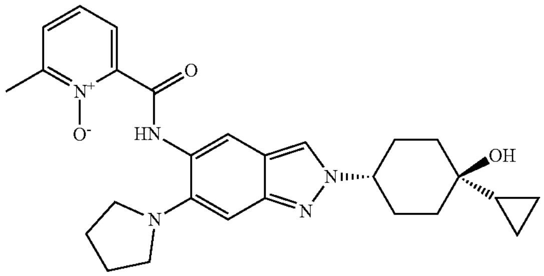

-continued
149
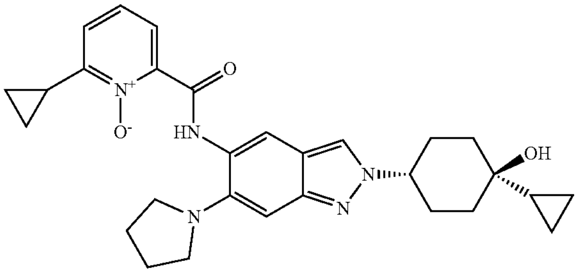
150
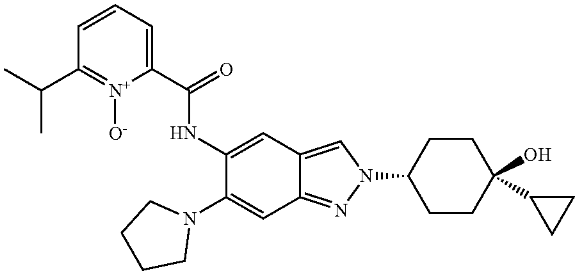
151
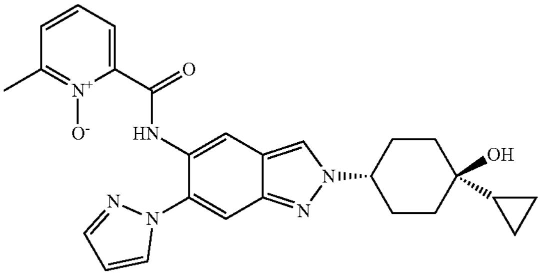
152
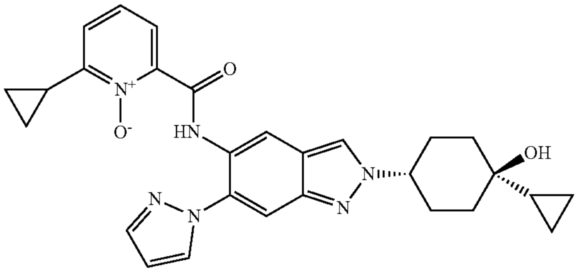
153
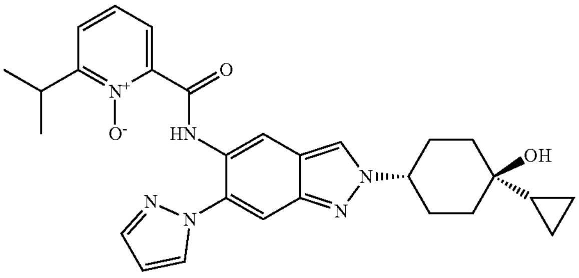
-continued
154
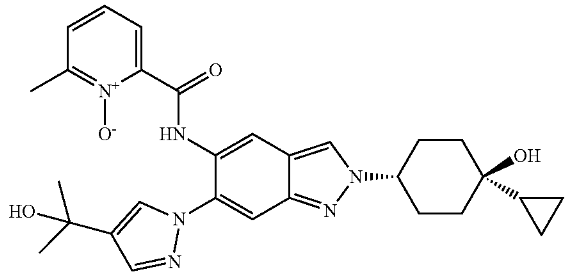
155
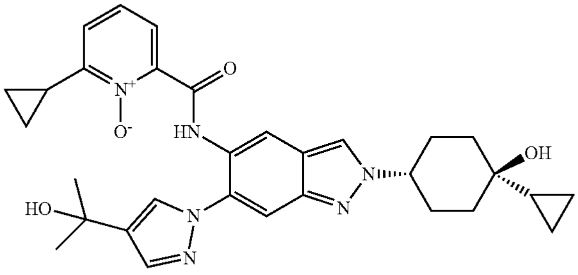
156
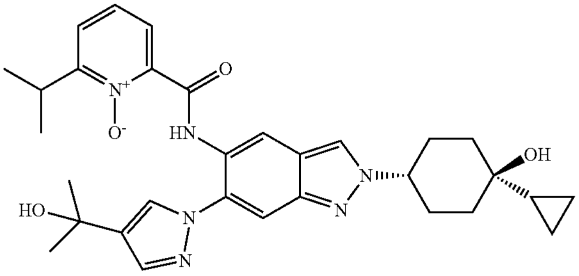
157
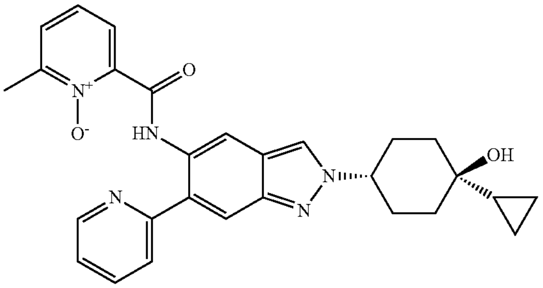
158
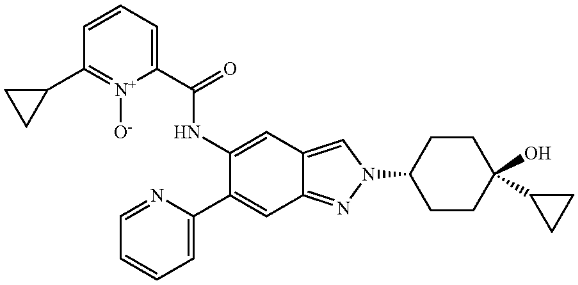

-continued
159
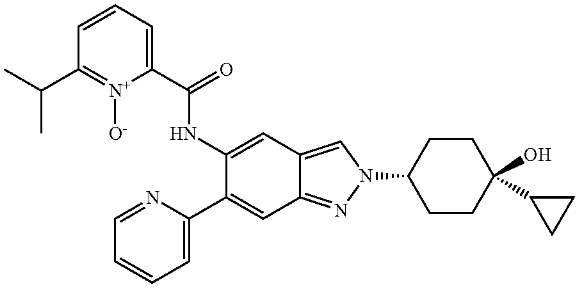
160
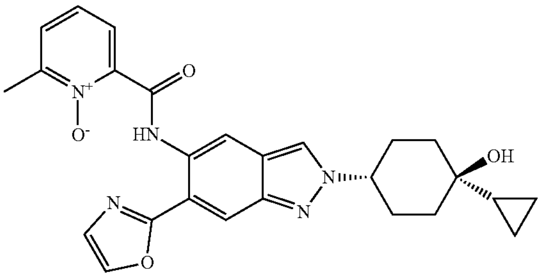
161
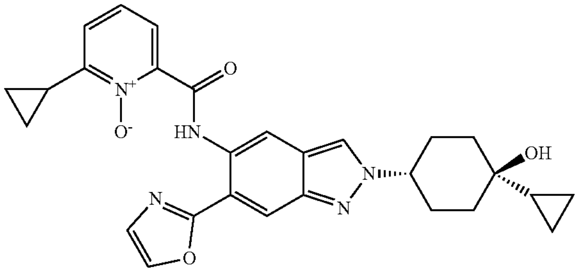
162
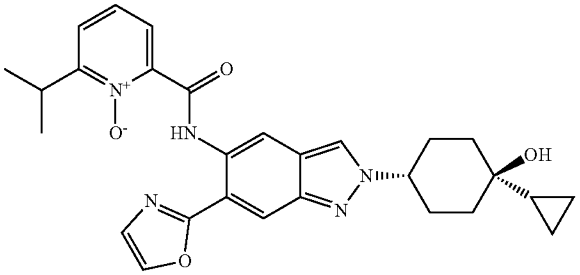
163
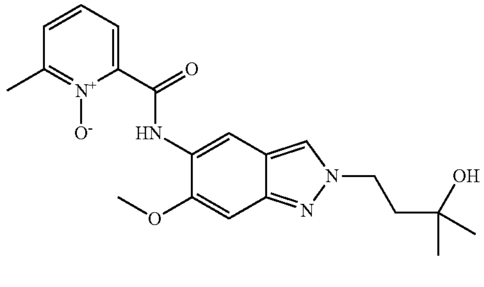
-continued
164
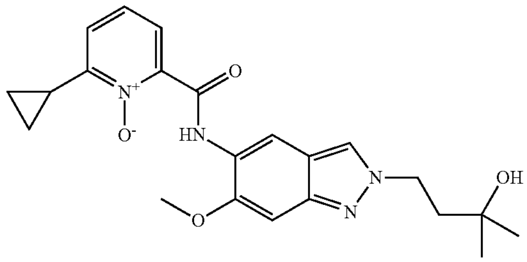
165
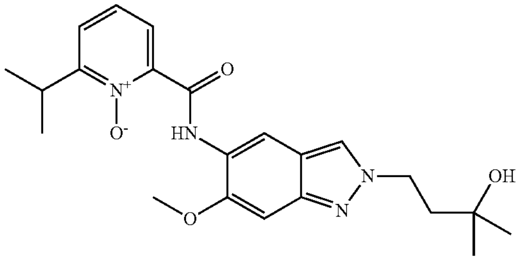
166
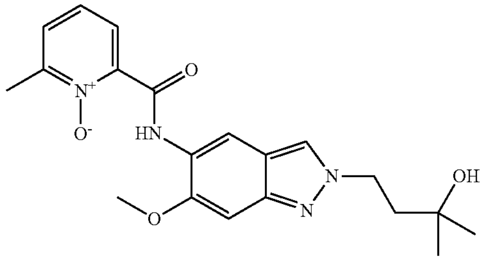
167
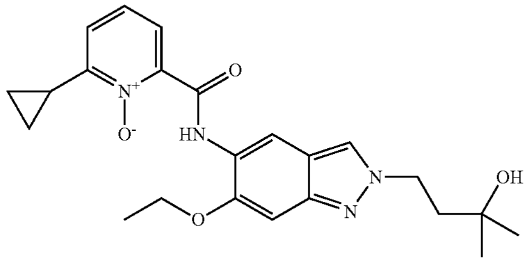
168
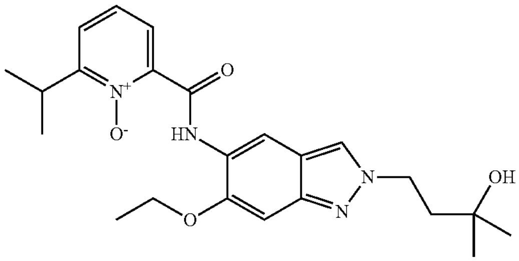

-continued
169
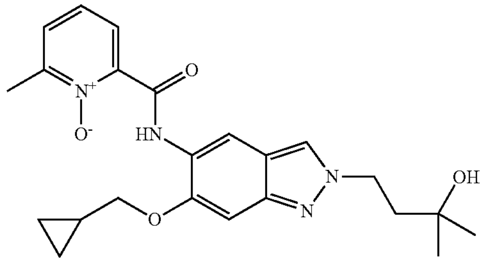
170
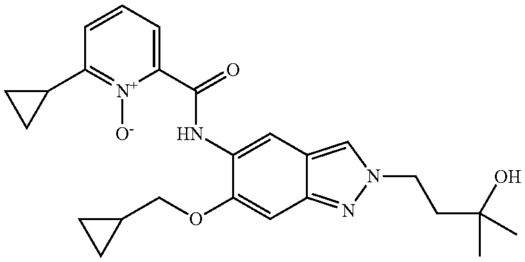
171
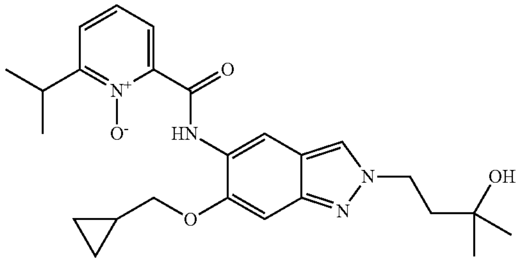
172
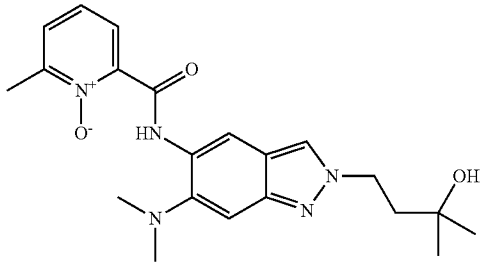
173
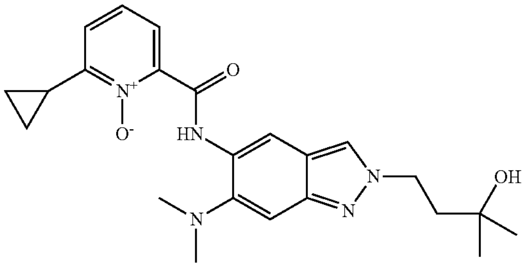
174
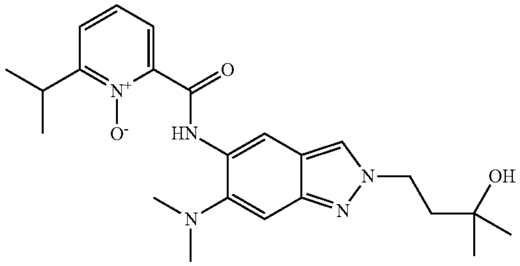
-continued
175
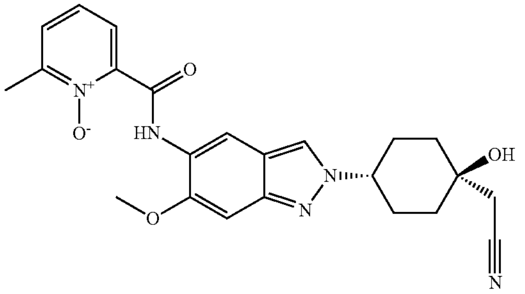
176
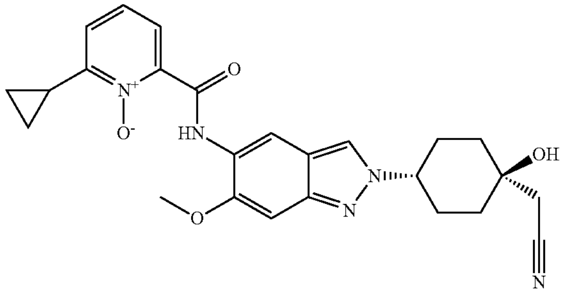
177
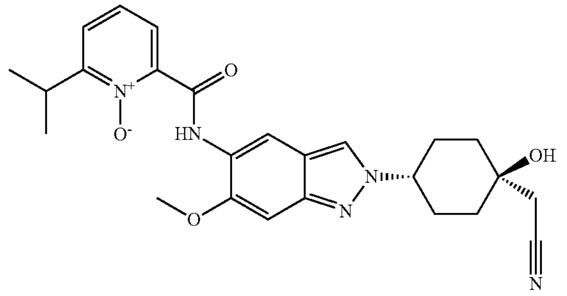
178
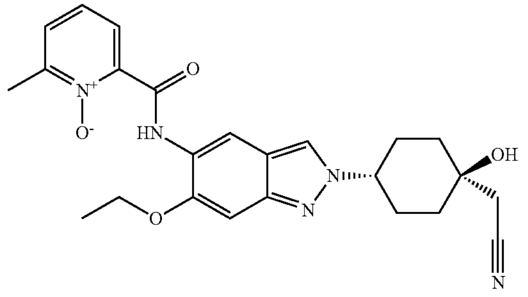
179
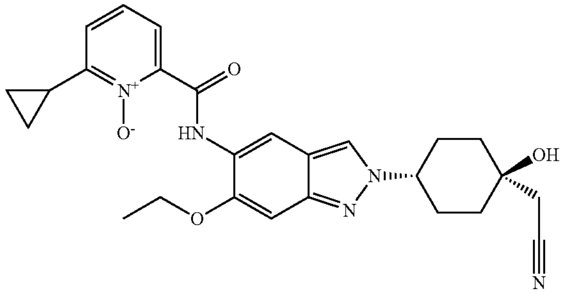

-continued
180
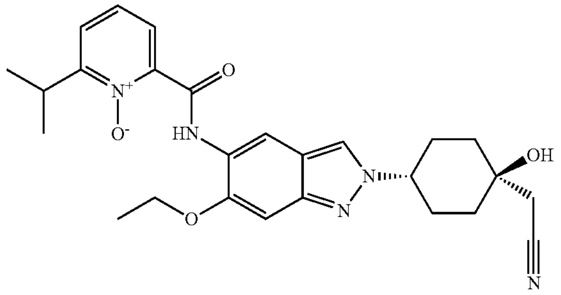
181
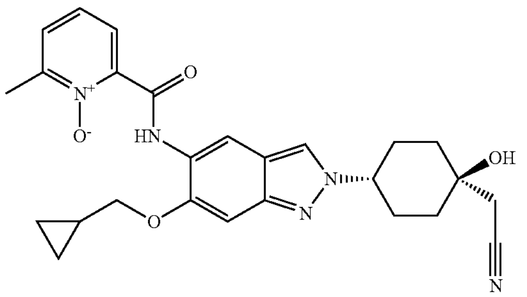
182
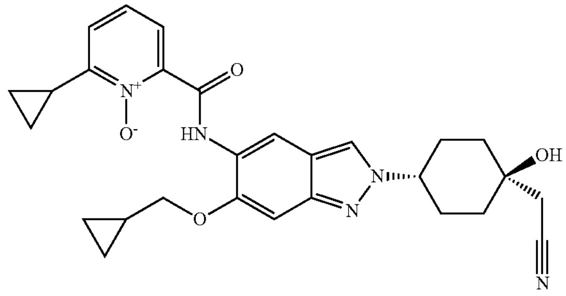
183
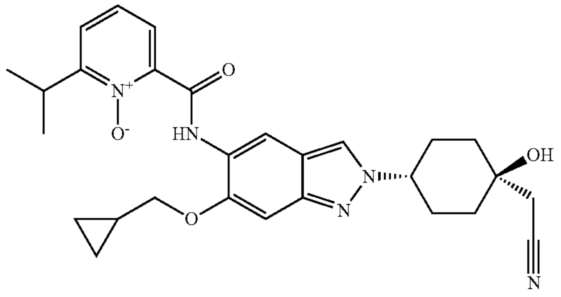
184
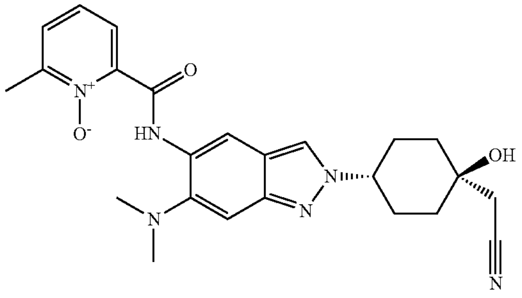
-continued
185
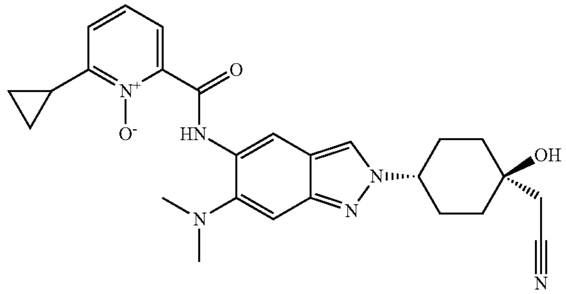
186
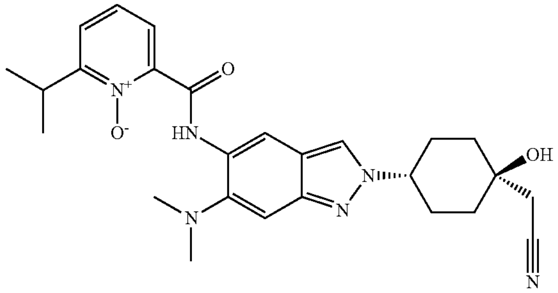
187
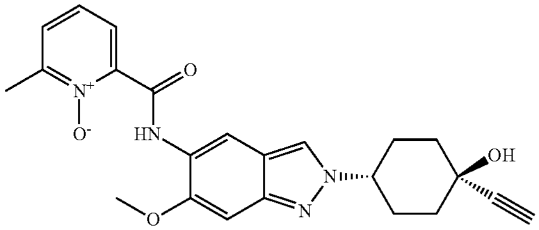
188
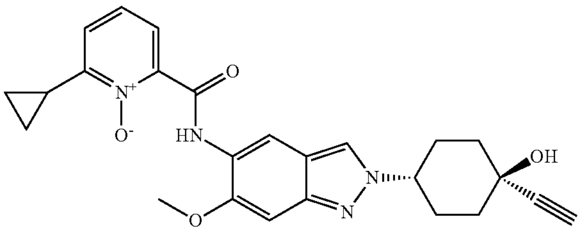
189
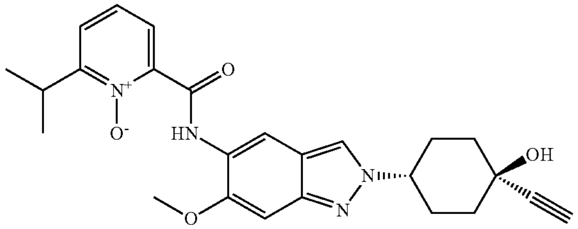

-continued
190
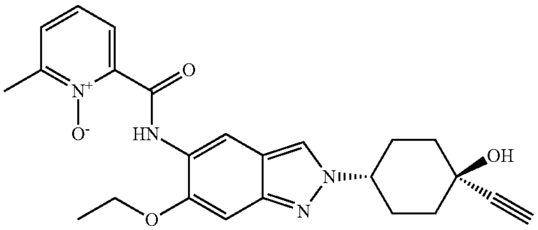
191
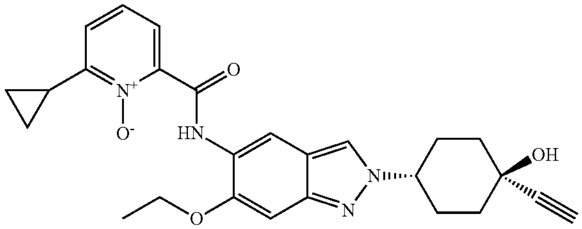
192
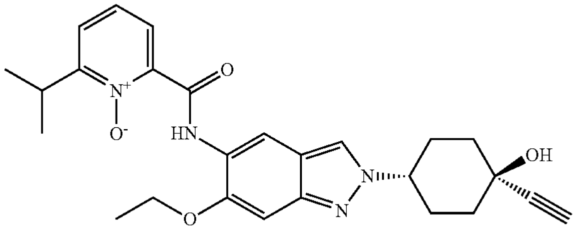
193
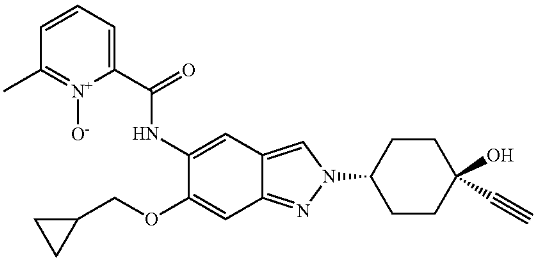
194
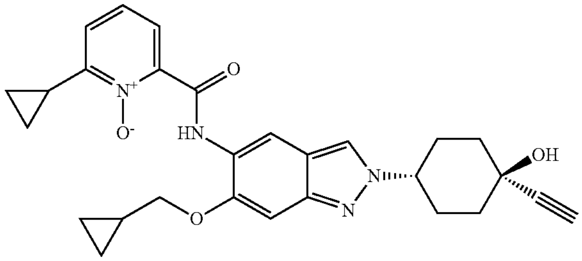
195
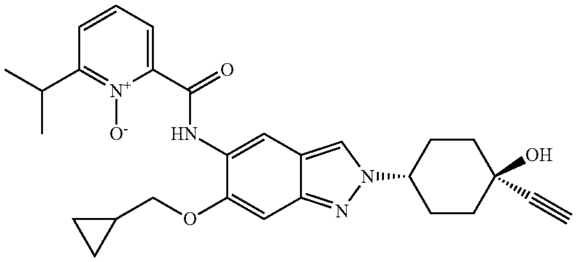
-continued
196
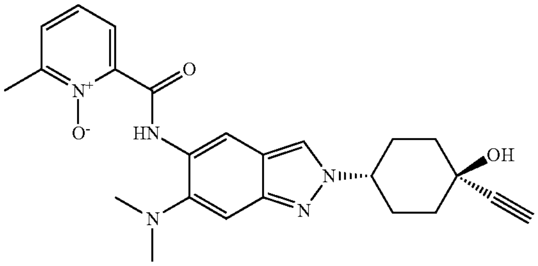
197
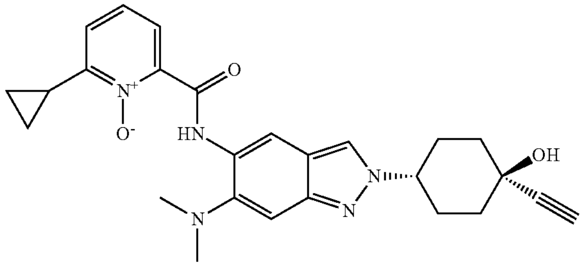
198
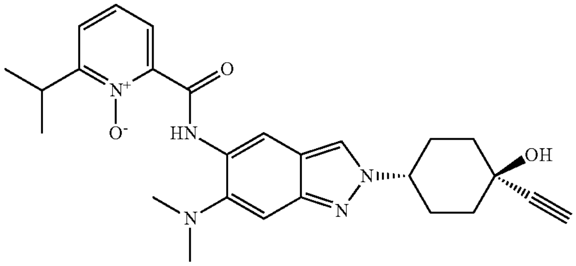
199
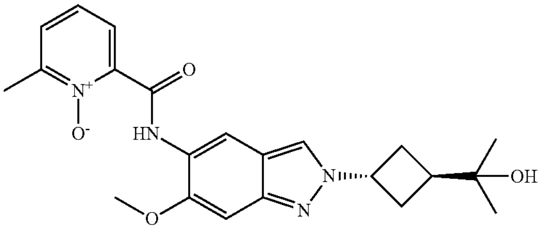
200
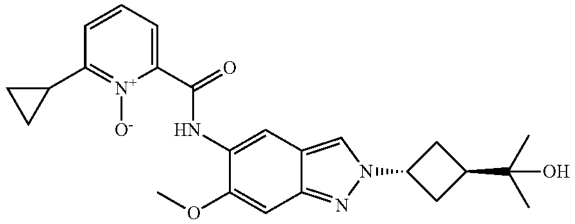
201
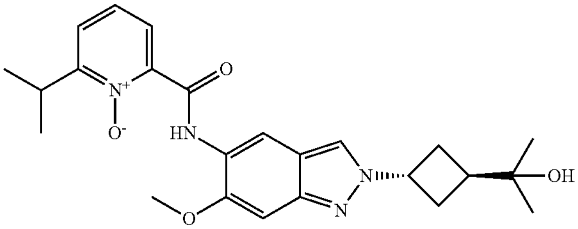

-continued
202
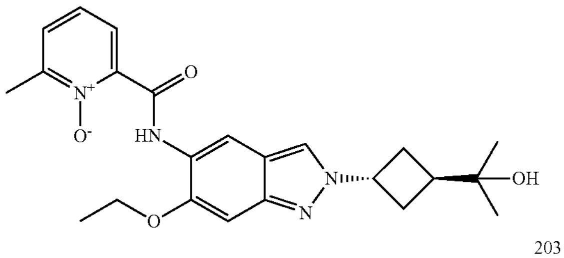
203
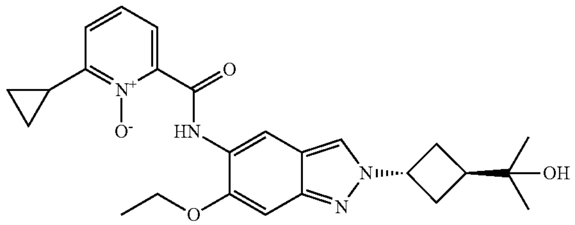
204
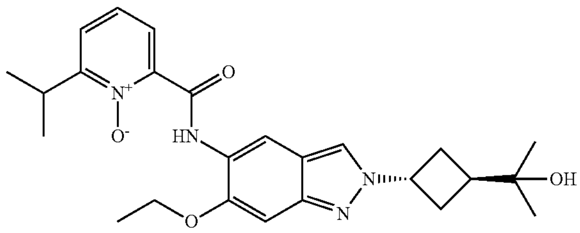
205
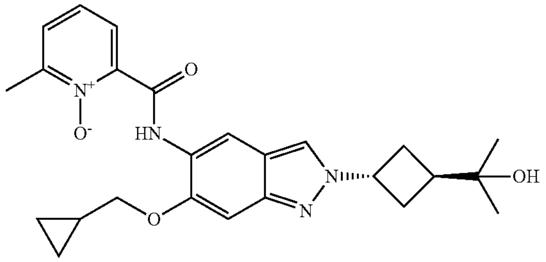
206
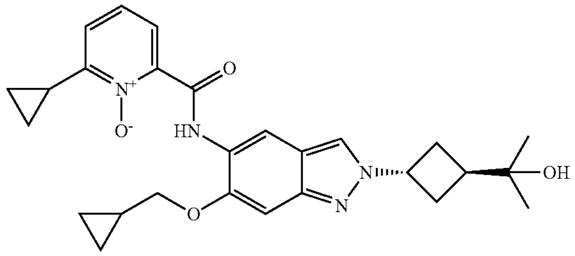
207
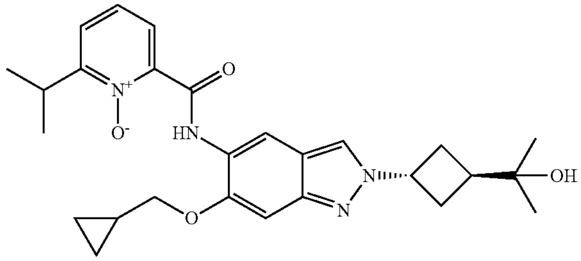
-continued
208
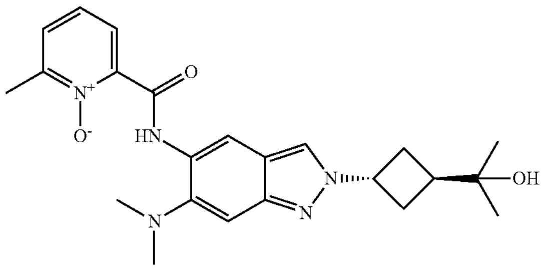
209
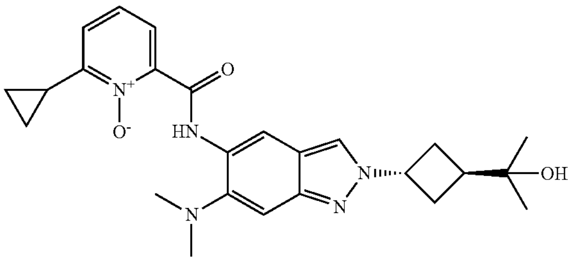
210
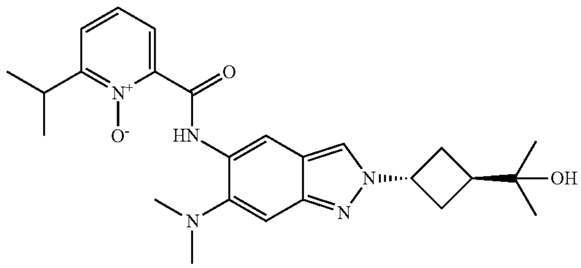
211
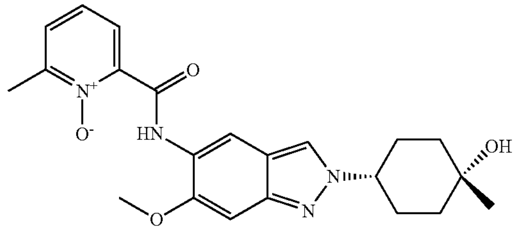
212
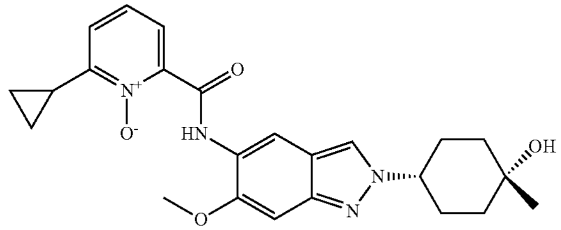
213
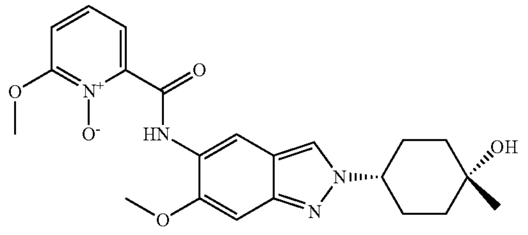

-continued
214
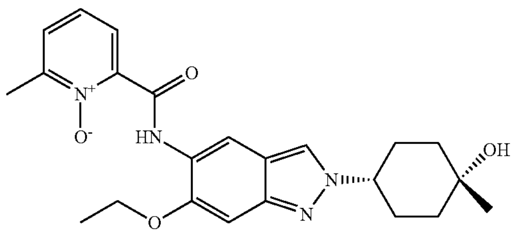
215
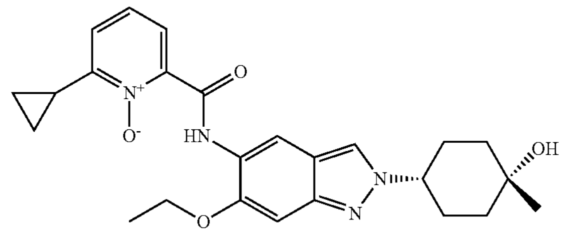
216
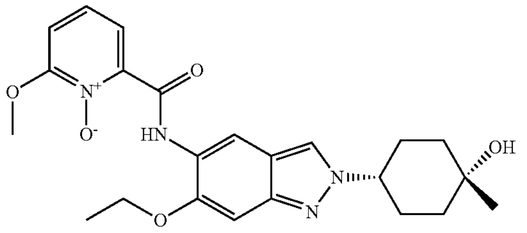
217
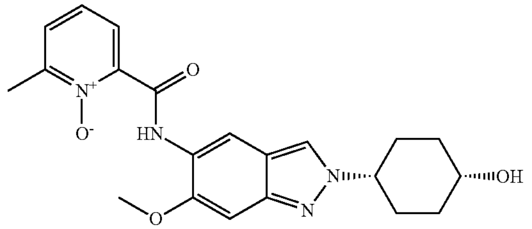
218
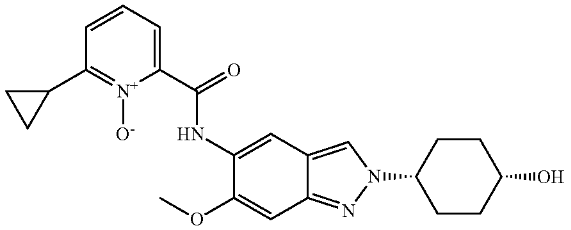
219
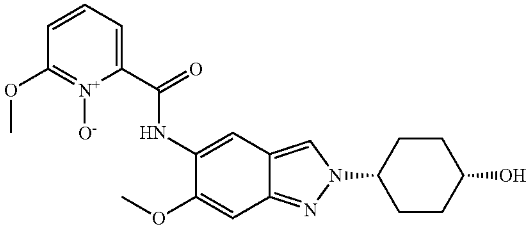
-continued
220
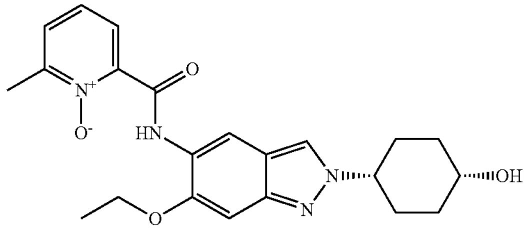
221
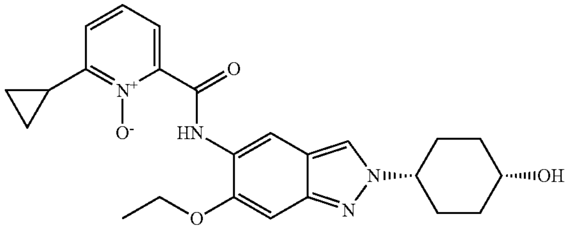
222
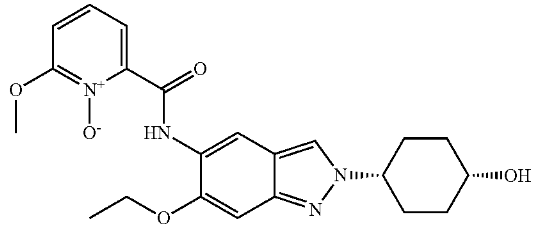
223
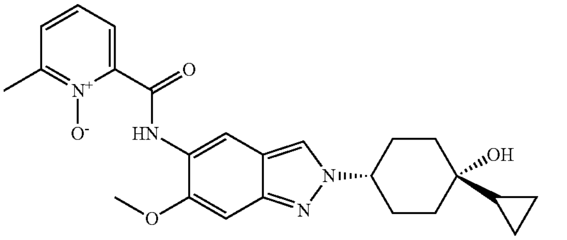
224
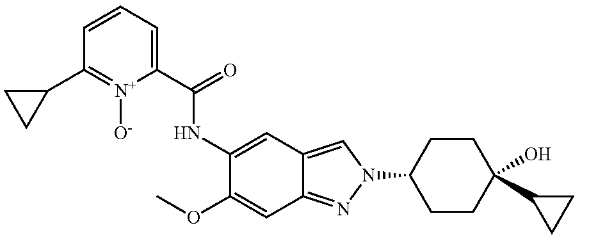
225
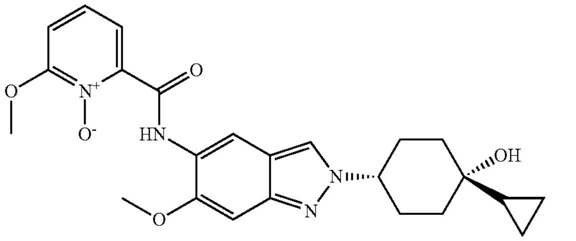

-continued
226
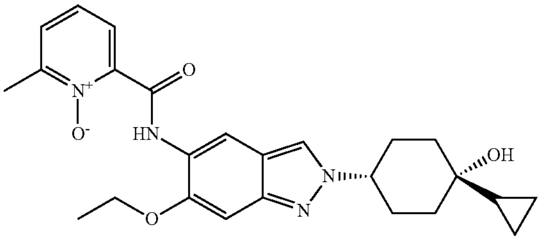
227
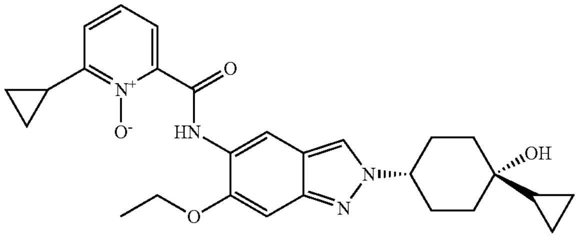
228
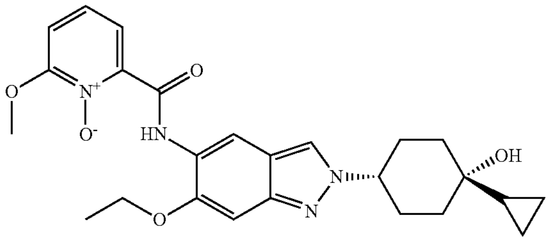
229
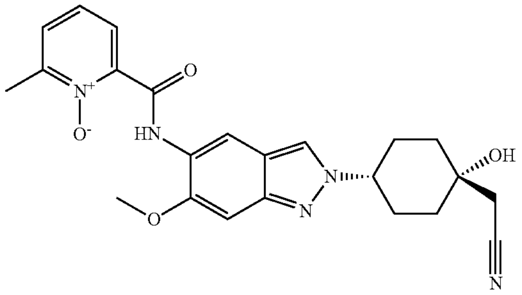
230
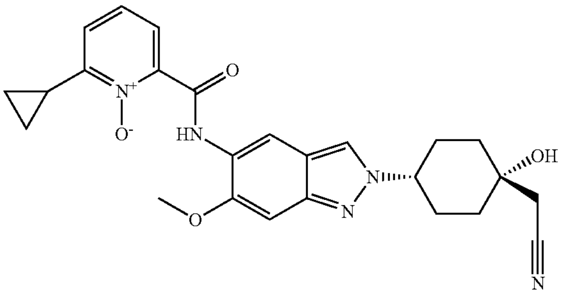
-continued
231
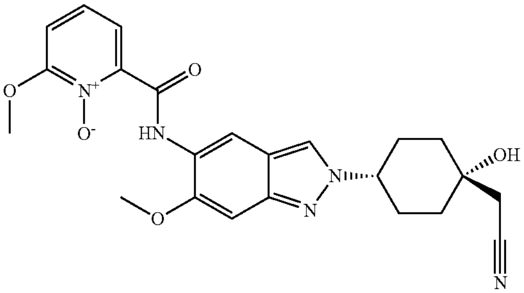
232
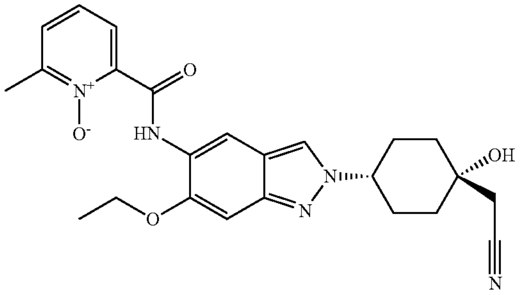
233
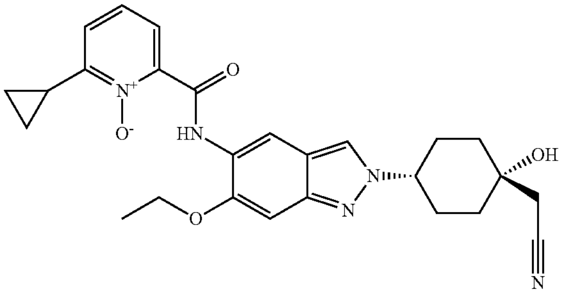
234
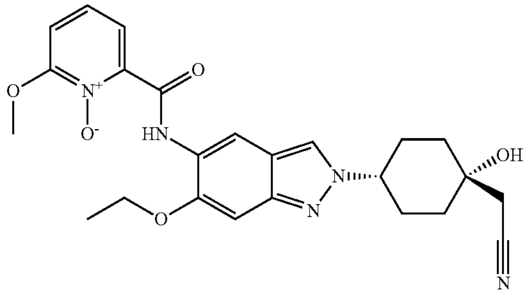
235
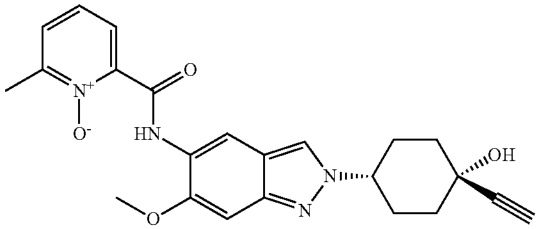

-continued
236
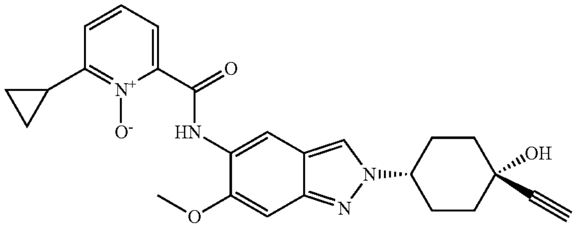
237
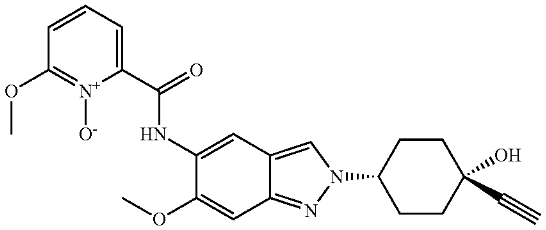
238
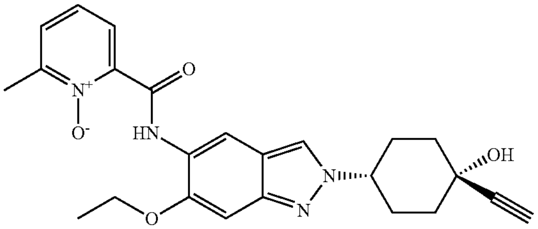
239
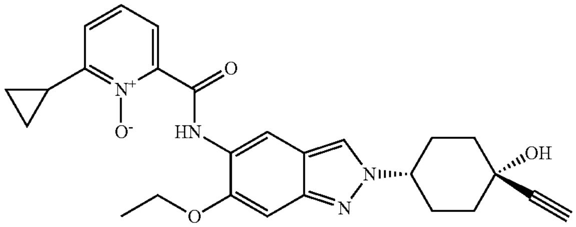
240
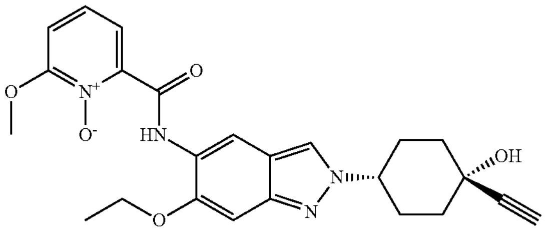
241
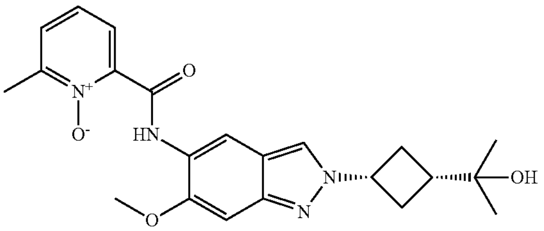
-continued
242
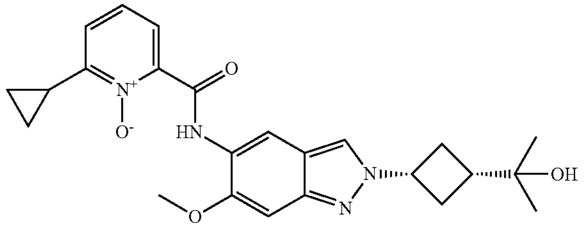
243
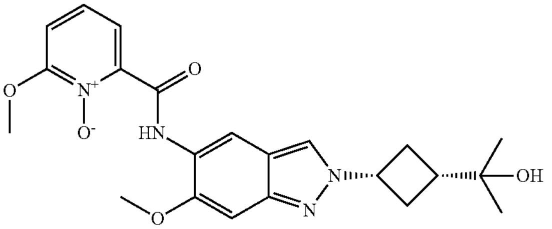
244
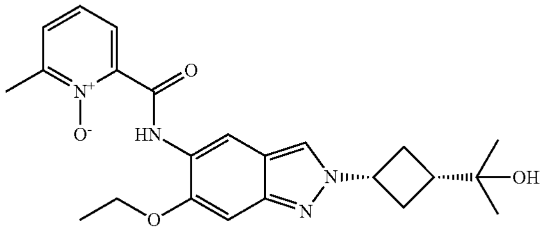
245
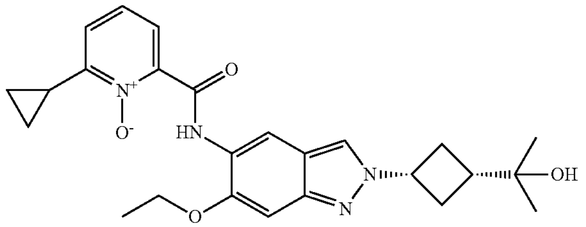
246
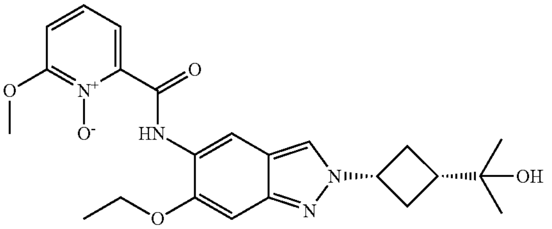
247
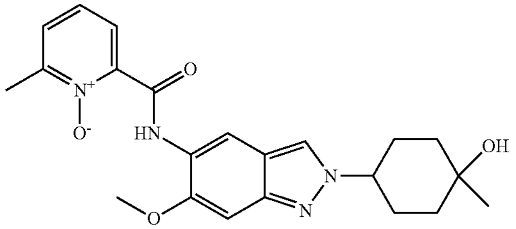

-continued
248
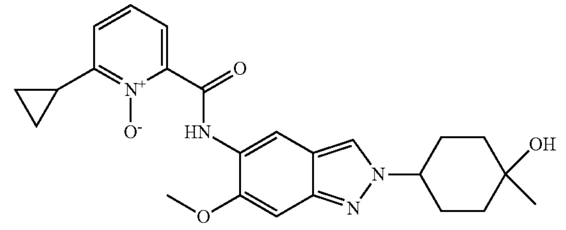
249
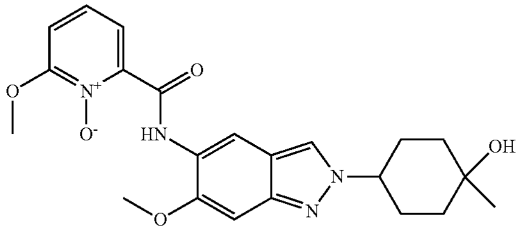
250
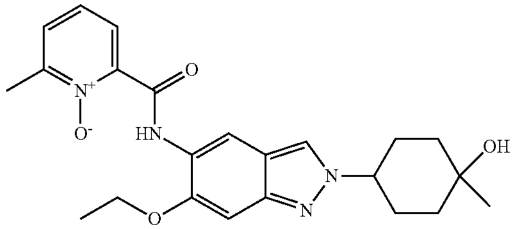
251
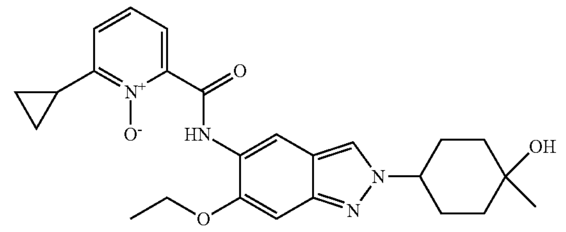
252
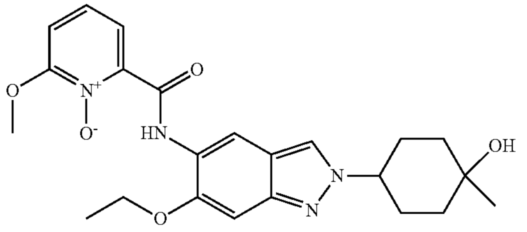
253
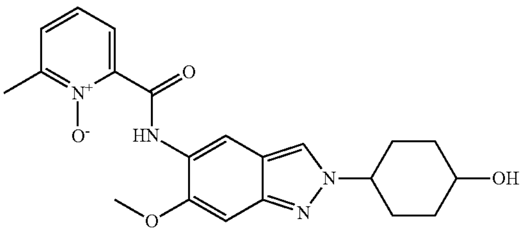
-continued
254
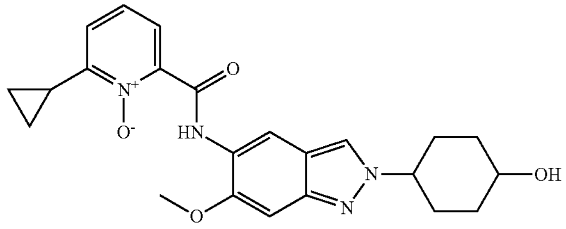
255
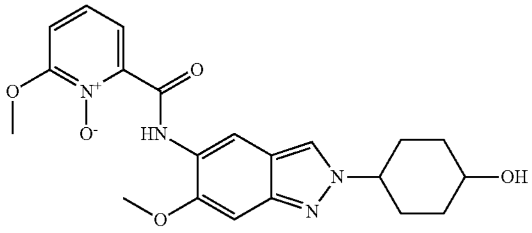
256
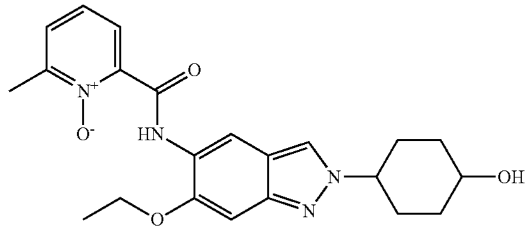
257
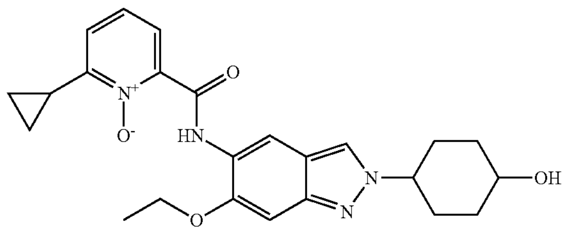
258
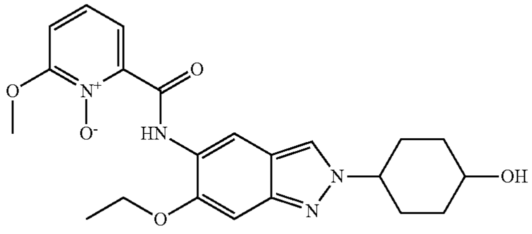
259
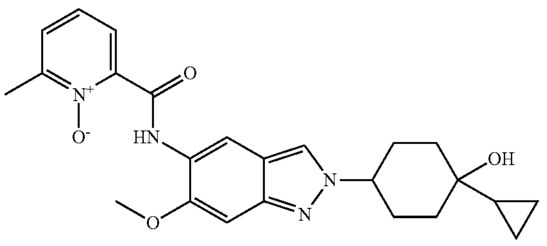

-continued
260
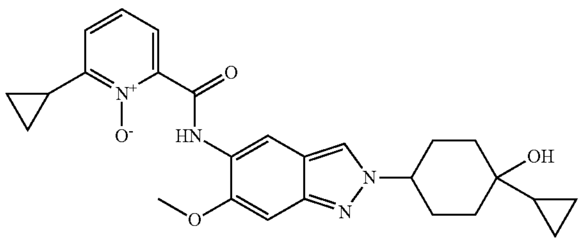
261
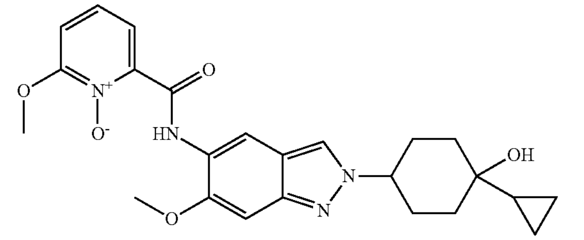
262
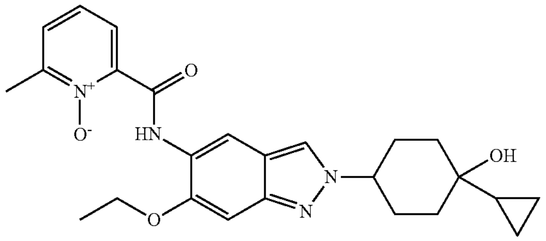
263
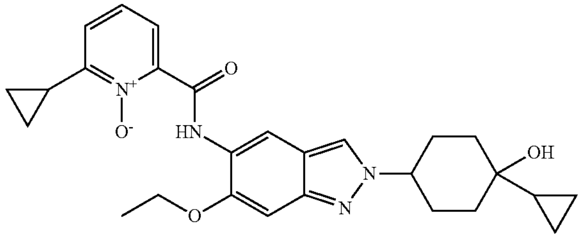
264
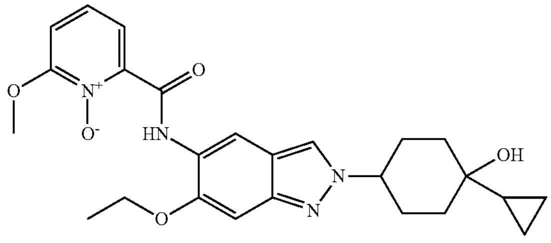
265
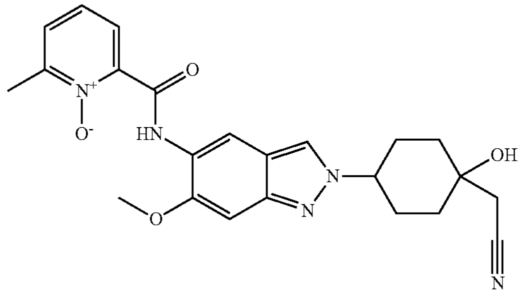
-continued
266
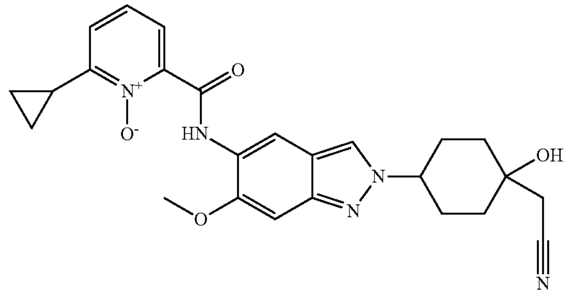
267
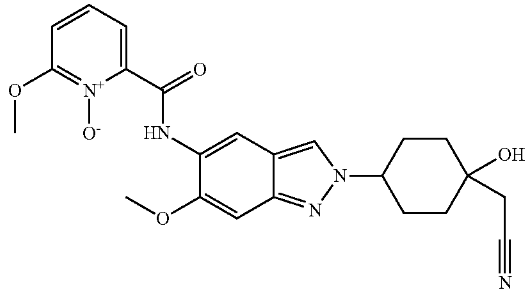
268
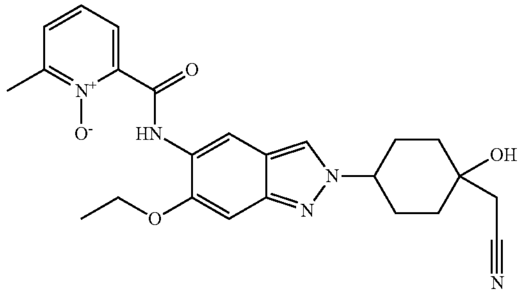
269
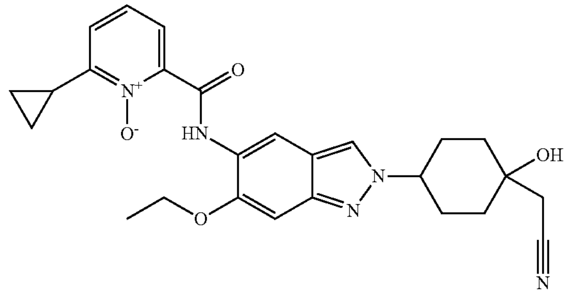
270
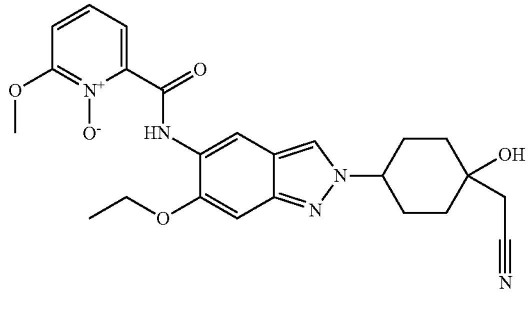

-continued
271
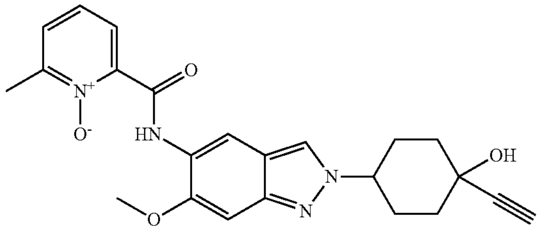
272
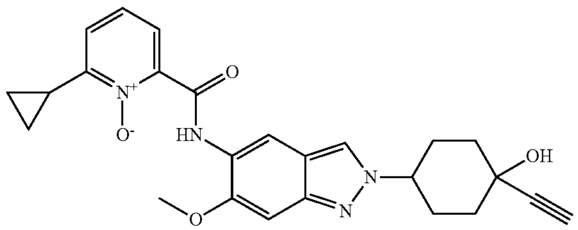
273
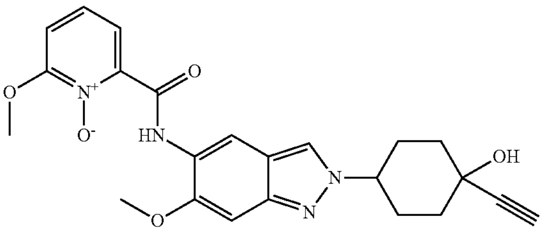
274
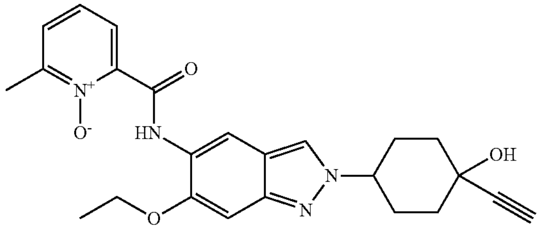
275
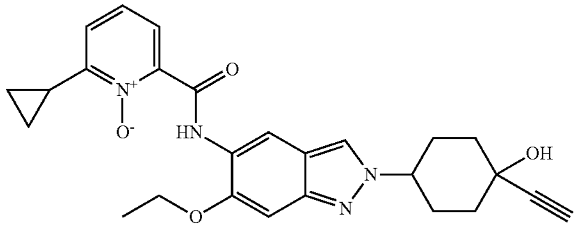
276
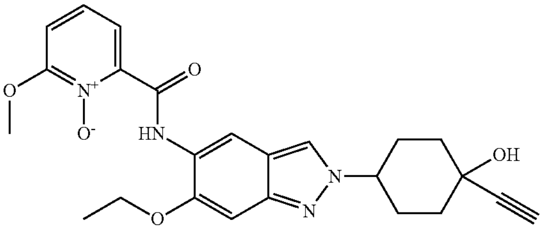
-continued
277
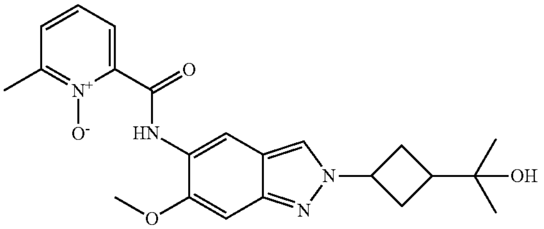
278
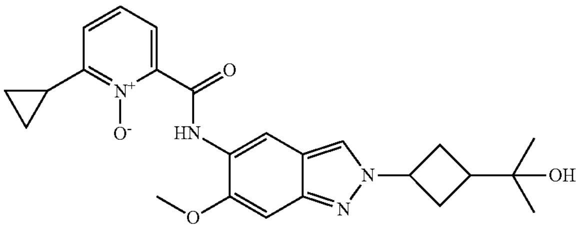
279
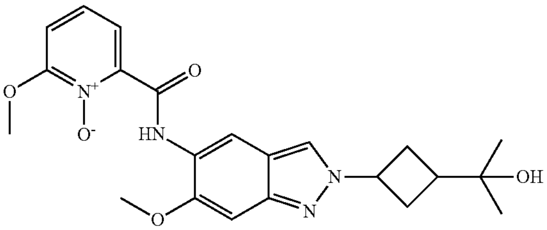
280
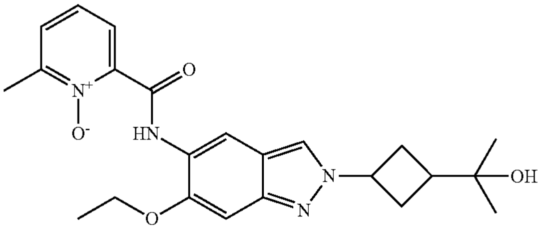
281
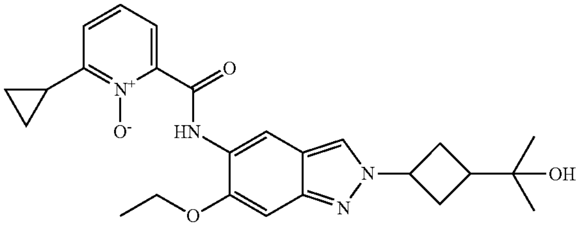
282
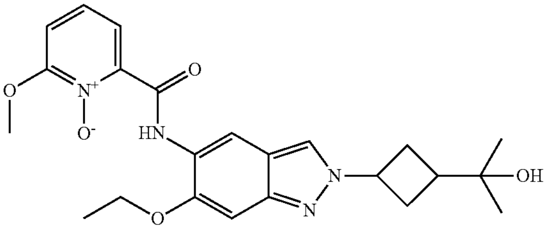

-continued

283

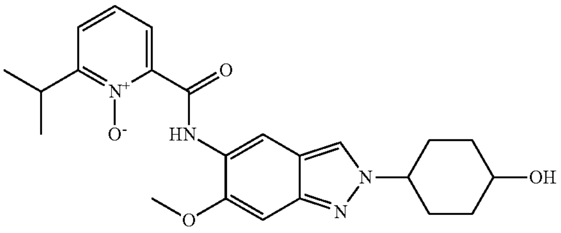

284

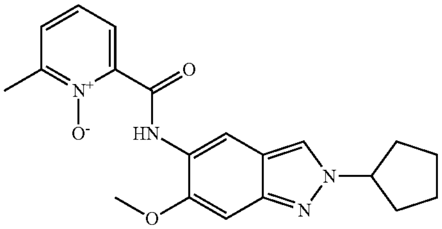

285

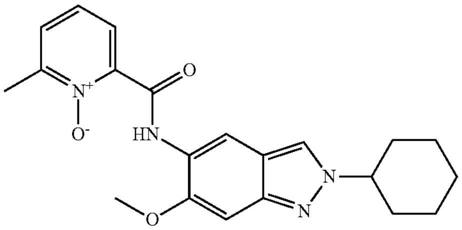

286

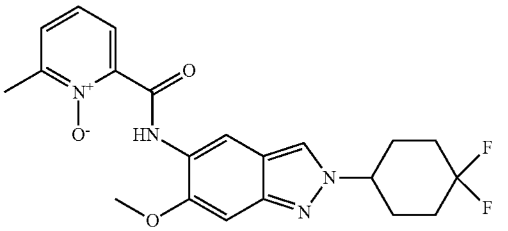

287

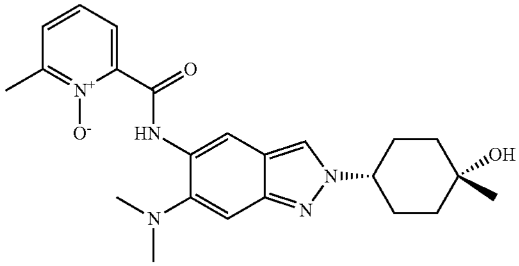

288

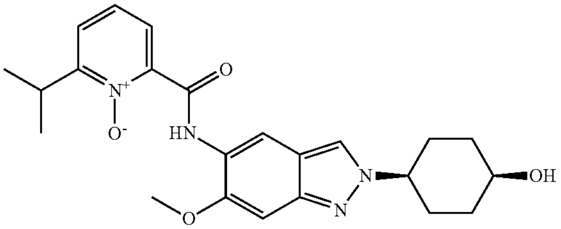

-continued

289

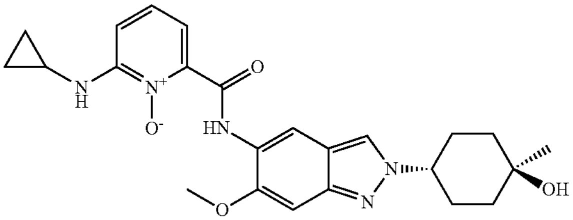

290

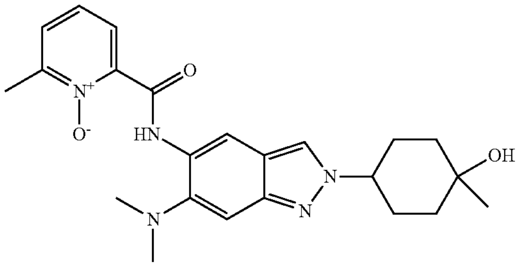

291

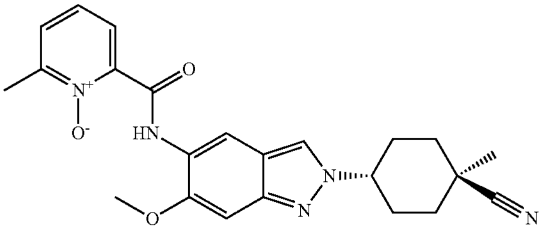

292

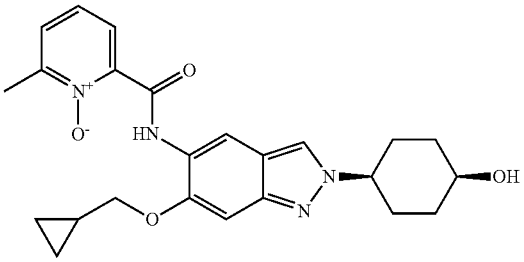

The present invention provides a preparation method for the compound of formula I (including formula Ia-Ie) or the stereoisomer, the racemate, the tautomer, the isotopically labeled compound, the prodrug or the pharmaceutically acceptable salt thereof, but the preparation method is not limited to the method described below.

In some embodiments, the preparation method may comprise:

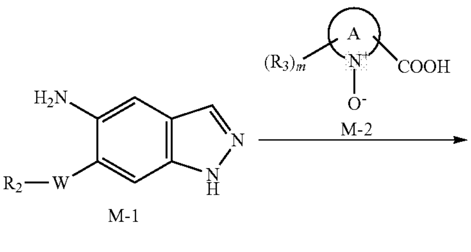

-continued

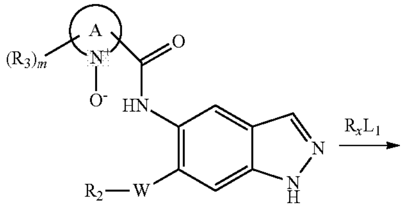

M-3

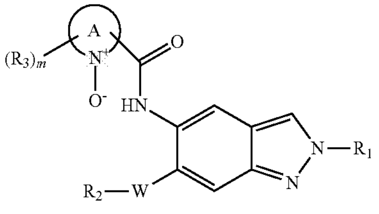

formula I (a1) reacting M-1 and M-2 to give M-3, wherein the reaction may be performed in the presence of EDCl·HCl and pyridine: and (a2) reacting M-3 and $R_xL_1$, wherein $R_x$ is selected from $R_1$ and a group of $R_1$ having hydroxyl with the hydroxyl substituted with

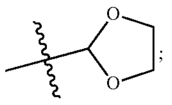 [SMILES: *C1OCCO1]

when $R_x$ is a group of $R_1$ having hydroxyl with the hydroxyl substituted with

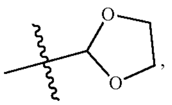

the reaction requires to be performed in the presence of an acid and a reductant to give the formula I, wherein the acid may be HCl, and the reductant may be sodium borohydride; $R_1$, $R_2$, $R_3$, m and W in the above steps are as defined in formula I, the L, is a leaving group and may be selected from halogen and —OTs.

In some embodiments, the preparation method may comprise:

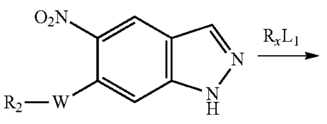

N-1

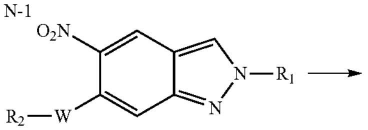

N-2

-continued

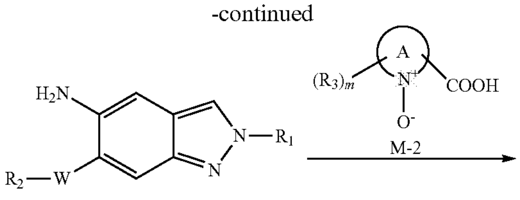

N-3

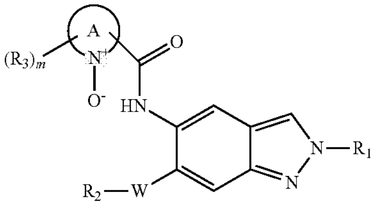

formula I (b1) reacting N-1 and $R_xL_1$, wherein $R_x$ is selected from $R_1$ and a group of $R_1$ having hydroxyl with the hydroxyl substituted with

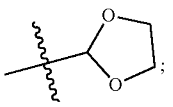 [SMILES: *C1OCCO1 ; ";"]

when $R_x$ is a group of $R_1$ having hydroxyl with the hydroxyl substituted with

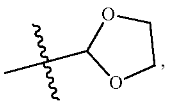

the reaction requires to be performed in the presence of an acid and a reductant to give N-2, wherein the acid may be HC, and the reductant may be sodium borohydride;

(b2) reducing the N-2 obtained in the above step to give N-3, wherein a reductant may be Pd/C; and (b3) reacting the N-3 and M-2 to give the formula I.

$R_1$, $R_2$, $R_3$, m and W in the above steps are as defined in formula I, the $L_1$ is a leaving group and may be selected from halogen and —OTs.

The present invention further provides a pharmaceutical composition comprising the compound of formula I or the stereoisomer, the racemate, the tautomer, the isotopically labeled compound, the prodrug or the pharmaceutically acceptable salt thereof disclosed herein.

In some embodiments, the pharmaceutical composition disclosed herein further comprises a therapeutically effective amount of the compound of formula I or the stereoisomer, the racemate, the tautomer, the isotopically labeled compound, the prodrug or the pharmaceutically acceptable salt thereof disclosed herein, and a pharmaceutically acceptable carrier.

The present invention further provides use of the compound of formula I or the stereoisomer, the racemate, the tautomer, the isotopically labeled compound, the prodrug or the pharmaceutically acceptable salt thereof in preparing IRAK inhibitor.

The present invention further provides use of the compound of formula I or the stereoisomer, the racemate, the tautomer, the isotopically labeled compound, the prodrug or the pharmaceutically acceptable salt thereof in preparing a medicament for preventing and/or treating diseases or disorders mediated by IRAK.

According to an embodiment of the present invention, the IRAK-mediated diseases or disorders are selected from tumors, gout, systemic lupus erythematosus, multiple sclerosis, metabolic syndrome, atherosclerosis, myocardial infarction, sepsis, inflammatory bowel disease, asthma, allergy, and the like.

The present invention further provides use of the compound of formula I or the stereoisomer, the racemate, the tautomer, the isotopically labeled compound, the prodrug or the pharmaceutically acceptable salt thereof in preparing a medicament for preventing and/or treating diseases or disorders associated with interleukin-1 receptor-associated kinase.

The present invention further provides a method for preventing and/or treating IRAK-mediated diseases or disorders, comprising administering to an individual in need thereof a therapeutically effective amount of the compound of formula I or the stereoisomer, the racemate, the tautomer, the isotopically labeled compound, the prodrug or the pharmaceutically acceptable salt thereof, or the pharmaceutical composition.

In some embodiments, the IRAK is IRAK4-associated kinase.

The present invention further provides a method for preventing and/or treating interleukin-1 receptor-associated diseases, comprising administering to an individual in need thereof a therapeutically effective amount of the compound of formula I or the stereoisomer, the racemate, the tautomer, the isotopically labeled compound, the prodrug or the pharmaceutically acceptable salt thereof, or the pharmaceutical composition.

According to an embodiment of the present invention, the diseases or disorders associated with interleukin-1 receptor-associated kinase are selected from tumors, gout, systemic lupus erythematosus, multiple sclerosis, metabolic syndrome, atherosclerosis, myocardial infarction, sepsis, inflammatory bowel disease, asthma, rheumatoid arthritis, septicemia, autoimmune disease, allergy, and the like.

The method of the present invention may comprise administering the compounds disclosed herein alone or in combination with one or more other chemotherapeutic agents. Multiple drugs may be administered simultaneously or successively.

Definitions and Abbreviations of Terms

Unless otherwise stated, the definitions of groups and terms described in the specification and claims of the present application, including definitions thereof as examples, exemplary definitions, preferred definitions, definitions documented in tables, definitions of specific compounds in the examples, and the like, may be arbitrarily combined and incorporated with each other. The definitions of groups and the structures of the compounds in such combinations and incorporations should fall within the scope of the present specification.

When a numerical range defined by "integer" is recited in the specification and claims of this application, it shall be construed as reciting both endpoints of the range and every integer within the range. For example, "an integer of 0 to 6" shall be construed to include every integer of 0, 1, 2, 3, 4, 5 and 6. The term "more" refers to three or more.

The optionally substituted with a substituent described herein encompasses both unsubstituted and substituted with one or more substituents, for example, "optionally substituted with one, two or more R" means that it may be not substituted (unsubstituted) with one R or substituted with one, two or more R. The term "halogen" refers to F, Cl, Br and I. In other words, F, Cl, Br and I may be described as "halogen" in the specification.

The term "aliphatic hydrocarbyl" includes saturated or unsaturated, and linear or branched or cyclic hydrocarbyl groups. The aliphatic hydrocarbyl may be selected from alkyl, alkenyl, alkynyl, and the like, has preferably 1-12 or 1-10 carbon atoms, and more preferably 1-6 carbon atoms, and specifically may include but is not limited to the following groups: methyl, ethyl, n-propyl, isopropyl, n-butyl, isobutyl, tert-butyl, n-pentyl, isopentyl, neopentyl, n-hexyl, ethenyl, 1-propenyl, 2-propenyl, 1-methylethenyl, 1-butenyl, 1-ethylethenyl, 1-methyl-2-propenyl, 2-butenyl, 3-butenyl, 2-methyl-1-propenyl, 2-methyl-2-propenyl, 1-pentenyl, 1-hexenyl, ethynyl, 1-propynyl, 2-propynyl, 1-butynyl, 1-methyl-2-propynyl, 3-butynyl, 1-pentynyl, 1-hexynyl, cyclopropyl, cyclobutyl, cyclopentyl and cyclohexyl;

the "aliphatic hydrocarbyl" may optionally comprise one, two or more heteroatoms (which may be construed as optional insertion of heteroatoms into any C—C bond and C—H bond of the aliphatic hydrocarbyl). Suitable heteroatoms will be apparent to those skilled in the art and include, for example, sulfur, nitrogen, oxygen, phosphorus and silicon. The aliphatic hydrocarbyl comprising heteroatoms may be selected from the following groups: ($C_1$-$C_6$)aliphatic hydrocarbyloxy, ($C_1$-$C_6$)aliphatic hydrocarbylthio, ($C_1$-$C_6$)aliphatic hydrocarbyloxy($C_1$-$C_6$)aliphatic hydrocarbyl, ($C_1$-$C_6$) aliphatic hydrocarbylthio($C_1$-$C_6$)aliphatic hydrocarbyl, N—($C_1$-$C_3$)aliphatic hydrocarbylamino($C_1$-$C_6$)aliphatic hydrocarbyl, and N,N-di-($C_1$-$C_3$)aliphatic hydrocarbylamino($C_1$-$C_6$)aliphatic hydrocarbyl, for example, methoxy, ethoxy, propoxy, butoxy, pentoxy, methoxymethyl, ethoxymethyl, propoxymethyl, methoxyethyl, ethoxyethyl, propoxyethyl, methoxypropyl, ethoxypropyl, propoxypropyl, N-methylaminomethyl, N-methylaminoethyl, N-ethylaminoethyl, N,N-dimethylaminomethyl, N,N-dimethylaminoethyl, and N,N-diethylaminoethyl; the "aliphatic hydrocarbyl" moieties contained in the other groups are defined as above.

The term "$C_{3-12}$ cycloalkyl" refers to a saturated or unsaturated monovalent monocyclic or bicyclic hydrocarbon ring having 3-12 carbon atoms, and is preferably a "$C_{3-10}$ cycloalkyl". The term "$C_{3-10}$ cycloalkyl" refers to a saturated monovalent monocyclic or bicyclic hydrocarbon ring having 3, 4, 5, 6, 7, 8, 9 or 10 carbon atoms. The $C_{3-10}$ cycloalkyl may be a monocyclic hydrocarbyl such as cyclopropyl, cyclobutyl, cyclopentyl, cyclohexyl, cycloheptyl, cyclooctyl, cyclononyl or cyclodecyl, or may be a bicyclic hydrocarbyl such as a decahydronaphthalene ring.

The term "3-12 membered heterocyclyl" refers to a saturated or unsaturated monovalent monocyclic or bicyclic ring comprising 1-5 heteroatoms independently selected from N, O and S. The groups comprising heteroatoms are not aromatic, and the 3-12 membered heterocyclyl is preferably a "3-10 membered heterocyclyl". The term "3-10 membered heterocyclyl" refers to a saturated monovalent monocyclic or bicyclic ring comprising 1-5, preferably 1-3, heteroatoms selected from N, O and S. The heterocyclyl may be connected to the rest of the molecule through any one of the carbon atoms or the nitrogen atom (if present). In particular, the heterocyclyl may include, but is not limited to: 4 membered rings such as azetidinyl or oxetanyl; 5 membered rings such as tetrahydrofuryl, tetrahydrothienyl, dioxolyl, pyrrolidinyl, imidazolidinyl, pyrazolidinyl or pyrrolinyl; 6 membered rings such as tetrahydropyranyl, piperidinyl, morpholinyl, dithianyl, thiomorpholinyl, piperazinyl or trithianyl; or 7 membered rings such as diazepanyl. Optionally, the heterocyclyl may be benzo-fused. The heterocyclyl may be bicyclic, such as but not limited to a 5,5 membered ring such as a hexahydrocyclopenta[c]pyrrol-2(1H)-yl ring, or a 5,6 membered bicyclic ring such as a hexahydropyrrolo [1,2-a]pyrazin-2(1H)-yl ring. The ring containing nitrogen atoms may be partially unsaturated, i.e., it may comprise one or more double bonds, such as but not limited to 2,5-dihydro-1H-pyrrolyl, 4H-[1,3,4]thiadiazinyl, 4,5-dihydrooxazolyl or 4H-[1,4]thiazinyl, or it may be benzo-fused, such as but not limited to dihydroisoquinolinyl. According to the present invention, the 3-12 membered heterocyclyl may be further selected from the following groups:

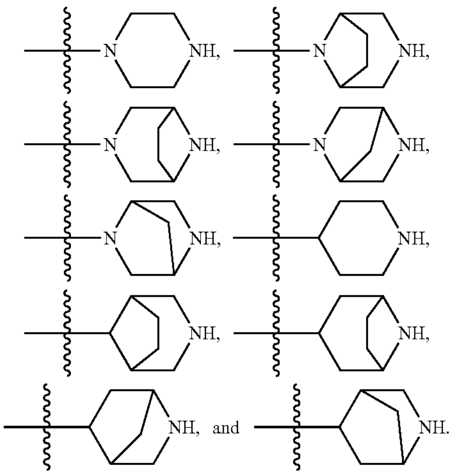

The term "$C_{6-20}$ aryl" preferably refers to an aromatic or partially aromatic monocyclic, bicyclic or tricyclic monovalent hydrocarbon ring containing 6-20 carbon atoms, and is preferably "$C_{6-14}$ aryl". The term "$C_{6-14}$ aryl" preferably refers to an aromatic or partially aromatic monovalent monocyclic, bicyclic or tricyclic hydrocarbon ring having 6, 7, 8, 9, 10, 11, 12, 13 or 14 carbon atoms ("$C_{6-14}$ aryl"), in particular a ring having 6 carbon atoms ("$C_6$ aryl"), such as phenyl; or a biphenyl, a ring having 9 carbon atoms ("$C_9$ aryl") such as indanyl or indenyl, a ring having 10 carbon atoms ("$C_{10}$ aryl") such as tetrahydronaphthyl, dihydronaphthyl or naphthyl, a ring having 13 carbon atoms ("$C_{13}$ aryl") such as fluorenyl, or a ring having 14 carbon atoms ("$C_{14}$ aryl") such as anthracenyl.

The term "5-14 membered heteroaryl" refers to an aromatic monovalent monocyclic, bicyclic or tricyclic ring which has 5, 6, 7, 8, 9, 10, 11, 12, 13 or 14 ring atoms, in particular 5, 6, 9 or 10 carbon atoms, comprises 1-5, preferably 1-3 heteroatoms independently selected from N, O and S, and may be benzo-fused in each case. In particular, the heteroaryl is selected from thienyl, furyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl and the like and benzo derivatives thereof, such as benzofuranyl, benzothienyl, benzoxazolyl, benzoisoxazolyl, benzimidazolyl, benzotriazolyl, indazolyl, indolyl, and isoindolyl; or pyridinyl, pyridazinyl, pyrimidinyl, pyrazinyl, triazinyl and the like and benzo derivatives thereof, such as quinolyl, quinazolinyl, and isoquinolyl; or azocinyl, indolizinyl, purinyl and the like and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, and the like.

Unless otherwise specified, heterocyclyl or heteroaryl includes all possible isomeric forms thereof, e.g. positional isomers thereof. Accordingly, for some illustrative non-limiting examples, pyridinyl or pyridinylene includes pyridin-2-yl, pyridinylene-2-yl, pyridin-3-yl, pyridinylene-3-yl, pyridin-4-yl, and pyridinylene-4-yl; thienyl or thienylene includes thien-2-yl, thien-2-ylene, thien-3-yl, and thien-3-ylene. The "3-12 membered heterocyclyl" and "5-14 membered heteroaryl" disclosed herein may further comprise 5-12 membered heterocyclyl or 5-14 membered heteroaryl containing N, that is N-containing 5-12 membered heterocyclyl or 5-14 membered heteroaryl may be selected from corresponding groups defined by the "3-12 membered heterocyclyl" and "5-14 membered heteroaryl".

According to the structure, the compounds disclosed herein may be chiral and may therefore exist in various enantiomeric forms. These compounds may therefore exist in racemic or optically active form. The compounds disclosed herein or intermediates thereof may be separated into enantiomers by chemical or physical methods well known to those skilled in the art, or used in this form for synthesis. In the case of racemic amines, diastereoisomers are prepared from mixtures by reaction with optically active resolving agents. Examples of suitable resolving agents are optically active acids such as R- or S-tartaric acid, diacetyltartaric acid, dibenzoyltartaric acid, mandelic acid, malic acid, lactic acid, suitable N-protected amino acids (e.g., N-benzoylproline or N-benzenesulfonylproline) or various optically active camphorsulfonic acids. Enantiomeric resolution by chromatography can be advantageously performed with the aid of optically active resolving agents, such as dinitrobenzoylphenylglycine, cellulose triacetate or other carbohydrate derivatives or chirally derivatized methacrylate polymers immobilized on silica gel. Suitable eluents for this purpose are mixtures of solvent containing water or alcohol, for example, hexane/isopropanol/acetonitrile.

A pharmaceutically acceptable salt may be, for example, acid addition salts of the compounds disclosed herein having a nitrogen atom in the chain or ring with sufficient basicity, for example, acid addition salts formed with the following inorganic acids: hydrochloric acid, hydrofluoric acid, hydrobromic acid, hydroiodic acid, sulfuric acid, pyrosulfuric acid, phosphoric acid or nitric acid; hydrosulfates; or acid addition salts with the following organic acids: formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectinic acid, peroxosulfuric acid, 3-phenylpropionic acid, picric acid, pivalic acid, 2-hydroxyethanesulfonic acid, itaconic acid, sulfamic acid, trifluoromethanesulfonic acid, dodecylsulfuric acid, ethanesulfonic acid, benzenesulfonic acid, p-toluenesulfonic acid, methanesulfonic acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptoic acid, glycerophosphoric acid, aspartic acid, sulfosalicylic acid, hemisulfuric acid, or thiocyanic acid.

In addition, another suitable pharmaceutically acceptable salt of the compounds disclosed herein having sufficient acidity is an alkali metal salt (e.g., sodium salt or potassium salt), an alkaline earth metal salt (e.g., calcium salt or magnesium salt), an ammonium salt, or a salt formed with an organic base which provides a physiologically acceptable cation, for example a salt formed with: a sodium ion, a potassium ion, N-methylglucamine, dimethylglucamine, ethylglucamine, lysine, dicyclohexylamine, 1,6-hexanediamine, ethanolamine, glucosamine, meglumine, sarcosine, serinol, trihydroxymethylaminomethane, aminopropanediol, or 1-amino-2,3,4-butanetriol. As an example, the pharmaceutically acceptable salts include salts formed by the group —COOH with the following: a sodium ion, a potassium ion, a calcium ion, a magnesium ion. N-methylglucamine, dimethylglucamine, ethylglucamine, lysine, dicyclohexylamine, 1,6-hexanediamine, ethanolamine, glucosamine, meglumine, sarcosine, serinol, trishydroxymethylaminomethane, aminopropanediol, or 1-amino-2,3,4-butanetriol.

In addition, the basic nitrogen-containing groups may be quaternized with the following agents: lower alkyl halides such as methyl, ethyl, propyl and butyl chlorides, bromides and iodides; dialkyl sulfates such as dimethyl sulfate, diethyl sulfate, dibutyl sulfate, and dipentyl sulfate; long chain halides such as decyl, lauryl, myristyl and stearyl chlorides, bromides and iodides; and aralkyl halides such as benzyl and phenethyl bromides. As an example, pharmaceutically acceptable salts include hydrochloride, sulfate, nitrate, bisulfate, hydrobromide, acetate, oxalate, citrate, mesylate, formate, meglumine, and the like. Since the compounds disclosed herein may have a plurality of salt-forming sites, the "pharmaceutically acceptable salt" includes not only a salt formed at 1 salt-forming site of the compounds disclosed herein but also salts formed at 2, 3 or all of the salt-forming sites thereof. For this purpose, the molar ratio of the compound of formula I to a radical ion (anion) of an acid or a cation of a base required for salt formation may vary within a wide range, and may be, for example, 4:1 to 1:4, such as 3:1, 2:1, 1:1, 1:2, and 1:3. According to the present invention, the pharmaceutically acceptable anions include anions selected from those generated by the ionization of inorganic or organic acids. The "inorganic acid" includes, but is not limited to, hydrochloric acid, hydrofluoric acid, hydrobromic acid, hydroiodic acid, sulfuric acid, pyrosulfuric acid, phosphoric acid, or nitric acid. The "organic acid" includes, but is not limited to, formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectinic acid, peroxosulfuric acid, 3-phenylpropionic acid, picric acid, pivalic acid, 2-hydroxyethanesulfonic acid, itaconic acid, sulfamic acid, trifluoromethanesulfonic acid, dodecylsulfuric acid, ethanesulfonic acid, benzenesulfonic acid, p-toluenesulfonic acid, methanesulfonic acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptoic acid, glycerophosphoric acid, aspartic acid, sulfosalicylic acid, hemisulfuric acid, or thiocyanic acid.

According to the position and nature of the various substituents, the compounds disclosed herein may also comprise one or more asymmetric centers. Asymmetric carbon atoms may exist in either the (R) or (S) configuration. When there is only one asymmetric center, a racemic mixture is generated, and when there are multiple asymmetric centers, a diastereoisomeric mixture is generated. In some cases, asymmetry may also exist due to hindered rotation about a particular bond, for example, the two substituted aromatic rings of a particular compound connected by the central bond may be asymmetric. Furthermore, the substituents may exist in cis- or trans-isomeric forms.

The compounds disclosed herein also include all possible stereoisomers thereof, either in the form of a single stereoisomer or in the form of any mixture of the stereoisomers (e.g., R- or S-isomers, or F- or Z-isomers) in any proportion. Single stereoisomers (e.g., single enantiomers or single diastereoisomers) of the compounds disclosed herein may be separated by any suitable method in the prior art (e.g., chromatography, particularly, e.g., chiral chromatography).

The term "tautomer" refers to functional isomers resulting from the rapid movement of an atom in a molecule between two positions. The compounds disclosed herein may exhibit the tautomerism. Tautomeric compounds may exist in two or more interconvertible forms. Prototropic tautomers result from the migration of a covalently bonded hydrogen atom between two atoms. Tautomers generally exist in an equilibrium form. Trying to separate a single tautomer usually lead to a mixture, the physicochemical properties of which are consistent with the mixture of the compound. The position of the equilibrium depends on the chemical properties of the molecule. For example, in many aliphatic aldehydes and ketones such as acetaldehyde, the keto form predominates; whereas in phenol, the enol form predominates. The present invention comprises all tautomeric forms of the compound.

In the present invention, the compounds involved also include isotopically labeled compounds, which are identical to the compound of formula I, but have one or more atoms substituted with atoms with the atomic mass or mass number different from the atomic mass or mass number of those usually found in nature. Examples of isotopes that can be incorporated into the compounds disclosed herein include isotopes of H, C, N, O, S, F and Cl, such as $^{2}H$, $^{3}H$, $^{13}C$, $^{11}C$, $^{14}C$, $^{15}N$. $^{18}O$, $^{17}O$, $^{32}P$, $^{35}S$, $^{18}F$, and $^{36}Cl$. The compound or the prodrug thereof, or the pharmaceutically acceptable salts thereof comprising the above isotopes and/or other isotopes of other atoms are within the scope of the present invention. Certain isotopically labeled compounds disclosed herein, e.g., those into which radioactive isotopes such as $^{3}H$ and $^{14}C$. are incorporated, are useful in drug and/or substrate tissue distribution assays. Tritium (i.e., $^{3}H$) and carbon 14 (i.e., $^{14}C$) isotopes are particularly preferred for their ease of preparation and detectability. Furthermore, substitution with heavier isotopes such as deuterium (i.e., $^{2}H$) may afford certain therapeutic advantages (e.g., increased in vivo half-life or reduced dose) resulting from greater metabolic stability and hence may be preferred in some circumstances. The compounds disclosed herein as claimed may be particularly limited to substitution with deuterium or tritium. Furthermore, the lack of separate specification of a hydrogen in a substituent as the term deuterium or tritium does not mean that the deuterium or tritium is excluded, on the contrary, the deuterium or tritium can also be included.

The term "effective amount" or "therapeutically effective amount" refers to an amount of the compounds disclosed herein sufficient to effect the intended use, including but not limited to the treatment of a disease as defined below. The therapeutically effective amount may vary depending on the following factors: the intended use (in vitro or in vivo), or the subject and diseases or conditions being treated, such as weight and age of the subject, severity of the diseases or conditions and mode of administration, which can be readily determined by one of ordinary skill in the art. The specific dosage will vary depending on the following factors: the selected particular compound, the dosage regimen to be followed, whether to administer in combination with other compounds, the schedule of administration, the tissue to be administered and the physical delivery system carried.

The term "excipient" refers to a pharmaceutically acceptable inert ingredient. Examples of types of excipients include, without limitation, binders, disintegrants, lubricants, glidants, stabilizers, fillers, diluents, and the like. Excipients are capable of enhancing the handling characteristics of the pharmaceutical formulation, i.e., making the formulation more amenable to direct compression by increasing flowability and/or adhesiveness. Examples of typical pharmaceutically acceptable carriers suitable for use in the above formulations include: saccharides, such as lactose, sucrose, mannitol, and sorbitol; starches, such as corn starch, tapioca starch and potato starch; cellulose and its derivatives, such as sodium carboxymethylcellulose, ethyl cellulose and methyl cellulose; calcium phosphates, such as dicalcium phosphate and tricalcium phosphate; sodium sulfate; calcium sulfate; polyvinylpyrrolidone; polyvinyl alcohol: stearic acid; alkaline earth metal stearate, such as magnesium stearate and calcium stearate; vegetable oils such as peanut oil, cottonseed oil, sesame oil, olive oil and corn oil; nonionic, cationic and anionic surfactants; a glycol polymer; fatty alcohols; and grain hydrolysis solids and other nontoxic compatible excipients commonly available in pharmaceutical formulations, such as fillers, binders, disintegrants, buffers, preservatives, antioxidants, lubricants, and colorants.

The term "solvate" refers to forms of the compounds disclosed herein in which a complex is formed by coordination of the compound in the solid or liquid state with solvent molecules. Hydrate is a particular form of the solvate in which the coordination occurs with water. In the present invention, the preferred solvate is a hydrate. Further, pharmaceutically acceptable solvates (hydrates) of the compound of formula I disclosed herein refer to co-crystals and clathrates formed of the compound of formula I and one or more molecules of water or other solvents in stoichiometric amounts. Available solvents for solvates include, but arc not limited to water, methanol, ethanol, ethylene glycol and acetic acid.

The term "prodrug", also known as "drug precursor", refers to a compound that is converted in vivo to the compound of the above general formula or of a particular compound. Such conversion is affected by hydrolysis of the prodrug in the blood or by enzymatic conversion of the prodrug into the parent structure in the blood or tissue. The prodrug disclosed herein may be esters, and in the present invention, the esters that may be used as prodrugs include phenyl esters, aliphatic ($C_{1-24}$) esters, acyloxymethyl esters, carbonates, carbamates and amino acid esters. For example, compounds disclosed herein containing hydroxyl/carboxyl can be acylated to give a prodrug. Other prodrugs include phosphate esters, and those phosphate esters are obtained by phosphorylating via the hydroxyl on the parent structure.

Reagent Names Corresponding to English Abbreviations of the Reagents

| English Abbreviations of Reagents | Reagent Names |
|---|---|
| m-CPBA | m-chloroperoxybenzoic acid |
| DCM | Dichloromethane |
| DIPEA | N,N-diisopropylethylamine |
| DMF | N,N-dimethylformamide |
| HATU | O-(7-azabenzotriazol-1-yl)-N,N,N',N'-tetramethyluronium hexafluorophosphate |
| EDCI•HCl | 1-(3-Dimethylaminopropyl)-3-ethylcarbodiimide hydrochloride |
| Py | Pyridine |
| DMAP | 4-dimethylaminopyridine |
| EA | Ethyl acetate |
| TsCl or TosCl | p-Toluenesulfonyl chloride |
| NMP | N-methylpyrrolidin-2-one |
| PE | Petroleum ether |
| DAST | Diethylaminosulfur trifluoride |

Beneficial Effects

1) The present invention provides a compound of general formula I with a novel structure, and experiments prove that the compound disclosed herein has a significant inhibition effect on IRAK4 activity, and has a good selective inhibition effect on IRAK4 activity relative to other kinases;
2) the compound disclosed herein has good medication safety, wide applicability and low toxicity, and the experiments prove that the compound of the present invention has a very low inhibition rate on human hERG, has no obvious time-dependent inhibition on human CYP3A4, has a moderate protein binding rate to plasma of human, rats and mice, and has little binding difference between species; at the same time, the compounds disclosed herein has no obvious inhibition effect on the 5 human CYP subtypes:
3) the compound disclosed herein has significant inhibitory effect on TNF-α release in LPS-induced Balb/c female mice;
4) the compound disclosed herein has good pharmacokinetic characteristics, shows excellent exposure and retention time in animals, and has suitable half-life and good drug absorption.

DETAILED DESCRIPTION

The technical scheme of the present invention will be further illustrated in detail with reference to the following specific examples. It should be understood that the following examples are merely exemplary illustration and explanation of the present invention, and should not be construed as limiting the protection scope of the present invention. All techniques implemented based on the aforementioned contents of the present invention are encompassed within the protection scope of the present invention.

Unless otherwise specified, the starting materials and reagents used in the following examples are all commercially available products or can be prepared by known methods.

Example 1: Synthesis of Compound 001

Reaction Formula:

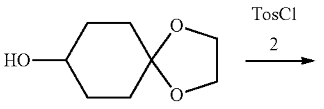

1

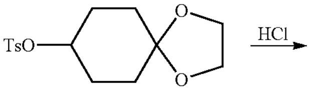

3

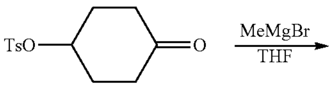

4

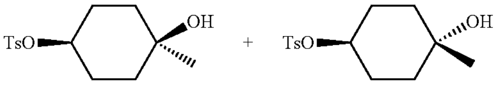

5 6

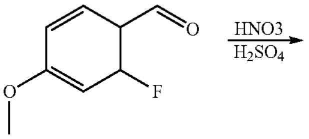

7

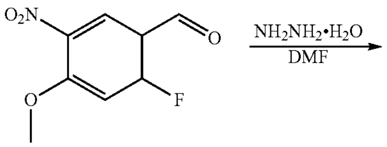

8

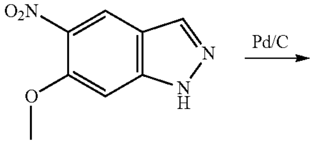

9

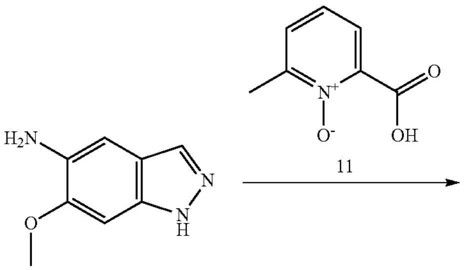

10

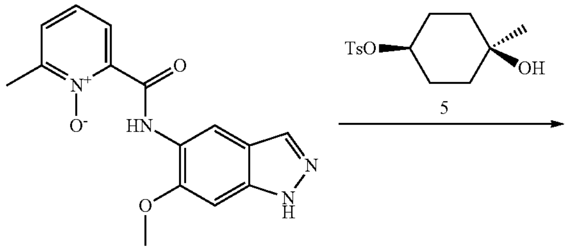

12

-continued

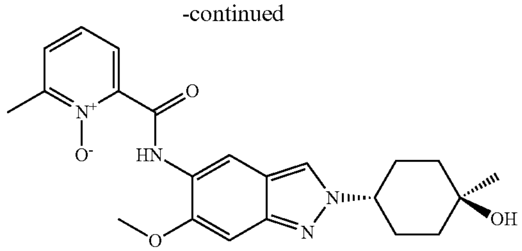

001

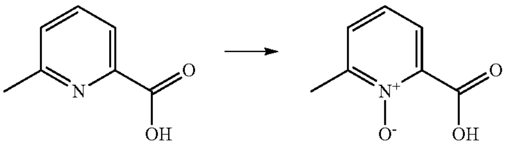

13 11

1. Synthesis of Compound 3

DMAP (42.5 g), compound 2 (63.4 g) and triethylamine (63.9 g) were added sequentially to a solution of compound 1 (50 g) in dichloromethane (500 mL) at 15° C. The reaction system was stirred at 25° C. for 18 h. The reaction solution was added with dichloromethane (200 mL), and washed with water (300 mL×2) and 1 M hydrochloric acid (300 mL×3). The organic phase was dehydrated over anhydrous sodium sulfate, filtered and concentrated under reduced pressure to give compound 3 (98 g, yield: 99%).

2. Synthesis of Compound 4

1 M hydrochloric acid (300 mL) was added into a solution of compound 3 (50 g) in tetrahydrofuran (300 mL) at 15° C. The reaction system was stirred at 25° C. for 20 h. At 0° C., the reaction solution was adjusted to pH 9 with 1 M sodium hydroxide solution. Ethyl acetate (200 mL×3) was added for extraction. The extracts were washed with saturated sodium chloride solution (300 mL), dehydrated over anhydrous sodium sulfate, filtered and concentrated under reduced pressure. The residue was slurried with petroleum ether (150 mL) to give compound 4 (39 g yield: 91%).

3. Synthesis of Compounds 5&6

A solution of compound 4 (34.5 g) in tetrahydrofuran (200 mL) was dropwise added into a solution of methylmagnesium bromide (85.8 mL) in tetrahydrofuran (500 mL) at −40° C. The reaction system was stirred at −40° C. for 4 h. After the reaction was quenched with saturated ammonium chloride solution (100 mL), ethyl acetate (500 mL×3) was added for extraction, and the extracts were washed with saturated saline (300 mL), dehydrated over anhydrous sodium sulfate, filtered and concentrated under reduced pressure. The residue was purified on silica gel column chromatography (petroleum ether:ethyl acetate=5:1) to give compound 5 (4.3 g, yield: 10%), compound 6 (7.0 g yield: 17%) and the mixture (12 g).

Compound 5

$^1H$ NMR (400 MHz, $CDCl_3$): δ 7.79 (d, J=8.0 Hz, 2H), 7.32 (d, J=8.4 Hz, 2H), 4.52-4.41 (m, 11H), 2.44 (s, 3H), 1.95-1.80 (m, 2H), 1.77-1.61 (m, 4H), 1.46-1.35 (m, 2H), 1.19 (s, 3H).

Compound 6

$^1H$ NMR (400 MHz, $CDCl_3$): δ 7.79 (d, J=8.4 Hz, 2H), 7.33 (d, J=8.0 Hz, 2H), 4.74-4.64 (m, 1H), 2.44 (s, 3H), 1.92-1.79 (m, 2H), 1.77-1.62 (m, 4H), 1.49-1.38 (m, 2H), 1.23 (s, 3H).

4. Synthesis of Compound 8

A solution of nitric acid (1.6 mL, 70%) in concentrated sulfuric acid (1.6 mL, 98%) was added dropwise to a solution of compound 7 (2.0 g) in concentrated sulfuric acid (12 mL, 98%) at −15° C. The reaction system was stirred at −15° C. for 2 h after the completion of addition. The reaction solution was slowly poured into ice water, stirred for 5 min and filtered under vacuum. The filter cake was washed with water, and the solid was collected and dried under reduced pressure to give compound 8 (2.5 g, yield: 97%).

5. Synthesis of Compound 9

Hydrazine hydrate (2.4 mL, 98%) was added into a solution of compound 8 (2.0 g) in DMF (20 mL). After the completion of addition, the reaction system was heated to 120° C., stirred for 16 h, and cooled to room temperature. The reaction system was slowly poured into ice water, stirred, and filtered under vacuum. The filter cake was washed with water, and the solid was collected and dried under reduced pressure to give compound 9 (1.3 g, yield: 67%).

6. Synthesis of Compound 10

Compound 9 (12.4 g) and palladium on carbon (7 g, 10%) were added sequentially to 400 mL of ethyl acetate at 15° C. The reaction system was stirred for 18 h at 15° C. in hydrogen atmosphere after the completion of addition. After palladium on carbon in the reaction solution was filtered, the filtrate was dehydrated and concentrated to give compound 10 (10.4 g, yield: 99%).

7. Synthesis of Compound 12

EDCl·HCl (2.6 g) was added into a solution of compound 10 (1.5 g) and compound 11 (1.4 g) in Py (15 mL) at 25° C. The reaction system was stirred at 25° C. for 16 h. The reaction solution was dehydrated and concentrated, and the residue was slurried with MeOH:$H_2O$=20 mL:20 mL to give compound 12 (1.3 g, yield: 48%).

8. Synthesis of Compound 001

2-((2-((1r,4r)-4-hydroxy-4-methylcyclohexyl)-6-methoxy-2H-indazol-5-yl)carbamoyl)-6-methylpyridine 1-oxide

001

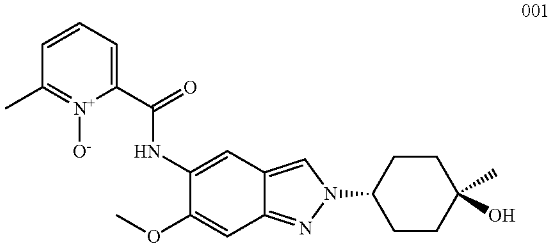 [SMILES: COc1cc2nn([C@H]3CC[C@](C)(O)CC3)cc2cc1NC(=O)c1cccc(C)[n+]1[O-]]

Cesium carbonate (985 mg) was added into a solution of compound 12 (300 mg) and compound 5 (344 mg) in DMF (5 mL) at 25° C. The reaction system was stirred at 90° C. for 16 h. The reaction solution was added into water (30 mL) and extracted with ethyl acetate (10 mL×3). The organic phase was concentrated under reduced pressure. The residue was purified by preparative high performance liquid chromatography ($CH_3CN$:$H_2O$ (0.1% $NH_4HCO_3$)=15-45%, UV: 214 nm, flowrate: 15 mL/min) to give compound 001 (70 mg, yield: 17%).

$^1H$ NMR (400 MHz, DMSO-d6): δ 14.16 (s, 1H), 8.78 (s, 1H), 8.34 (s, 1H), 8.32-8.30 (m, 1H), 7.77 (d, J=7.6 Hz, 1H), 7.58 (t, J=8.0 Hz, 1H), 7.13 (s, 1H), 4.45 (s, 1H), 4.43-4.40 (m, 1H), 3.95 (s, 3H), 2.53 (s, 3H), 2.09-2.00 (m, 4H), 1.68-1.58 (m, 4H), 1.22 (s, 3H). LCMS: Rt=3.646 min, $[M+H]^+$=411.1.

9. Synthesis of Compound 11 m-CPBA (25 g) was added into a solution of compound 13 (10 g) in DCM (200 mL) at 25° C. The reaction system was stirred at 25° C. for 16 h. The reaction solution was filtered, and the filtrate was quenched with a saturated solution prepared from sodium sulfite (15.6 g). The reaction system was stirred for 2 h and extracted. The aqueous phase was adjusted to pH<7 with hydrochloric acid and extracted with DCM (50 mL×3). The organic phases were combined and concentrated, and the residue was slurried with EA (300 mL) to give compound 11 (10.1 g, yield: 90%).

Example 2: Synthesis of Compound 010

Reaction Formula:

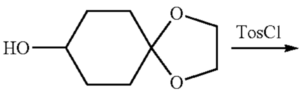

1

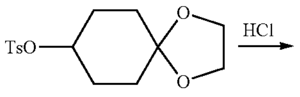

2

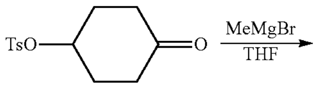

3

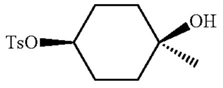

+

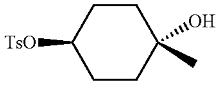

4

5

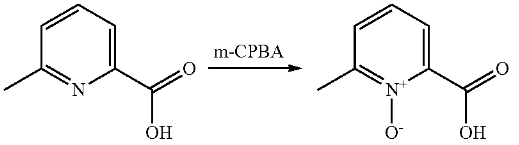

6

7

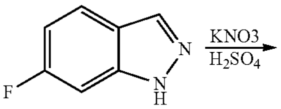

8

-continued

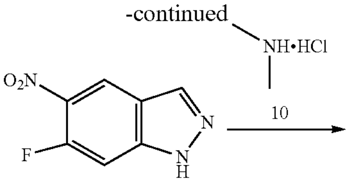

9

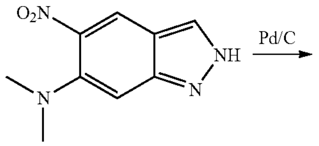

11

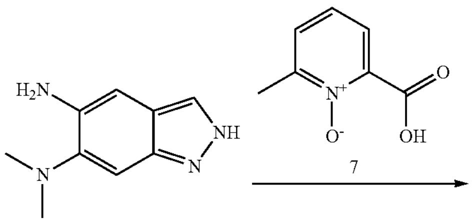

12

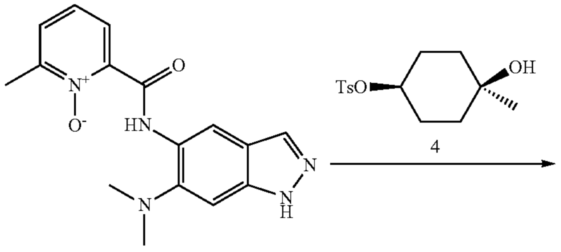

13

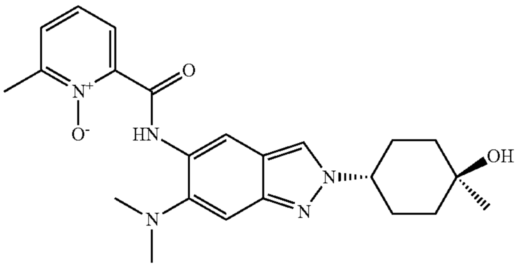

010

1. Synthesis of Compound 2

DMAP (42.5 g), TsCl (63.4 g) and triethylamine (63.9 g) were added sequentially to a solution of compound 1 (50 g) in dichloromethane (500 mL) at 15° C. The reaction system was stirred at 25° C. for 18 h. The reaction solution was added with dichloromethane (200 mL), and washed with water (300 mL×2) and 1 M hydrochloric acid (300 mL×3). The organic phase was dehydrated over anhydrous sodium sulfate, filtered and concentrated under reduced pressure to give compound 2 (98 g, yield: 99%).

2. Synthesis of Compound 3

1 M hydrochloric acid (300 mL) was added into a solution of compound 2 (50 g) in tetrahydrofuran (300 mL) at 15° C. The reaction system was stirred at 25° C. for 20 h. At 0° C., the reaction solution was adjusted to pH=9 with 1 M sodium hydroxide solution. Ethyl acetate (200 mL×3) was added for extraction. The extracts were washed with saturated sodium chloride solution (300 mL), dehydrated over anhydrous sodium sulfate, filtered and concentrated under reduced pressure. The residue was slurried with petroleum ether (150 mL) to give compound 3 (39 g, yield: 91%).

3. Synthesis of Compounds 4&5

A solution of compound 3 (34.5 g) in tetrahydrofuran (200 mL) was dropwise added into a solution of methylmagnesium bromide (85.8 mL) in tetrahydrofuran (500 mL) at −40° C. The reaction system was stirred at −40° C. for 4 h. After the reaction was quenched with saturated ammonium chloride solution (100 mL), ethyl acetate (500 mL×3) was added for extraction, and the extracts were washed with saturated saline (300 mL), dehydrated over anhydrous sodium sulfate, filtered and concentrated under reduced pressure. The residue was purified on silica gel column chromatography (petroleum ether:ethyl acetate=5:1) to give compound 4 (4.3 g, yield: 10%), compound 5 (7.0 g, yield: 17%) and the mixture (12 g).

Compound 4

$^{1}H$ NMR (400 MHz, $CDCl_3$): δ 7.79 (d, J=8.0 Hz, 2H), 7.32 (d, J=8.4 Hz, 2H), 4.52-4.41 (m, 1H), 2.44 (s, 3H), 1.95-1.80 (m, 2H), 1.77-1.61 (m, 4H), 1.46-1.35 (m, 2H), 1.19 (s, 3H).

Compound 5

$^{1}H$ NMR (400 MHz, $CDCl_3$): δ 7.79 (d, J=8.4 Hz, 2H), 7.33 (d, J=8.0 Hz, 2H), 4.74-4.64 (m, 1H), 2.44 (s, 3H), 1.92-1.79 (m, 2H), 1.77-1.62 (m, 4H), 1.49-1.38 (m, 2H), 1.23 (s, 3H).

4. Synthesis of Compound 7 m-CPBA (25 g) was added into a solution of compound 6 (10 g) in DCM (200 mL) at 25° C. The reaction system was stirred at 25° C. for 16 h. The reaction solution was filtered, and the filtrate was quenched with a saturated solution prepared from sodium sulfite (15.6 g). The reaction system was stirred for 2 h and extracted. The aqueous phase was adjusted to pH<7 with hydrochloric acid and extracted with DCM (50 mL×3). The organic phases were combined and concentrated, and the residue was slurried with EA (300 mL) to give compound 7 (10.1 g, yield: 90%).

5. Synthesis of Compound 9

80 mL concentrated sulfuric acid was added into a 500 mL three-necked bottle. The reaction system was cooled to −7° C., slowly added with compound 8 (10 g) and stirred for 5 min at −7° C. and then the reaction system was cooled to −15° C., slowly added with potassium nitrate (8.9 g), and stirred at −15° C. for 1 h. The mixed reaction solution was poured into 1.2 L ice water. The precipitated solid was filtrated, and filter cake was dissolved in 2 L ethyl acetate. The reaction solution was added with 4 L sodium bicarbonate solution to adjust pH>7, and extracted with ethyl acetate (2 L×3). The organic phase was concentrated and dehydrated, and the residue was purified on a silica gel column (DCM:MeOH=300:1) to give compound 9 (12.3 g, yield: 27%).

6. Synthesis of Compound 11

Compound 9 (400 mg), compound 10 (1.81 g) and DIPEA (2.86 g) were added sequentially to 20 mL of DMF at room temperature. The reaction solution was stirred overnight at 80° C. in a closed container. After the reaction was completed, water was added, followed by three extractions with ethyl acetate. The extracts were concentrated under reduced pressure and purified on silica gel column (DCM: $CH_3OH$=200:1) to give compound 11 (570 mg, yield: 83%).

7. Synthesis of Compound 12

Compound 11 (80 mg), Pd/C (5 mg) were added sequentially to 10 mL of DMF at room temperature. The reaction solution was stirred overnight at 55° C. in hydrogen atmosphere. After the reaction was completed, the reaction solution was filtrated, and the filtrate was concentrated under reduced pressure and purified on a silica gel column (DCM: $CH_3OH$=100:1) to give compound 12 (60 mg, yield: 65%).

8. Synthesis of Compound 13

EDCl·HCl (950 mg) was added into a solution of compound 12 (580 mg) and compound 7 (505 mg) in Py (01 mL) at 25° C. The reaction system was stirred at 40° C. for 16 h. The reaction solution was concentrated and evaporated, and the residue was purified on a silica gel column (PE:EA=1:1) to give compound 13 (550 mg, yield: 55%).

9. Synthesis of Compound 010

2-((6-(dimethylamino)-2-((1r,4r)-4-hydroxy-4-methylcyclohexyl)-2H-indazol-5-yl)carbamoyl)-6-methylpyridine 1-oxide

010

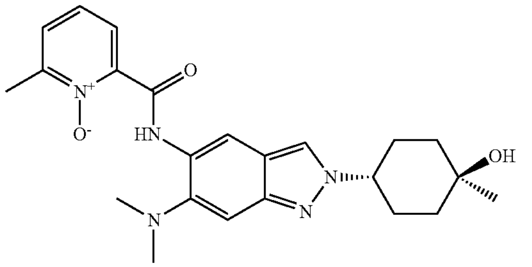

Cesium carbonate (936 mg) was added into a solution of compound 13 (300 mg) and compound 4 (409 mg) in DMF (6 mL) at 25° C. The reaction system was stirred at 90° C. for 16 h. The reaction solution was added into water (30 mL) and extracted with ethyl acetate (10 mL×3). The organic phase was concentrated under reduced pressure. The residue was purified by preparative high performance liquid chromatography ($CH_3CN$:$H_2O$ (0.1% $NH_4HCO_3$)=20-70%, UV: 214 nm, flowrate: 15 mL/min) to give compound 010 (59 mg, yield: 14%).

$^1$H NMR (400 MHz, DMSO-$d_6$): δ 14.01 (s, 1H), 8.80 (s, 1H), 8.34 (s, 1H), 8.33-8.30 (m, 1H), 7.77-7.74 (m, 1H), 7.56 (t, J=7.6 Hz, 1H), 7.33 (s, 1H), 4.44-4.41 (m, 2H), 2.72 (s, 6H), 2.52 (s, 3H), 2.06-2.01 (m, 4H), 1.68-1.55 (m, 4H), 1.23 (s, 3H). LCMS: Rt=3.318 min, [M+H]$^+$=424.2.

Example 3: Synthesis of Compound 013

Reaction Formula:

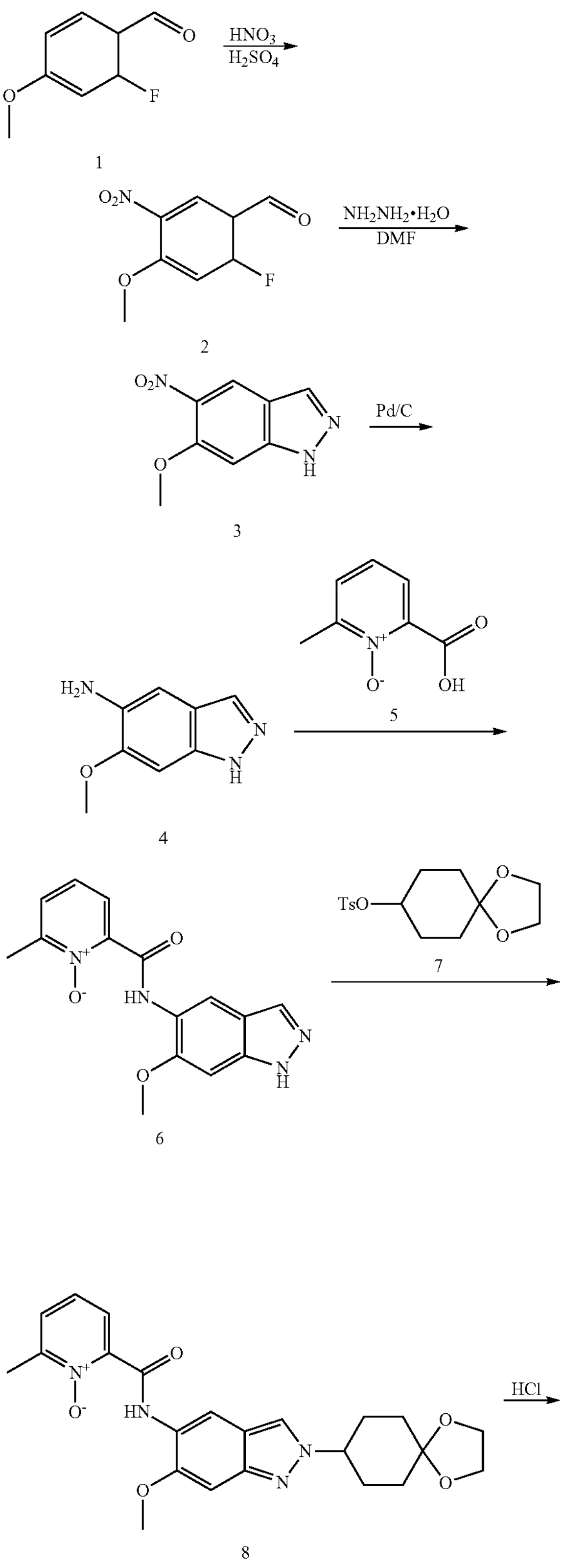

-continued

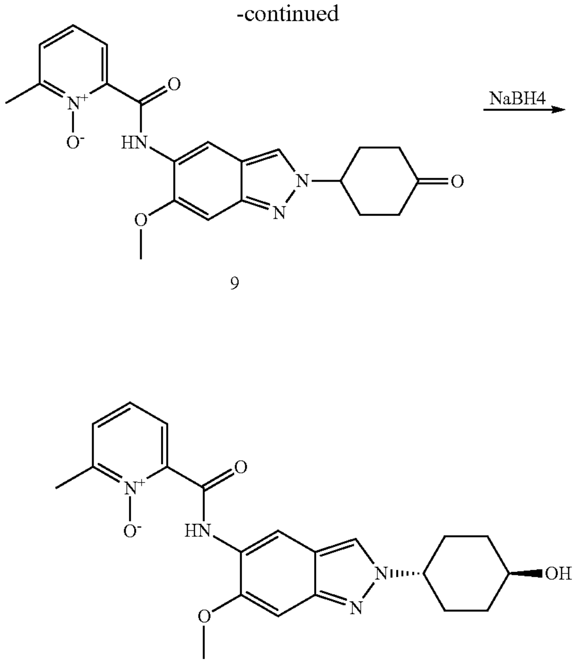

9

013

1. Synthesis of Compound 2

A solution of nitric acid (1.6 mL, 70%) in concentrated sulfuric acid (1.6 mL, 98%) was added dropwise to a solution of compound 1 (2.0 g) in concentrated sulfuric acid (12 mL, 98%) at −15° C. The reaction system was stirred at −15° C. for 2 h after the completion of addition. The reaction solution was slowly poured into ice water, stirred for 5 min and filtered under vacuum. The filter cake was washed with water, and the solid was collected and dried under reduced pressure to give compound 2 (2.5 g, yield: 97%).

2. Synthesis of Compound 3

Hydrazine hydrate (2.4 mL, 98%) was added into a solution of compound 2 (2.0 g) in DMF (20 mL). After the completion of addition, the reaction system was heated to 120° C., stirred for 16 h, and cooled to room temperature. The reaction system was slowly poured into ice water, stirred, and filtered under vacuum. The filter cake was washed with water, and the solid was collected and dried under reduced pressure to give compound 3 (1.3 g, yield: 67%).

3. Synthesis of Compound 4

Compound 3 (12.4 g) and palladium on carbon (7 g, 10%) were added sequentially to 400 mL of ethyl acetate at 15° C. The reaction system was stirred for 18 h at 15° C. in hydrogen atmosphere after the completion of addition. After palladium on carbon in the reaction solution was filtered, the filtrate was dehydrated and concentrated to give compound 4 (10.4 g, yield: 99%).

4. Synthesis of Compound 6

EDCl·HCl (2.6 g) was added into a solution of compound 4 (1.5 g) and compound 5 (1.4 g) in Py (15 mL) at 25° C. The reaction system was stirred at 25° C. for 16 h. The reaction solution was dehydrated and concentrated, and the residue was slurried with $MeOH:H_2O$=20 mL:20 mL to give compound 6 (1.3 g, yield: 48%).

5. Synthesis of Compound 8

Cesium carbonate (3.3 g) was added into a solution of compound 6 (1 g) and compound 7 (1.3 g) in DMF (20 mL) at 25° C. The reaction system was stirred at 90° C. for 16 h. The reaction solution was added into water (50 mL) and extracted with ethyl acetate (30 mL×3). The organic phase was concentrated under reduced pressure. The residue was purified by preparative high performance liquid chromatography ($CH_3CN:H_2O$ (0.1% $NH_4HCO_3$)=20-60%, UV: 214 nm, flowrate: 15 mL/min) to give compound 8 (370 mg, yield: 25%).

6. Synthesis of Compound 9

5 mL 2 M hydrochloric acid was added into a solution of compound 8 (350 mg) in dioxane (5 mL) at 25° C. The reaction system was stirred at 25° C. for 16 h. The reaction solution was adjusted to pH>7 with sodium carbonate solution and extracted with ethyl acetate (10 mL×3). The organic phase was concentrated under reduced pressure to give compound 9 (150 mg, yield: 48%).

7. Synthesis of Compound 013

2-((2-((1r,4r)-4-hydroxycyclohexyl)-6-methoxy-2H-indazol-5-yl)carbamoyl)-6-methylpyridine 1-oxide

013

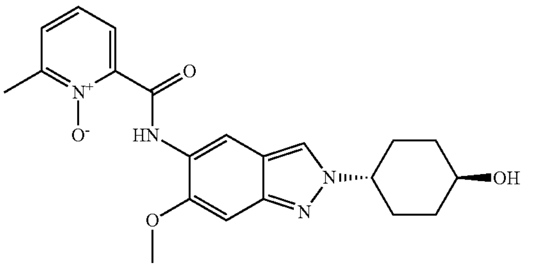

Sodium borohydride (25 mg) was added into a solution of compound 9 (130 mg) in methanol (2 mL) at 0° C. The reaction system was stirred at 25° C. for 2 h. The reaction solution was quenched with ammonium chloride solution (10 mL) and extracted with ethyl acetate (5 mL×3). The organic phase was concentrated under reduced pressure. The residue was purified by preparative high performance liquid chromatography ($CH_3CN:H_2O$ (0.1% $NH_4HCO_3$)=10-60%, UV: 214 nm, flowrate: 15 ml/min) to give compound 013 (54 mg, yield: 41%).

$^1H$ NMR (400 MHz, DMSO-$d_6$): δ 14.16 (s, 1H), 8.78 (s, 1H), 8.31-8.29 (m, 2H), 7.78-7.76 (m, 1H), 7.58 (t, J=8.0 Hz, 1H), 7.10 (s, 1H), 4.71 (d, J=4.4 Hz, 1H), 4.40-4.34 (m, 1H), 3.95 (s, 3H), 3.57-3.50 (m, 1H), 2.53 (s, 3H), 2.09-2.06 (m, 2H), 1.97-1.88 (m, 4H), 1.45-1.34 (m, 2H). LCMS: Rt=2.541 min, $[M+H]^+$=397.2.

Example 4: Synthesis of Compounds 016 and Compound 220

Reaction Formula:

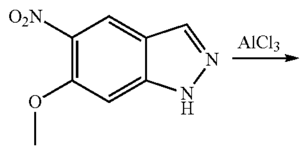

1

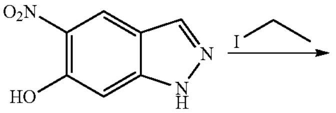

2

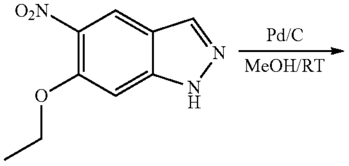

3

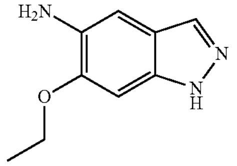

4

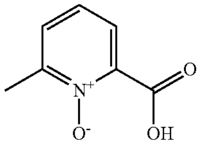

5

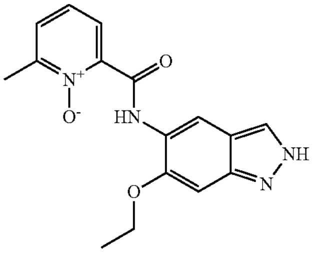

6

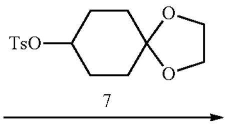

7

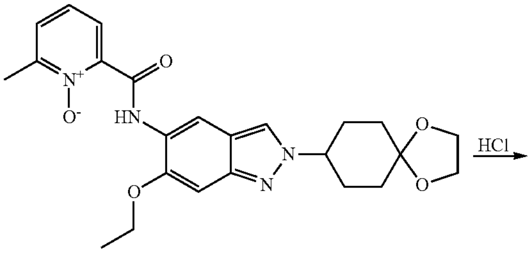

8

-continued

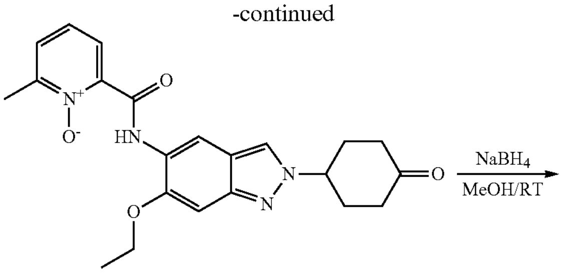

9

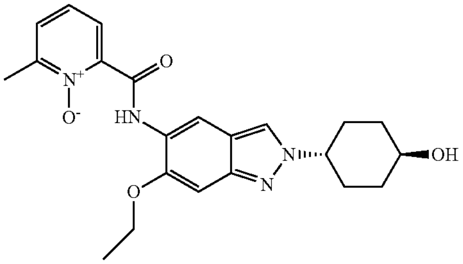

016

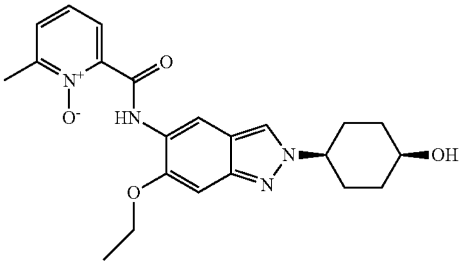

220

1. Synthesis of Compound 2

Compound 1 (2 g) and $AlCl_3$ (4.13 g) were sequentially added into dichloromethane (150 mL) at 18° C. The reaction system was stirred at 55° C. for 18 h. The reaction solution was quenched with water (50 mL), extracted with dichloromethane (150 mL) and then extracted with ethyl acetate (150 mL×3). The organic phase was concentrated and dehydrated, and the residue was slurried with dichloromethane (30 mL) to give compound 2 (1.6 g, yield: 86%).

2. Synthesis of Compound 3

Potassium carbonate (93 mg) was added into a solution of compound 2 (0.1 g) and iodoethane (105 mg) in DMF (2 mL) at 25° C. The reaction system was stirred at 60° C. for 16 h. The reaction solution was added into water (20 mL). The reaction solution was extracted with ethyl acetate (5 mL×3). The organic phase was concentrated under reduced pressure. The residue was purified on a silica gel column (petroleum ether:ethyl acetate=2:1) to give compound 3 (0.1 g, yield: 86%).

3. Synthesis of Compound 4

Pd/C (0.3 g) was added into a solution of compound 3 (1.1 g) in methanol (100 mL) at 25° C. The reaction system was stirred at 25° C. for 16 h in hydrogen atmosphere at 76f)

Torr. The reaction solution was filtered, and the filtrate was concentrated by rotary evaporation to give compound 4 (0.71 g, yield: 76%).

4. Synthesis of Compound 6

Compound 5 (558 mg) was added into a solution of compound 4 (710 mg) and EDCl (840 mg) in pyridine (25 mL) at 25° C. The reaction system was stirred at 25° C. for 16 h. The reaction solution was added into water (100 mL). The reaction solution was extracted with ethyl acetate (30 mL×3). The organic phase was concentrated under reduced pressure. The residue was purified on a silica gel column (dichloromethane:methanol=60:1) to give compound 6 (0.67 g, yield: 54%).

5. Synthesis of Compound 8

Compound 6 (630 mg) was added into a solution of compound 7 (945 mg) and Cesium carbonate (1.97 g) in DMF (25 mL) at 25° C. The reaction system was stirred at 90° C. for 16 h. The reaction solution was added into water (100 mL) and extracted with ethyl acetate (30 mL×3). The organic phase was concentrated under reduced pressure. The residue was purified by preparative high performance liquid chromatography ($CH_3CN:H_2O$ (0.1% $NH_4HCO_3$)=5-95%, UV: 214 nm, flowrate: 15 mL/min) to give compound 8 (160 mg, yield: 18%).

6. Synthesis of Compound 9

The compound 8 (180 mg) was dissolved in a mixed solution of dioxane (30 mL) and 2 M hydrochloric acid (10 mL) at 25° C. The reaction system was stirred at 45° C. for 16 h. The reaction solution was adjusted to pH>7 with saturated sodium bicarbonate solution and extracted with ethyl acetate (30 mL×3). The organic phase was concentrated by rotary evaporation to give compound 9 (180 mg, yield: 97%).

7. Synthesis of Compound 016

2-((6-ethoxy-2-((1r,4r)-4-hydroxycyclohexyl)-2H-indazol-5-yl)carbamoyl)-6-methylpyridine 1-oxide and Compound 220

2-((6-ethoxy-2-((1s,4s)-4-hydroxycyclohexyl)-2H-indazol-5-yl)carbamoyl)-6-methylpyridine 1-oxide

016

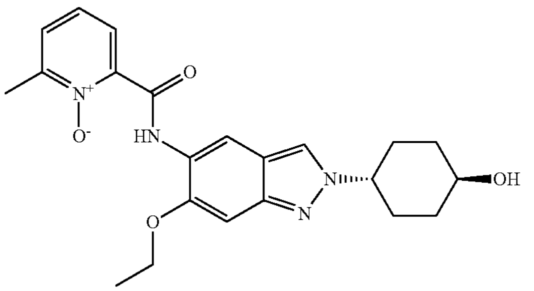

-continued

220

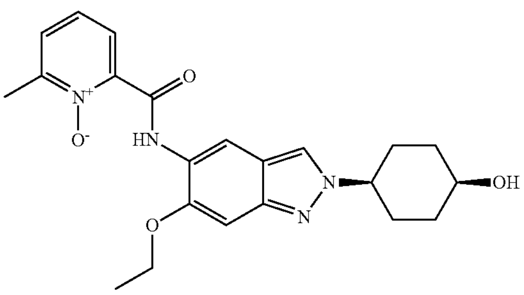

Sodium borohydride (50 mg) was added into a solution of compound 9 (180 mg) in methanol (20 mL) at 0° C. The reaction system was stirred at 25° C. for 1 h. The reaction solution was quenched with ammonium chloride solution (10 mL) and extracted with ethyl acetate (20 mL×3). The organic phase was concentrated under reduced pressure. The residue was purified by preparative high performance liquid chromatography ($CH_3CN:H_2O$ (0.1% $NH_4HCO_3$)=20-50%, UV: 214 nm, flowrate: 15 mL/min) to give compound 016 (retention time Rt=11.25 min, 123 mg, yield: 68%) and compound 220 (retention time Rt=11.75 min, 30 mg, yield: 17%).

Compound 016

$^1$H NMR (400 MHz, $CDCl_3$): δ 14.30 (s, 1H), 8.88 (s, 1H), 8.45 (d, J=7.6 Hz, 1H), 7.83 (s, 1H), 7.43-7.36 (m, 2H), 7.03 (s, 1H), 4.37-4.30 (m, 1H), 4.24 (q, J=6.8 Hz, 2H), 3.82-3.80 (m, 1H), 2.63 (s, 3H), 2.28 (d, J=12.8 Hz, 2H), 2.18 (d, J=14.8 Hz, 2H), 2.06 (q, J=13.2 Hz, 2H), 1.65-1.56 (m, 3H), 1.55-1.50 (m, 2H).

LCMS: Rt=2.486 min, $[M+H]^+$=411.2.

Compound 220

$^1$H NMR (400 MHz, $CDCl_3$): δ 14.30 (s, 1H), 8.89 (s, 1H), 8.45 (d, J=7.6 Hz, 1H), 7.89 (s, 1H), 7.43-7.36 (m, 2H), 7.04 (s, 1H), 4.41-4.35 (m, 1H), 4.24 (q, J=8.8 Hz, 2H), 4.14 (br s, 1H), 2.63 (s, 3H), 2.35 (q, J=8.8 Hz, 2H), 2.08 (d, J=8.4 Hz, 2H), 1.98 (d, J=13.2 Hz, 2H), 1.75 (t, J=13.2 Hz, 2H), 1.64 (t, J=6.8 Hz, 3H). LCMS: Rt=2.642 min, $[M+H]^+$ =411.2.

Example 5: Synthesis of Compound 025

Reaction Formula:

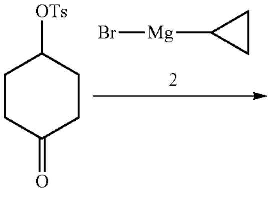

1

-continued

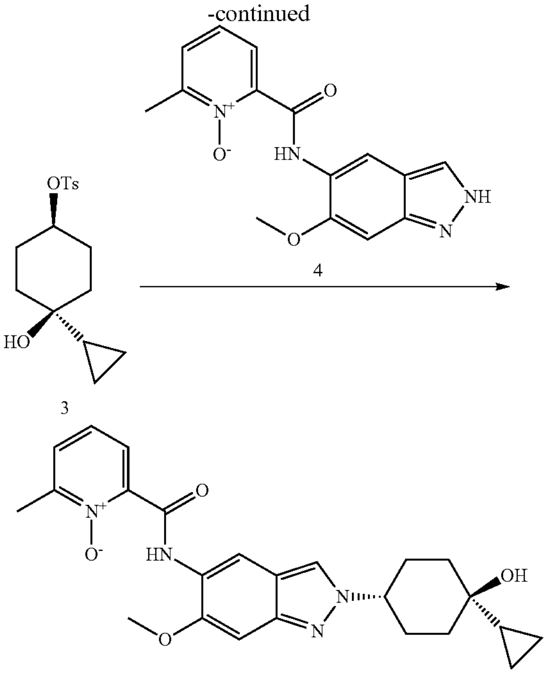

025

1. Synthesis of Compound 3

A solution of compound 1 (3 g) in tetrahydrofuran (10 mL) was dropwise added into a solution of compound 2 (45 mL) in tetrahydrofuran (100 mL) at −40° C. The reaction system was stirred at 0° C. for 8 h. After the reaction was quenched with saturated ammonium chloride solution (200 mL), ethyl acetate (200 mL×3) was added for extraction, and the extracts were washed with saturated saline (400 mL), dehydrated over anhydrous sodium sulfate, filtered and concentrated under reduced pressure. The residue was purified on silica gel column chromatography (petroleum ether: ethyl acetate=5:1) to give compound 3 (1.5 g, yield: 44%).

2. Synthesis of Compound 025

2-((2-((1r,4r)-4-cyclopropyl-4-hydroxycyclohexyl)-6-methoxy-2H-indazol-5-yl)carbamoyl)-6-methylpyridine 1-oxide

025

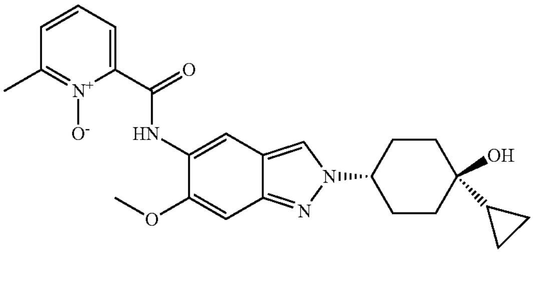

Cesium carbonate (820 mg) was added into a solution of compound 4 (300 mg) and compound 3 (374 mg) in NMP (30 mL) at 25° C. The reaction system was stirred at 90° C.

for 16 h. The reaction solution was cooled and added with water (100 mL). Ethyl acetate was added for extraction (80 mL×4). The organic phase was concentrated under reduced pressure. The residue was purified by preparative high performance liquid chromatography ($CH_3CN:H_2O$ (0.1% $NH_4HCO_3$)=5-95%, UV: 214 nm, flowrate: 15 mL/min) to give compound 025 (79 mg, yield: 18%).

$^1H$ NMR (400 MHz, $CDCl_3$): δ 14.13 (s, 1H), 8.89 (s, 1H), 8.45 (d, J=12 Hz, 1H), 7.89 (s, 1H), 7.42-7.37 (m, 2H), 7.07 (s, 1H), 4.49-4.41 (m, 1H), 4.05 (s, 3H), 2.64 (s, 3H), 2.38-2.22 (m, 4H), 1.92-1.88 (m, 2H), 1.72-1.64 (m, 2H), 1.31-1.26 (m, 1H), 0.98 (s, 1H), 0.43-0.41 (m, 4H). LCMS: Rt=3.198, $[M+H]^+$=437.2.

Example 6: Synthesis of Compound 163

Reaction Formula:

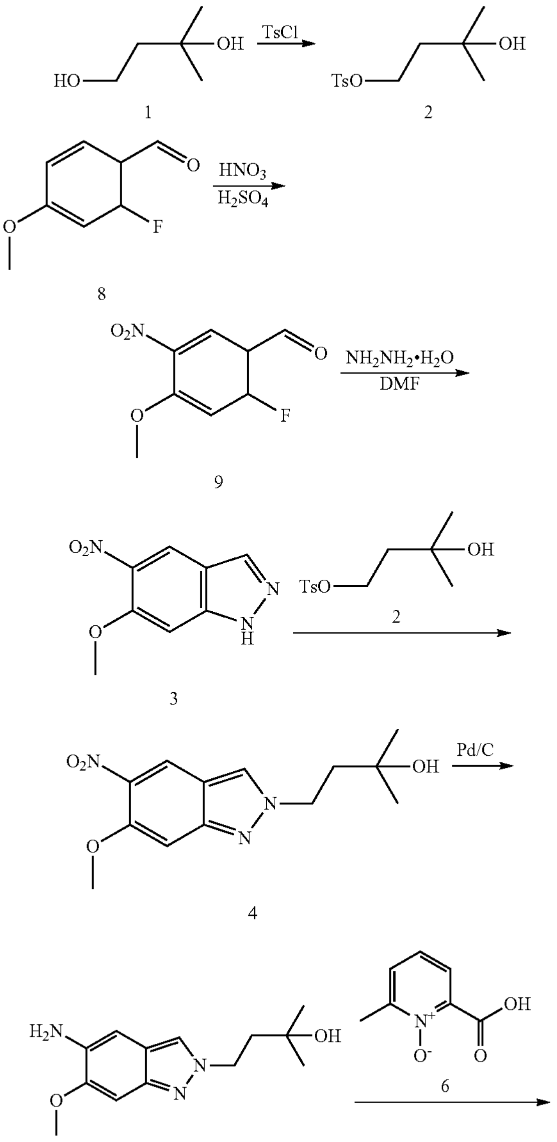

5

-continued

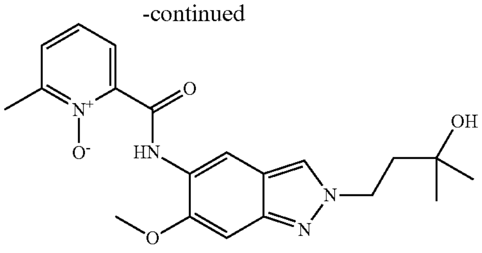

163

1. Synthesis of Compound 2 p-toluenesulfonyl chloride (11.8 g) was added into a solution of compound 1 (6.1 g), triethylamine (14.8 g) and DMAP (7.2 g) in DCM (120 mL) at 15° C. The reaction system was stirred at 10° C. for 16 h. The reaction solution was washed with 1 N HCl (100 mL×3). The organic phase was dried and concentrated to give compound 2 (13.1 g, yield: 84%).

2. Synthesis of Compound 9

A solution of nitric acid (1.6 mL) in concentrated sulfuric acid (1.6 mL, 98%) was added dropwise to a solution of compound 8 (2.0 g) in concentrated sulfuric acid (12 mL, 98%) at −15° C. The reaction system was stirred at −15° C. for 2 h after the completion of addition. The reaction solution was slowly poured into ice water, stirred for 5 min and filtered under vacuum. The filter cake was washed with water, and the solid was collected and dried under reduced pressure to give compound 9 (2.5 g, yield: 97%).

3. Synthesis of Compound 3

Hydrazine hydrate (2.4 mL, 98%) was added into a solution of compound 8 (2.0 g) in DMF (20 mL). After the completion of addition, the reaction system was heated to 120° C. stirred for 16 h, and cooled to room temperature. The reaction system was slowly poured into ice water, stirred, and filtered under vacuum. The filter cake was washed with water, and the solid was collected and dried under reduced pressure to give compound 3 (1.3 g, yield: 67%).

4. Synthesis of Compound 4

DIPEA (13.4 g) was added into a solution of compound 3 (4.0 g) and compound 2 (10.7 g) in toluene (80 mL) at 15° C. The reaction system was stirred at 130° C. for 48 h. The reaction solution was added into water (100 mL) and extracted with ethyl acetate (50 mL×3). The organic phase was concentrated under reduced pressure. The residue was purified by preparative high performance liquid chromatography ($CH_3CN$:$H_2O$ (0.1% $NH_4HCO_3$)=10-50%, UV: 214 nm, flowrate: 15 mL/min) to give compound 4 (2.5 g, yield: 43%).

5. Synthesis of Compound 5

Pd/C (400 mg) was added into a solution of compound 4 (1.3 g) in ethyl acetate (30 mL) at 30° C. and the reaction system was stirred for 16 h in hydrogen atmosphere. The organic phases were combined, and the reaction solution was filtered and concentrated under reduced pressure to give compound 5 (1.9 g, yield: 95%).

6. Synthesis of Compound 163

2-((2-(3-hydroxy-3-methylbutyl)-6-methoxy-2H-indazol-5-yl)carbamoyl)-6-methylpyridine 1-oxide

163

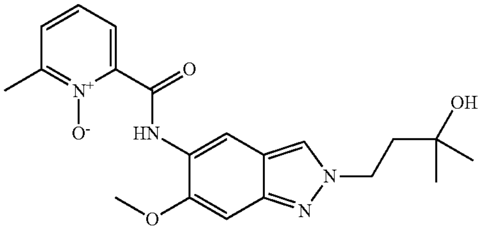

HATU (273 mg) and $Et_3N$ (145 mg) were added into a solution of compound 5 (120 mg) and compound 6 (81 mg) in DMF (2 mL) at 30° C. The reaction system was stirred at 30° C. for 18 h. The reaction solution was concentrated under reduced pressure, and the crude product was further purified by preparative high performance liquid chromatography ($CH_3CN$:$H_2O$ (0.1% $NH_4HCO_3$)=5-95%, UV: 214 nm, flowrate: 15 mL/min) to give compound 163 (110 mg, yield: 60%).

$^1H$ NMR (400 MHz, DMSO-$d_6$): δ 14.13 (s, 1H), 8.78 (s, 1H), 8.31-8.28 (m, 2H), 7.77-7.75 (m, 1H), 7.60-7.55 (m, 1H), 7.09 (s, 1H), 4.50 (s, 1H), 4.44-4.40 (m, 2H), 3.93 (s, 3H), 2.53 (s, 3H), 2.04-2.00 (m, 2H), 1.15 (s, 6H). LCMS: Rt=2.784 min, $[M+H]^+$=385.2.

Example 7: Synthesis of Compound 284

Reaction Formula:

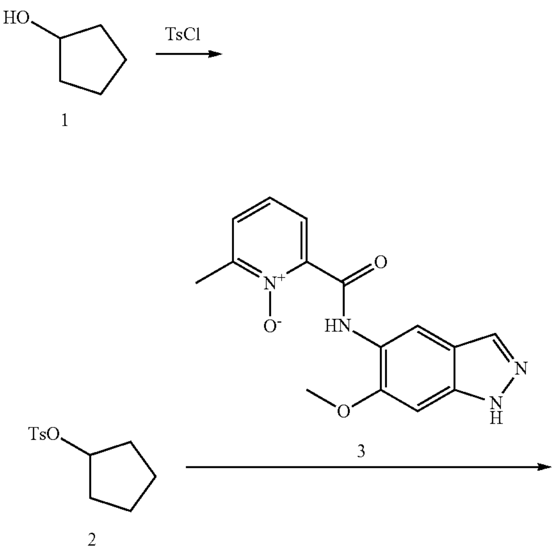

-continued

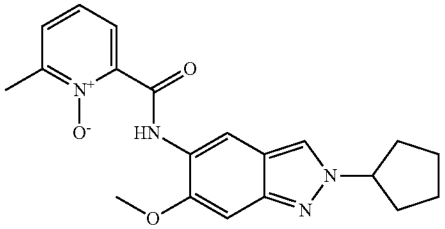

284

1. Synthesis of Compound 2 p-toluenesulfonyl chloride (2.3 g) was added into a solution of compound 1 (1 g), triethylamine (2.9 g) and DMAP (1.4 g) in DCM (20 mL) at 25° C. The reaction system was stirred at 25° C. for 16 h. The reaction solution was washed with 1 N HCl (200 mL×3). The organic phase was dried and concentrated to give compound 2 (2.1 g, yield: 75%).

2. Synthesis of Compound 284

2-((2-cyclopentyl-6-methoxy-2H-indazol-5-yl)carbamoyl)-6-methylpyridine 1-oxide

284

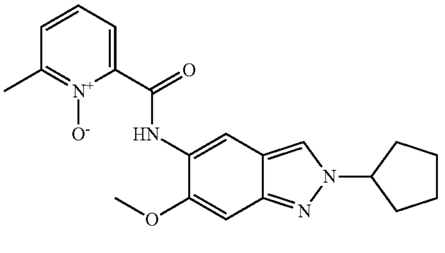

Cesium carbonate (1.6 g) was added into a solution of compound 3 (500 mg) and compound 2 (485 mg) in DMF (10 mL) at 25° C. The reaction system was stirred at 90° C. for 16 h. The reaction solution was added into water (50 mL) and extracted with ethyl acetate (30 mL×3). The organic phase was concentrated under reduced pressure. The residue was purified by preparative high performance liquid chromatography ($CH_3CN:H_2O$ (0.1% $NH_4HCO_3$)=25-60%, UV: 214 nm, flowrate: 15 mL/min) to give compound 284 (123 mg, yield: 20%).

$^1$H NMR (400 MHz, DMSO-$d_6$): δ 14.15 (s, 1H), 8.78 (s, 1H), 8.32-8.29 (m, 2H), 7.77-7.75 (m, 1H), 7.57 (t, J=7.6 Hz, 1H), 7.13 (s, 1H), 4.97-4.90 (m, 1H), 3.96 (s, 3H), 2.53 (s, 3H), 2.22-2.13 (m, 2H), 2.10-2.01 (m, 2H), 1.92-1.82 (m, 2H), 1.74-1.65 (m, 2H). LCMS: Rt=3.562 min, $[M+H]^+$=367.2.

Example 8: Synthesis of Compound 285

Reaction Formula:

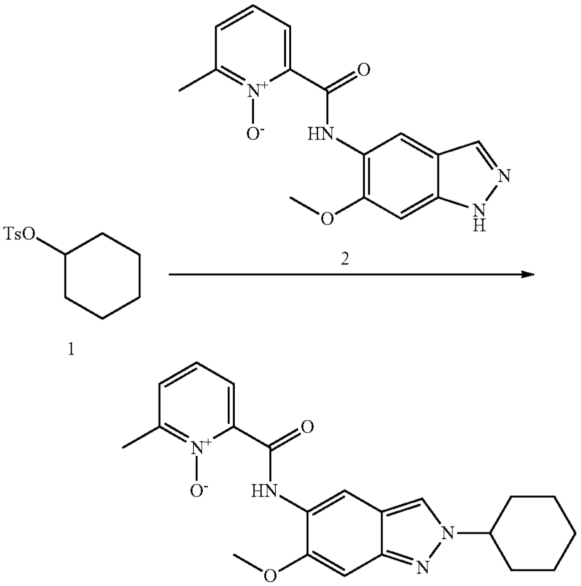

2

1

285

1. Synthesis of Compound 285

2-((2-cyclohexyl-6-methoxy-2H-indazol-5-yl)carbamoyl)-6-methylpyridine 1-oxide

285

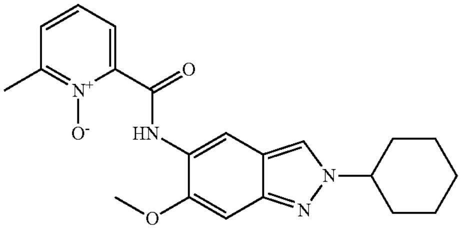

Cesium carbonate (1.3 g) was added into a solution of compound 2 (400 mg) and compound 1 (511 mg) in NMP (8 mL) at 25° C. The reaction system was stirred at 90° C. for 16 h. The reaction solution was added into water (30 mL) and extracted with ethyl acetate (10 mL×3). The organic phase was concentrated under reduced pressure. The residue was purified by preparative high performance liquid chromatography ($CH_3CN:H_2O$ (0.1% $NH_4HCO_3$)=25-75%, UV: 214 nm, flowrate: 15 mL/min) to give compound 285 (68 mg, yield: 13%).

$^1$H NMR (400 MHz, DMSO-$d_6$): δ 14.15 (s, 1H), 8.79 (s, 1H), 8.32-8.29 (m, 2H), 7.78-7.76 (m, 1H), 7.58 (t, J=8.0 Hz, 1H), 7.11 (s, 1H), 4.40-4.34 (m, 1H), 3.95 (s, 3H), 2.53 (s, 3H), 2.11-2.07 (m, 2H), 1.90-1.80 (m, 4H), 1.70 (d, J=12.8 Hz, 1H), 1.50-1.40 (m, 2H), 1.31-1.23 (m, 1H). LCMS: Rt=3.971 min, $[M+H]^+$=381.2.

Example 9: Synthesis of Compound 286

Reaction Formula:

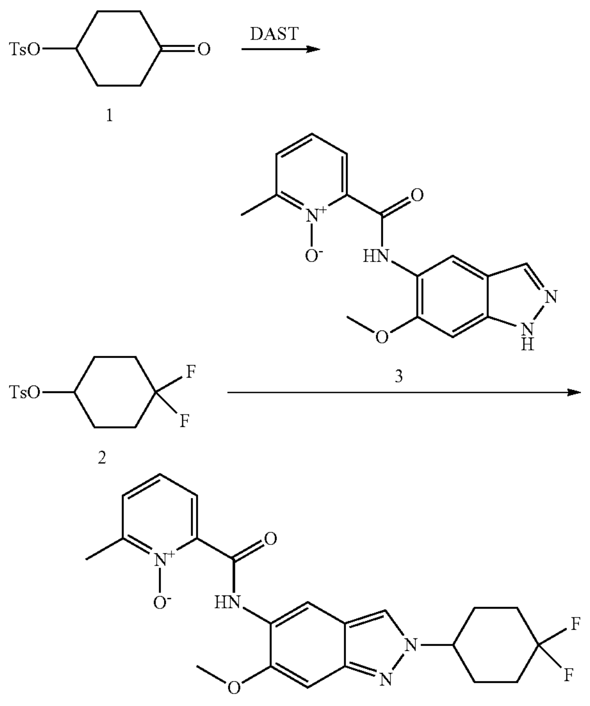

286

1. Synthesis of Compound 2

DAST (6 g) was added into a solution of compound 1 (2 g) in DCM (70 mL) at 0° C. The reaction system was stirred at 25° C. for 3 h. The reaction solution was added into water (50 mL). The reaction solution was extracted with dichloromethane (30 mL×2). The organic phase was concentrated under reduced pressure. The residue was purified on a silica gel column (PE:EA=10:1) to give compound 2 (1.8 g, yield: 82%).

2. Synthesis of Compound 286

2-((2-(4,4-difluorocyclohexyl)-6-methoxy-2H-indazol-5-yl)carbamoyl)-6-methylpyridine 1-oxide

286

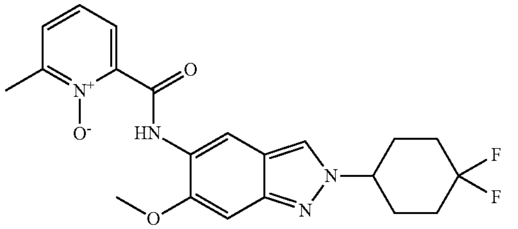

Cesium carbonate (1.6 g) was added into a solution of compound 3 (500 mg) and compound 2 (731 mg) in NMP (10 mL) at 25° C. The reaction system was stirred at 90° C. for 16 h. The reaction solution was added into water (30 mL) and extracted with ethyl acetate (10 mL×3). The organic phase was concentrated under reduced pressure. The residue was purified by preparative high performance liquid chromatography ($CH_3CN:H_2O$ (0.1% $NH_4HCO_3$)=40-70%, UV: 214 nm, flowrate: 15 mL/min) to give compound 286 (129 mg, yield: 18%).

$^1H$ NMR (400 MHz, DMSO-$d_6$): δ 14.17 (s, 1H), 8.80 (s, 11H), 8.35 (s, 1H), 8.32-8.29 (m, 1H), 7.78-7.76 (m, 1H), 7.58 (t, J=8.0 Hz, 1H), 7.13 (s, 1H), 4.68-4.57 (m, 1H), 3.97 (s, 3H), 2.53 (s, 3H), 2.32-2.07 (m, 8H). LCMS: Rt=3.692 min, $[M+H]^+$=417.2.

Example 10: Synthesis of Compound 287

Reaction Formula:

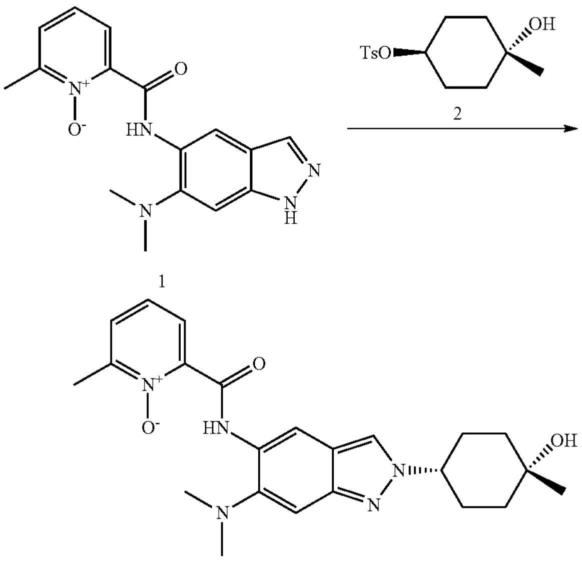

287

1. Synthesis of Compound 287

2-((6-(dimethylamino)-2-((1s,4s)-4-hydroxy-4-methylcyclohexyl)-2H-indazol-5-yl)carbamoyl)-6-methylpyridine 1-oxide

287

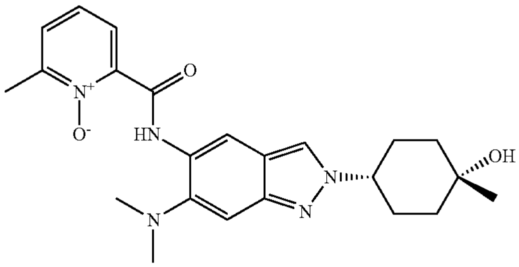

Cesium carbonate (800 mg) was added into a solution of compound 1 (255 mg) and compound 2 (350 mg) in NMP (5 mL) at 25° C. The reaction system was stirred at 90° C.

for 16 h. The reaction solution was added into water (30 mL) and extracted with ethyl acetate (10 mL×3). The organic phase was concentrated under reduced pressure. The residue was purified by preparative high performance liquid chromatography ($CH_3CN$:$H_2O$ (0.1% $NH_4HCO_3$)=35-60%, UV: 214 nm, flowrate: 15 mL/min) to give compound 287 (51 mg, yield: 15%).

$^1$H NMR (400 MHz, $CDCl_3$): δ 14.03 (s, 1H), 8.92 (s, 1H), 8.46 (d, J=8.0 Hz, 1H), 7.89 (s, 1H), 7.41-7.35 (m, 3H), 4.37-4.31 (m, 1H), 2.84 (s, 6H), 2.63 (s, 3H), 2.37-2.27 (m, 2H), 2.11-2.05 (m, 2H), 1.93-1.85 (m, 2H), 1.61-1.58 (m, 2H), 1.33 (s, 3H). LCMS: Rt=3.298 min, $[M+H]^+$=424.3.

Example 11: Synthesis of Compounds 015 and Compound 288

Reaction Formula:

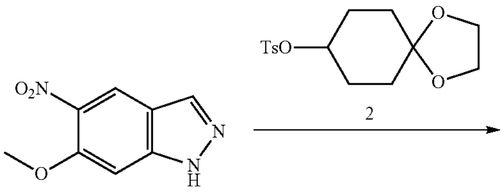

1

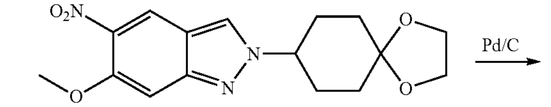

3

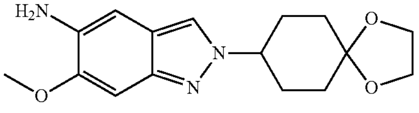

4

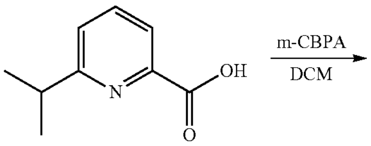

5

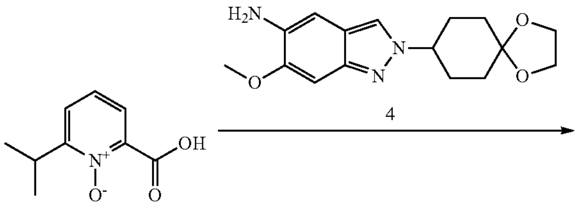

6

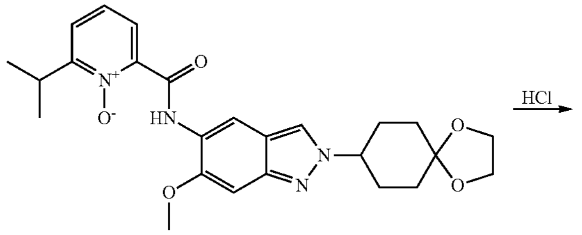

7

-continued

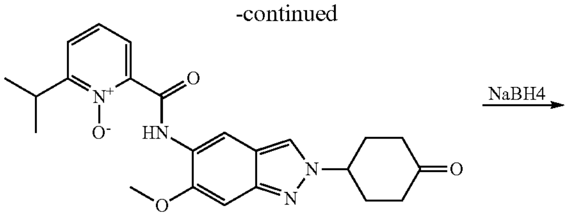

8

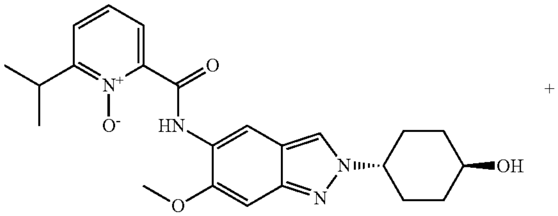

015

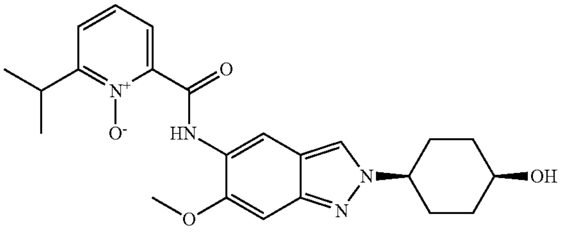

288

1. Synthesis of Compound 3

Compound 1 (5 g), compound 2 (26 g) and cesium carbonate (29 g) were sequentially added into DMF (400 mL) at 20° C. The reaction system was stirred at 90° C. for 24 h in nitrogen atmosphere. The reaction solution was cooled to 20° C., added with water (800 mL) and extracted with ethyl acetate (800 mL×3). The organic phase was washed with saturated sodium chloride solution (500 mL×3), dehydrated over anhydrous sodium sulfate, filtered and concentrated under reduced pressure. The residue was purified on silica gel column chromatography (petroleum ether:ethyl acetate=1:1) and slurried with MTBE (50 mL) to give compound 3 (1.2 g, yield: 14%).

2. Synthesis of Compound 4

Pd/C (0.1 g) was added into a solution of compound 3 (1.1 g) in ethyl acetate (200 mL) at 25° C. and the reaction system was stirred for 16 h in hydrogen atmosphere. The reaction solution was filtered and concentrated under reduced pressure to give compound 4 (901 mg, yield: 90%).

3. Synthesis of Compound 6

Compound 5 (900 mg) was dissolved in dichloromethane (20 mL), and the reaction solution was slowly added with mCPBA (2.5 g). The reaction system was stirred at 25° C. for 16 h. The reaction solution was filtered. The residue was quenched with aqueous sodium sulfite. The reaction solution was adjusted to pH<7 with hydrochloric acid and extracted with dichloromethane (50 mL×3). The organic phase was concentrated, and purified by silica gel column chromatography (petroleum ether:ethyl acetate=1:1) to give compound 6 (0.68 g, yield: 69%).

4. Synthesis of Compound 7

HATU (376 mg) and DIPEA (128 mg) were added into a solution of compound 6 (164 mg) and compound 4 (250 mg) in DMF (10 mL) at 25° C. The reaction system was stirred for 16 h. The reaction solution was added with water (100 mL) and extracted with EA (20 mL×3). The extracts were washed with saturated sodium chloride solution (200 mL), dehydrated over anhydrous sodium sulfate, filtered and concentrated under reduced pressure. The residue was purified on silica gel column chromatography (dichloromethane: methanol=40:1) and slurried to give compound 7 (480 mg, yield: 99%).

5. Synthesis of Compound 8

4 M hydrochloric acid (10 mL) was added into a solution of compound 7 (480 mg) in dioxane (10 mL) at 0° C. The reaction system was stirred at 30° C. for 16 h. cooled to 0° C., adjusted to pH=8 with saturated $NaHCO_3$ solution, extracted with EA (40 mL×5), washed with saturated NaCl (200 mL), dehydrated over anhydrous sodium sulfate, filtered and concentrated under reduced pressure to give compound 8 (435 mg, yield: 99%).

7. Synthesis of Compound 015

2-((2-((1r,4r)-4-hydroxycyclohexyl)-6-methoxy-2H-indazol-5-yl)carbamoyl)-6-isopropylpyridine 1-oxide and Compound 288

2-((2-((1s,4s)-4-hydroxycyclohexyl)-6-methoxy-2H-indazol-5-yl)carbamoyl)-6-isopropylpyridine 1-oxide

015

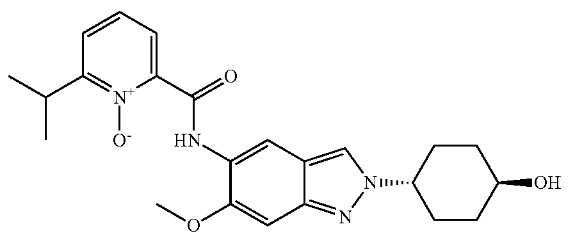

288

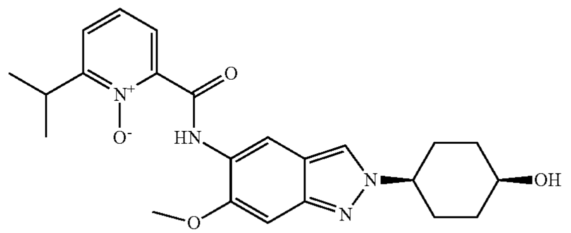

Sodium borohydride (118 mg) was added into a solution of compound 8 (435 mg) in methanol (20 mL) at 0° C. The reaction system was stirred at 30° C. for 16 h. The reaction solution was adjusted to pH=7 with saturated ammonium chloride, extracted with DCM (40 mL×5) and washed with saturated NaCl (200 mL). The residue was purified by preparative high performance liquid chromatography ($CH_3CN:H_2O$ (0.1% $NH_4 \cdot HCO_3$)=30-70%, UV: 214 nm, flowrate: 15 mL/min) to give compound 015 (Retention time Rt=28.13 min, 171 mg, yield: 39%) and compound 288 (Retention time Rt=29.25 min, 44 mg, yield: 10%).

Compound 015

$^1$H NMR (400 MHz, $CDCl_3$): δ 14.18 (s, 1H), 8.88 (s, 1H), 8.44 (d, J=5.2 Hz, 1H), 7.83 (s, 1H), 7.47-7.40 (m, 2H), 7.05 (s, 1H), 4.34-4.33 (m, 1H), 4.04 (s, 3H), 3.99-3.95 (m, 1H), 3.82-3.80 (m, 1H), 2.30-2.26 (m, 2H), 2.19-2.16 (m, 2H), 2.05 (q, J=9.2 Hz, 2H), 1.60-1.50 (m, 2H), 1.36 (s, 3H).1.35 (s, 3H). LCMS: Rt=3.531, $[M+H]^+$=425.2.

Compound 288

$^1$H NMR (400 MHz, $CDCl_3$): δ 14.17 (s, 1H), 8.88 (s, 1H), 8.44 (d, J=5.2 Hz, 1H), 7.89 (s, 1H), 7.47-7.40 (m, 2H), 7.06 (s, 1H), 4.39-4.37 (m, 1H), 4.14 (s, 1H), 4.05 (s, 3H), 3.99-3.95 (m, 1H), 2.38-2.34 (m, 2H), 2.09-2.04 (m, 2H), 2.01-1.96 (m, 2H), 1.80-1.76 (m, 2H), 1.36 (s, 3H).1.35 (s, 3H).

LCMS: Rt=3.472, $[M+H]^+$=425.2.

Example 12: Synthesis of Compounds 014 and Compound 218

Reaction Formula:

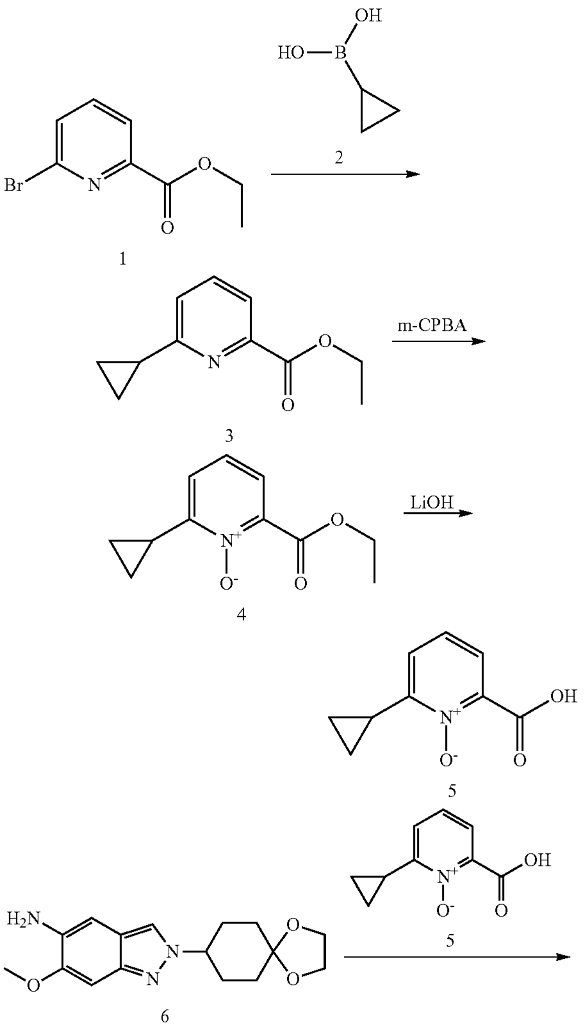

-continued

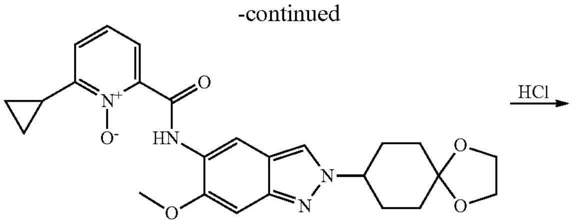

7

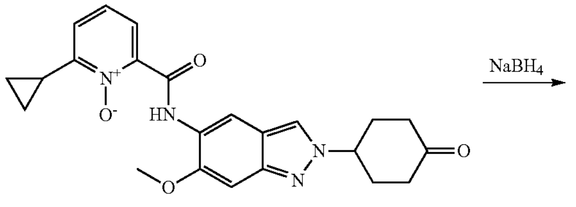

8

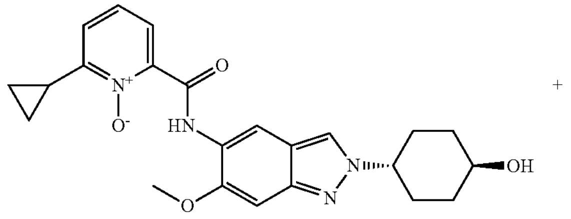

014

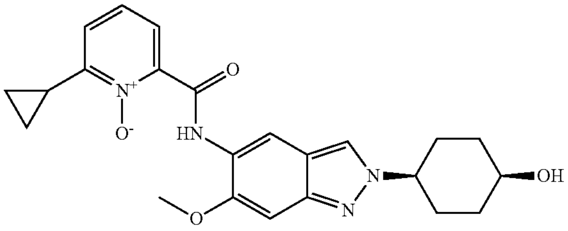

218

1. Synthesis of Compound 3

$Pd(dppf)Cl_2$ (113 mg) and $K_3PO_4$ (13.4 g) were added into a solution of compound 1 (7.3 g) and compound 2 (6.5 g) in toluene (70 mL). The reaction system was stirred at 100° C. for 16 h in nitrogen atmosphere. The reaction solution was cooled and concentrated under reduced pressure. The residue was purified with thin-layer chromatography (petroleum ether:ethyl acetate=20:1) to give compound 3 (1.2 g, yield: 20%).

2. Synthesis of Compound 4 m-CPBA (5.7 g) was added into a solution of compound 3 (1.1 g) in DCM (100 mL) at 25° C. The reaction system was stirred at 25° C. for 48 h. The reaction solution was quenched with a saturated solution prepared from sodium sulfite (2.4 g). The organic phase was washed with saturated sodium bicarbonate (100 mL×3), dehydrated over anhydrous sodium sulfate, filtered and concentrated under reduced pressure to give compound 4 (1.1 g, yield: 92%).

3. Synthesis of Compound 5

Compound 4 (1.2 g) and $LiOH{\cdot}H_2O$ (730 mg) were sequentially added into $THF/H_2O$ (30 mL/10 mL) in nitrogen atmosphere. The reaction system was stirred at 30° C. for 4 h after the completion of addition. The reaction solution was added with water (50 mL). The aqueous phase was adjusted to pH=7 with 1 N HCl. The reaction solution was extracted with ethyl acetate (100 mL×3), washed with saturated brine (200 mL), dried over anhydrous sodium sulfate, filtered under vacuum, and concentrated under reduced pressure to give compound 5 (844 mg, yield 84%).

4. Synthesis of Compound 7

DECI (427 mg) was added into a solution of compound 6 (450 mg) and compound 5 (319 mg) in pyridine (35 mL) at 25° C. The reaction system was stirred for 16 h. The solvent was completely removed under reduced pressure. The reaction solution was added with water (100 mL) and extracted with DCM (100 mL×3). The extracts were washed with saturated sodium chloride solution (200 mL), dehydrated over anhydrous sodium sulfate, filtered and concentrated under reduced pressure. The residue was slurried with ethyl acetate (10 mL) to give compound 7 (314 mg, yield: 45%).

5. Synthesis of Compound 8

4 M hydrochloric acid (250 mL) was added into a solution of compound 7 (289 mg) in tetrahydrofuran (25 mL) at 0° C. The reaction system was stirred at 30° C. for 16 h, cooled to 0° C., adjusted to pH=8 with saturated $NaHCO_3$ solution, and extracted with DCM (40 mL×5). The extracts were washed with saturated NaCl (200 mL), dehydrated over anhydrous sodium sulfate, filtered and concentrated under reduced pressure to give compound 8 (249 mg, yield: 95%).

6. Synthesis of Compound 014

2-cyclopropyl-6-((2-((1r,4r)-4-hydroxycyclohexyl)-6-methoxy-2H-indazol-5-yl)carbamoyl)pyridine 1-oxide and Compound 218 Synthesis of 2-cyclopropyl-6-((2-((1s,4s)-4-hydroxycyclohexyl)-6-methoxy-2H-indazol-5-yl)carbamoyl)pyridine 1-oxide

014

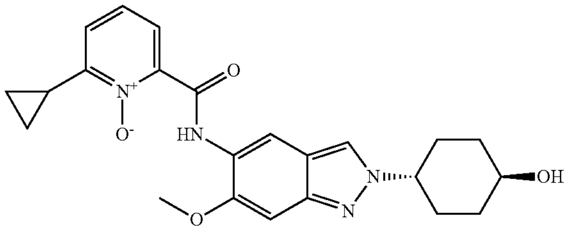

218

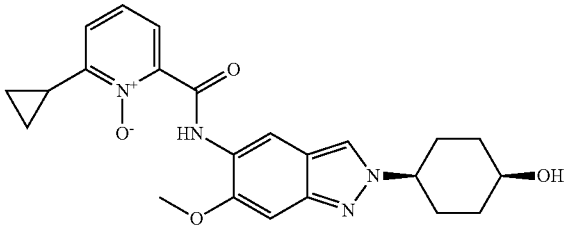

Sodium borohydride (67 mg) was added into a solution of compound 8 (249 mg) in methanol (20 mL) at 0° C. The reaction system was stirred at 30° C. for 16 h. The reaction solution was adjusted to pH=7 with saturated ammonium chloride, and extracted with DCM (40 mL×5). The extracts were washed with saturated NaCl (200 mL). The residue was purified by preparative high performance liquid chromatography ($CH_3CN$:$H_2O$ (0.1% $NH_4HCO$)=30-70%, UV: 214 nm, flowrate: 15 mL/min) to give compound 014 (Retention time Rt=7.99 min, 108 mg, yield: 43%) and compound 218 (Retention time Rt=8.50 min, 14 mg, yield: 5%).

Compound 014

$^1$H NMR (400 MHz, $CDCl_3$): δ 14.26 (s, 1H), 8.87 (s, 1H), 8.39 (d, J=8.0 Hz, 1H), 7.82 (s, 1H), 7.39-7.35 (m, 11H), 7.04 (s, 2H), 4.37-4.29 (m, 1H), 4.04 (s, 3H), 3.83-3.75 (m, 1H), 2.88-2.80 (m, 1H), 2.28-2.25 (m, 2H), 2.18-2.15 (m, 2H), 2.09-2.00 (m, 2H), 1.58-1.48 (m, 2H), 1.29-1.26 (m, 2H), 0.84-0.82 (m, 2H).

LCMS: Rt=3.312, $[M+H]^+$=423.2.

Compound 218

$^1$H NMR (400 MHz, $CDCl_3$): δ 14.20 (s, 1H), 8.88 (s, 1H), 8.40 (d, J=8.0 Hz, 1H), 7.80 (s, 1H), 7.38-7.26 (m, 1H), 7.06 (s, 2H), 4.69 (s, 1H), 4.41-4.35 (m, 1H), 4.14 (s, 11H), 4.05 (s, 3H), 2.89-2.80 (m, 1H), 2.41-2.31 (m, 2H), 2.08-2.04 (m, 2H), 2.00-1.96 (m, 2H), 1.80-1.72 (m, 2H), 1.28-1.26 (m, 2H), 0.84-0.83 (m, 2H).

LCMS: Rt=2.807, $[M+H]^+$=423.2.

Example 13: Synthesis of Compound 187

Reaction Formula:

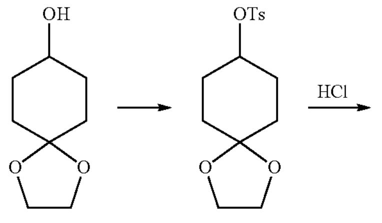

1 2

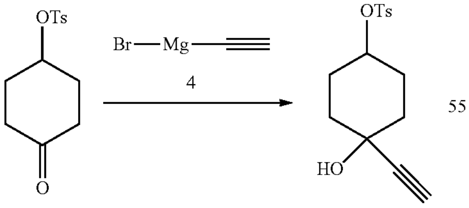

3 5

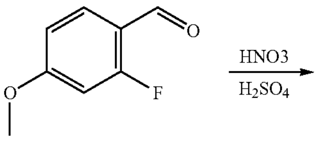

6

-continued

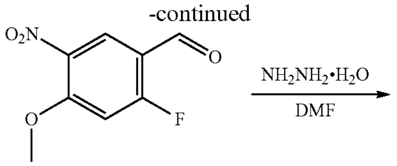

7

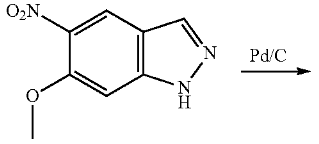

8

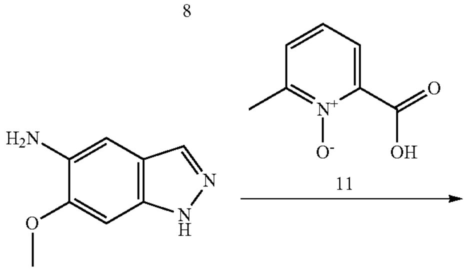

9

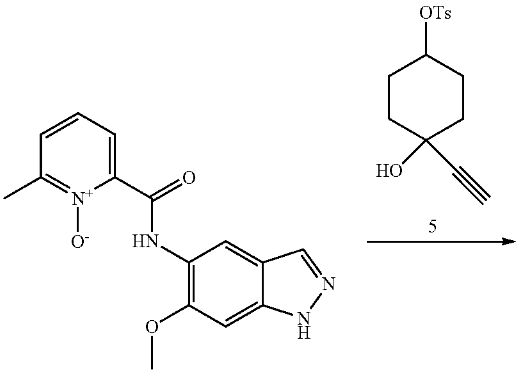

10

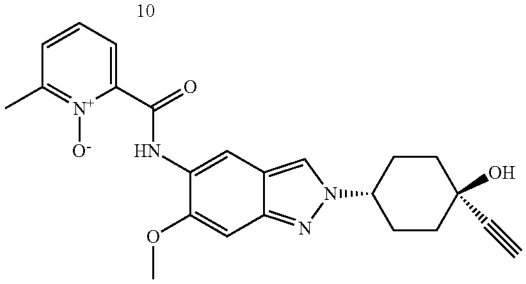

187

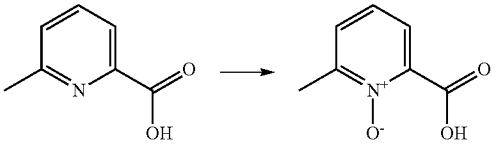

12 11

1. Synthesis of Compound 2

DMAP (42.5 g), TsCl (63.4 g) and triethylamine (63.9 g) were added sequentially to a solution of compound 1 (50 g) in dichloromethane (500 mL) at 15° C. The reaction system was stirred at 25° C. for 18 h. The reaction solution was added with dichloromethane (200 mL), and washed with water (300 mL×2) and 1 M hydrochloric acid (300 mL×3). The organic phase was dehydrated over anhydrous sodium sulfate, filtered and concentrated under reduced pressure to give compound 2 (98 g, yield: 99%).

2. Synthesis of Compound 3

1 M hydrochloric acid (300 mL) was added into a solution of compound 2 (50 g) in tetrahydrofuran (300 mL) at 15° C. The reaction system was stirred at 25° C. for 20 h. At 0° C., the reaction solution was adjusted to pH=9 with 1 M sodium hydroxide solution. Ethyl acetate (200 mL×3) was added for extraction. The extracts were washed with saturated sodium chloride solution (300 mL), dehydrated over anhydrous sodium sulfate, filtered and concentrated under reduced pressure. The residue was slurried with petroleum ether (150 mL) to give compound 3 (39 g, yield: 91%).

3. Synthesis of Compound 5

Compound 3 (74.6 mL) was dropwise added into a solution of compound 4 (5.0 g) in tetrahydrofuran (100 mL) at −40° C. The reaction system was stirred at −40° C. for 4 h. After the end of reaction, as detected by TLC, the reaction was quenched with saturated ammonium chloride solution (50 mL), ethyl acetate (100 mL×3) was added for extraction, and the extracts were washed with saturated sodium chloride solution (50 mL), dehydrated over anhydrous sodium sulfate, filtered and concentrated under reduced pressure.

The residue was purified on silica gel column chromatography (petroleum ether:ethyl acetate=5:1) to give compound 5 (900 mg, yield: 16%).

4. Synthesis of Compound 7

Concentrated sulfuric acid (80 mL) was added into a 1 L three-necked flask. The reaction system was stirred at −12° C. for 5 min (part of the concentrated sulfuric acid was in an icing state), then slowly added with compound 6 (10 g) at −12° C., and reacted without great temperature fluctuation. The reaction solution was stirred at −12° C. for 5 min, then added dropwise slowly with a mixed solution of nitric acid (8 mL) and concentrated sulfuric acid (8 mL) at about −12° C. and stirred for 1.5 h at about −12° C. The starting material was consumed completely as detected by a dot plate. The reaction solution was slowly poured into ice water, stirred at low temperature for 20 min, filtered and washed with water. The filtrate was evaporated to dryness under reduced pressure to give compound 7 (13 g, yield: 100%).

5. Synthesis of Compound 8

Compound 7 (30 g) was dissolved in DMF (450 mL), and slowly dropwise added with hydrazine hydrate (36.3 mL, 98%) at 0° C. The reaction solution was stirred at 120° C. for 18 h. After the reaction was completed, the reaction solution was cooled, then slowly poured into ice water, stirred for 10 min, filtered and washed with water. The filtrate was evaporated to dryness under reduced pressure to give compound 8 (20 g, yield: 69%).

6. Synthesis of Compound 9

Compound 8 (10 g) and palladium on carbon (5 g, 10%) were sequentially added into ethyl acetate (200 mL). The reaction solution was stirred at 20° C. for 16 h in hydrogen atmosphere. After the reaction was completed, celite was added to filter out the palladium on carbon, and the reaction solution was concentrated, and dried to give compound 9 (8 g, yield: 94%).

7. Synthesis of Compound 11 m-CPBA (25 g) was added into a solution of compound 12 (10 g) in DCM (200 mL) at 25° C. The reaction system was stirred at 25° C. for 16 h. The reaction solution was filtered, and the filtrate was quenched with a saturated solution prepared from sodium sulfite (15.6 g). The reaction system was stirred for 2 h and extracted. The aqueous phase was adjusted to pH<7 with hydrochloric acid and extracted with DCM (50 mL×3). The organic phases were combined and concentrated, and the residue was slurried with EA (300 mL) to give compound 11 (10.1 g, yield: 90%).

8. Synthesis of Compound 10

EDCl·HCl (2.6 g) was added into a solution of compound 9 (1.5 g) and compound 11 (1.4 g) in Py (15 mL) at 25° C. The reaction system was stirred at 25° C. for 16 h. The reaction solution was dehydrated and concentrated, and the residue was slurried with MeOH:$H_2O$=20 mL:20 mL to give compound 10 (1.3 g, yield: 48%).

9. Synthesis of Compound 187

2-((2-((1r,4r)-4-ethynyl-4-hydroxycyclohexyl)-6-methoxy-2H-indazol-5-yl)carbamoyl)-6-methylpyridine 1-oxide

187

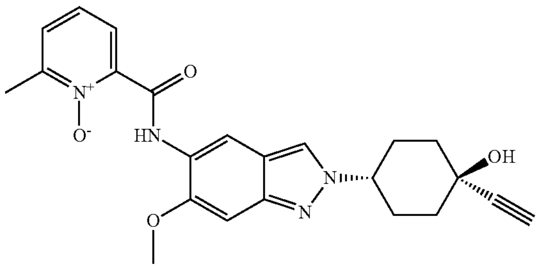

Compound 10 (300 mg), compound 5 (444 mg) and cesium carbonate (820 mg) were sequentially added into NMP (10 mL) at 30° C. The reaction system was stirred at 90° C. for 18 h. After the reaction was completed, as detected by LCMS, the reaction solution was cooled to 30° C. added with water (15 mL) to quench reaction, and extracted with ethyl acetate (10 mL×3). The extracts were washed with saturated sodium chloride (10 mL), dehydrated over anhydrous sodium sulfate, filtered and concentrated under reduced pressure. The residue was purified by preparative high performance liquid chromatography ($CH_3CN$: $H_2O$ (0.1% $NH_4HCO_3$)=5-90%, UV: 214 nm, flowrate: 15 mL/min) to give compound 187 (85 mg, yield: 20%).

$^1H$ NMR (400 MHz, $CDCl_3$): δ 14.14 (s, 1H), 8.89 (s, 1H), 8.46 (dd, $J_1$=7.6 Hz, $J_2$=2.8 Hz, 1H), 7.87 (s, 1H), 7.45-7.37 (m, 2H), 7.07 (s, 1H), 4.44-4.33 (m, 1H), 4.06 (s, 3H), 2.69-2.60 (m, 4H), 2.33-2.27 (m, 4H), 2.25-2.17 (m, 2H), 1.90-1.79 (m, 2H). LCMS: Rt=3.162 min, $[M+H]^+$=421.2.

Example 14: Synthesis of Compounds 019 and Compound 292

Reaction Formula:

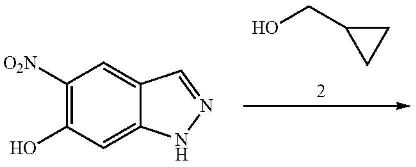

1

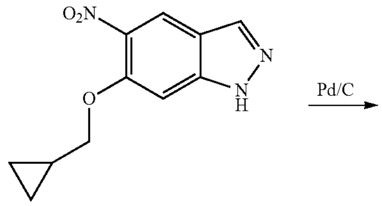

3

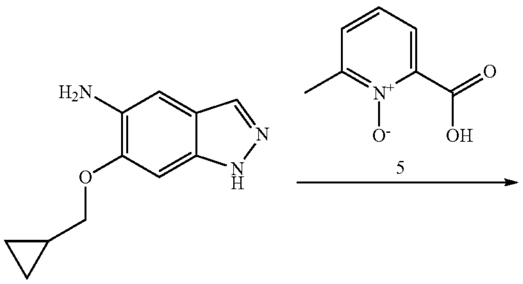

4

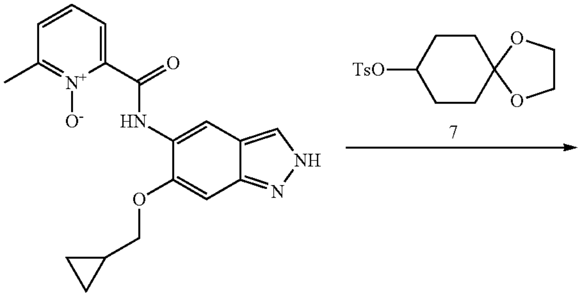

6

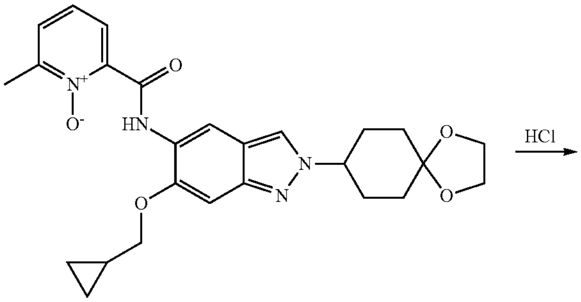

8

-continued

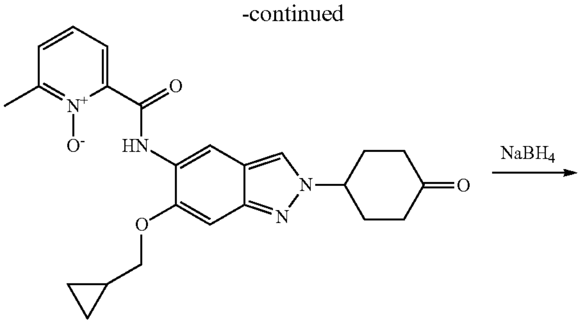

9

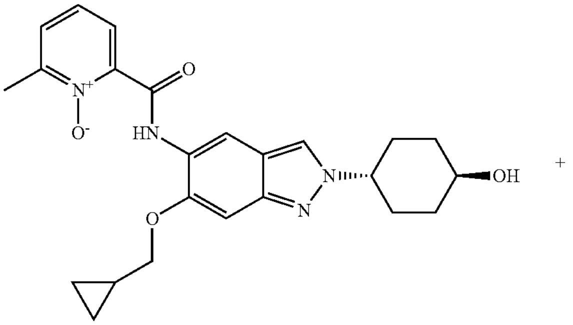

019

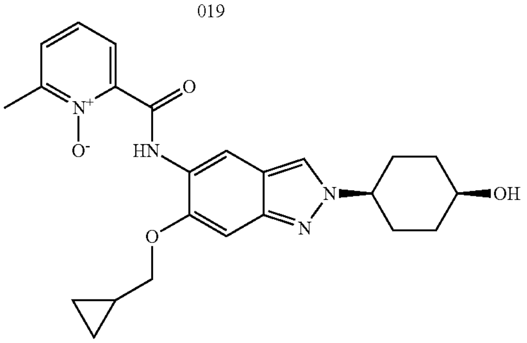

292

1. Synthesis of Compound 3

$PPh_3$ (15 g) was added into a solution of compound 1 (7 g) and compound 2 (3.37 g) in THF (200 mL) in ice bath. The reaction system was stirred for 10 min. DIAD (3.1 g) was slowly dropwise added into the reaction solution, and the reaction system was stirred at 30° C. for 18 h. The reaction solution was added with water (50 mL) and extracted with ethyl acetate (40 mL×4). The organic phase was concentrated under reduced pressure. The residue was purified on silica gel column chromatography (PE:EA=10:1 to PE:EA=2:1) to give compound 3 (6.0 g, yield: 66%).

2. Synthesis of Compound 4

Pd/C (1.0 g, 10%) was added into a solution of compound 3 (6.5 g) in ethyl acetate (300 mL) at 15° C. and the reaction system was stirred at 30° C. for 18 h in hydrogen atmosphere at 760 Torr. The reaction solution was filtered and concentrated under reduced pressure to give compound 4 (4.5 g, yield: 80%).

3. Synthesis of Compound 6

EDCl·HCl (2.1 g) was added into a solution of compound 4 (1.5 g) and compound 5 (1.1 g) in pyridine (30 mL) at 25°

C. The reaction system was stirred at 25° C. for 16 h. The reaction solution was concentrated and evaporated, and the residue was purified on a silica gel column (PE:EA=1:1) to give compound 6 (810 mg, yield: 32%).

4. Synthesis of Compound 8

Cesium carbonate (2.3 g) was added into a solution of compound 6 (810 mg) and compound 7 (1.1 g) in DMF (15 mL) at 25° C. The reaction system was stirred at 90° C. for 16 h. The reaction solution was added into water (50 mL) and extracted with ethyl acetate (30 mL×3). The organic phase was concentrated under reduced pressure. The residue was purified by preparative high performance liquid chromatography ($CH_3CN$:$H_2O$ (0.1% $NH_4HCO_3$)=30-55%, UV: 214 nm, flowrate: 15 mL/min) to give compound 8 (320 mg, yield: 28%).

5. Synthesis of Compound 9

4 mL 2 M hydrochloric acid was added into a solution of compound 8 (320 mg) in dioxane (4 mL) at 25° C. The reaction system was stirred at 25° C. for 16 h. The reaction solution was adjusted to pH>7 with sodium bicarbonate solution and extracted with ethyl acetate (10 mL×2). The organic phase was concentrated under reduced pressure to give compound 9 (250 mg, yield: 86%).

6. Synthesis of Compound 019

2-((6-(cyclopropylmethoxy)-2-((1r,4r)-4-hydroxycyclohexyl)-2H-indazol-5-yl)carbamoyl)-6-methylpyridine 1-oxide and Compound 292 2-((6-(cyclopropylmethoxy)-2-((1s,4s)-4-hydroxycyclohexyl)-2H-indazol-5-yl)carbamoyl)-6-methylpyridine 1-oxide

019

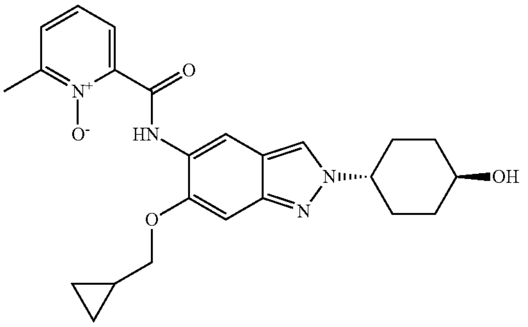

292

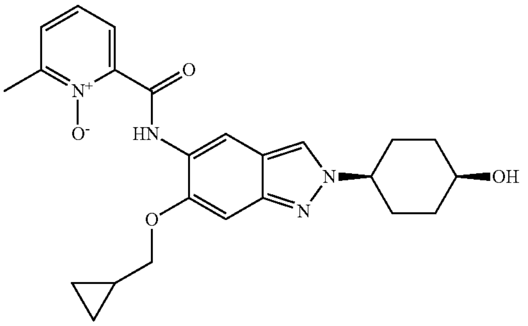

Sodium borohydride (44 mg) was added into a solution of compound 7 (250 mg) in methanol (5 mL) at 0° C. The reaction system was stirred at 25° C. for 2 h. The reaction solution was quenched with ammonium chloride solution (10 mL) and extracted with ethyl acetate (5 mL×3). The organic phase was concentrated under reduced pressure. The residue was purified by preparative high performance liquid chromatography ($CH_3CN$:$H_2O$ (0.1% $NH_4HCO_3$)=35-60%, UV: 214 nm, flowrate: 15 mL/min) to give compound 019 (retention time Rt=10.7 min, 77 mg, yield: 31%) and compound 292 (retention time Rt=11.1 min, 12 mg, yield: 5%).

Compound 019

$^1H$ NMR (400 MHz, DMSO-d6): δ 14.31 (s, 1H), 8.78 (s, 1H), 8.31-8.27 (m, 2H), 7.77-7.75 (m, 1H), 7.56 (t, J=7.6 Hz, 1H), 7.07 (s, 1H), 4.69 (s, 1H), 4.40-4.32 (m, 1H), 4.02 (d, J=6.8 Hz, 1H), 3.56-3.51 (m, 1H), 2.52 (s, 3H), 2.09-2.05 (m, 2H), 1.97-1.87 (m, 4H), 1.44-1.34 (m, 3H), 0.66-0.61 (m, 2H), 0.48-0.45 (m, 2H). LCMS: Rt=3.391 min, $[M+H]^+$=437.2.

Compound 292

$^1H$ NMR (400 MHz, DMSO-d6): δ 14.31 (s, 1H), 8.79 (s, 1H), 8.31-8.29 (m, 2H), 7.77-7.75 (m, 1H), 7.57 (t, J=7.6 Hz, 1H), 7.08 (s, 1H), 4.49 (d, J=6.8 Hz, 1H), 4.40-4.34 (m, 1H), 4.02 (d, J=6.8 Hz, 2H), 3.87 (s, 1H), 2.52 (s, 3H), 2.33-2.22 (m, 2H), 1.56-1.75 (m, 4H), 1.66-1.60 (m, 2H), 1.41-1.34 (m, 1H), 0.65-0.61 (m, 2H), 0.49-0.45 (m, 2H). LCMS: Rt=3.101 min, $[M+H]^+$=437.2.

Example 15: Synthesis of Compound 291

Reaction Formula:

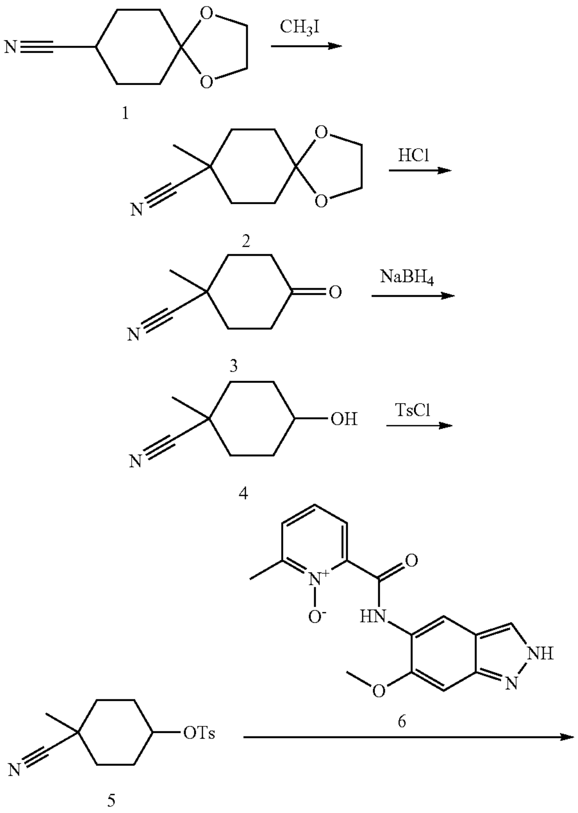

-continued

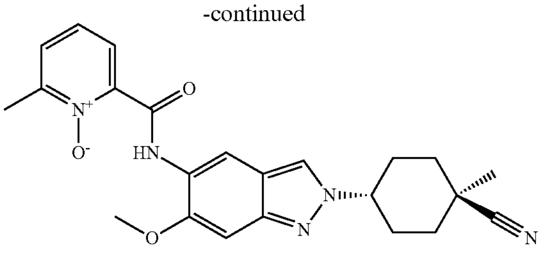

291

1. Synthesis of Compound 2

Compound 1 (800 mg) was dissolved in tetrahydrofuran (10 mL) at 0° C. LiHMDS (1 M THF solution, 5.50 mL) was slowly dropwise added into the reaction solution at 0° C., then the reaction solution was stirred for 60 min at 0° C. and slowly added with iodomethane (680 mg). The reaction system was reacted at 0° C. for 1.5 h. After the reaction was completed, the reaction solution was added with saturated ammonium chloride solution (10 mL) to quench reaction, then extracted with ethyl acetate (25 mL×2), and concentrated under reduced pressure. The residue was purified on a silica gel column (petroleum ether:ethyl acetate=7:1) to give compound 2 (420 mg, yield: 55%).

2. Synthesis of Compound 3

Compound 2 (700 mg) and 3 M HCl (18 mL) were sequentially added into tetrahydrofuran (18 mL) at 0° C. The reaction system was stirred at 50° C. for 5 h. After the reaction was completed, the reaction solution was added with aqueous sodium hydroxide solution (3 M) to adjust to pH=8, then extracted with dichloromethane (20 mL×2), and concentrated under reduced pressure. The residue was purified on a silica gel column (petroleum ether:ethyl acetate=4:1) to give compound 3 (420 mg, yield: 78%).

3. Synthesis of Compound 4

Compound 3 (390 mg) was dissolved in ethanol (8 mL) at 25° C. The reaction solution was added dropwise with a solution of sodium borohydride (112 mg) in ethanol (1 mL) at −70° C., and stirred at −70° C. for 1 h. After the reaction was completed, the reaction solution was added with water (8 mL) to quench reaction, and then extracted with ethyl acetate (15 mL×2). The organic phase was concentrated under reduced pressure. The residue was purified on silica gel column chromatography (petroleum ether:ethyl acetate=1:1) to give compound 4 (280 mg, yield: 66%).

4. Synthesis of Compound 5

Compound 4 (250 mg), TosCl (406 mg), DMAP (261 mg) and triethylamine (0.5 mL) were sequentially added into dichloromethane (8 mL) at 28° C. The reaction system was stirred at 28° C. for 18 h. After the reaction was completed, the reaction solution was concentrated and evaporated, and the residue was purified on silica gel column chromatography (petroleum ether:ethyl acetate=6:1) to give compound 5 (370 mg, yield: 64%).

5. Synthesis of Compound 291

2-((2-((1r,4r)-4-cyano-4-methylcyclohexyl)-6-methoxy-2H-indazol-5-yl)carbamoyl)-6-methylpyridine 1-oxide

291

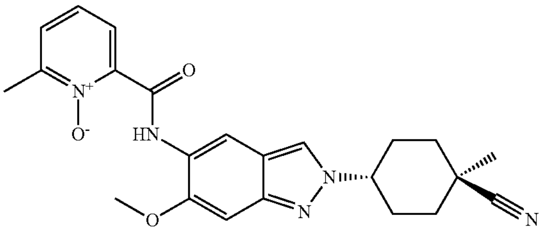

Compound 5 (296 mg), compound 6 (350 mg), and cesium carbonate (808 mg) were sequentially added into DMF (6 mL) at 25° C. The reaction system was stirred at 90° C. for 18 h after the completion of addition. After the reaction was completed, water (10 mL) was added to quench reaction, the reaction solution was extracted twice with ethyl acetate (40 mL). The organic phase was concentrated under reduced pressure. The residue was purified by preparative high performance liquid chromatography ($CH_3CN$:$H_2O$ (0.1% $NH_4HCO_3$)=5-95%, UV: 214 nm, flowrate: 15 mL/min) to give compound 291 (80 mg, yield: 19%).

$^1H$ NMR (400 MHz, $CDCl_3$): δ 14.14 (s, 1H), 8.88 (s, 1H), 8.45 (d, J=7.6 Hz, 1H), 7.87 (s, 1H), 7.44-7.38 (m, 2H), 7.06 (s, 1H), 4.53-4.50 (m, 1H), 4.06 (s, 3H), 2.63 (s, 3H), 2.46-2.39 (m, 2H), 2.28-2.20 (m, 2H), 2.02-1.88 (m, 4H), 1.45 (s, 3H). LCMS: Rt=3.310 min, $[M+H]^+$=420.2.

Example 16: Synthesis of Compound 002

Reaction Formula:

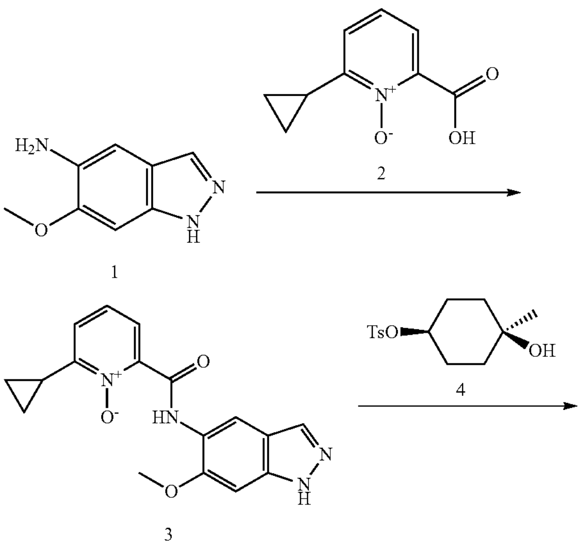

-continued

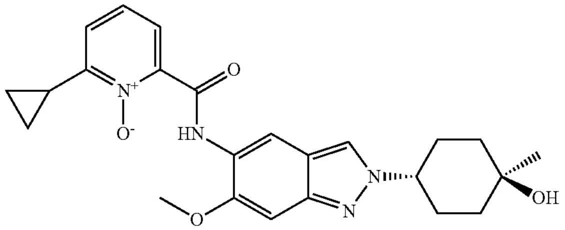

002

1. Synthesis of Compound 3

Compound 2 (1.0 g), compound 1 (0.91 g) and EDCl (1.6 g) were added into pyridine (15 mL) at 28° C. The reaction system was stirred at 28° C. for 18 h. After the reaction was completed, the reaction solution was concentrated under reduced pressure, and the residue was slurried with methanol and water to give the compound 3 (1.0 g, a yield: 56%).

2. Synthesis of Compound 002

2-cyclopropyl-6-((2-((1r,4r)-4-hydroxy-4-methylcyclohexyl)-6-methoxy-2H-indazol-5-yl)carbamoyl) Pyridine 1-oxide

002

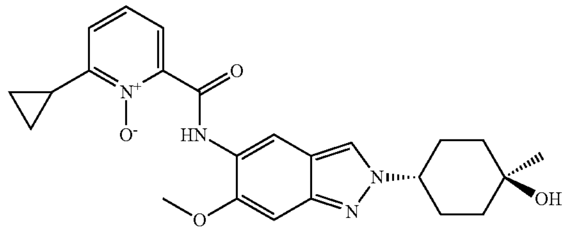

Compound 3 (500 mg), compound 4 (675 mg) and cesium carbonate (1.26 g) were sequentially added into DMF (10 mL) at 25° C. The reaction system was stirred at 90° C. for 18 h. After the reaction was completed, the reaction solution was cooled to 25° C., added with water (5 mL) to quench reaction, and extracted with ethyl acetate (15 mL×3). The extracts were washed with saturated brine (10 mL), dehydrated over anhydrous sodium sulfate, filtered and concentrated under reduced pressure. The residue was purified by high performance liquid chromatography ($CH_3CN$: $H_2O$=20-45%, UV: 214 nm, flowrate; 15 mL/min) to give compound 002 (130 mg, yield: 19%).

$^1H$ NMR (400 MHz, $CDCl_3$): δ 14.22 (s, 1H), 8.89 (s, 1H), 8.40 (dd, $J_1$=2.0 Hz, J=8.0 Hz, 1H), 7.87 (s, 1H), 7.37 (t, J=8.0 Hz, 1H), 7.14-7.01 (m, 2H), 4.46-4.34 (m, 1H), 4.05 (s, 3H), 2.91-2.81 (m, 1H), 2.30-2.08 (m, 4H), 1.93-1.82 (m, 2H), 1.76-1.69 (m, 2H), 1.39 (s, 3H), 1.32-1.23 (m, 2H), 0.89-0.76 (m, 2H). LCMS: Rt=2.859 min, $[M+H]^+$=437.2.

Example 17: Synthesis of Compound 289

Reaction Formula:

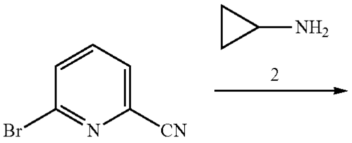

1

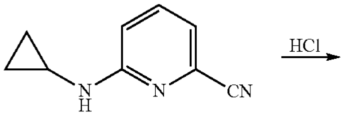

3

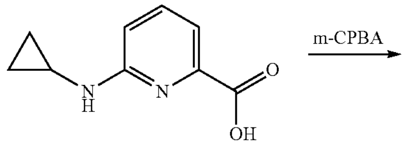

4

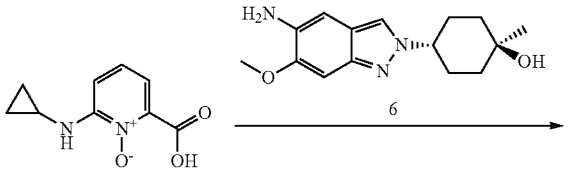

5

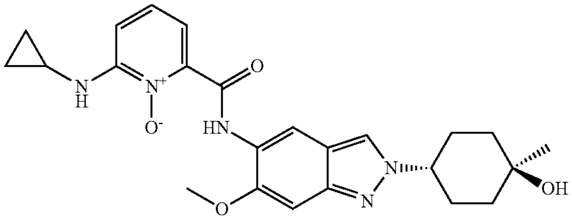

289

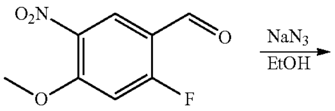

10

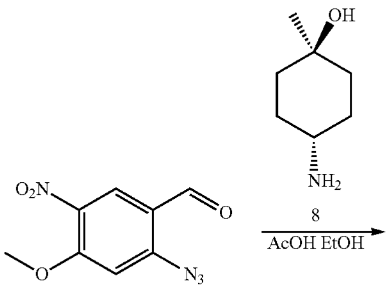

9

-continued

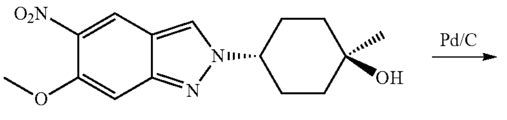

7

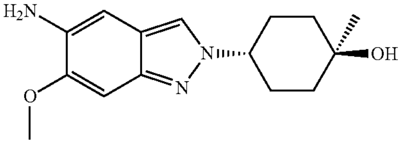

6

1. Synthesis of Compound 3

Compound 1 (5.0 g), compound 2 (2.3 g), cesium carbonate (13.4 g), $Pd_2(dba)_3$ (0.25 g) and BINAP (0.51 g) were sequentially added into methylbenzene (100 mL) at 26° C. The reaction system was stirred at 80° C. for 18 h in nitrogen atmosphere. After the reaction was completed, the reaction solution was cooled to 26° C., added with water (100 mL), and extracted with ethyl acetate (200 mL×3). The extracts were washed with saturated brine (100 mL), dried over anhydrous sodium sulfate, concentrated under reduced pressure. The residue was purified on silica gel column chromatography (petroleum ether:ethyl acetate=10:1) to give compound 3 (1.3 g, yield: 30%).

2. Synthesis of Compound 4

Potassium hydroxide (4.58 g) was added into a solution of compound 3 (1.3 g) in ethanol/water (40 mL/10 mL). The reaction system was stirred at 90° C. for 16 h. The reaction solution was adjusted to pH=6 with 1 M hydrochloric acid, and extracted with ethyl acetate (100 mL×3). The extracts were washed with water (50 mL) and saturated brine (100 mL), dried over anhydrous sodium sulfate and concentrated under reduced pressure to give compound 4 (1.12 g, yield: 77%).

3. Synthesis of Compound 5 m-CPBA (1.86 g) was added into a solution of compound 4 (360 mg) in dichloromethane (50 mL) at 26° C. The reaction system was stirred at 26° C. for 3 days. After the reaction was completed, the reaction solution was filtered, the filtrate was added with saturated sodium sulfite solution, adjusted to pH<7 with hydrochloric acid, stirred at 26° C. for 2 h, and extracted with dichloromethane (200 mL×3). The extracts were washed with saturated brine (100 mL), dehydrated over anhydrous sodium sulfate, filtered and concentrated under reduced pressure. The residue was purified by silica gel preparative thin layer chromatography (dichloromethane:methanol=20:1) to give compound 5 (60 mg, yield: 15%).

4. Synthesis of Compound 289

2-(cyclopropylamino)-6-((2-((1r,4r)-4-hydroxy-4-methylcyclohexyl)-6-methoxy-2H-indazol-5-yl)carbamoyl)pyridine 1-oxide

289

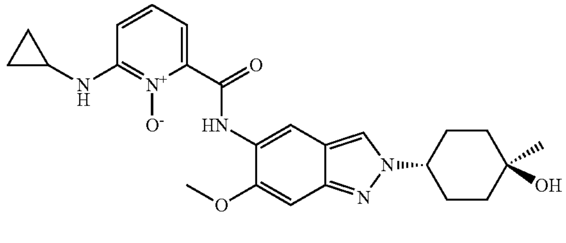

Compound 5 (49 mg), compound 6 (69 mg), HATU (118 mg), and DIPEA (66 mg) were added into DMF (5 mL). The reaction system was stirred at 25° C. for 18 h. The reaction solution was concentrated under reduced pressure, and the residue was purified by preparative high performance liquid chromatography ($CH_3CN$:$H_2O$=30-95%, UV: 214 nm, flow-rate: 15 mL/min) to give compound 289 (95 mg, yield: 83%).

$^1H$ NMR (400 MHz, $CDCl_3$): δ 14.29 (s, 1H), 8.89 (s, 1H), 7.86 (t, J=6.4 Hz, 2H), 7.41 (t, J=8.0 Hz. 1H), 7.15 (s, 2H), 7.07 (s, 1H), 4.43-4.38 (m, 1H), 4.04 (s, 3H), 2.61 (br s, 1H), 2.25-2.13 (m, 4H), 1.89-1.85 (m, 1H), 1.75-1.64 (m, 4H), 1.39 (s, 3H), 0.93-0.90 (m, 2H), 0.74-0.72 (m, 2H). LCMS: Rt=3.308 min, $[M+H]^+$=452.2.

5. Synthesis of Compound 9

$NaN_3$ (13.2 g) was added into a solution of compound 10 (34 g) in ethanol (350 mL) at 0° C. The reaction system was stirred at 25° C. for 16 h, which was directly used in the next step after the completion of reaction.

6. Synthesis of Compound 7

Acetic acid (30.6 g) and compound 8 (22 g) were added into a solution of compound 9 (0.17 mol) in ethanol (350 mL) at 25° C. The reaction system was stirred at 25° C. for 10 min. The reaction solution was refluxed at 80° C. and reacted for 16 h. After the reaction was completed, part reaction solution was concentrated, slurried with water (70 mL) and filtrated to give a solid. The solid was added into ethanol (200 mL), heated to reflux and dissolve, added with n-heptane (200 mL), slurried for 2 h and filtrated to give compound 7 (35 g, 67% yield over two steps).

7. Preparation of Compound 6

Pd/C (150 mg) was added into a solution of compound 7 (300 mg) in ethyl acetate (50 mL) at 25° C. The reaction system was stirred at 25° C. for 16 h. After the reaction was completed, the reaction solution was filtrated and concentrated under reduced pressure to give compound 6 (260 mg, yield 96%).

Example 18. Synthesis of Compound 175

Reaction Formula:

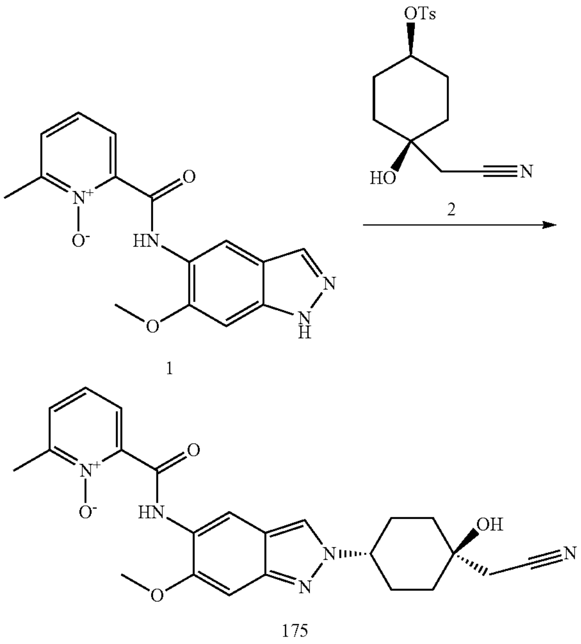

1. Synthesis of Compound 175

2-((2-((1r,4r)-4-(cyanomethyl)-4-hydroxycyclohexyl)-6-methoxy-2H-indazol-5-yl)carbamoyl)-6-methylpyridine 1-oxide

175

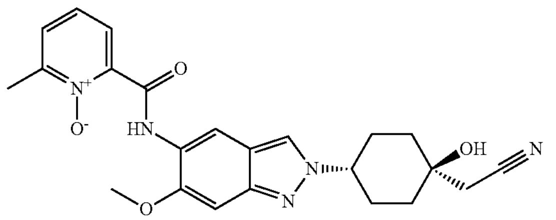

Cesium carbonate (1.4 g) was added into a solution of compound 1 (520 mg) and compound 2 (806 mg) in DMF (10 mL) at 25° C. The reaction system was stirred at 90° C. for 16 h. The reaction solution was poured into water (50 mL) and extracted with ethyl acetate (30 mL×3). The organic phase was concentrated under reduced pressure. The residue was purified by preparative high performance liquid chromatography ($CH_3CN$:$H_2O$ (0.1% $NH_4HCO_3$)=20-40%, UV: 214 nm, flowrate: 15 mL/min) to give compound 175 (64 mg, yield: 8%).

$^1$H NMR (400 MHz, DMSO-$d_6$): δ 14.16 (s, 1H), 8.79 (s, 1H), 8.37 (s, 1H), 8.32-8.29 (m, 1H), 7.78-7.76 (m, 1H), 7.58 (t, J=8.0 Hz, 1H), 7.11 (s, 1H), 5.20 (s, 1H), 4.49-4.45 (m, 1H), 3.95 (s, 3H), 2.82 (s, 2H), 2.53 (s, 3H), 2.14-2.01 (m, 4H), 1.84-1.80 (m, 2H), 1.71-1.64 (m, 2H). LCMS: Rt=9.367 min. $[M+H]^+$=436.2.

Example 19: Synthesis of Compound 176

Reaction Formula:

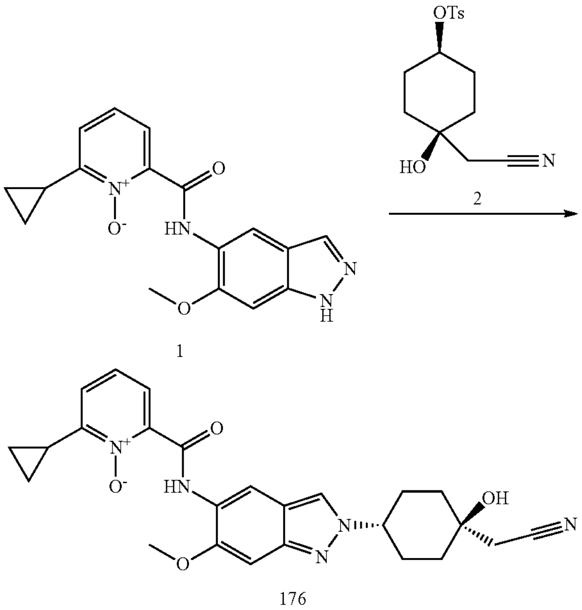

1. Synthesis of Compound 176

2-((2-((1r,4r)-4-(cyanomethyl)-4-hydroxycyclohexyl)-6-methoxy-2H-indazol-5-yl)carbamoyl)-6-cyclopropylpyridine 1-oxide

176

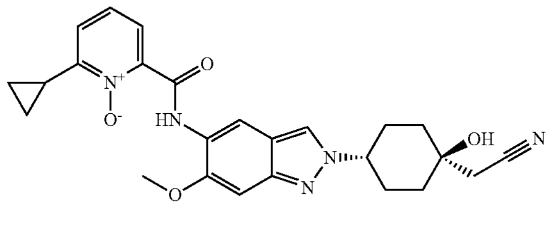

Compound 8 (420 mg), compound 9 (601 mg) and cesium carbonate (1.06 g) were sequentially added into DMF (10 mL) at 25° C. The reaction system was stirred at 90° C. for 16 h. After the reaction was completed, the reaction solution was cooled to 25° C., added with water (5 mL) to quench reaction, and extracted with ethyl acetate (10 mL×3). The extracts were washed with saturated brine (10 mL), dehydrated over anhydrous sodium sulfate, filtered and concentrated under reduced pressure. The residue was purified by high performance liquid chromatography ($CH_3CN$: $H_2O$=25-55%, UV: 214 nm, flowrate; 15 mL/min) and by silica gel preparative thin layer chromatography (dichloromethane:methanol=20:1) to give compound 176 (25 mg, yield: 4%).

$^1$H NMR (400 MHz, $CDCl_3$): δ 14.25 (s, 1H), 8.89 (s, 1H), 8.39 (dd, $J_1$=2.0 Hz, $J_2$=8.0 Hz, 1H), 7.86 (s, 1H), 7.38 (t, J=8.0 Hz, 1H), 7.09-7.03 (m, 2H), 4.53-4.43 (m, 1H), 4.05 (s, 3H), 2.90-2.81 (m, 1H), 2.76 (s, 2H), 2.33-2.17 (m,

4H), 2.13-2.03 (m, 2H), 1.99-1.93 (m, 1H), 1.89-1.73 (m, 2H), 1.30-1.26 (m, 2H), 0.88-0.80 (m, 2H). LCMS: Rt=3.553 min, $[M+H]^+$=462.2.

Example 20: Synthesis of Compound 042

Reaction Formula:

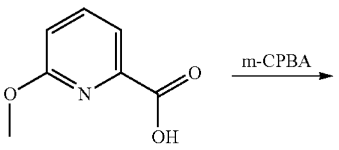

1

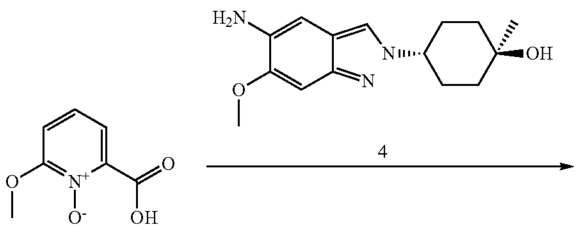

4

2

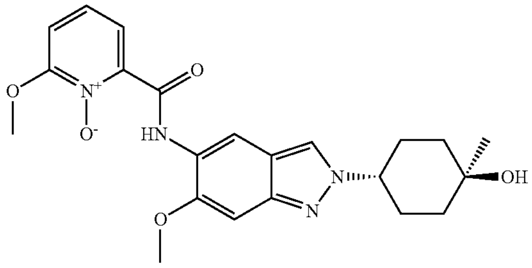

042

1. Synthesis of Compound 2 m-CPBA (13.3 g) was added into a solution of compound 1 (5.0 g) in dichloromethane (50 mL) at 25° C. The reaction system was stirred at 25° C. for 18 h. The reaction solution was filtered, the filtrate was added with saturated aqueous sodium sulfite (8.2 g) solution, stirred at 25° C. for 2 h, and extracted with dichloromethane (50 mL×3). The extracts were washed with saturated brine (50 mL), dehydrated over anhydrous sodium sulfate, filtered and concentrated under reduced pressure. The residue was slurried with ethyl acetate and purified to give compound 2 (600 mg, yield: 11%).

2. Synthesis of Compound 042

2-((2-((1r,4r)-4-hydroxy-4-methylcyclohexyl)-6-methoxy-2H-indazol-5-yl)carbamoyl)-6-methoxy-pyridine 1-oxide

042

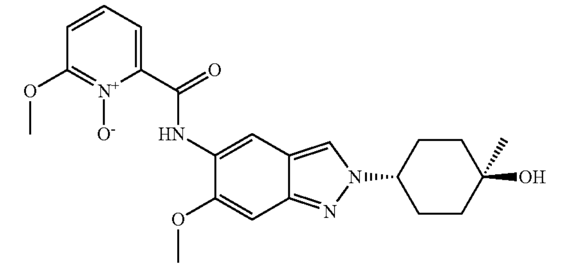

Compound 2 (92 mg), compound 4 (150 mg), HATU (311 mg) and triethylamine (165 mg) were added into DMF (5 mL) at 25° C. The reaction system was stirred at 25° C. for 16 h. After the reaction was completed, the reaction solution was added with water (5 mL) to quench reaction, and extracted with ethyl acetate (5 mL×3). The extracts were washed with saturated brine (10 mL), dehydrated over anhydrous sodium sulfate, and concentrated under reduced pressure. The residue was purified by high performance liquid chromatography ($CH_3CN:H_2O$=10-40%, UV: 214 nm, flowrate: 15 mL/min) to give compound 042 (96 mg, yield: 41%).

$^1H$ NMR (400 MHz, $CDCl_3$): δ 14.15 (s, 1H), 8.89 (s, 1H), 8.22 (dd, $J_1$=2.0 Hz, $J_2$=8.0 Hz, 1H), 7.86 (s, 1H), 7.49 (t, J=8.0 Hz, 1H), 7.11-7.02 (m, 2H), 4.44-4.34 (m, 1H), 4.16 (s, 3H), 4.03 (s, 3H), 2.29-2.08 (m, 4H), 1.91-1.82 (m, 2H), 1.73-1.69 (m, 2H), 1.39 (s, 3H). LCMS: Rt=2.713 min, [M+H]=427.2.

Example 21: Synthesis of Compound B

N-(2-((1r,4r)-4-hydroxy-4-methylcyclohexyl)-6-methoxy-2H-indazol-5-yl)-6-methylpicolinamide

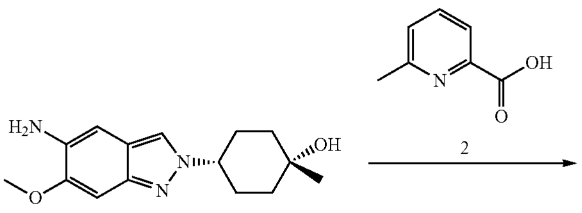

2

1

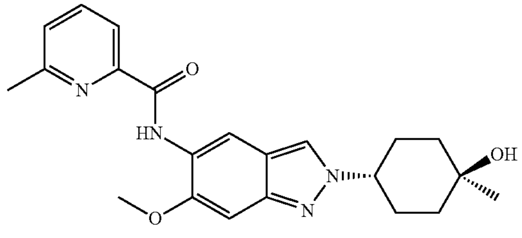

B

Compound 1 (150 mg), compound 2 (75 mg), HATU (249 mg), and DIPEA (141 mg) were sequentially added into DMF (5 mL) at 25° C. The reaction system was stirred at 25° C. for 16 h. The reaction solution was added with water (50 mL), and extracted with ethyl acetate (10 mL×3). The extracts were washed with saturated brine (10 mL), dehydrated over anhydrous sodium sulfate, filtered and concentrated under reduced pressure. The residue was purified by high performance liquid chromatography ($CH_3CN$: $H_2O$=30-95%, UV: 214 nm, flowrate: 15 mL/min) to give a white solid (170 mg, yield: 79%).

1H NMR (400 MHz, $CDCl_3$): δ 10.82 (s, 1H), 8.85 (s, 1H), 8.10 (d. J=7.6 Hz, 1H), 7.87 (s, 1H), 7.78 (t, J=7.6 Hz, 1H), 7.32 (d, J=7.2 Hz, 11H), 7.08 (s, 1H), 4.43-4.37 (m, 1H), 4.03 (s, 3H), 2.66 (s, 3H), 2.27-2.13 (m, 4H), 1.89 (br s, 1H), 1.76-1.68 (m, 4H), 1.40 (s, 3H). LCMS: Rt=3.604 min, [M+H]+=395.2.

Biological Evaluation

The following test examples are used for further explaining the present invention, but are not intended to limit the scope of the present invention.

The structure of compound A in biological test examples:

A

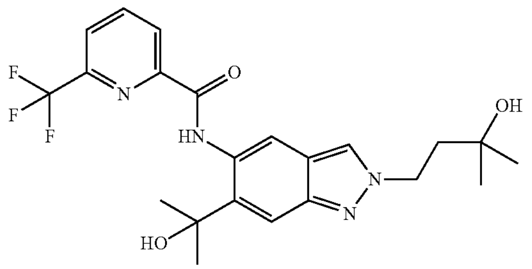

The structure of compound B synthesized in Example 21 in biological test examples:

B

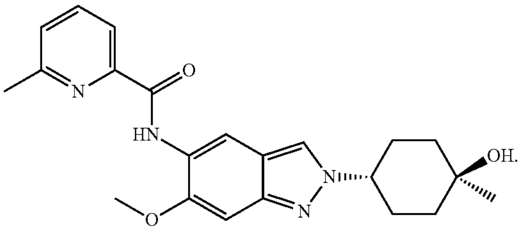

Test Example 1. Determination of Inhibition of Human IRAK4 by the Compounds Disclosed Herein Major Materials ATP (Sigma, CAT No. A7699-1G)
DMSO (Sigma, CAT No. D2650)
EDTA (Sigma, CAT No. E5134)
HEPES (Sigma. CAT No. V900477-500G)
DTT (Sigma, CAT No. D0632-25g)
Brij-35 (Sigma, CAT No. B4184)
96-well plate (Corning, CAT No. 3365)
384-well plate (Corning, CAT No. 3573)

Procedures

The inhibitory activity of the compounds on IRAK4 at the Km concentration of ATP was measured in IRAK4 MSA (Mobility-Shift Assay, a mobility detection of microfluidic chip technology) as described below.

A recombinant fusion protein of N-terminal GST (glutathione-S-transferase) and human IRAK4 was used as enzyme (GST-IRAK4, kinase IRAK4 (Cama, CAT No. 09-145)) at a final concentration of 1 nM; ATP (Sigma. CAT No. A7699-1G) was at a final concentration of 37 μM;

the substrates used for the kinase reaction were 5-FAM (5-carboxyfluorescein)-labeled polypeptide (5-FAM-IPTSPITTTYFFFKKK-COOH) and substrate peptide FAM-P8 (GL Biochem, CAT No. 112396) at final concentrations of 5 μM.

In this assay, 500 μM stock solutions of the compounds were prepared in 100% DMSO, and serially 4-fold diluted to the 10th concentration gradient with 100% DMSO, followed by a 10-fold dilution in the compound buffer (50 mM HEPES, pH 7.5, 0.00015% Brij-35) to give intermediate dilutions of the compounds at a final concentration of 10 μM–0.04 nM containing 10% DMSO. 5 μL of the intermediate dilution was transferred into a black 384-well plate.

IRAK4 was diluted to 2.5 nM in the kinase buffer (50 mM HEPES, pH 7.5, 0.00015% Brij-35, 2 mM DTT). 10 μL of the IRAK4 dilution was transferred to the 384-well plate and co-incubated with the compound for 10-15 min.

The substrate and ATP were diluted to 12.5 μM and 92.5 μM with reaction buffer (50 mM HEPES, pH 7.5, 0.00015% Brij-35, 10 mM $MgCl_2$), respectively. 10 μL of the dilution was transferred to a 384-well plate and incubated at 28° C. for 1 h. The reaction was terminated by adding 25 μL of 50 mM EDTA to the 384-well plate.

The inhibition rate of IRAK4 by the compounds was calculated by measuring the rate of phosphorylated substrate using a Caliper EZ Reader (PerkinElmer) and the $IC_{50}$ was calculated by XL-fit software. Results show that the compounds disclosed herein have significant inhibition effect on IRAK4 activity, and the $IC_{50}$ (nM) is less than 100, preferably less than 30. In particular, some exemplary compound activity values are as follows:

$IC_{50}$ values for the compounds disclosed herein inhibiting human IRAK4 activity are shown in Table 1.

TABLE 1

$IC_{50}$ for inhibiting human IRAK4 activity

| Compound ID | $IC_{50}$ (nM) |
|---|---|
| Compound B | 30.0 |
| 001 | 6.0 |
| 002 | 3.7 |
| 010 | 11.0 |
| 013 | 7.6 |
| 014 | 2.5 |
| 015 | 5.4 |
| 016 | 8.1 |
| 019 | 8.1 |
| 025 | 13.0 |
| 163 | 23.0 |
| 175 | 7.1 |
| 176 | 4.3 |
| 187 | 9.2 |
| 218 | 8.3 |
| 220 | 14.0 |
| 284 | 28.0 |
| 285 | 5.9 |
| 286 | 14.0 |
| 287 | 13.0 |

TABLE 1-continued

| IC$_{50}$ for inhibiting human IRAK4 activity | |
|---|---|
| Compound ID | IC$_{50}$ (nM) |
| 288 | 13.0 |
| 289 | 1.7 |
| 291 | 14.0 |
| 292 | 14 |

Test Example 2. Determination of Inhibition of Human IRAK1 by the Compounds Disclosed Herein This assay evaluated the inhibitory effect of the compounds on human IRAK1 activity with the same materials as in Test Example 1.

The inhibitory activity of the compounds on IRAK1 at the Km concentration of ATP was measured in IRAK1 MSA (Mobility-Shift Assay, a mobility detection of microfluidic chip technology) as described below. A recombinant fusion protein of N-terminal GST (glutathione-S-transferase) and human IRAK1 was used as enzyme (GST-IRAK1, kinase IRAK1, Cama) at a final concentration of 3 nM: ATP (Sigma) was at a final concentration of 97 μM; the substrates used for the kinase reaction were 5-FAM (5-carboxyfluorescein)-labeled polypeptide (5-FAM-IPTSPITTYFFFKKK-COOH) and substrate peptide FAM-P8 (GL Biochem) at final concentrations of 5 μM.

In this assay, 500 μM stock solutions of the compounds were prepared in 100% DMSO, and serially 4-fold diluted to the 10th concentration gradient with 100% DMSO, followed by a 10-fold dilution in the compound buffer (50 mM HEPES, pH 7.5, 0.00015% Brij-35) to give intermediate dilutions of the compounds at a final concentration of 10 μM–0.04 nM containing 10% DMSO. 5 μL of the intermediate dilution was transferred into a black 384-well plate.

IRAK1 was diluted to 7.5 nM in the kinase buffer (50 mM HEPES, pH 7.5, 0.00015% Brij-35, 2 mM DTT). 10 μL of the IRAK1 dilution was transferred to the 384-well plate and co-incubated with the compound for 10-15 min.

The substrate and ATP were diluted to 12.5 μM and 242.5 μM with reaction buffer (50 mM HEPES, pH 7.5, 0.00015% Brij-35, 10 mM $MgCl_2$), respectively. 10 μL of the dilution was transferred to a 384-well plate and incubated at 28° C. for 1 h. The reaction was terminated by adding 25 μL of 50 mM EDTA to the 384-well plate.

The inhibition of IRAK1 by the compounds was calculated by measuring the rate of phosphorylated substrate using a Caliper EZ Reader (PerkinElmer) and the IC$_{50}$ was calculated by XL-fit software. Results show that the compounds disclosed herein have significant selective inhibitory activity on IRAK4, and the IC$_{50}$ (nM) ratio of IRAK1 to IRAK4 is more than 500, preferably more than 200. In particular, some exemplary compound activity values are shown below: IC$_{50}$ values for the compounds disclosed herein inhibiting human IRAK1 activity are shown in Table 2.

TABLE 2

| IC$_{50}$ for inhibiting hitman IRAKI activity | | |
|---|---|---|
| Compound ID | IRAKI IC$_{50}$ (nM) | IRAKI IC$_{50}$ (nM)/ IRAK4 IC$_{50}$ (nM) |
| 163 | 2993 | 130.1 |
| 001 | 4039 | 673.2 |

As can be seen from Table 2, the compounds disclosed herein have significant selectivity for human IRAK4 compared to IRAK1.

Test Example 3. Experiments for Determining hERG of the Compounds Disclosed Herein This experiment evaluated the cardiac safety of the compounds disclosed herein, and an HEK-293 cell line stably expressing hERG potassium ion channel was used for detection.

Instruments:

Amplifier: purchased from HEKA (Germany), EPC10

Micromanipulator: purchased from Sutter Instruments (USA), MP225

Micropipette puller: purchased from Sutter Instruments (USA), P97

Microscope: purchased from Nikon, TE300

Capillary glass tubing: purchased from Sutter Instruments (USA), BF150-86-10

Data acquisition and analysis software: PatchMaster, Igor Pro 6.0 and GraphPad Prism 5.0

Procedures:

Test compound stocks were diluted in DMSO into 0.3 mM, 1 mM, and 3 mM dilutions. Test compound stocks were diluted in an extracellular buffer (140 mM NaCl, 3.5 mM KCl, 1 mM $MgCl_2$, 2 mM $CaCl_2$, 10 mM glucose, 10 mM HEPES, 1.25 mM $NaH_2PO_4$, adjusted to pH 7.4 with NaOH) to give working solutions of the test compounds at concentrations of 0.3 μM, 1 μM, 3 μM, 10 μM and 30 μM. The working solutions of the test compounds were ultrasonically treated for 20 min.

Patch clamping: Under an inverted microscope, recording electrodes were controlled by micromanipulator to contact with the cell. A negative voltage was applied to create a G-omega shaped connection. After forming the G-omega shaped connection, a rapid capacitance compensation was given. Under the continuous negative voltage, the cell membrane was ruptured to form a whole-cell recording configuration. In the whole-cell recording configuration, slow capacitance compensation was given, and the values of membrane capacitance and series resistance were recorded.

Voltage stimulation scheme for cellular hERG potassium current: The cell membrane clamping voltage was −80 mV; the voltage was first elevated from −80 mV to +30 mV, held for 2.5 sec, and rapidly raised to and held at −50 mV for 4 sec, thus exciting the hERG channel tail current. Data acquisition was performed every 10 sec. −50 mV was used for drain current detection.

The cover glasses planted with cells were placed in the recording chamber of an inverted microscope. Negative control and test compounds flowed through the recording chamber in an ascending order of concentration by gravity perfusion to quickly act on the cells. During the recording, the extracellular buffer was continuously circulated by a vacuum pump. The current detected in a cell in the negative control was used as the background for the cell. Each concentration was allowed to act for 5 min or until the current was stabilized. All experiments were performed at room temperature.

Data Analysis:

The current of each concentration was normalized first $$\left(\frac{\text{Peak tail current compound}}{\text{Peak tail current vehicle}}\right),$$

and then the inhibition rate was calculated $$\left(\left(1-\frac{\text{Peak tail current compound}}{\text{Peak tail current vehicle}}\right)\right).$$

Basic statistics were calculated for each concentration, including mean, standard deviation (SD), standard error (SE), and replicates (n). The dose-dependent curve was fitted with the following equation and the half maximal inhibitory concentration ($IC_{50}$) of the test compounds was calculated:

Wherein C represents the test compound concentration. $IC_{50}$ represents the half maximal inhibitory concentration, and h represents the Hill coefficient. Curve fitting and calculation of $IC_{50}$ were done by GraphPad Prism 5.0 software.

Results show low inhibition rates of the compounds disclosed herein for human hERG, which are even significantly superior to the control compound A. The inhibition rate of the compounds at 30 μM for hERG is less than 50%, preferably less than 30% of that of the compound A. In particular, some exemplary compound inhibition rate values are as follows:

TABLE 3

30 μM inhibition for hERG

| Compound ID | Inhibition for hERG (30 μM) |
|---|---|
| A | 27.10% ± 1.74% |
| 163 | 8.73% ± 1.37% |
| 001 | 5.09% ± 2.43% |

As can be seen from Table 3, the compounds disclosed herein have low inhibition rates for human hERG while have significant superiority to the compound A.

Test Example 4. Determination of Time-Dependent Inhibition (TDI) Data of the Compounds Disclosed Herein This study was intended to investigate the time-dependent inhibition effect of the compounds on CYP3A4 in human P450 superfamily. The mixed human liver microsomes used in this assay were purchased from Corning (USA).

The test compounds were co-incubated with the human liver microsomes and a probe substrate midazolam (CYP3A4), and the concentration of the test compounds was set at 30 μM. The reaction was initiated by adding coenzyme NADPH, and terminated by adding acetonitrile dossolved with internal standard in advance. After the proteins were precipitated, the supernatant was centrifuged. The characteristic metabolite 1-hydroxy-midazolam (CYP3A4) in the supernatant was analyzed by LC-MS/MS. The influence of the test compounds on production of the characteristic metabolites was finally analyzed on the basis of the data obtained. A selective inhibitor (verapamil for CYP3A4-M) was used as positive control.

Results show that the compounds in the examples of the present invention have no significant time-dependent inhibition on human CYP3A4. In particular, TDI values of some exemplary compound are as follows:

TABLE 4

Time-dependent inhibition (TDI) on human CYP3A4 at a concentration of 30 μM

| Compound ID | TDI (3A4, 30 μM) |
|---|---|
| 001 | −3.68% |
| 014 | +3.85% |

Test Example 5. Determination of Plasma Protein Binding (PPB) Data of the Compounds Disclosed Herein The experiment is intended to determine plasma protein binding (PPB) data of the test compounds disclosed herein.

In the PPB experiment, the final administration matrix contained the test compound or a reference compound with a concentration of 1 μM and DMSO with a content of 0.2%.

Collecting samples in initial time: 25 μL of the matrix containing the compound was added into a blank 96-well collecting plate, and the plate was stored at −20° C.

An equilibrated dialysis device was prepared. 100 μL of buffer was added to the receiving side of the equilibrium dialysis plate. Then 100 μL of the administration matrix containing the compound or the reference compound was added into an administration side of the equilibrium dialysis plate. The prepared equilibrium dialysis plate was placed in a 37° C. shaker to be shaken for 5 h at 60 rpm.

Sample was prepared at the end of cultivation (5 h): Preparing sample in the receiving side: 25 μL of sample from a receiving side was taken out and placed in a 96-well sample collecting plate, and 25 μL of a corresponding matrix (blank plasma) was added for mixing: 200 μL of ACN containing an internal standard was added, shaken for 10 minutes at 600 rpm, and centrifuged at 5594 g for 15 min.

Preparing sample in the administration side: 25 μL of the sample containing test compound and reference compound from the administration side was taken out and 25 μL of a blank buffer was added for mixing; 200 μL of ACN containing an internal standard was added, shaken for 10 minutes at 600 rpm, and centrifuged at 5594 g for 15 min.

Preparing sample in initial time: the sample containing test compound and reference compound was re-melted at 37° C. in initial time and then mixed with the corresponding matrix (blank buffer) in the same volume (25 μL); 200 μL of ACN containing an internal standard was added, shaken for 10 minutes at 600 rpm, and centrifuged at 5594 g for 15 min.

After all the samples were centrifuged, 50 μL of a supernatant was taken and added into 50 μL of ultrapure water for mixing, and the samples were sent to liquid chromatography-mass spectrometry. Results show that the compounds in the examples of the present invention have a moderate protein binding rate to plasma of human, rats and mice, and has little binding difference between species, which may even be significantly smaller than the control compound A. In particular, the PPB data for some exemplary compounds are as follow:

TABLE 5

| Plasma protein binding (PPB) data | | | |
|---|---|---|---|
| | Plasma protein binding (Bound %) Species | | |
| Compound ID | Human | Mouse | Rat |
| A | 99.02 | 85.18 | 86.99 |
| 013 | 80.90 | 76.20 | 81.70 |
| 001 | 81.00 | 79.90 | 84.70 |
| 163 | 81.66 | 83.78 | 80.59 |
| 016 | 86.90 | 87.70 | 90.10 |

Test Example 6. Inhibition of Cytokine TNF-α Release in LPS-Induced Balb/c Female Mice by the Compounds Disclosed Herein Procedures Female Balb/c mice were randomized into groups, each containing 4 mice, including a control+vehicle group, a model+vehicle group, a model+reference group and model+compound groups. The control animals received an intraperitoneal injection of normal saline (10 mL/kg) and the model animals received LPS stimulation (Sigma CAT #L2630, i.p., 10 mL/kg, 0.2 mg/kg). To the test compounds, DMSO, Solutol and 10 mM PBS were sequentially added to prepare a solution or suspension of required concentration for administration. For the vehicle, DMSO, Solutol and 10 mM PBS were mixed in a volume ratio of 5:15:80. The animals were administered through oral gavage (10 mL/kg) 16 h before LPS (or saline) stimulation at predetermined doses, and euthanized with $CO_2$ at 1.5 h after the stimulation for cardiac blood collection. The whole blood was not anticoagulated, incubated in wet ice for 1.5 h, and centrifuged at 2000×g at 4° C. for 10 min to separate the serum. Serum was frozen at −80° C. for TNF-α assay. Quantification of TNF-α was done by TNF-α ELISA kit according to the manufacturer's instructions. The readings of absorbance at A450 were measured with a microplate reader SpectraMax i3x (Molecular Device) for calculating the inhibition of the compounds, and $IC_{50}$ was calculated with GraphPad Prism 7.0 software. Test results show that the compounds in the examples of the present invention have significant inhibitory effect on cytokine TNF-α release in LPS-induced Balb/c female mice, and the inhibition rate is greater than 50%, preferably greater than 70%. In particular, some exemplary compound inhibition rate values are as follows:

TABLE 6

| Inhibition rate of cytokine TNF-α release in LPS-induced Balb/c female mice | |
|---|---|
| Compound ID | Inhibition rate (%) of TNF-α |
| 013 | 76.29 |
| 001 | 74.00 |
| 163 | 71.56 |
| 016 | 78.71 |

Test Example 7. Determination of Inhibition of Five Major CYP450 Enzyme Subtypes in Human Liver Microsomes by the Compounds Disclosed Herein This study was intended to investigate the inhibitory effect of the test compounds on 5 major enzymes in human P450 superfamily, CYP1A2, 2C9, 2C19, 2D6 and 3A4-M. The mixed human liver microsomes used in this assay were purchased from Corning (USA). The test compound (compound 14) was co-incubated at 7 concentrations with human liver microsomes and five probe substrates (phenacetin for CYP1a2, diclofenac for CYP2C9, mephenytoin for CYP2C19, dextromethorphan for CYP2D6, midazolam for CYP3A4-M, mixed). See the table below. The reaction was initiated by adding coenzyme NADPH, and terminated by adding acetonitrile containing internal standard. After the proteins were precipitated, the supernatant was centrifuged. The characteristic metabolites in the supernatant (acetaminophen for CYP1A2, 4-hydroxydiclofenac for CYP2C9, 4-hydroxymephenytoin for CYP2C19, dextrorphan for CYP2D6, 1-hydroxymidazolam for CYP3A4-M) were analyzed by LC-MS/MS. The influence of the test compounds on production of the characteristic metabolites was finally analyzed on the basis of the data obtained. A selective inhibitor (ketoconazole for CYP3A4-M) may be used as positive control. All samples were tested in duplicate.

Test results show that the compounds of the examples of the present invention all have no obvious inhibition effect on the 5 human CYP subtypes, and the inhibition effect on the 3 subtypes 1A2, 2C9 and 2C19 is obviously smaller than that of the control compound A. In particular, some exemplary compound inhibition rate values arc as follows:

TABLE 7

| Inhibition of the compounds for five major CYP450 enzyme subtypes in human liver microsomes CYP1A2, 2C9, 2C19, 2D6 and 3A4 ($IC_{50}$, nM) | | | | | |
|---|---|---|---|---|---|
| | Subtype | | | | |
| Compound ID | 1A2 | 2C9 | 2C19 | 2D6 | 3A4 |
| A | 2.91 | 19.06 | 23.48 | >30 | >30 |
| 001 | >30 | >30 | >30 | >30 | >30 |
| 163 | >30 | >30 | >30 | >30 | >30 |

Test Example 8. PK of the Compounds Disclosed Herein in Rat

The rats used for pharmacokinetic study in the preferred example in the present invention were male SPF-grade SD rats (B&K Universal, Shanghai).

Route of administration: a single dose by oral gavage or intravenous injection

Sampling points: 0.083 h, 0.25 h, 0.5 h, 1 h, 2 h, 4 h, 6 h, 8 h and 24 h after administration Sample processing: 0.2 mL of venous blood was collected, and let stand on ice before centrifugation to separate plasma (centrifugation conditions: 8000 rpm, 6 min, 4° C.). The separated plasma was stored at −80° C. before analysis.

Internal standard working solution: An appropriate amount of tolbutamide internal standard stock solution at 645,000 ng/mL was added into a volumetric flask, and was diluted to the volume with methanol. The solution was well mixed to give an internal standard working solution with a concentration of 50 ng/mL.

Sample pretreatment: 50 μL of plasma was added into a 1.5-mL centrifuge tube, and added with 250 μL of internal standard solution (methanol of the same volume for the blank control). The solution was well mixed by vortex, and centrifuged for 5 min at 14000 rpm. 200 μL of the supernatant was transferred into a 96-well sample feeding plate, and loaded onto a LC-MS/MS system.

LC Conditions:

Column: ACQUITY UPLC BEH C18 1.7 μm (50 mm×2.10 mm)

Mobile phase: A: 0.1% aqueous formic acid: B: 0.1% formic acid in acetonitrile

Flow rate: 0.5 mL/min

The data processing system was Analyst software (Applied Biosystems, USA, ver 1.5.5).

Results show that the compounds in the examples of the present invention have good pharmacokinetic characteristics on mice, show excellent exposure and retention time in animals, and have suitable half-life and good drug absorption. In particular, pharmacokinetics data of some exemplary compounds are as

TABLE 8

Pharmacokinetic study data for single oral gavage dosing of different compounds in ICR mice

| | | | PK for oral gavage | | | | | |
|---|---|---|---|---|---|---|---|---|
| Compound No. | Dose Dose (mpk) | Formulation Formulation | Time to peak $t_{max}$ (h) | Peak concentration $C_{max}$ (ng/mL) | Area under curve $AUC_{0-t}$ (ng/mL*h) | Area under curve $AUC_{0-\infty}$ (ng/mL*h) | Half life $t_{1/2}$ (h) | Average retention time MRT (h) |
| 163 | 40 | 15% solutol HS15 + 85% PBS | 4 | 25875 | 206683 | 206702 | 3.62 | 6.75 |
| 001 | 40 | 15% solutol HS15 + 85% PBS | 4 | 24153 | 293784 | 375482 | 11.47 | 15.31 |
| 013 | 40 | 15% solutol HS15 + 85% PBS | 1 | 18924 | 160198 | 182133 | 7.23 | 10.41 |

The examples of the present invention have been described above. However, the present invention is not limited to the above examples. Any modification, equivalent, improvement and the like made without departing from the spirit and principle of the present invention shall fall within the protection scope of the present invention.

The invention claimed is:

1. A compound of formula I, or a stereoisomer, a racemate, a tautomer, or a pharmaceutically acceptable salt thereof, Formula I

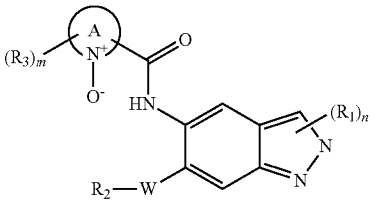

wherein:

ring A is 5-14 membered heteroaryl or 5-12 heterocyclyl containing at least one N;

$R_1$ and $R_3$ are each independently selected from the group consisting of hydrogen, halogen, CN, OH, and the following groups optionally substituted with one, two, or more R: ($C_1$-$C_{12}$) aliphatic hydrocarbyl, ($C_1$-$C_{12}$) aliphatic hydrocarbyl optionally comprising one, two, or more heteroatoms, $C_{3-12}$ cycloalkyl, 3-12 membered heterocyclyl, $C_6$-20 aryl or 5-14 membered heteroaryl, and —$NR_aR_b$;

$R_2$ is selected from the group consisting of halogen, CN, OH, and the following groups optionally substituted with one, two, or more R: ($C_1$-$C_{12}$) aliphatic hydrocarbyl, ($C_1$-$C_{12}$) aliphatic hydrocarbyl optionally comprising one, two, or more heteroatoms, $C_{3-12}$ cycloalkyl, 3-12 membered heterocyclyl, $C_{6-20}$ aryl or 5-14 membered heteroaryl, and —$NR_aR_b$;

W is selected from the group consisting of O, S, NH, and a single bond;

Ra and $R_b$ are each independently selected from the group consisting of H and ($C_1$-$C_{12}$) aliphatic hydrocarbyl;

each R is independently selected from the group consisting of halogen, CN, OH, SH, $NR_aR_b$, and the following groups optionally substituted with one, two, or more R': ($C_1$-$C_{12}$)aliphatic hydrocarbyl, ($C_1$-$C_{12}$) aliphatic hydrocarbyl optionally comprising one, two, or more heteroatoms, $C_{3-12}$ cycloalkyl, 3-12 membered heterocyclyl, and $C_6$-20 aryl or 5-14 membered heteroaryl;

each R' is independently selected from the group consisting of halogen, CN, OH, SH, and $NR_aR_b$;

n is selected from the group consisting of 1, 2, and 3; and m is selected from the group consisting of 1, 2, 3, 4, 5, and 6.

2. The compound of claim 1, wherein:

each "($C_1$-$C_{12}$) aliphatic hydrocarbyl optionally comprising one, two, or more heteroatoms" is independently selected from the group consisting of ($C_1$-$C_{12}$) aliphatic hydrocarbyloxy, ($C_1$-$C_{12}$) aliphatic hydrocarbylthio, ($C_1$-$C_6$) aliphatic hydrocarbyloxy ($C_1$-$C_6$) aliphatic hydrocarbyl, ($C_1$-$C_6$) aliphatic hydrocarbylthio($C_1$-$C_6$) aliphatic hydrocarbyl, N—($C_1$-$C_3$) aliphatic hydrocarbylamino ($C_1$-$C_6$) aliphatic hydrocarbyl, and N, N-di-($C_1$-$C_3$) aliphatic hydrocarbylamino ($C_1$-$C_6$) aliphatic hydrocarbyl;

ring A is selected from the group consisting of pyridine, pyrrole, piperidine, and tetrahydropyrrole;

each "($C_1$-$C_{12}$) aliphatic hydrocarbyl" is independently selected from the group consisting of ($C_1$-$C_6$)alkyl, ($C_2$-$C_6$)alkenyl, and ($C_2$-$C_6$)alkynyl;

each "halogen" is independently selected from the group consisting of F, Cl, Br, and I; and each "$C_{3-12}$ cycloalkyl" is independently selected from the group consisting of cyclopropyl, cyclobutyl, cyclopentyl, and cyclohexyl.

3. The compound of claim 1, wherein:

$R_1$, $R_2$, and $R_3$ are each independently selected from the group consisting of the following groups optionally substituted with one, two, or more R: methyl, ethyl, n-propyl, isopropyl, n-butyl, isobutyl, tert-butyl, n-pentyl, isopentyl, neopentyl, n-hexyl, ethenyl, 1-propenyl, 2-propenyl, 1-methylethenyl, 1-butenyl, 1-ethylethenyl, 1-methyl-2-propenyl, 2-butenyl, 3-butenyl, 2-methyl-1-propenyl, 2-methyl-2-propenyl, 1-pentenyl, 1-hexenyl, ethynyl, 1-propynyl, 2-propynyl, 1-butynyl, 1-methyl-2-propynyl, 3-butynyl, 1-pentynyl, 1-hexynyl, cyclopropyl, cyclobutyl, cyclopentyl, cyclohexyl, methoxy, ethoxyl, propoxy, butoxy, pentyloxy, methoxymethyl, ethoxylmethyl, propoxymethyl, methoxyethyl, ethoxylethyl, propoxyethyl, methoxypropyl, ethoxylpropyl, propoxypropyl, N-methylaminomethyl, N-methylaminoethyl, N-ethylaminoethyl, N,N-dimethylaminomethyl, N,N-dimethylaminoethyl, N,N-diethylaminoethyl, amino, N,N-dimethylamino, N,N-diethylamino, tetrahydropyrrolyl, piperidinyl, pyridyl, pyrazinyl, pyrrolyl, imidazolyl, pyrazolyl, oxazolyl, isoxazolyl,

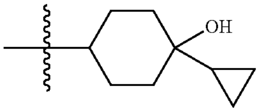,
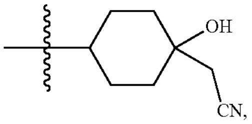,
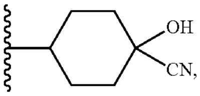,
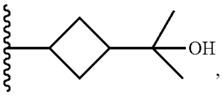,
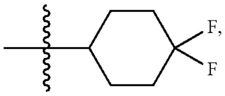,
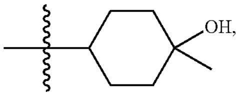,
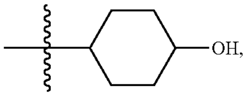,
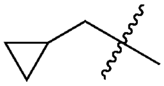,
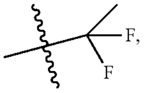,
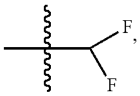,
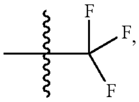,
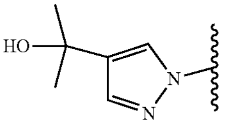,
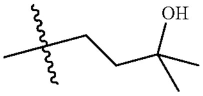, and
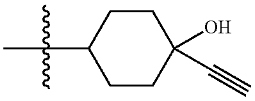;

and the "⌇" denotes the connection site of the group.

4. The compound of claim 1, which is a compound of formula Ia, formula Ib, formula Ic, formula Id, or formula Ie:

formula Ia

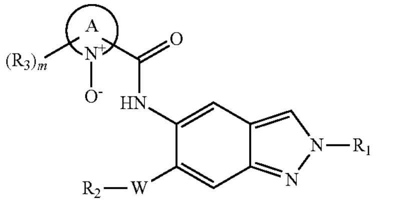

-continued formula Ib

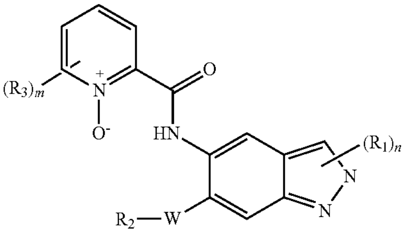

formula Ic

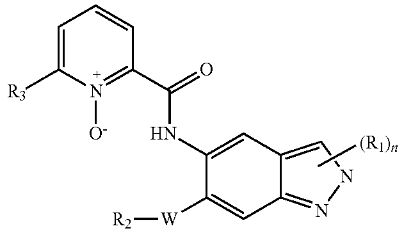

formula Id

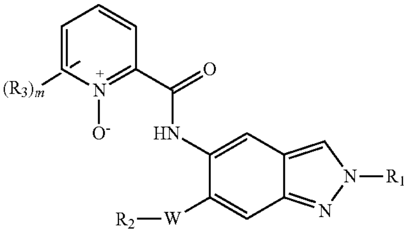

formula Ie

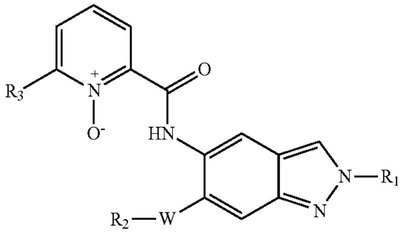

or a stereoisomer, a racemate, a tautomer, or a pharmaceutically acceptable salt thereof.

5. A compound selected from the group consisting of the following structures:

001

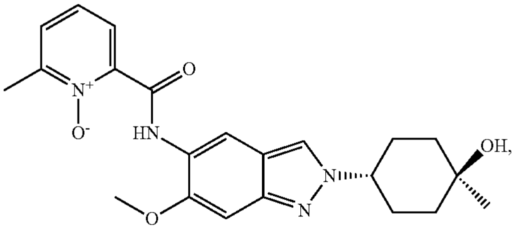

-continued
002
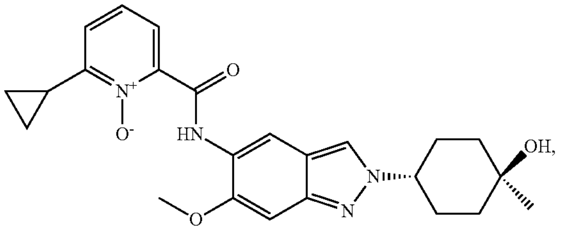
003
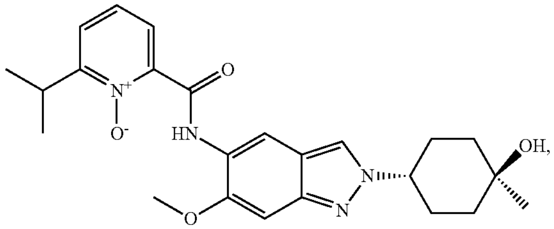
004
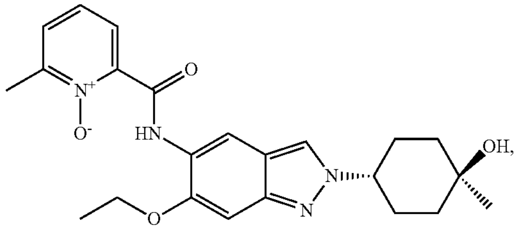
005
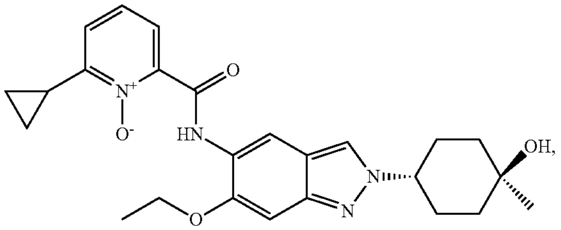
006
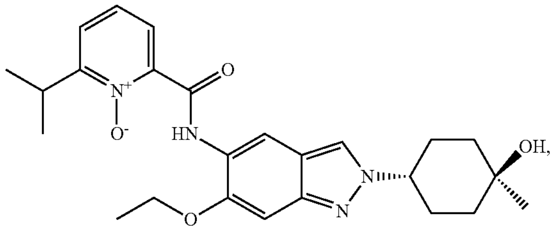
007
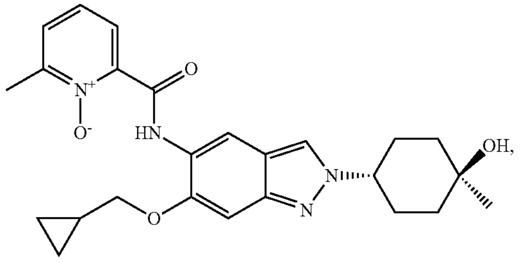
-continued
008
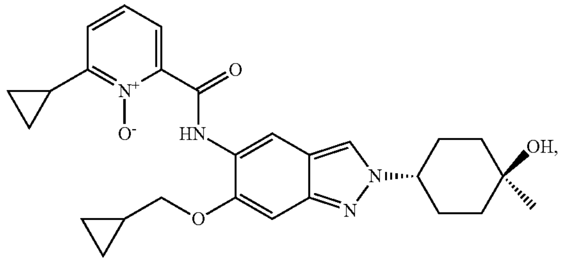
009
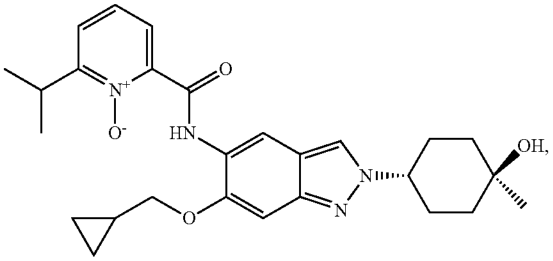
010
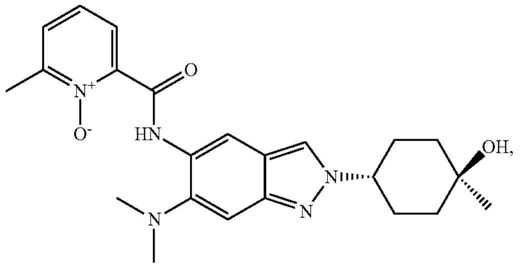
011
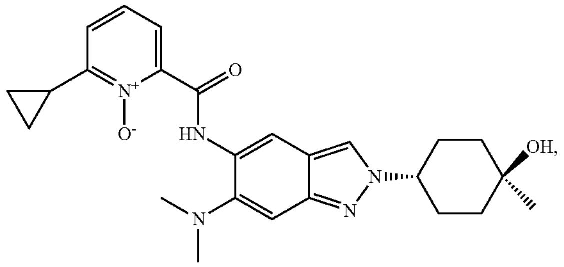
012
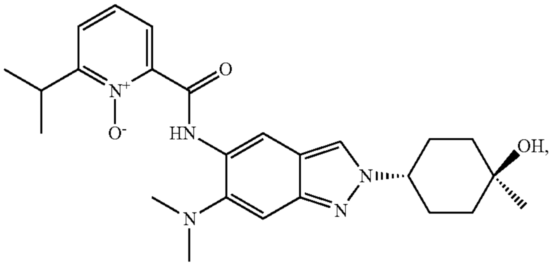

-continued
013
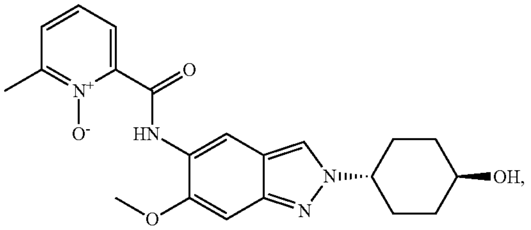
014
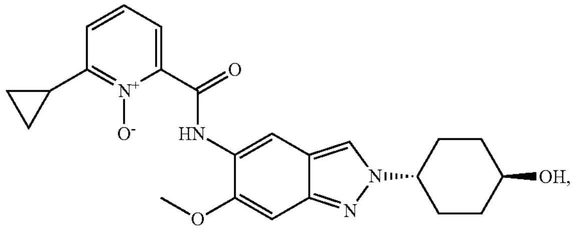
015
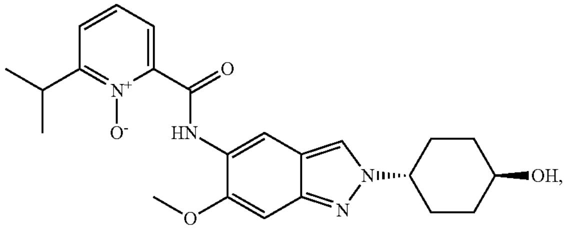
016
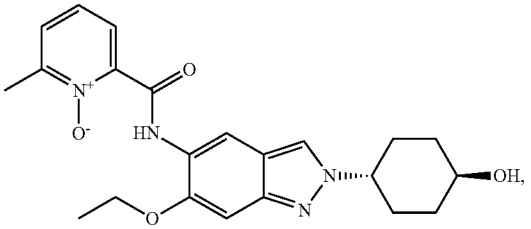
017
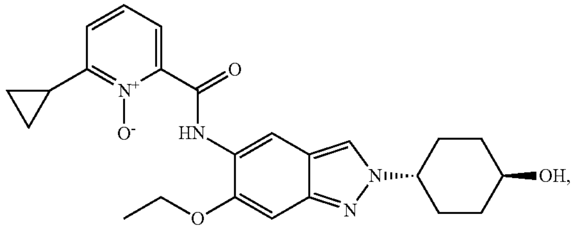
018
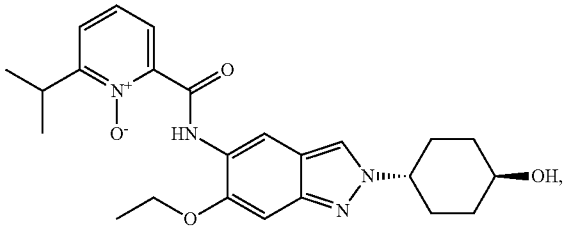
-continued
019
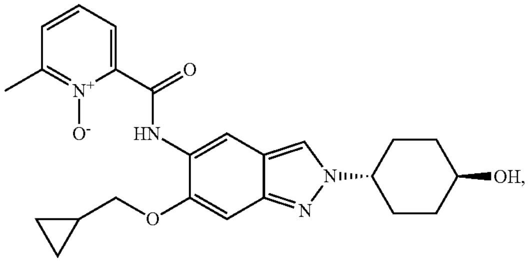
020
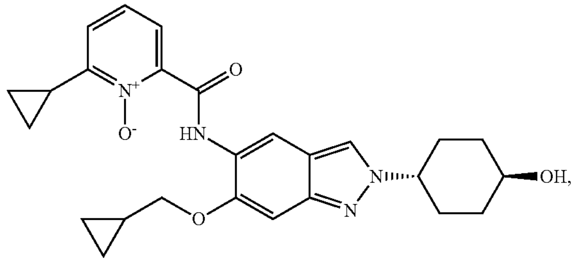
021
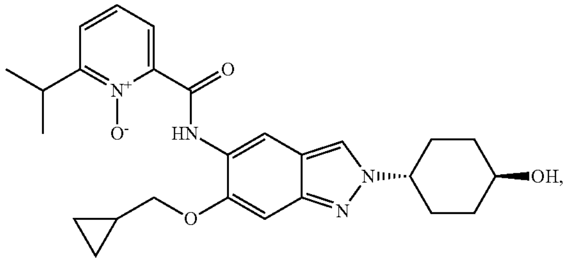
022
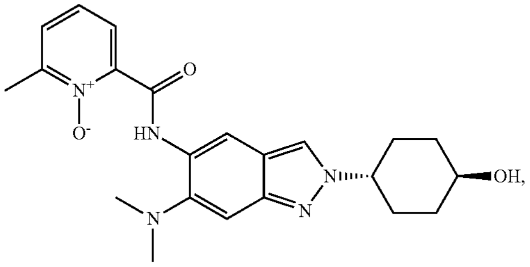
023
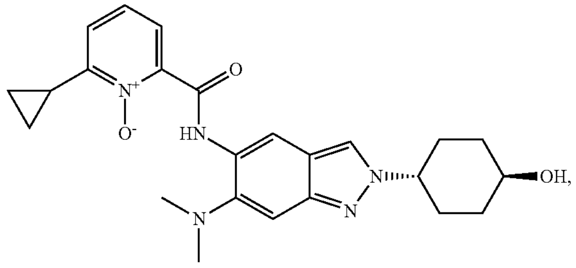

-continued
024
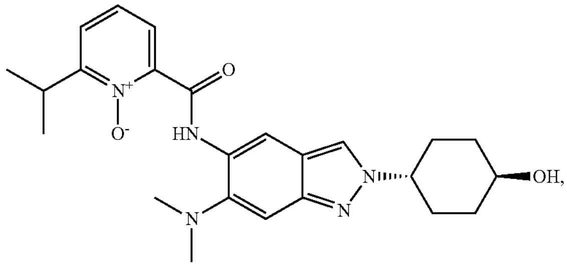
,
025
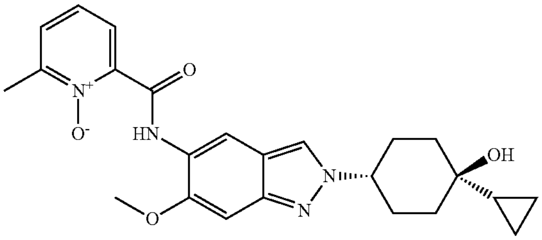
,
026
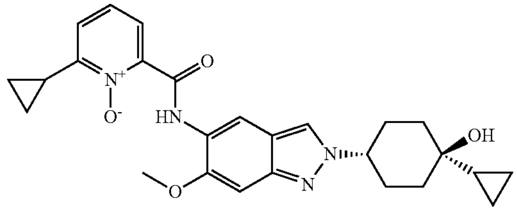
,
027
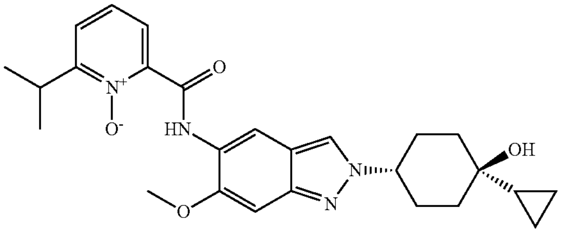
,
028
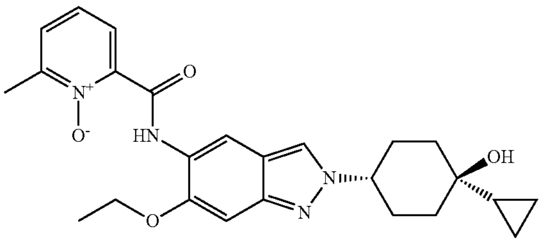
,
029
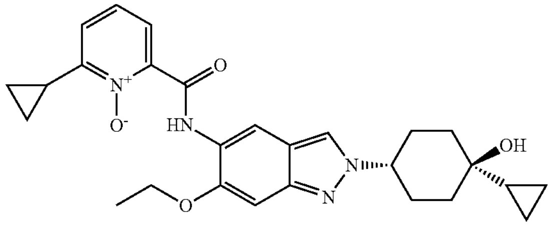
,
-continued
030
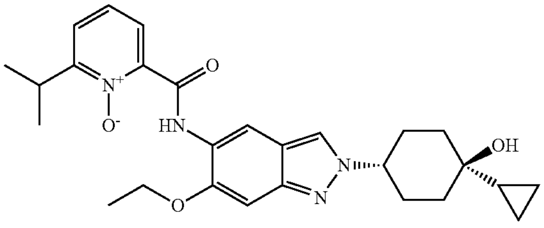
,
031
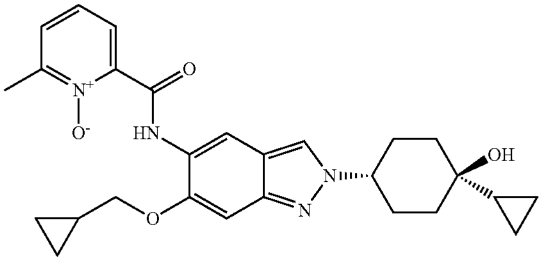
,
032
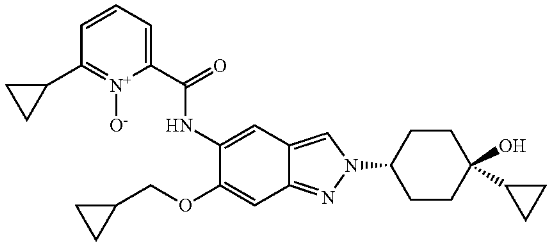
,
033
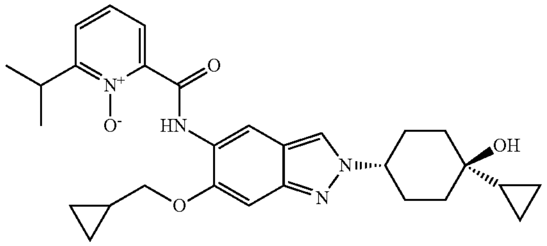
,
034
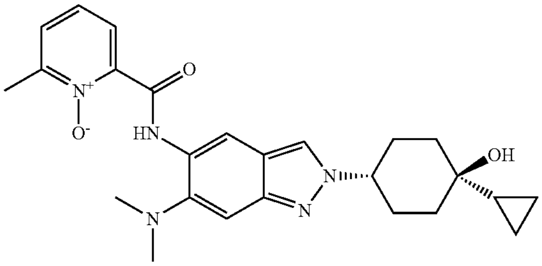
, -continued
035
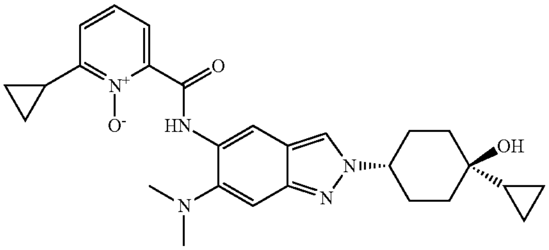
,
036
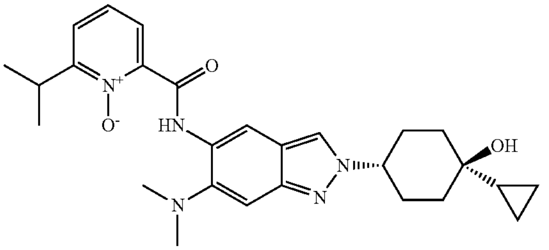
,
037
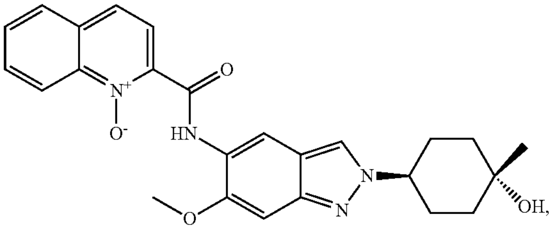
038
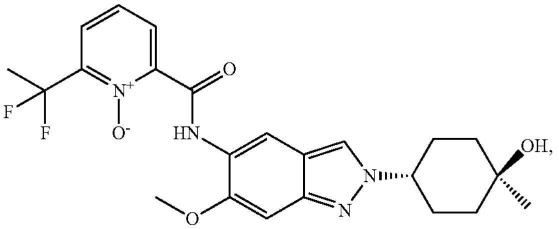
039
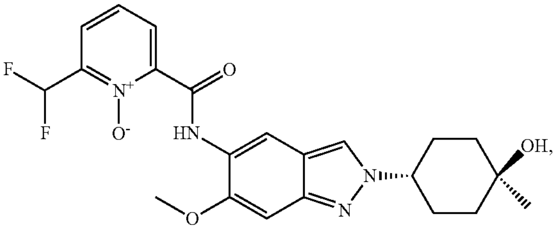
040
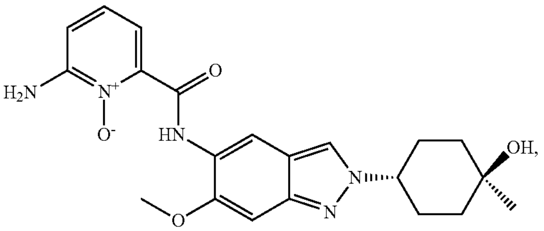
-continued
041
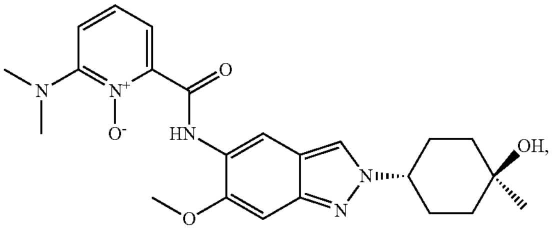
042
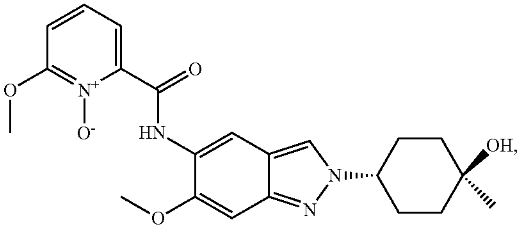
043
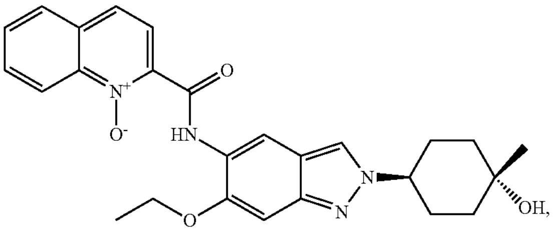
044
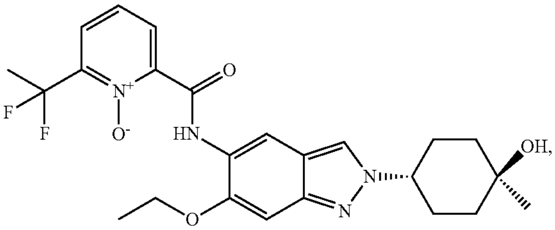
045
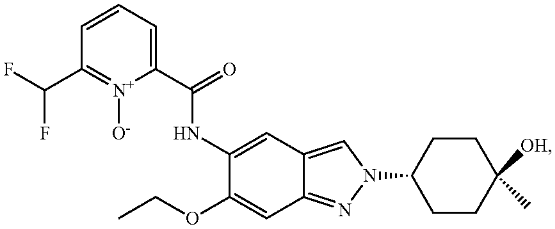
046
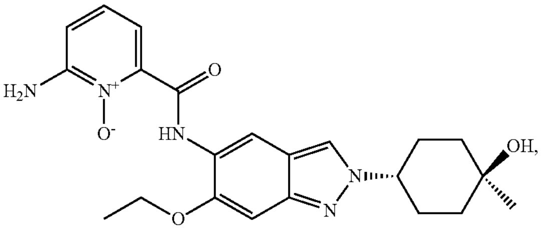

-continued
047
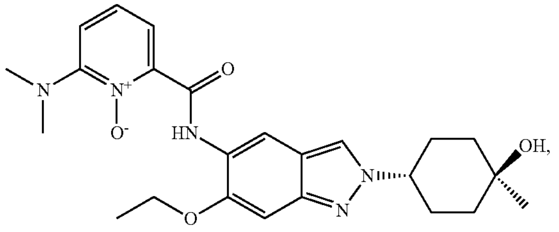
048
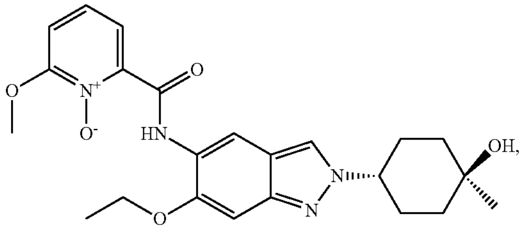
049
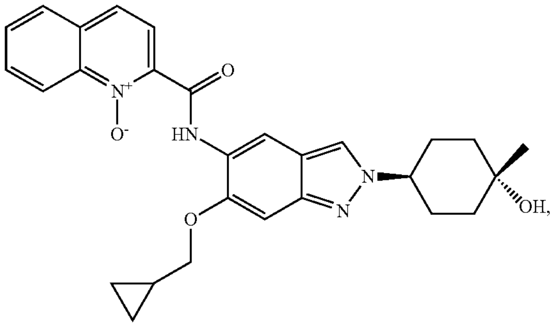
050
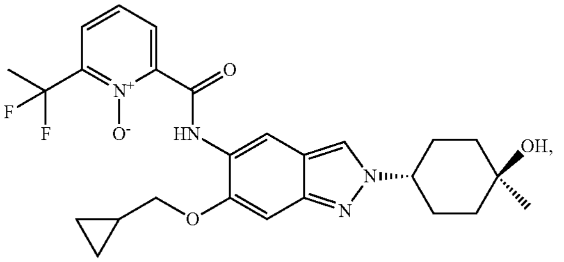
051
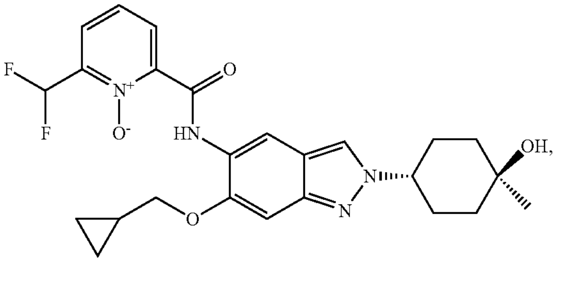
-continued
052
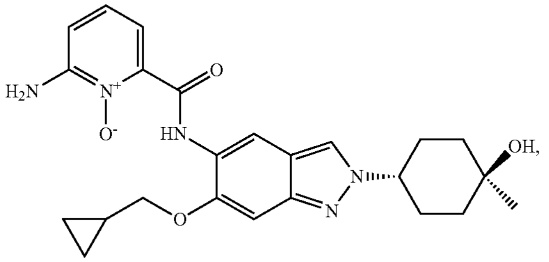
053
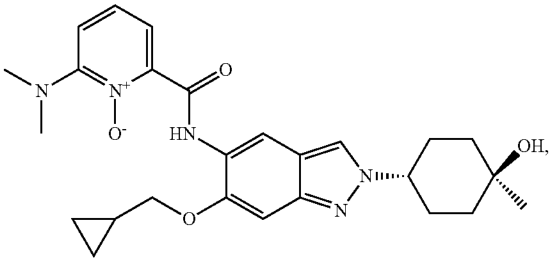
054
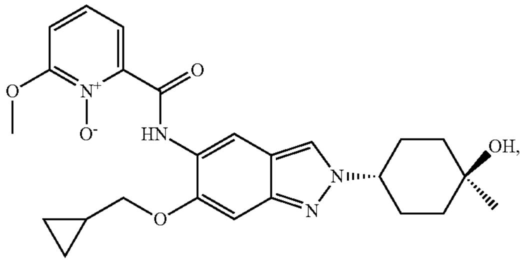
055
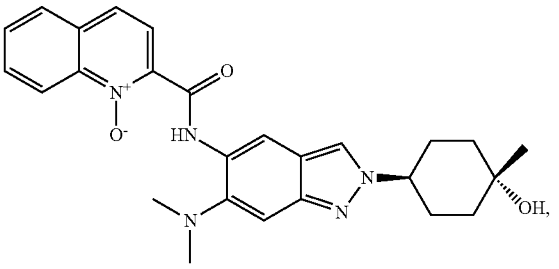
056
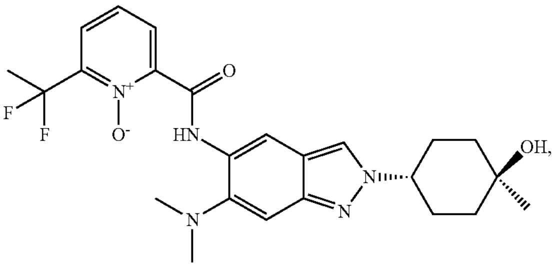

-continued
057
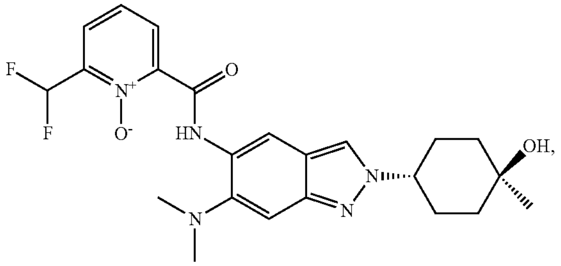
058
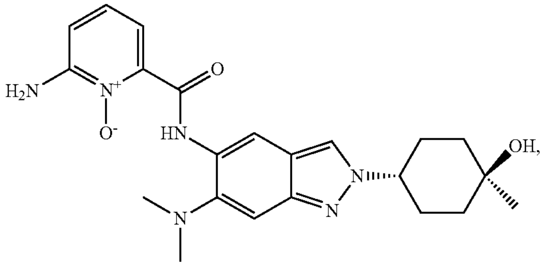
059
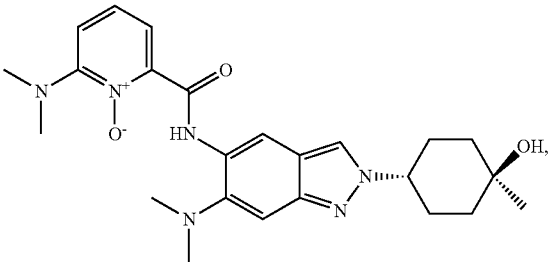
060
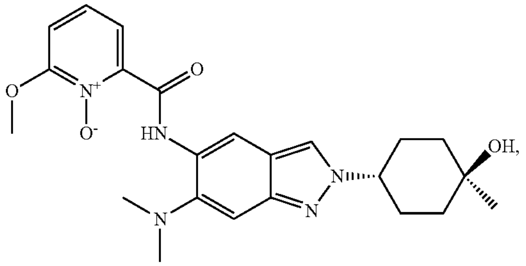
061
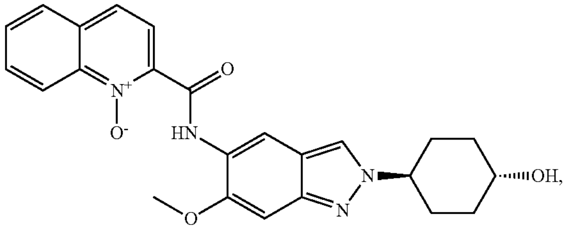
-continued
062
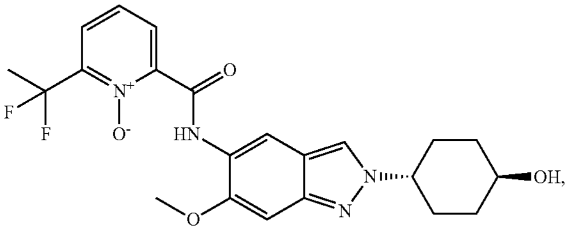
063
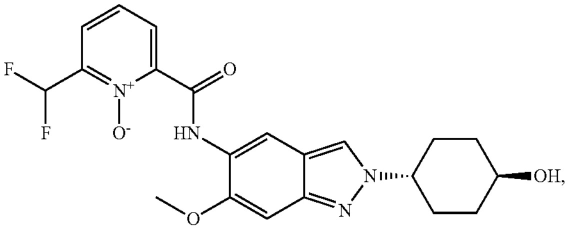
064
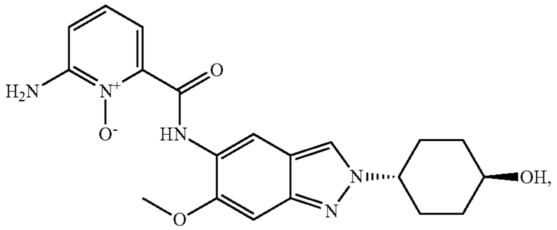
065
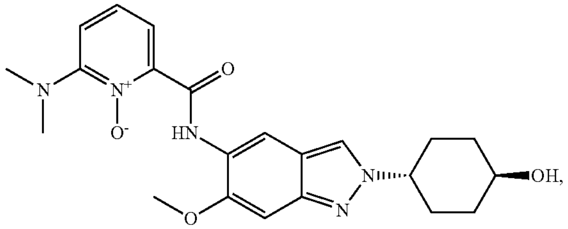
066
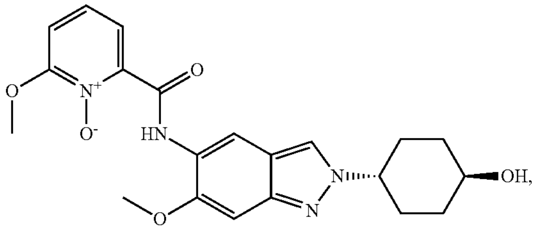
067
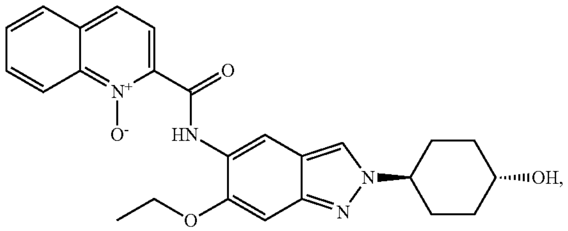

-continued
068
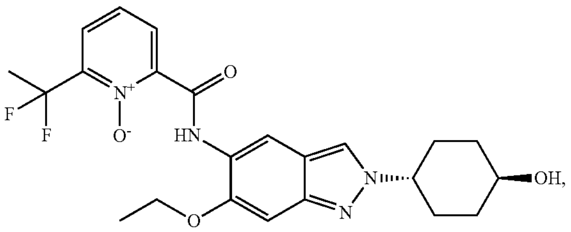
069
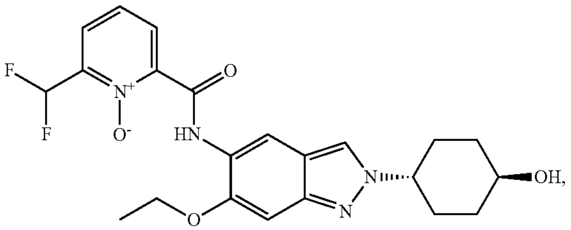
070
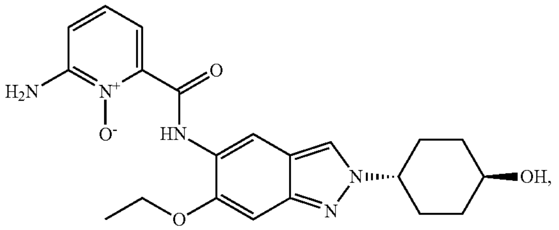
071
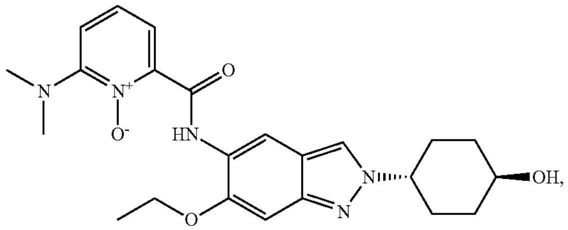
072
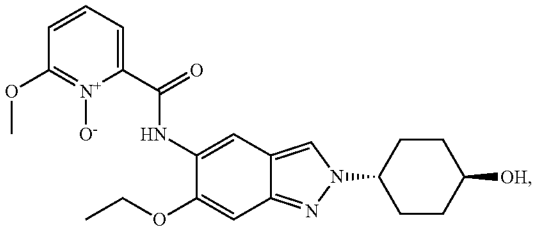
073
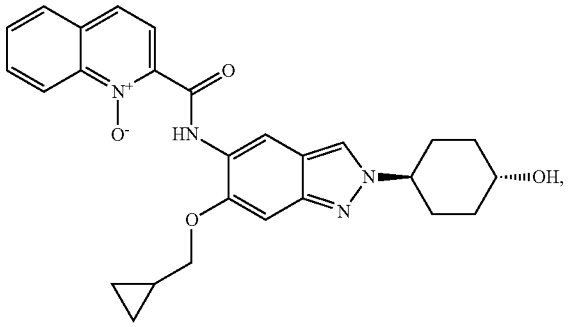
-continued
074
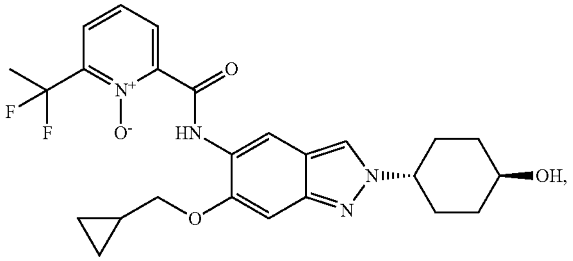
075
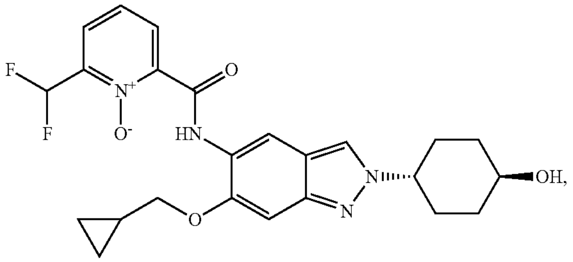
076
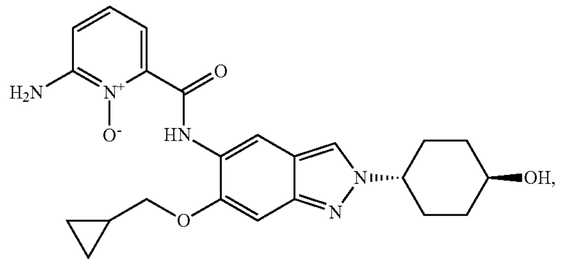
077
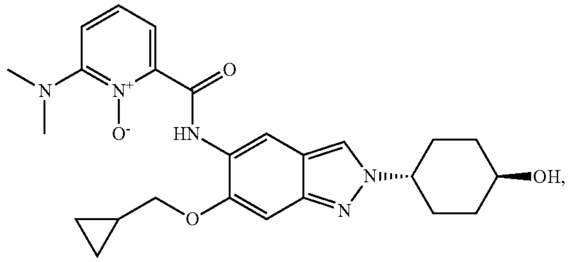
078
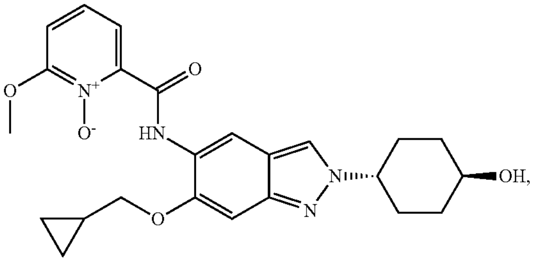

-continued
079
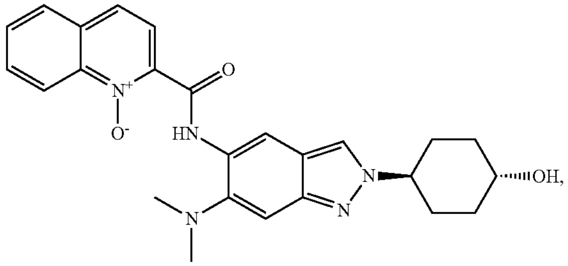
080
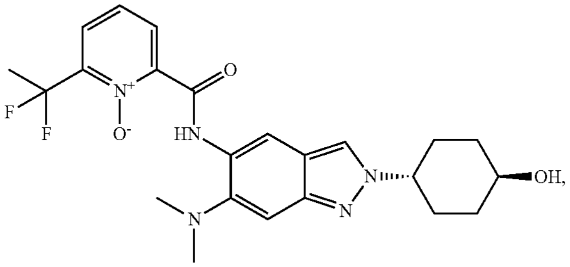
081
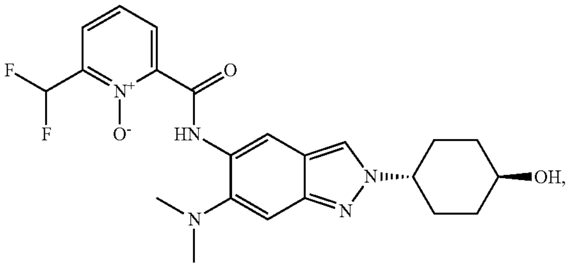
082
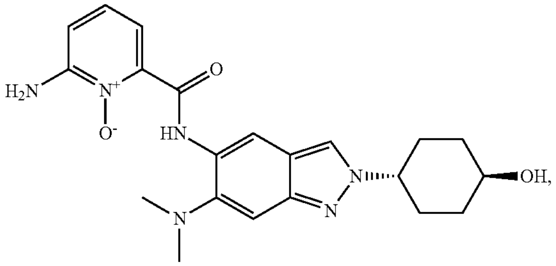
083
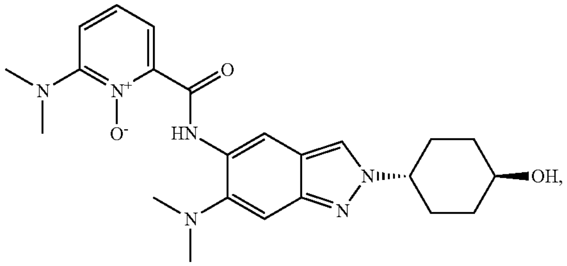
-continued
084
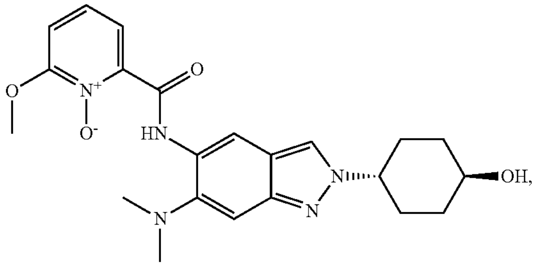
085
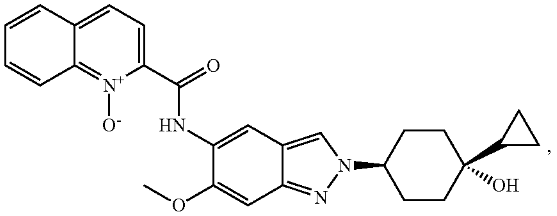
086
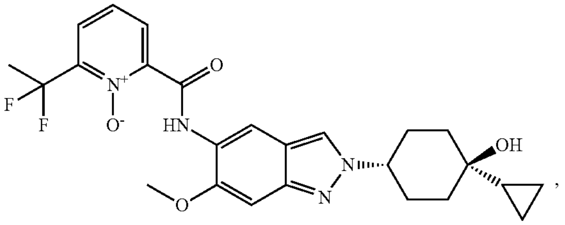
087
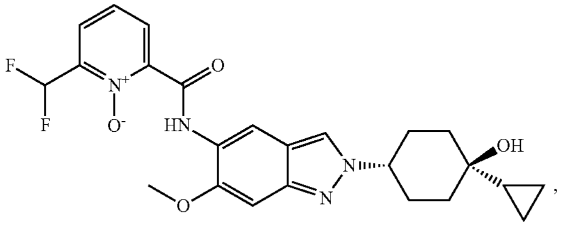
088
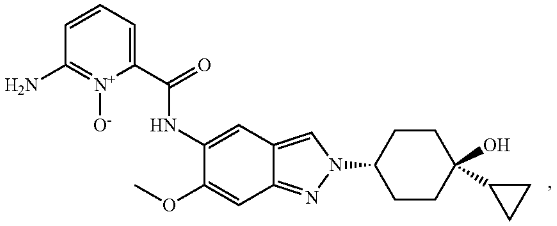
089
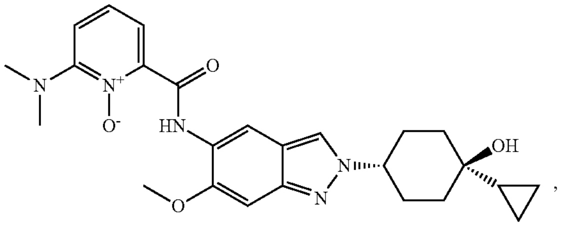

-continued
090
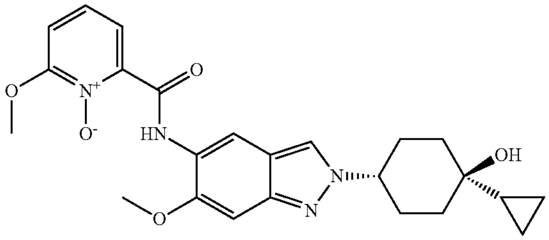,
091
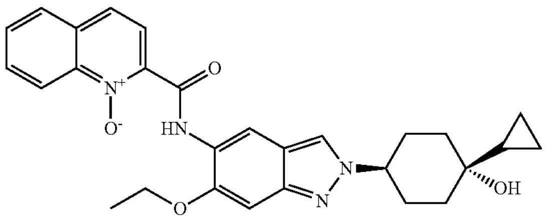,
092
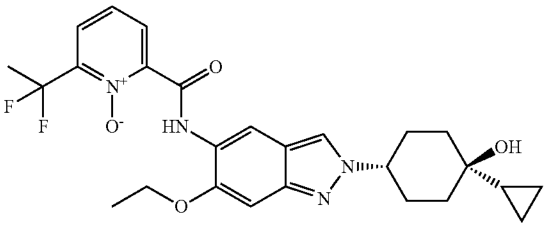,
093
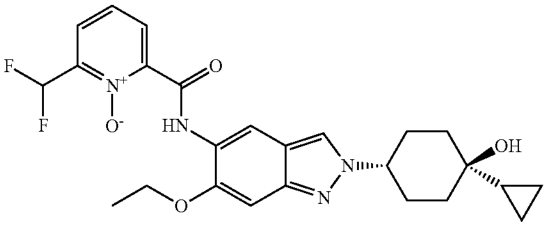,
094
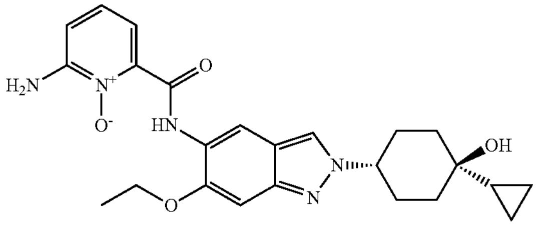,
095
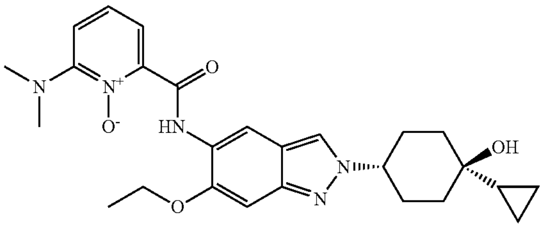,
-continued
096
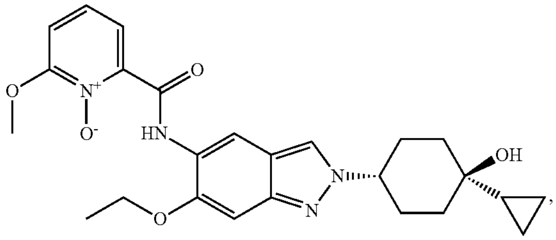,
097
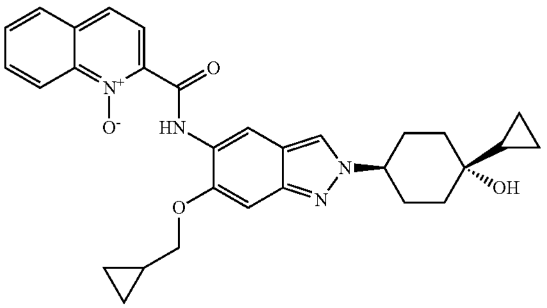,
098
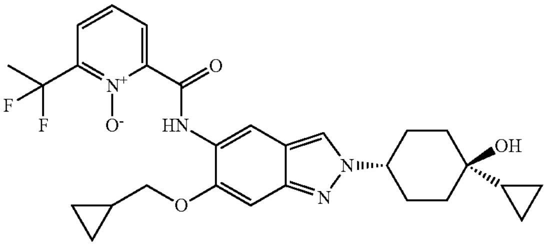,
099
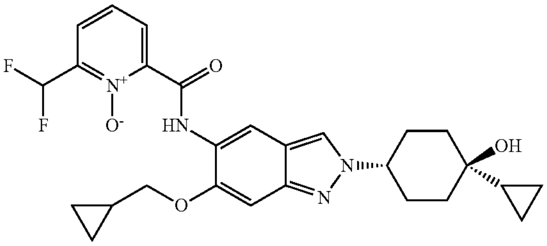,
100
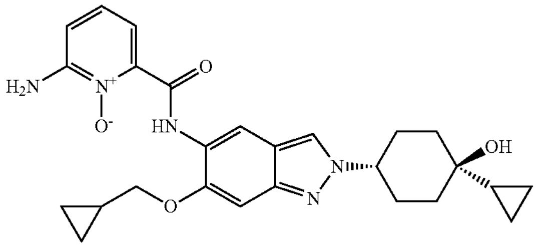, -continued
101
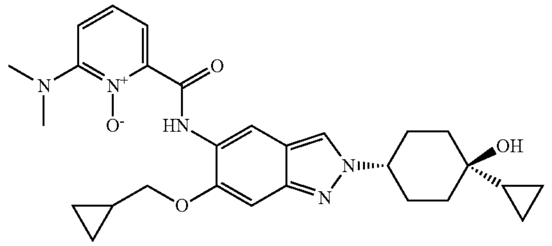
,
102
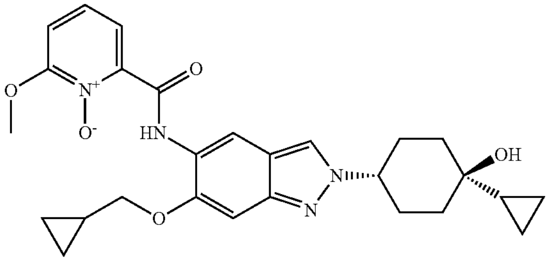
,
103
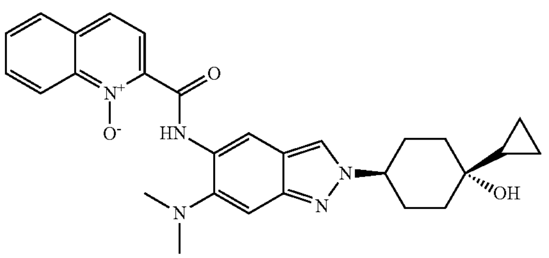
,
104
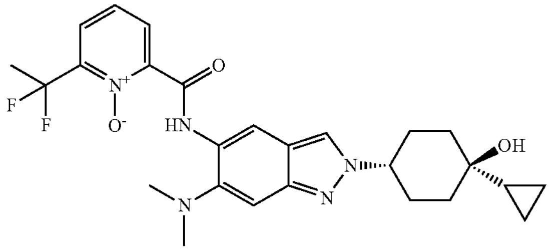
,
105
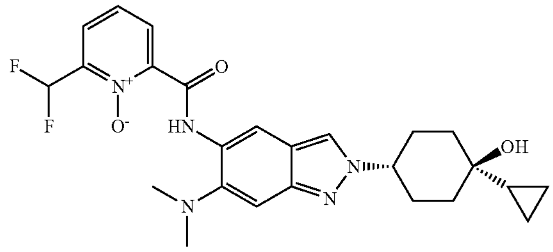
,
-continued
106
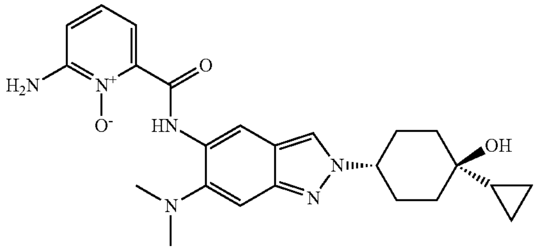
,
107
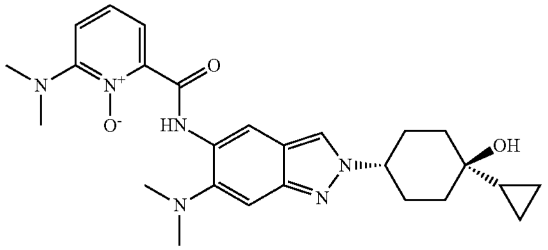
,
108
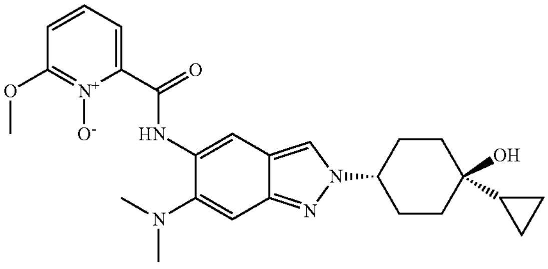
,
109
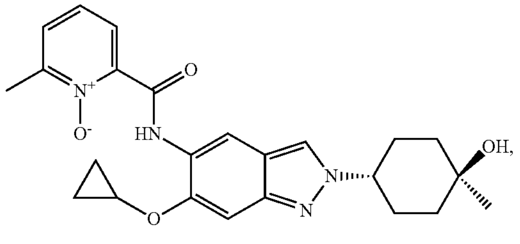
110
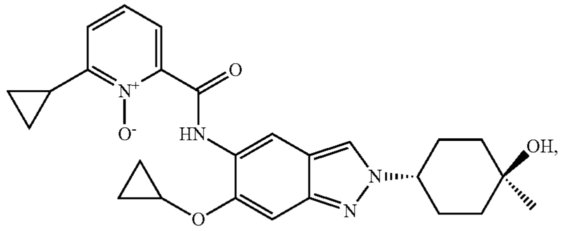
111
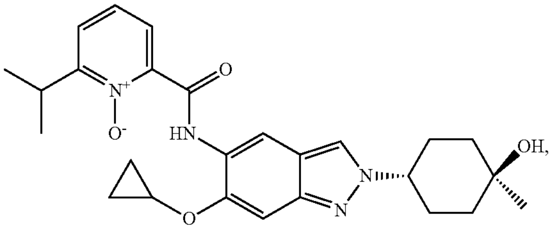

112
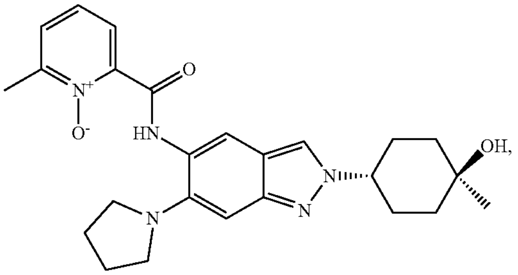
113
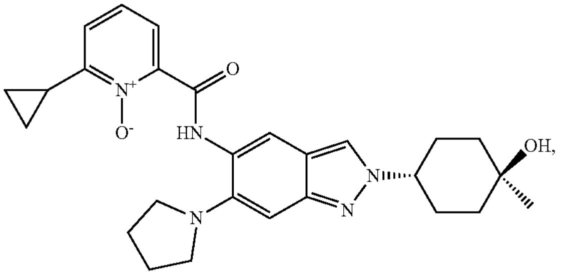
114
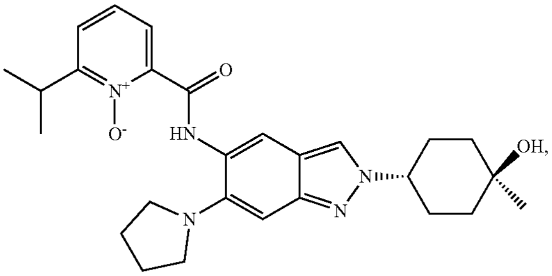
115
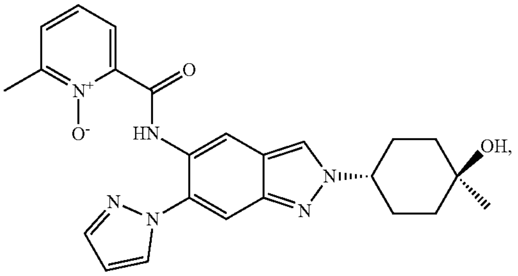
116
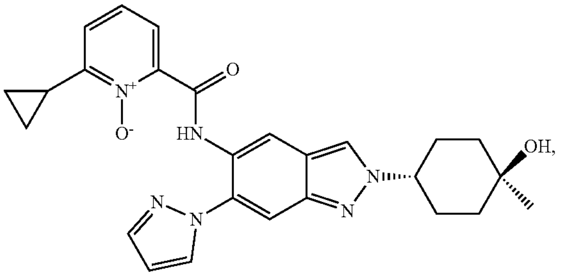
117
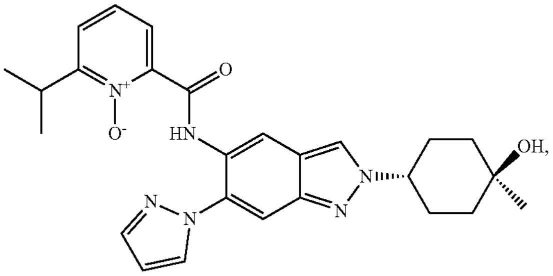
118
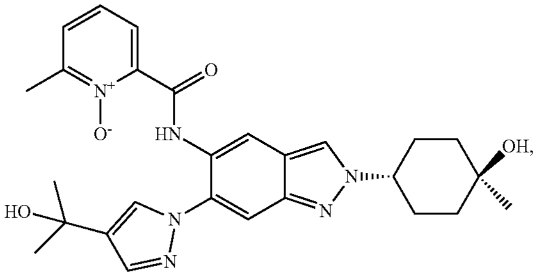
119
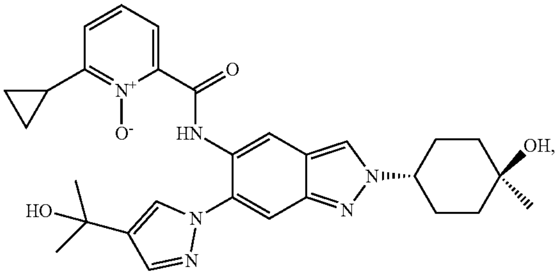
120
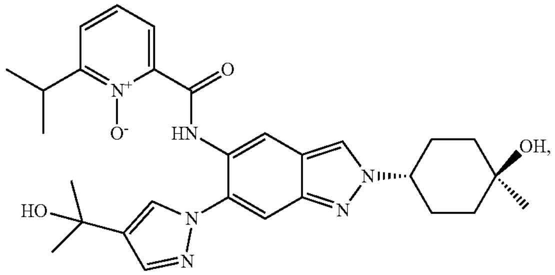
121
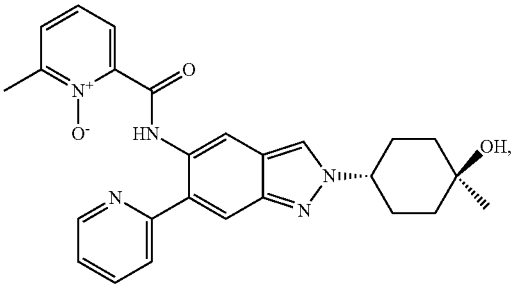

-continued
122
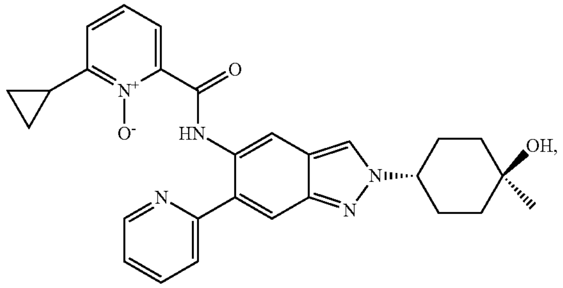
123
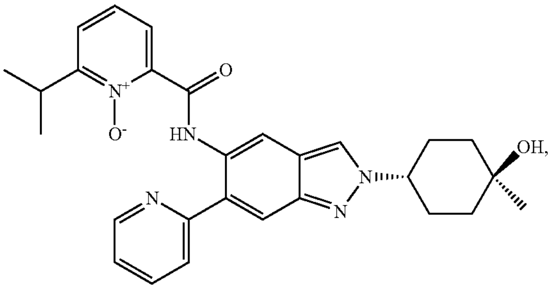
124
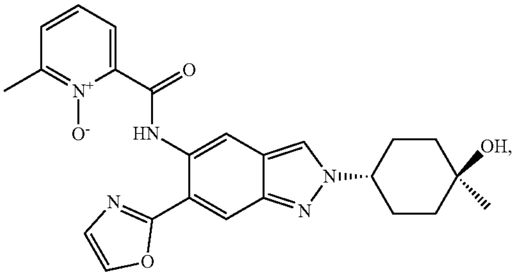
125
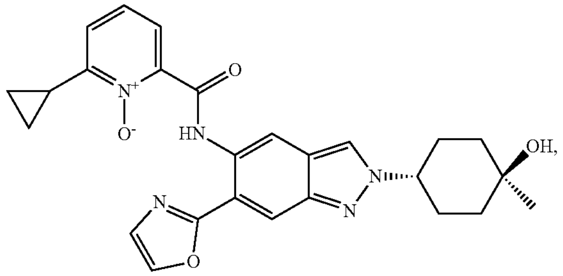
126
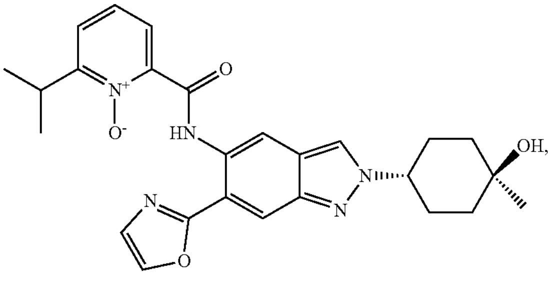
-continued
127
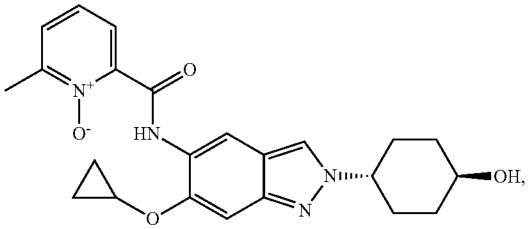
128
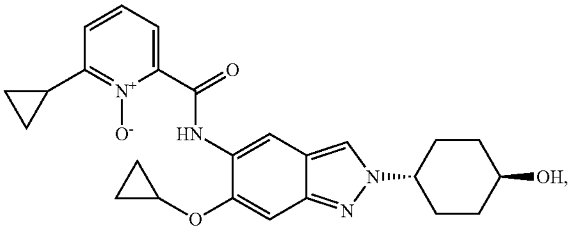
129
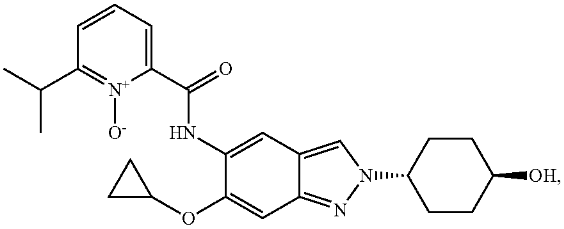
130
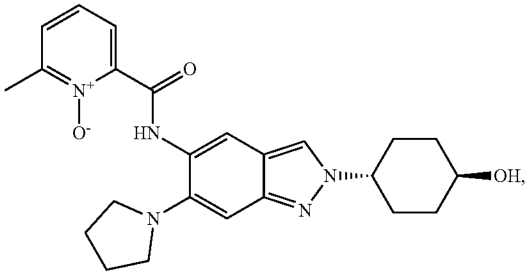
131
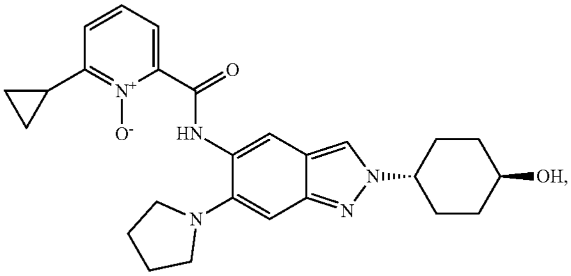

-continued
132
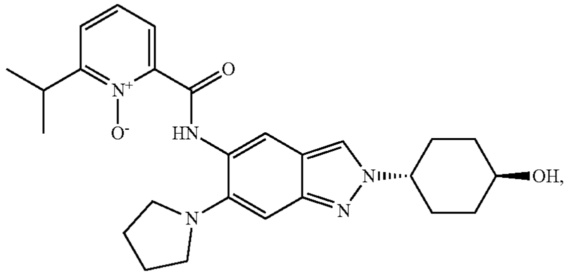
133
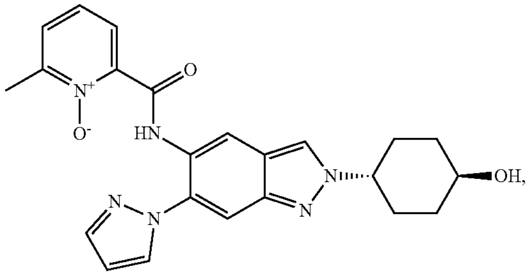
134
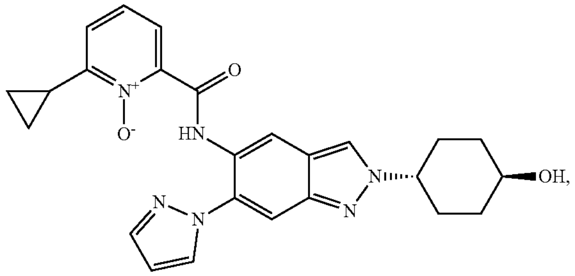
135
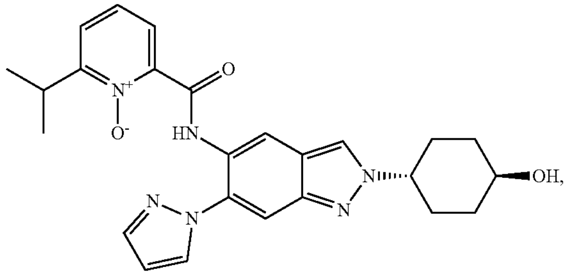
136
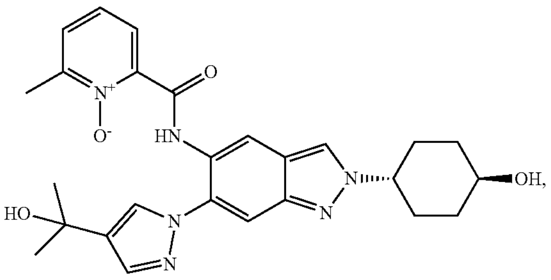
-continued
137
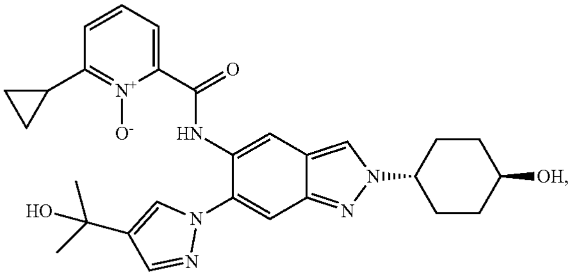
138
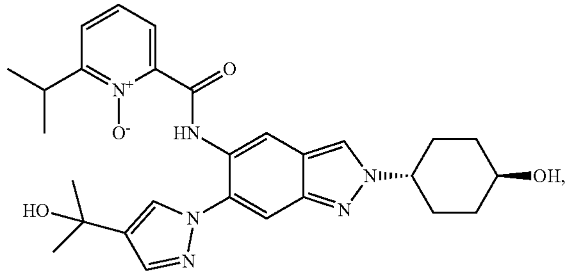
139
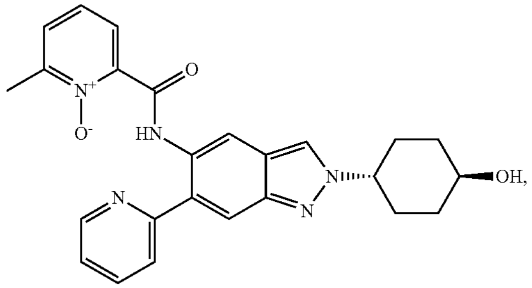
140
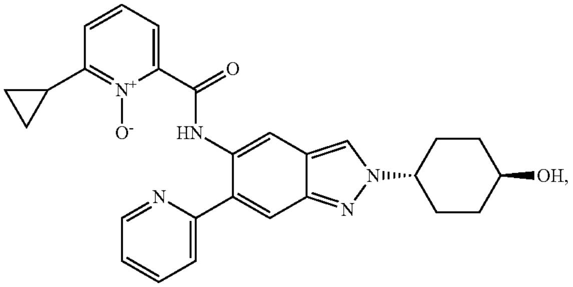
141
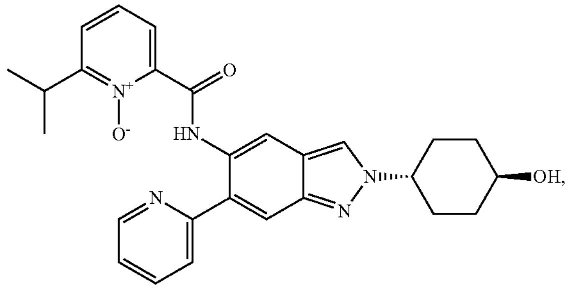

-continued
142
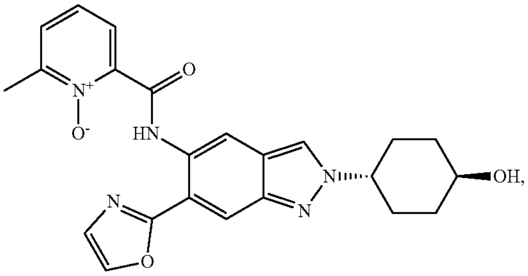
143
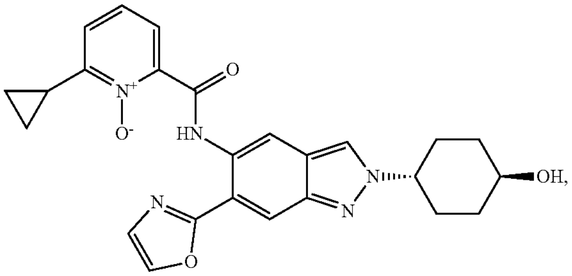
144
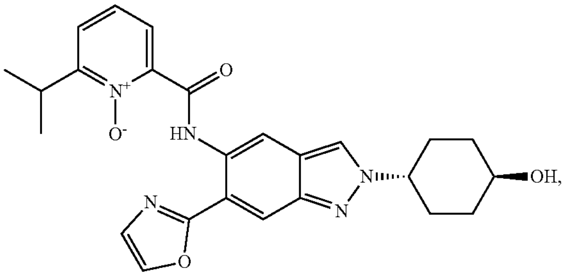
145
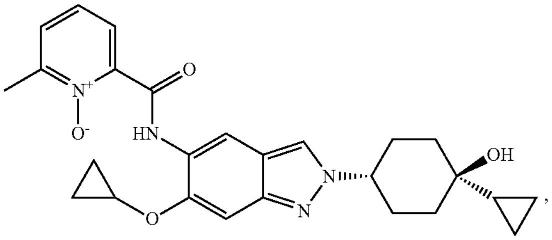
146
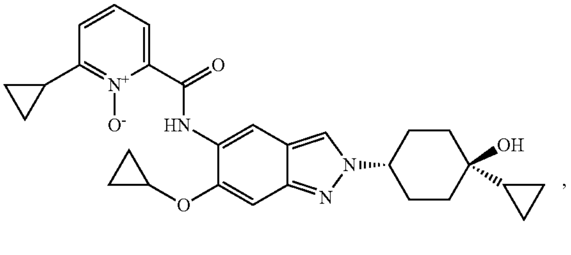
-continued
147
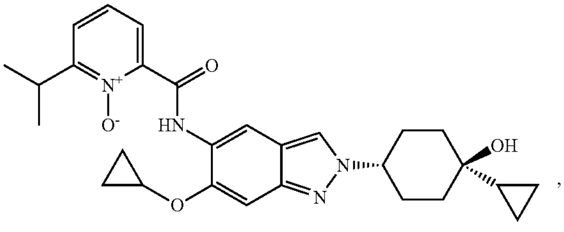
148
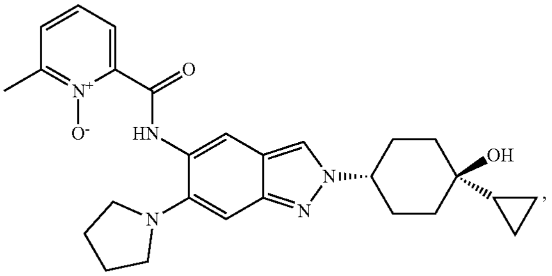
149
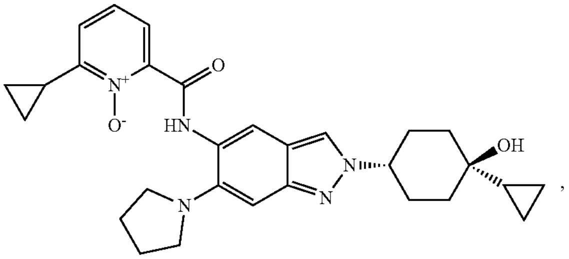
150
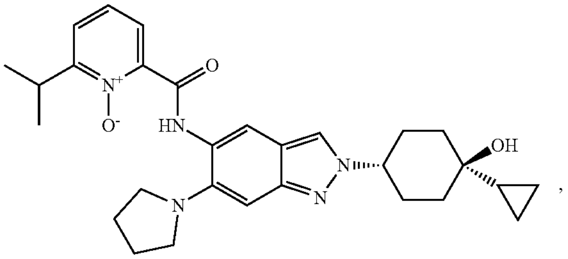
151
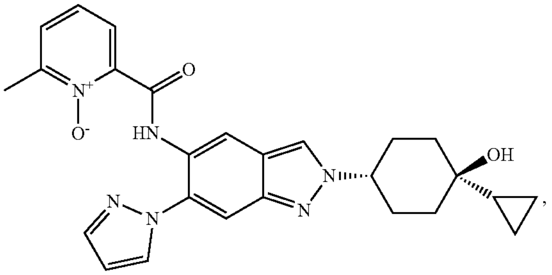

-continued
152
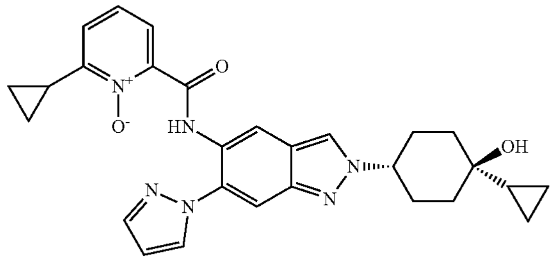
,
153
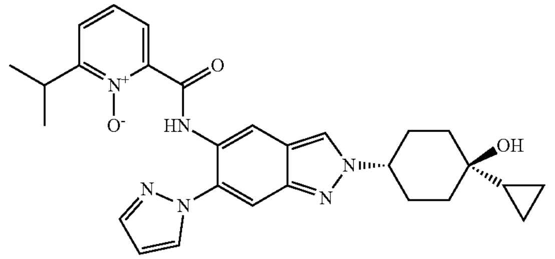
,
154
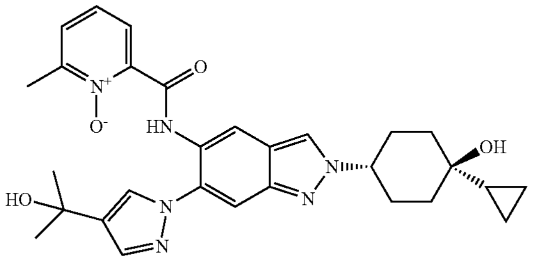
,
155
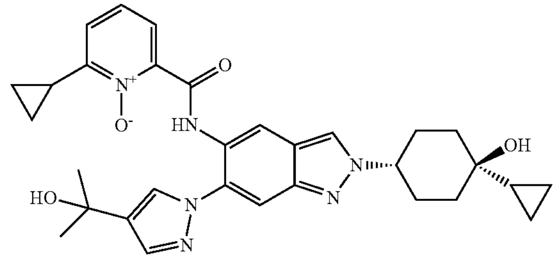
,
156
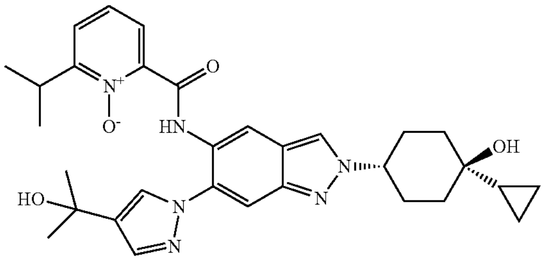
,
-continued
157
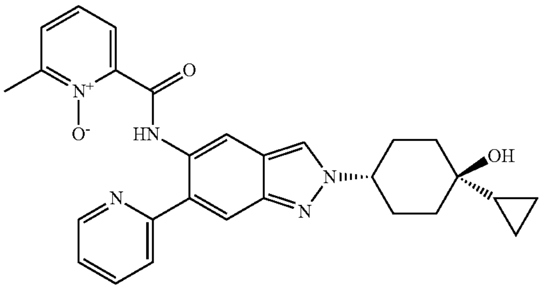
,
158
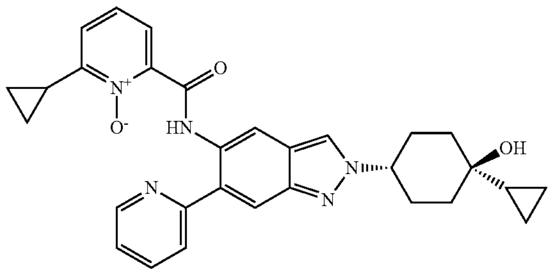
,
159
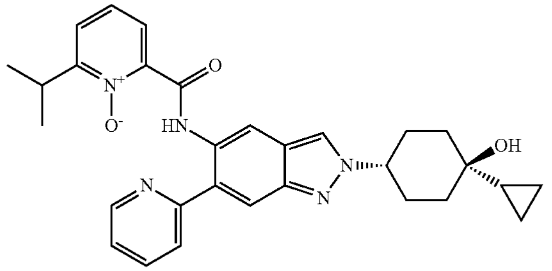
,
160
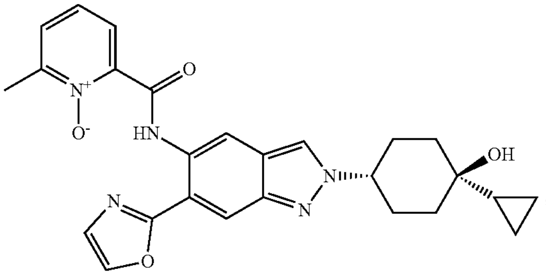
,
161
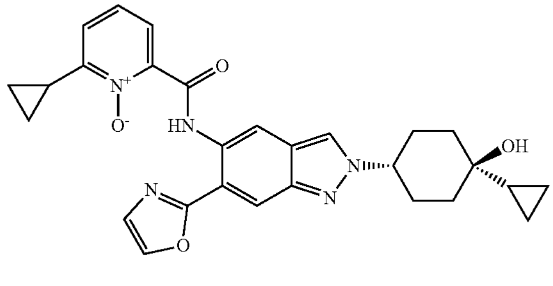
, -continued
162
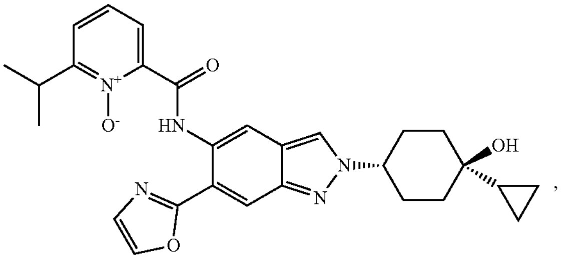
163
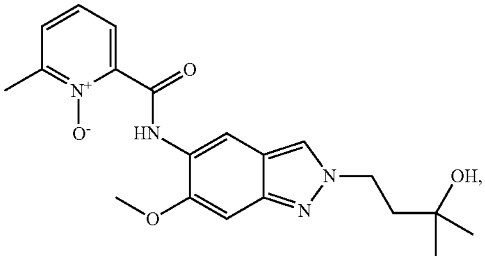
164
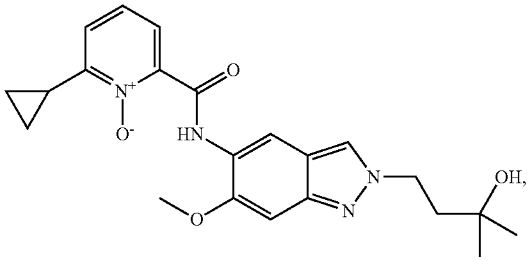
165
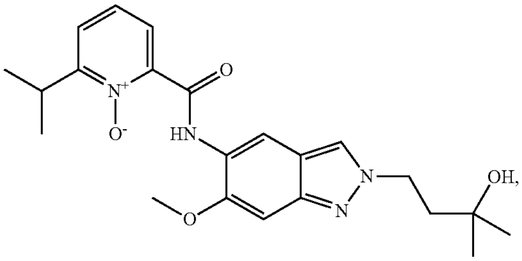
166
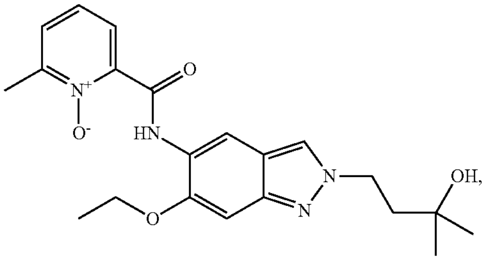
-continued
167
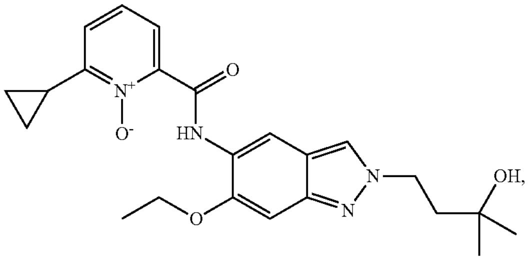
168
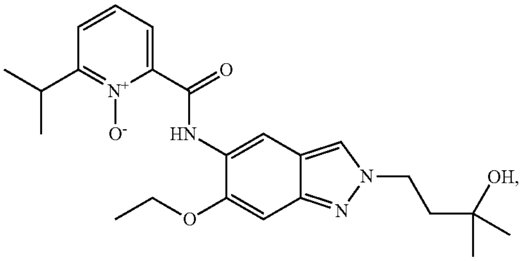
169
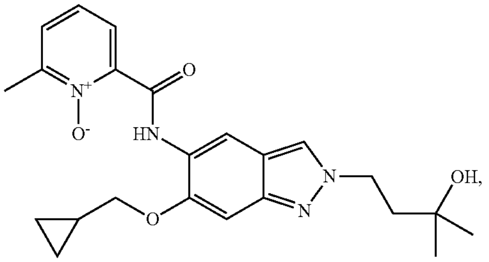
170
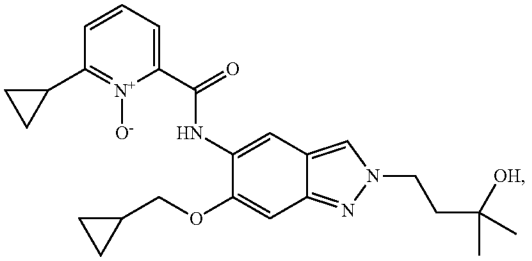
171
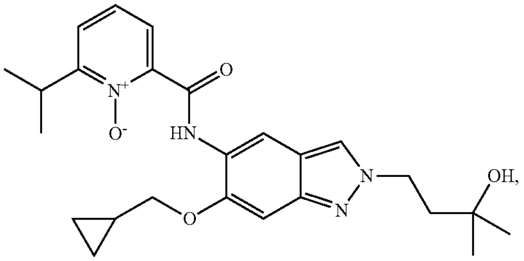

-continued
172
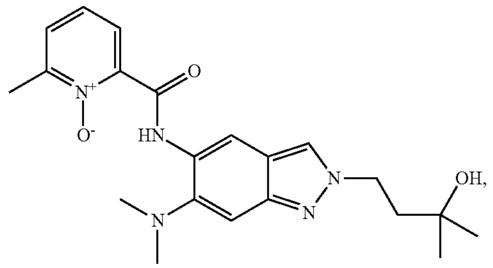
173
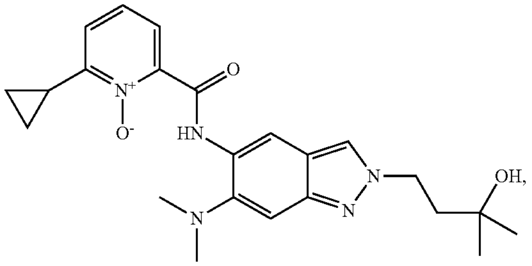
174
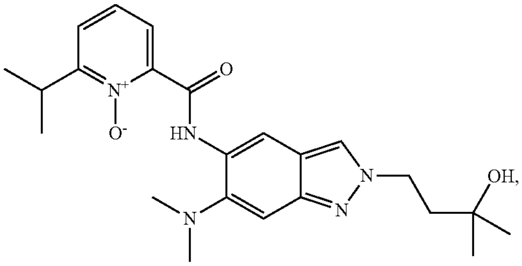
175
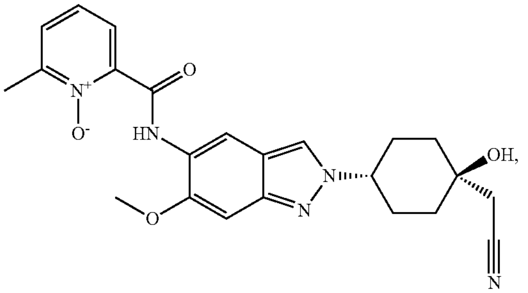
176
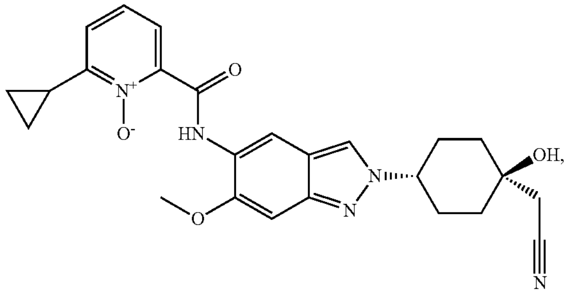
-continued
177
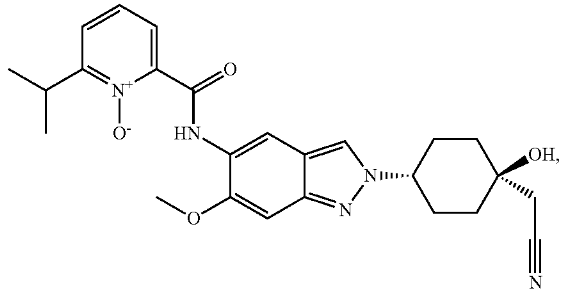
178
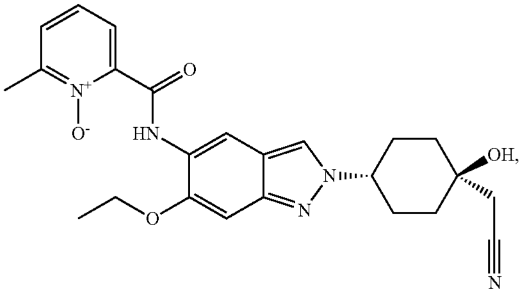
179
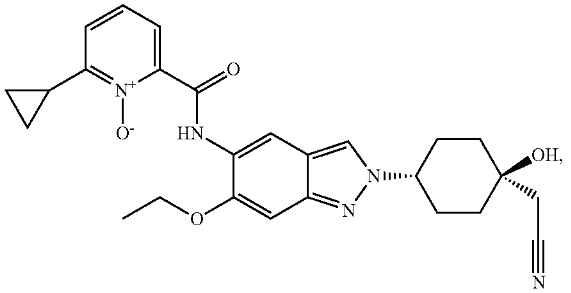
180
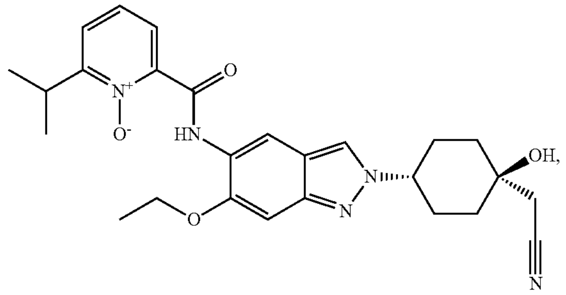
181
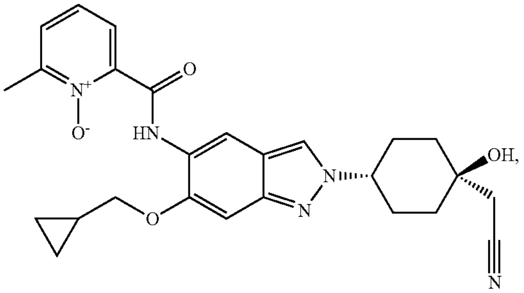

-continued
182
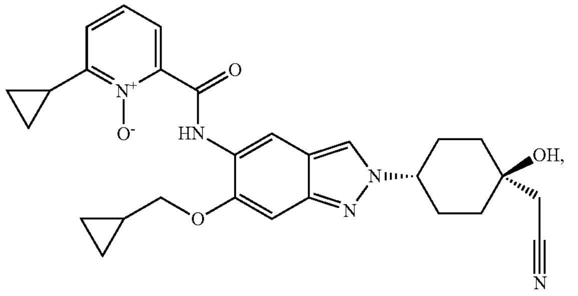
183
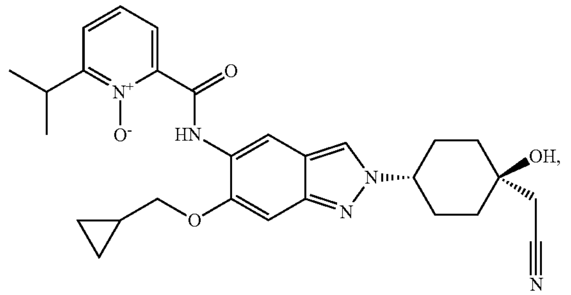
184
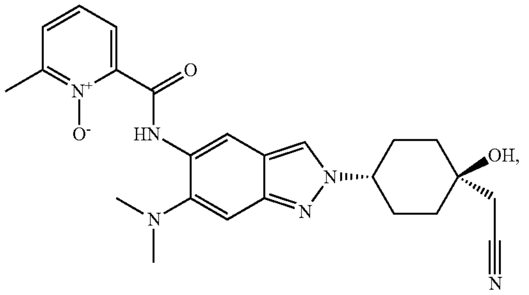
185
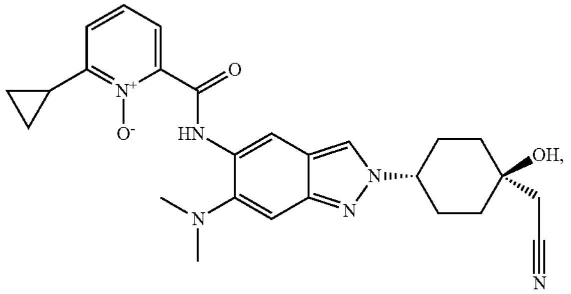
186
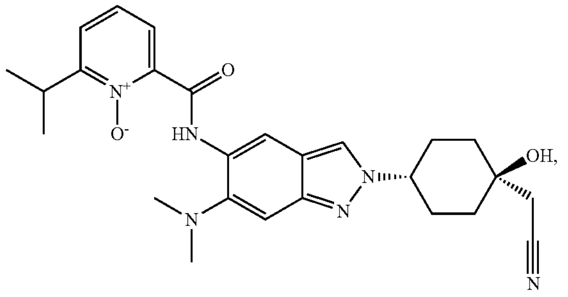
-continued
187
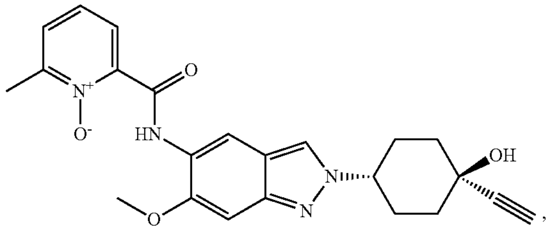
188
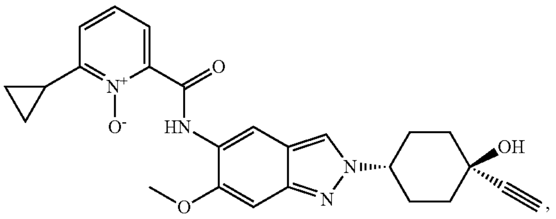
189
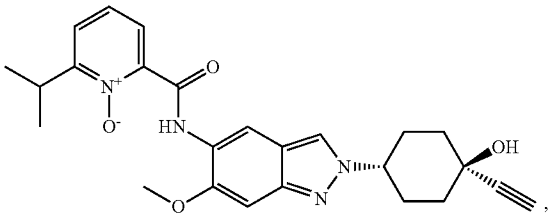
190
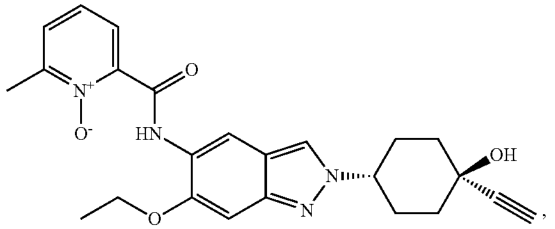
191
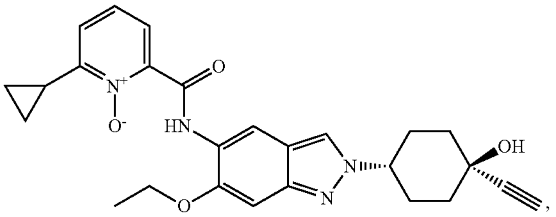
192
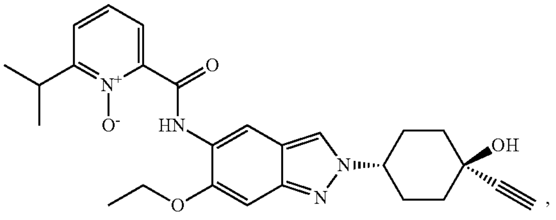

-continued
193
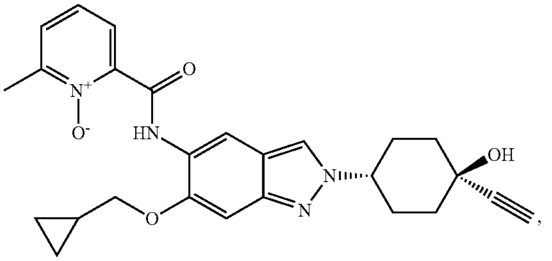
194
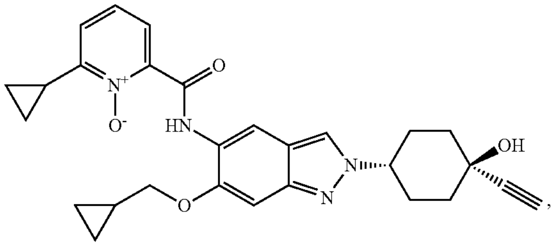
195
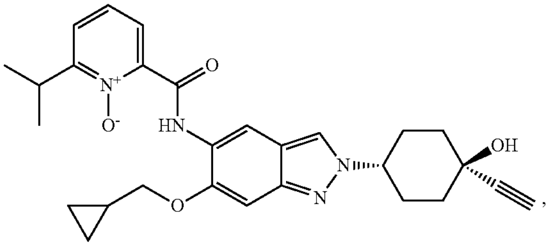
196
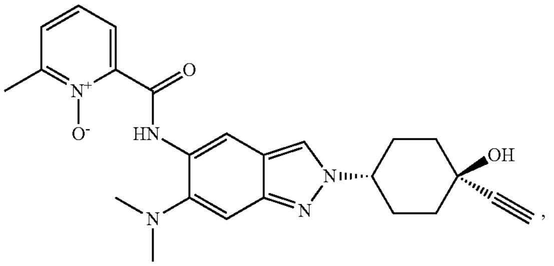
197
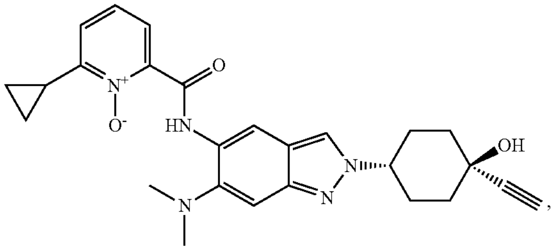
-continued
198
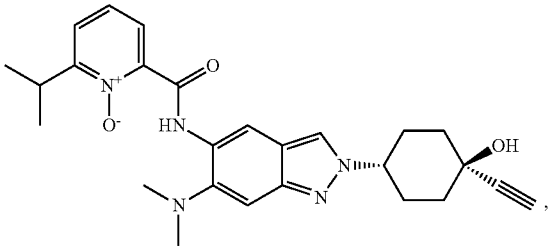
199
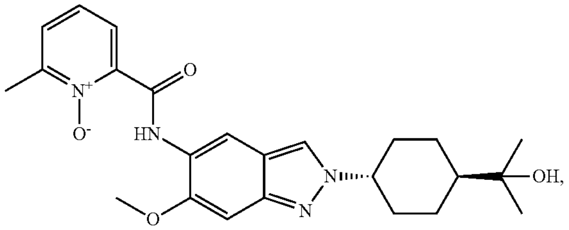
200
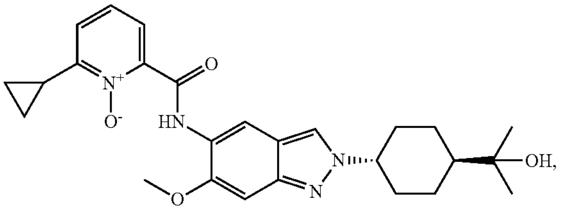
201
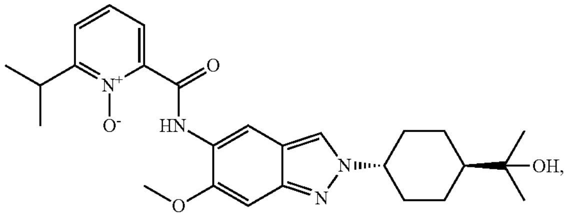
202
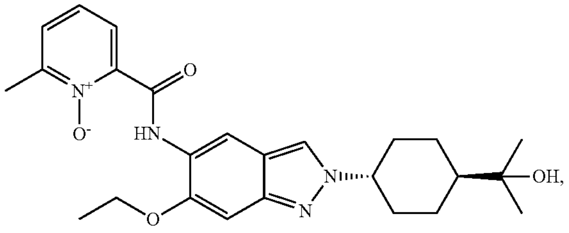
203
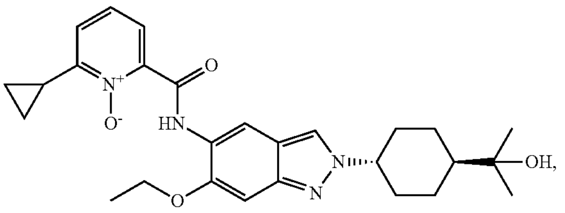

-continued
204
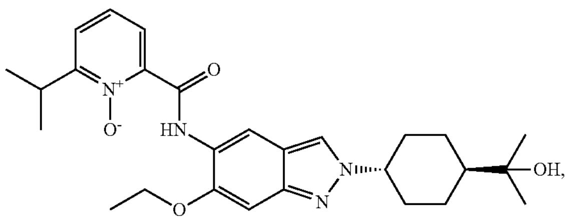
205
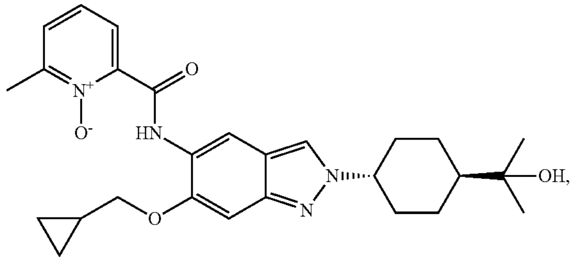
206
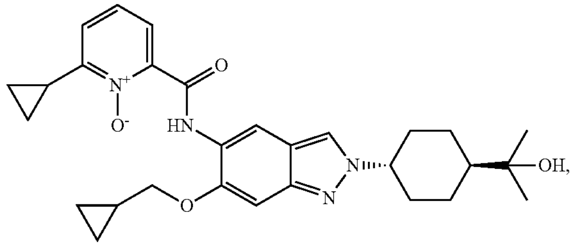
207
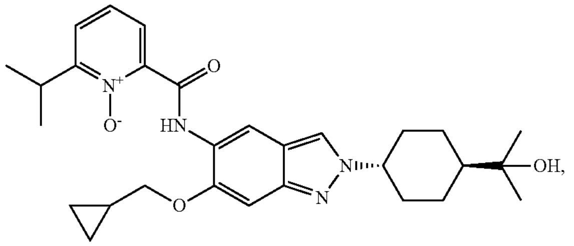
208
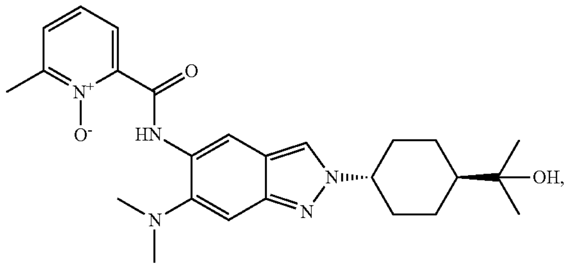
209
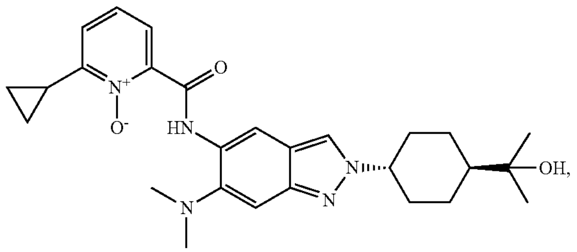
-continued
210
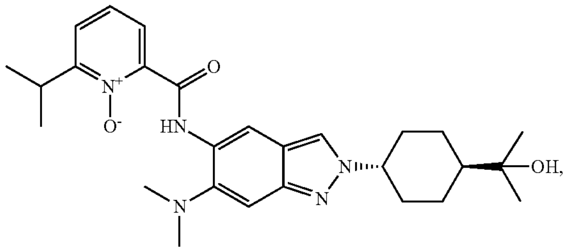
211
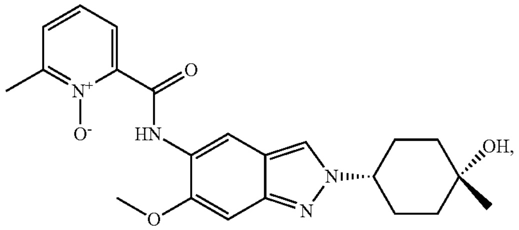
212
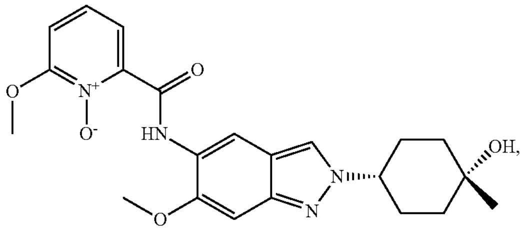
213
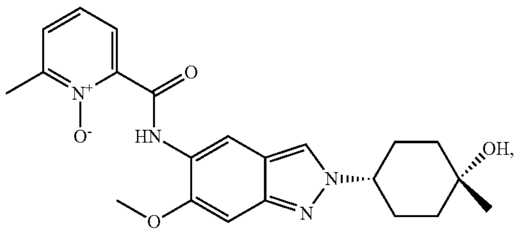
214
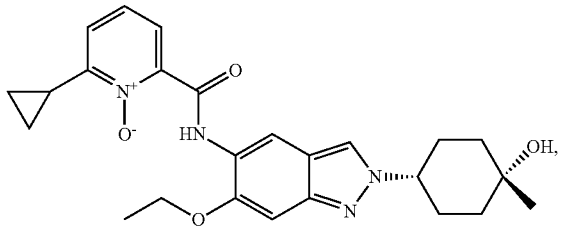
215
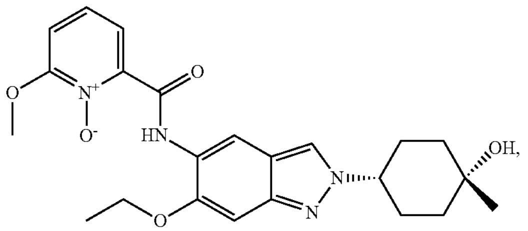

-continued
216
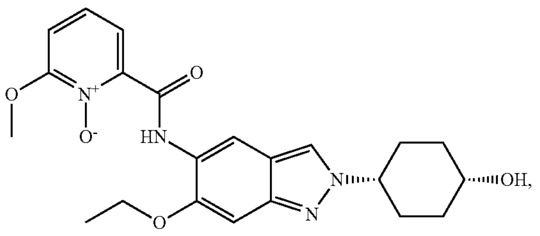
217
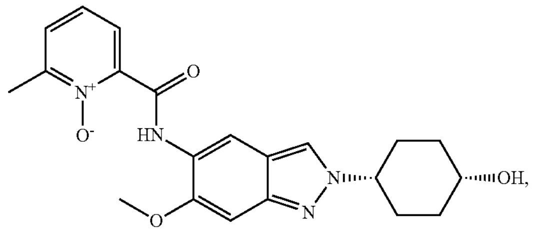
218
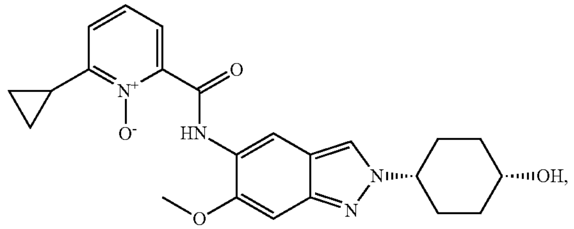
219
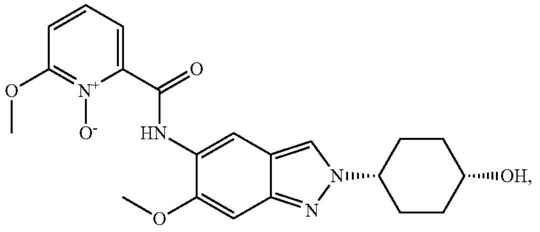
220
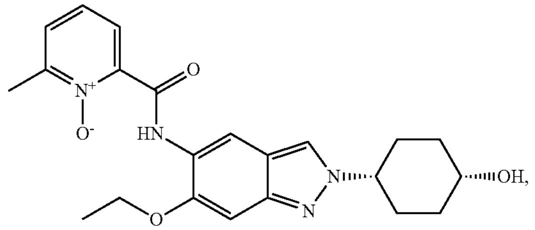
221
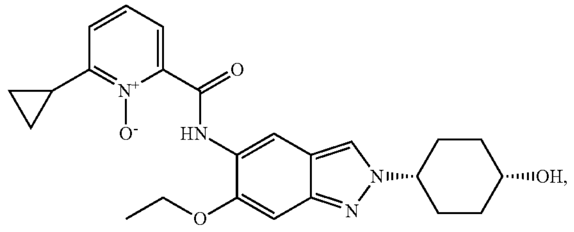
-continued
222
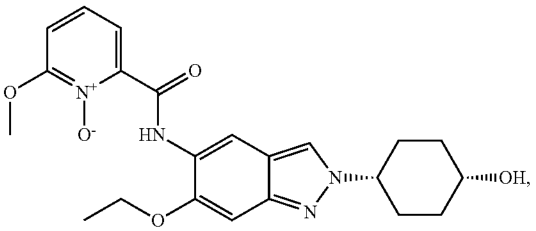
223
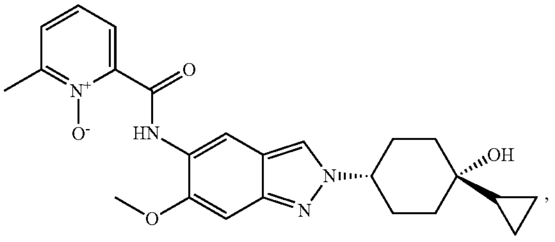
224
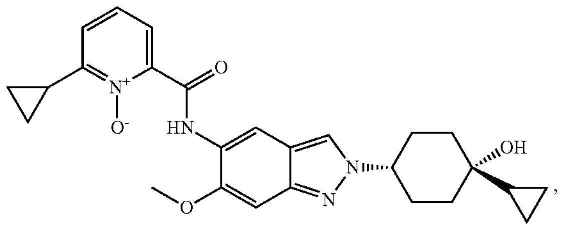
225
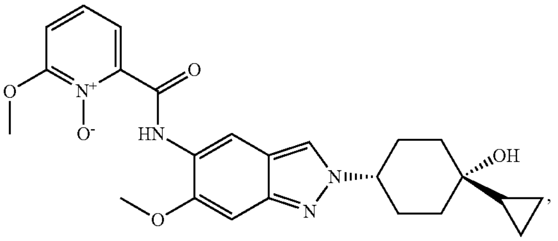
226
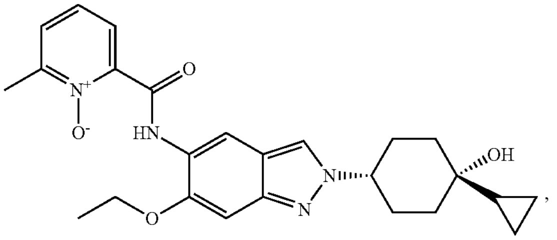
227
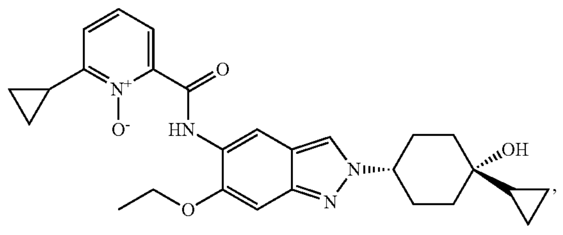

228
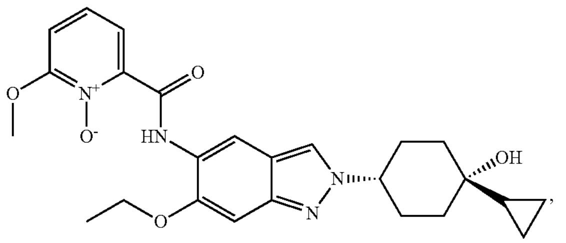
229
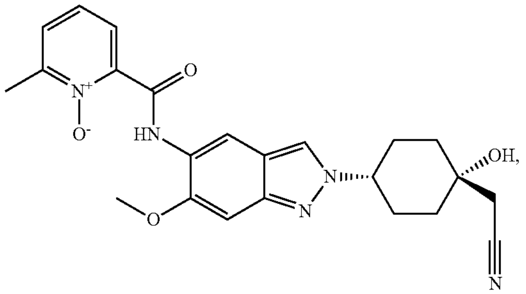
230
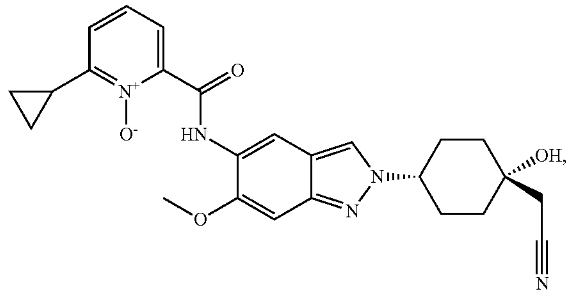
231
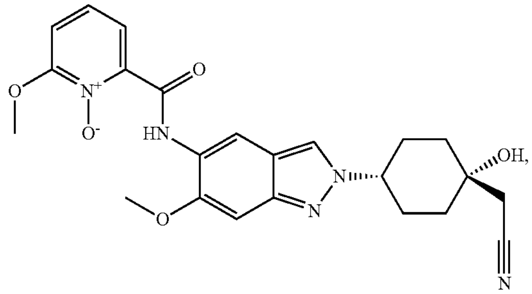
232
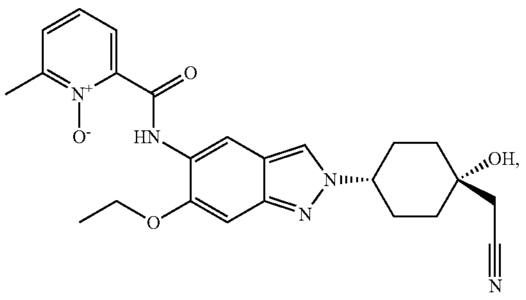
233
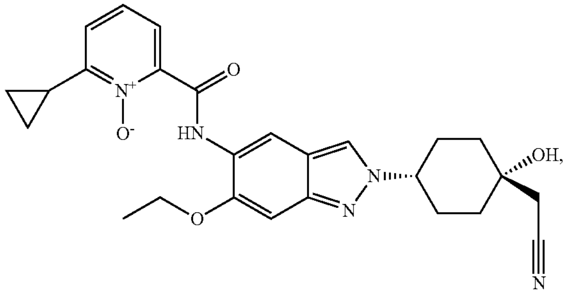
234
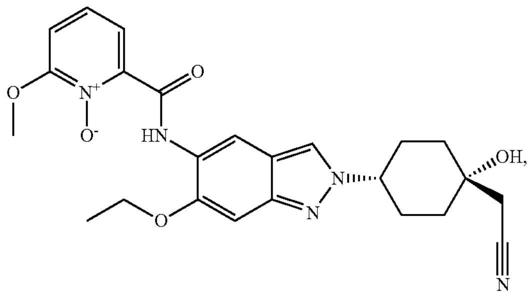
235
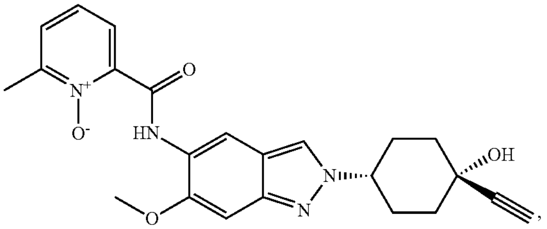
236
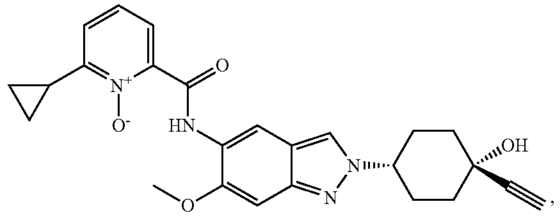
237
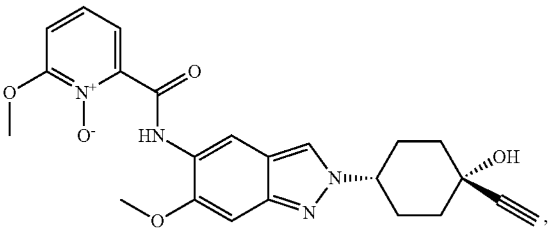

-continued
238
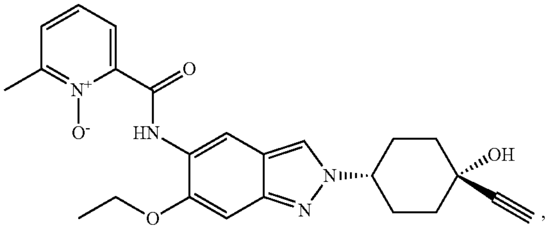
239
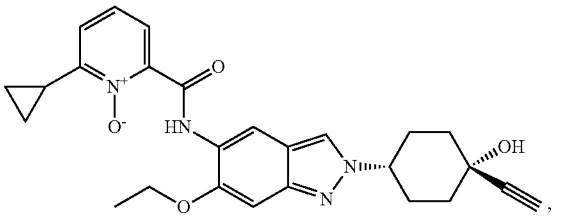
240
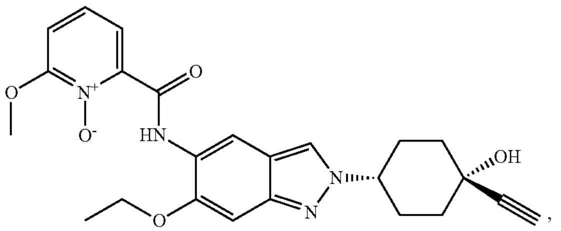
241
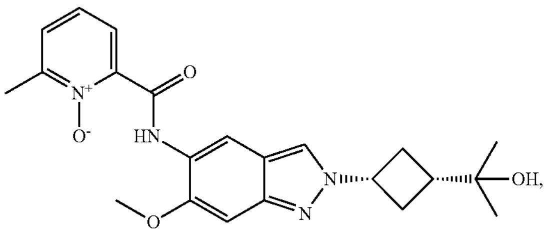
242
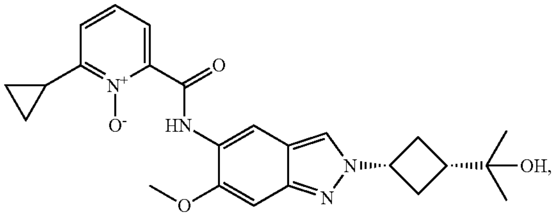
243
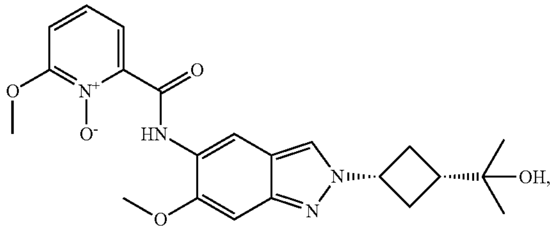
-continued
244
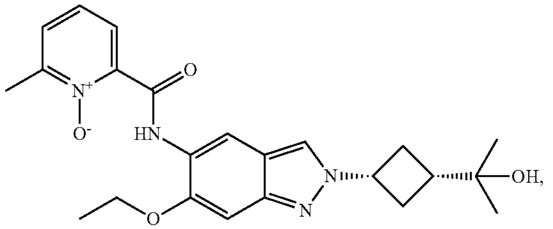
245
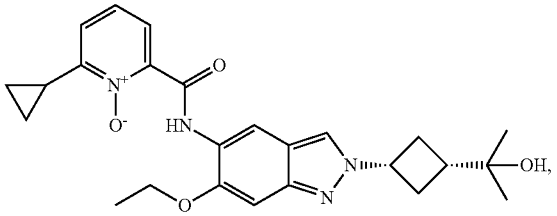
246
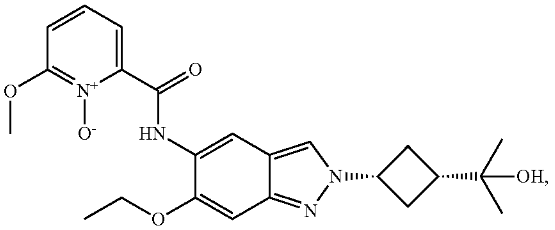
247
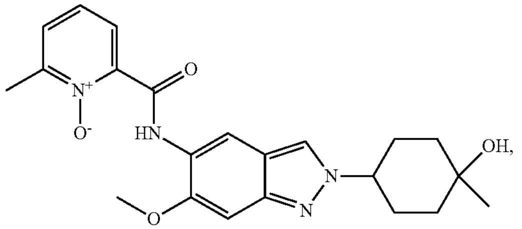
248
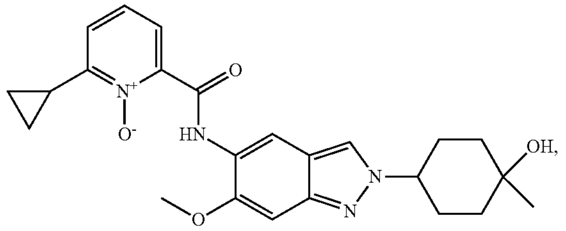
249
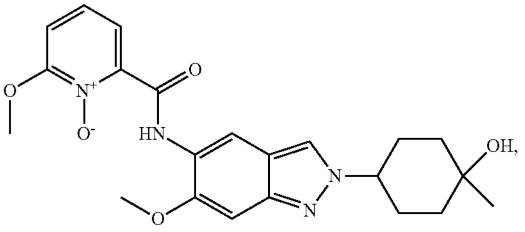

-continued
250
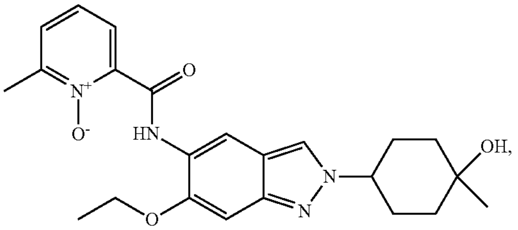
251
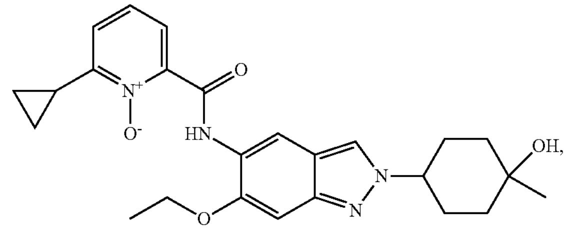
252
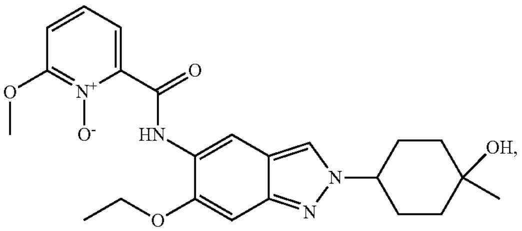
253
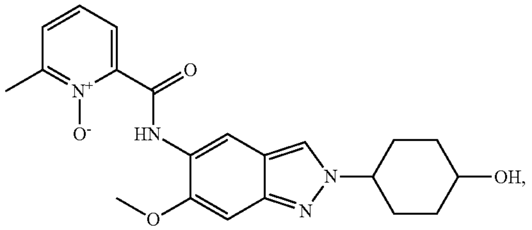
254
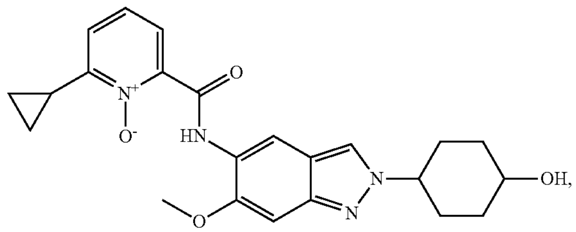
255
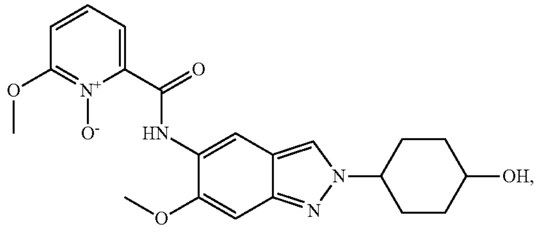
-continued
256
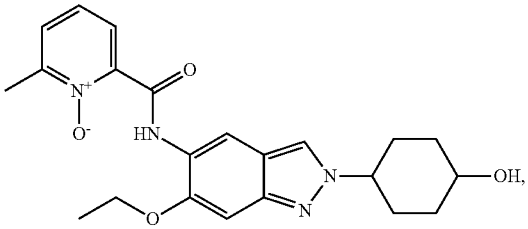
257
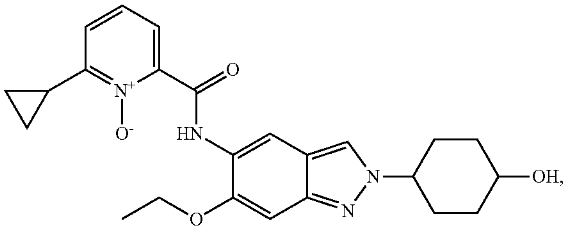
258
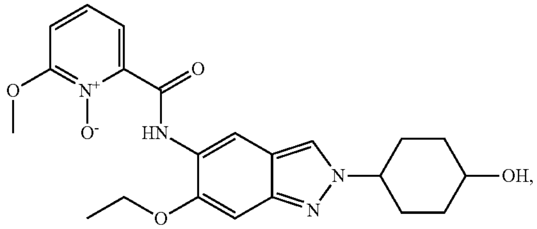
259
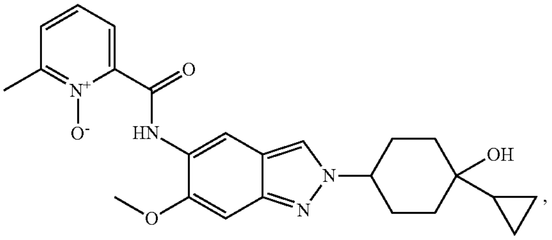
260
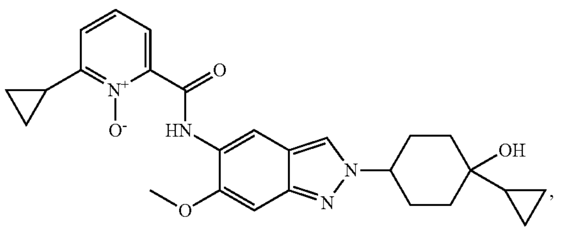
261
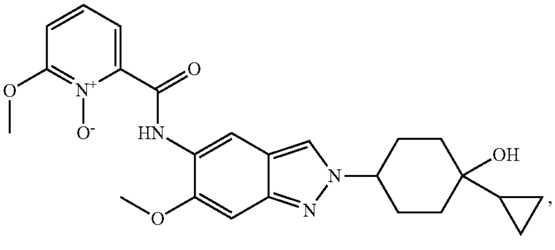

-continued
262
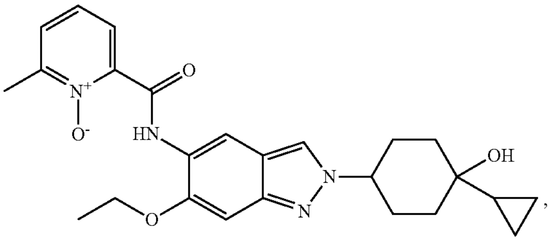
263
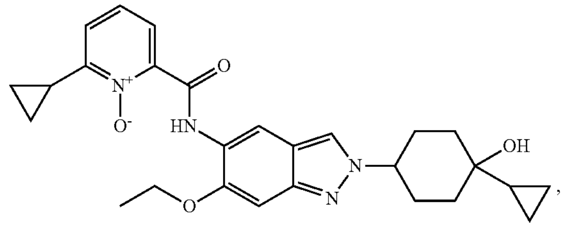
264
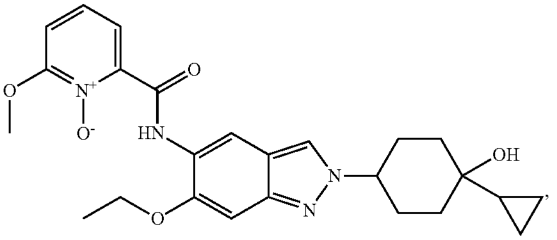
265
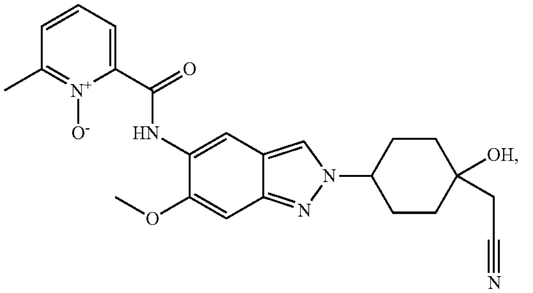
266
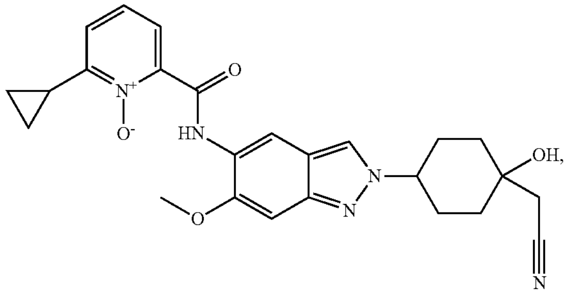
-continued
267
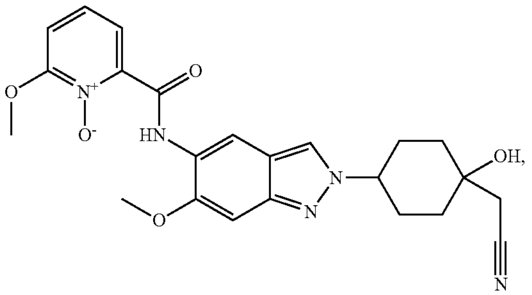
268
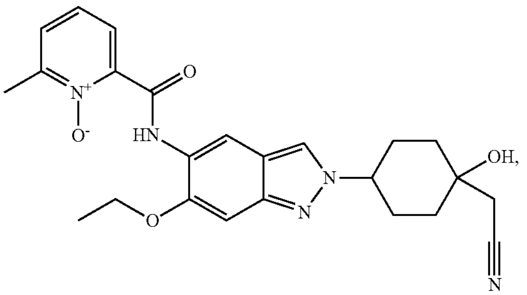
269
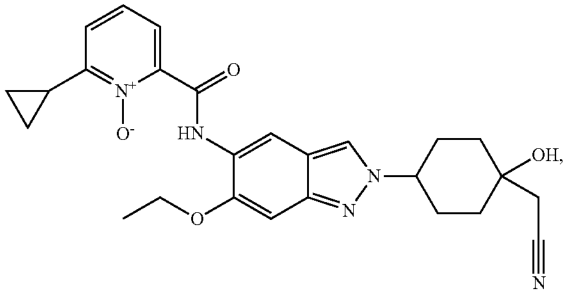
270
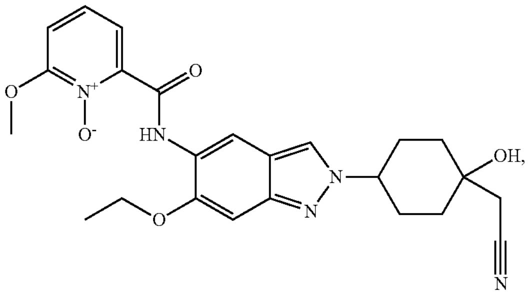
271
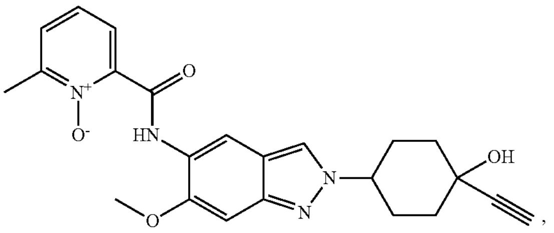

-continued
272
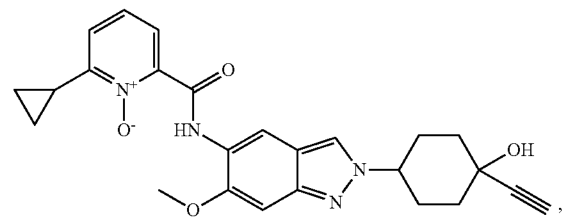
273
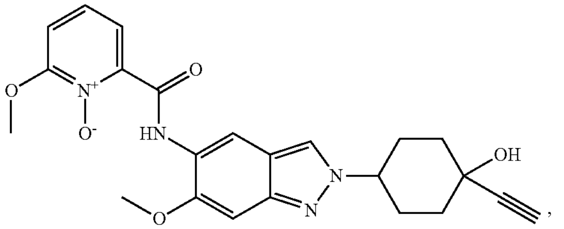
274
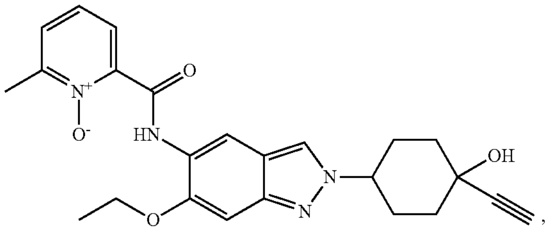
275
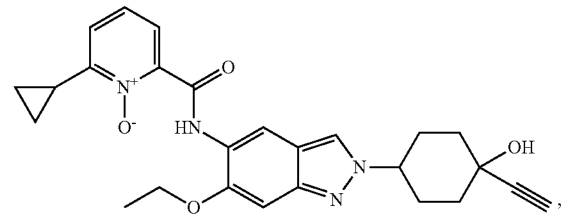
276
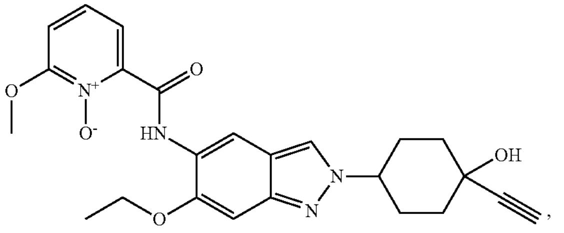
277
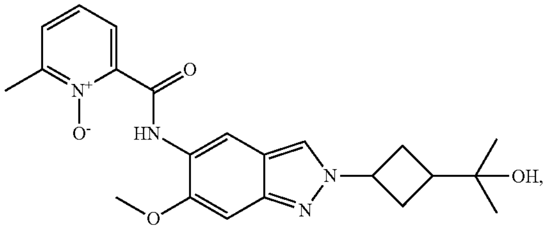
-continued
278
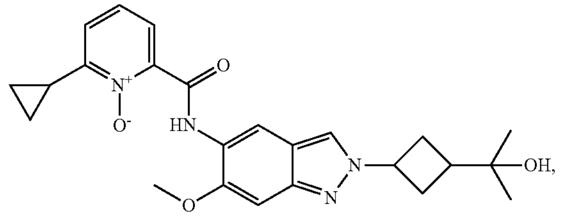
279
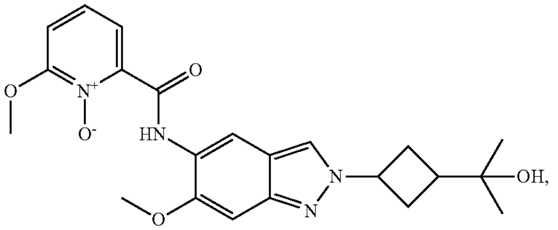
280
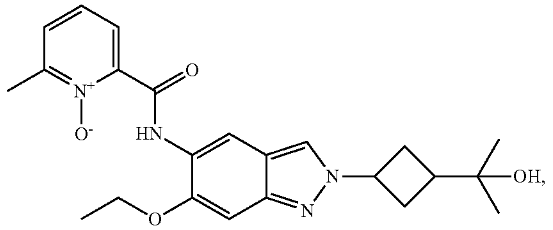
281
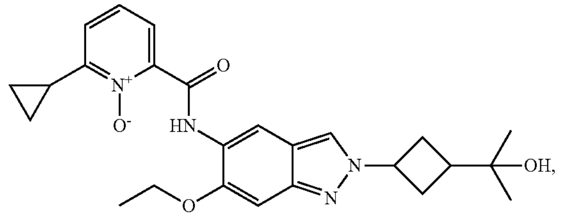
282
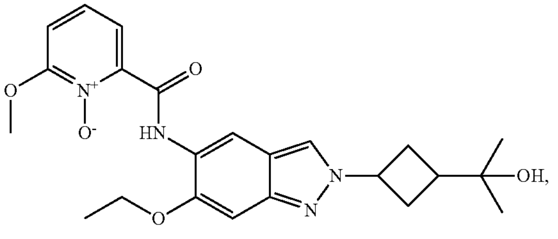
283
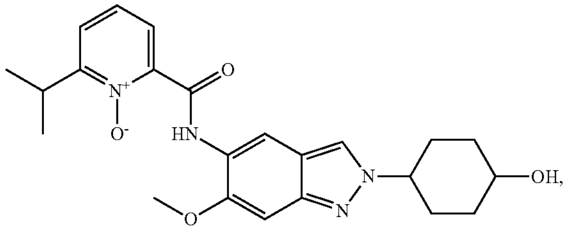

-continued

284

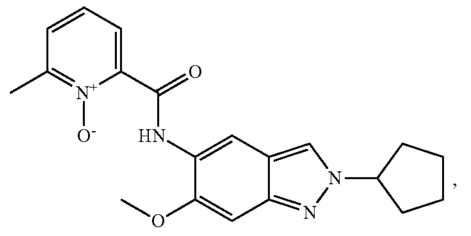

285

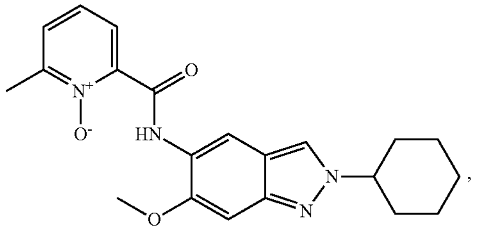

286

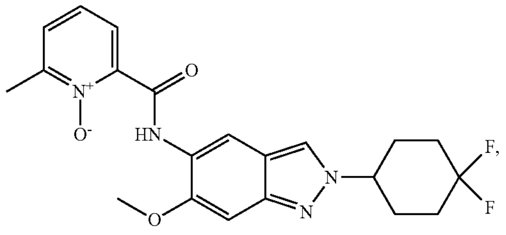

287

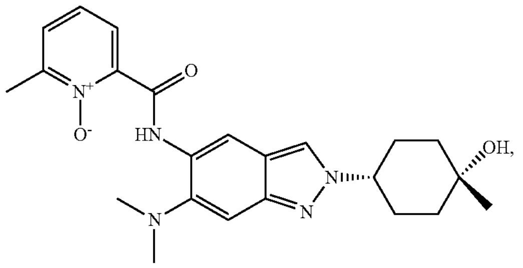

288

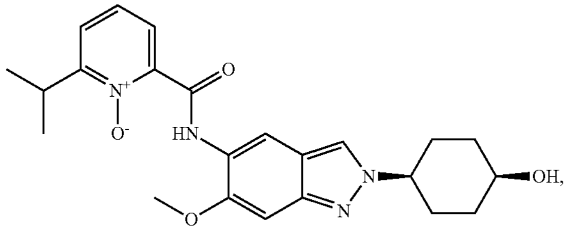

289

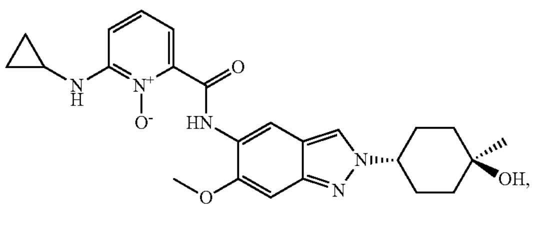

and

-continued

290

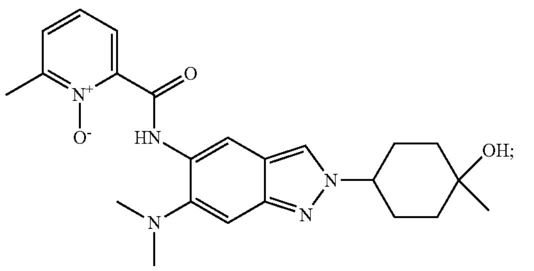

or a stereoisomer, a racemate, a tautomer, or a pharmaceutically acceptable salt thereof.

6. A pharmaceutical composition comprising the compound of claim 1.

7. The compound of claim 1, wherein ring A is 5-14 membered heteroaryl containing at least one N.

8. The compound of claim 1, wherein ring A is pyridine ring.

9. The compound of claim 1, wherein W is O.

10. The compound of claim 1, wherein $R_1$ is $C_{3-12}$ cycloalkyl optionally substituted with one, two, or more R.

11. The compound of claim 1, wherein $R_1$ is cyclopropyl, cyclobutyl, cyclopentyl, or cyclohexyl; each of which is optionally substituted with one or two R.

12. The compound of claim 1, wherein $R_1$

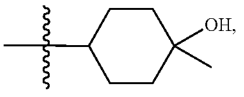 [SMILES: *C1CCC(C)(O)CC1]

is or a stereoisomer thereof.

13. The compound of claim 1, wherein $R_2$ is $(C_1\text{-}C_6)$ aliphatic hydrocarbyl, optionally substituted with one, two, or more R.

14. The compound of claim 1, wherein each instance of $R_3$ is independently $(C_1\text{-}C_6)$ aliphatic hydrocarbyl, optionally substituted with one, two, or more R.

15. The compound of claim 1, wherein each of $R_2$ and $R_3$ is independently methyl or ethyl; each of which is optionally substituted with one, two, or more R.

16. The compound of claim 1, wherein each instance of R is independently halogen, CN, OH, $NR_aR_b$, $(C_1\text{-}C_6)$ aliphatic hydrocarbyl, $C_{3-6}$ cycloalkyl, $(C_1\text{-}C_6)$ aliphatic hydrocarbyl comprising one or two heteroatoms, 3-6 membered heterocyclyl, $C_6$ aryl, or 5-6 membered heteroaryl; each of which is independently optionally substituted with one, two, or more R'.

17. The compound of claim 4, which is a compound of formula Ie:

fomula Ie

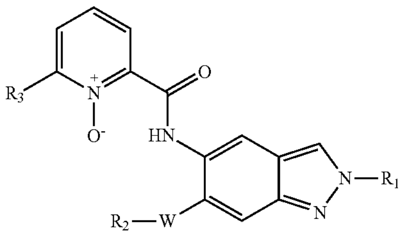

or a stereoisomer, a racemate, or a pharmaceutically acceptable salt thereof.
18. A compound, which is:
001
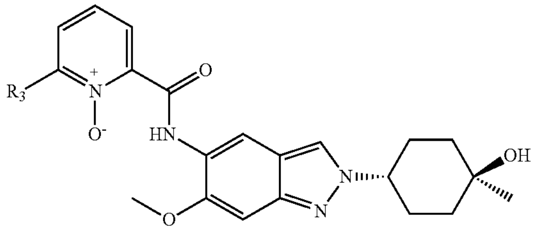
or a stereoisomer, a racemate, or a pharmaceutically acceptable salt thereof.
19. The compound of claim 18, which is:
001
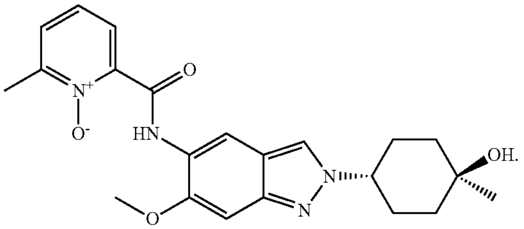
20. A pharmaceutical composition comprising the compound of claim 18.
* * * * *